(12) United States Patent
Fruchter et al.

(10) Patent No.: US 11,680,877 B2
(45) Date of Patent: Jun. 20, 2023

(54) TESTING FOR PARTICULATES

(71) Applicant: HERO SCIENTIFIC LTD., Jerusalem (IL)

(72) Inventors: Lazar Fruchter, Efrat (IL); Arie Oscar Holtz, Jerusalem (IL); Robert Eric Levitz, Beit Shemesh (IL); Leah Forgosh, Jerusalem (IL); Boaz Arieli, Mevaseret Tzion (IL)

(73) Assignee: HERO SCIENTIFIC LTD., Jerusalem (IL)

( * ) Notice: Subject to any disclaimer, the term of this patent is extended or adjusted under 35 U.S.C. 154(b) by 293 days.

(21) Appl. No.: 17/270,544

(22) PCT Filed: Sep. 5, 2019

(86) PCT No.: PCT/IL2019/050997
§ 371 (c)(1),
(2) Date: Feb. 23, 2021

(87) PCT Pub. No.: WO2020/049569
PCT Pub. Date: Mar. 12, 2020

(65) Prior Publication Data
US 2021/0215585 A1 Jul. 15, 2021

Related U.S. Application Data

(60) Provisional application No. 62/727,268, filed on Sep. 5, 2018.

(51) Int. Cl.
| C12N 15/10 | (2006.01) |
| C12N 15/115 | (2010.01) |
| G01N 33/53 | (2006.01) |
| G01N 1/40 | (2006.01) |
| C12Q 1/68 | (2018.01) |
| A61B 10/00 | (2006.01) |
| B01L 3/00 | (2006.01) |

(52) U.S. Cl.
CPC ....... *G01N 1/4077* (2013.01); *A61B 10/0051* (2013.01); *B01L 3/502* (2013.01); *B01L 2200/0668* (2013.01); *B01L 2300/0681* (2013.01); *B01L 2400/0478* (2013.01); *B01L 2400/0605* (2013.01); *G01N 2001/4088* (2013.01)

(58) Field of Classification Search
CPC .............. C12N 15/115; C12N 2310/16; C12Q 1/6811; C12Q 1/6818; C12Q 1/24
See application file for complete search history.

(56) References Cited

U.S. PATENT DOCUMENTS

| 1,856,811 A | 5/1932 | Inaki |
| 2,425,945 A | 8/1947 | Leach |
| 2,857,908 A | 10/1958 | Cornfield |
| 3,295,686 A | 1/1967 | Krueger |
| 3,449,081 A | 6/1969 | Hughes |
| 3,481,712 A | 12/1969 | Bernstein et al. |
| 3,745,090 A | 7/1973 | Chappelle |
| 3,897,902 A | 8/1975 | Yanez |
| 3,933,592 A | 1/1976 | Clendenning |
| 3,971,703 A | 7/1976 | Picciolo et al. |
| 4,144,134 A | 3/1979 | Plakas |
| 4,303,752 A | 12/1981 | Kolehmainen et al. |
| 4,421,848 A | 12/1983 | Whitlock |
| 4,503,149 A | 3/1985 | Boyd |
| 4,698,311 A | 10/1987 | Hall et al. |
| 4,729,846 A | 3/1988 | Matsui et al. |
| 4,829,005 A | 5/1989 | Friedman et al. |
| 4,863,602 A | 9/1989 | Johnson |
| 4,902,421 A | 2/1990 | Pascale et al. |
| 4,906,565 A | 3/1990 | Vossen |
| 5,073,272 A | 12/1991 | O'neill et al. |
| 5,077,012 A | 12/1991 | Guirguis |
| 5,139,031 A | 8/1992 | Guirguis |
| 5,186,897 A | 2/1993 | Eason et al. |
| 5,238,812 A | 8/1993 | Coulter et al. |
| 5,258,285 A | 11/1993 | Aegidius |
| 5,264,184 A | 11/1993 | Aysta et al. |

(Continued)

FOREIGN PATENT DOCUMENTS

| CN | 206910919 | 1/2018 |
| CN | 109567967 | 4/2019 |

(Continued)

OTHER PUBLICATIONS

Arnold, John C. and Victor Nizet. (2002). 27 Pharyngitis. Clin Infect Dis. 35: 113-125.
Bernheimer, A. W. and Pappenheimer A. M. Jr., "Factors necessary for massive growth of Group A hemolytic *Streptococcus*". Journal of Bacteriology, vol. 43(4), pp. 481/494 (1941).
Decelle JG & Taylor GR. (1976). Autoflora in the Upper Respiratory Tract of Apollo Astronauts. Applied and Environmental Microbiology. 32(5): 659-665.
Edwards E.A. et al., "Diagnosis of Group A Streptococcal Infections Directly from Throat Secretions," Journal of Clinical Microbiology Mar. 1982, p. 481-483 (1982).

(Continued)

*Primary Examiner* — Barry A Chestnut
(74) *Attorney, Agent, or Firm* — Sughrue Mion, PLLC

(57) ABSTRACT

A testing device (20, 120, 220, 290, 320, 420, 520, 620, 720, 820, 1020, 1120) is provided for testing for the presence of particulate in a liquid (22). The testing device (20, 120, 220, 290, 320, 420, 520, 620, 720, 820, 1020, 1120) includes a liquid container (30, 730) for containing the liquid (22); a filter (32, 132, 732), disposed in or downstream of the liquid container (30, 730); a liquid-pressure source (34, 734), which is arranged to apply pressure to drive the liquid (22) contained in the liquid container (30, 730) through the filter (32, 132, 732); and a filter chamber (36, 136, 236, 336, 736) that is (a) disposed downstream of the liquid container (30, 730), (b) shaped so as to define an inlet (38, 138, 238, 738, 838), and (c) in fluid communication with the filter (32, 132, 732). Other embodiments are also described.

34 Claims, 62 Drawing Sheets

(56) References Cited

U.S. PATENT DOCUMENTS

| | | |
|---|---|---|
| 5,339,829 A | 8/1994 | Thieme et al. |
| 5,376,337 A | 12/1994 | Seymour |
| 5,403,551 A | 4/1995 | Galloway et al. |
| 5,405,527 A | 4/1995 | Covington |
| 5,427,739 A | 6/1995 | Meserol et al. |
| 5,429,742 A | 7/1995 | Gutman et al. |
| 5,576,185 A | 11/1996 | Coulter et al. |
| 5,595,653 A | 1/1997 | Good et al. |
| 5,634,885 A | 6/1997 | Kiro |
| 5,690,825 A | 11/1997 | Parton |
| 5,695,989 A | 12/1997 | Kalamasz |
| 5,736,351 A | 4/1998 | Miller et al. |
| 5,776,341 A | 7/1998 | Barnard et al. |
| 5,868,928 A | 2/1999 | Bradley |
| 5,888,729 A | 3/1999 | Kacian et al. |
| 5,891,702 A | 4/1999 | Sakakibara et al. |
| 5,897,492 A | 4/1999 | Feller et al. |
| 5,905,029 A | 5/1999 | Andreotti et al. |
| 5,908,751 A | 6/1999 | Higo et al. |
| 5,980,456 A | 11/1999 | Falcone |
| 6,004,766 A | 12/1999 | Atrache et al. |
| 6,015,681 A | 1/2000 | Ralls et al. |
| 6,045,913 A | 4/2000 | Castle |
| 6,090,572 A | 7/2000 | Crosby |
| 6,140,040 A | 10/2000 | Palm et al. |
| 6,152,887 A | 11/2000 | Blume |
| 6,174,704 B1 | 1/2001 | Chu et al. |
| 6,197,598 B1 | 3/2001 | Schrier et al. |
| 6,200,767 B1 | 3/2001 | Sakakibara et al. |
| 6,207,445 B1 | 3/2001 | Crosby |
| 6,221,655 B1 | 4/2001 | Fung et al. |
| 6,251,660 B1 | 6/2001 | Muir et al. |
| 6,265,229 B1 | 7/2001 | Fodstad et al. |
| 6,451,260 B1 | 9/2002 | Dusterhoft et al. |
| 6,465,201 B1 | 10/2002 | Presente et al. |
| 6,531,578 B1 | 3/2003 | Webber et al. |
| 6,565,749 B1 | 5/2003 | Hou et al. |
| 6,576,460 B1 | 6/2003 | Baeumner et al. |
| 6,588,681 B2 | 7/2003 | Rothrum et al. |
| 6,641,543 B1 | 11/2003 | Osgoodby |
| 6,660,489 B2 | 12/2003 | Schrecengost et al. |
| 6,677,129 B1 | 1/2004 | Blume |
| 6,767,714 B2 | 7/2004 | Nazareth et al. |
| 6,811,971 B2 | 11/2004 | Klepp et al. |
| 6,824,560 B2 | 11/2004 | Pelton |
| 6,846,648 B2 | 1/2005 | Maes |
| 6,861,067 B2 | 3/2005 | Mcghee et al. |
| 6,911,148 B1 | 6/2005 | Demmer et al. |
| 6,967,261 B1 | 11/2005 | Soerens et al. |
| 6,991,898 B2 | 1/2006 | O'connor |
| 7,005,143 B2 | 2/2006 | Abuelyaman et al. |
| 7,045,913 B2 | 5/2006 | Ebrahim et al. |
| 7,052,831 B2 | 5/2006 | Fletcher et al. |
| 7,060,223 B2 | 6/2006 | Dicesare et al. |
| 7,083,911 B2 | 8/2006 | Wood et al. |
| 7,141,033 B2 | 11/2006 | Kanjilal et al. |
| 7,160,689 B2 | 1/2007 | Matsumoto et al. |
| 7,282,181 B2 | 10/2007 | Hudak et al. |
| 7,338,692 B2 | 3/2008 | Smith et al. |
| 7,422,868 B2 | 9/2008 | Fan et al. |
| 7,485,609 B2 | 2/2009 | Reddy et al. |
| 7,553,417 B2 | 6/2009 | Waller, Jr. et al. |
| 7,618,591 B2 | 11/2009 | Slowey et al. |
| 7,642,060 B2 | 1/2010 | Nagar et al. |
| 7,682,688 B2 | 3/2010 | Smith |
| 7,682,835 B2 | 3/2010 | Giordano |
| 7,824,732 B2 | 11/2010 | Sahouani et al. |
| 7,837,939 B2 | 11/2010 | Tung et al. |
| 7,927,548 B2 | 4/2011 | Slowey et al. |
| 7,935,161 B1 | 5/2011 | Adams et al. |
| 7,993,283 B1 | 8/2011 | Altschul |
| 8,030,088 B2 | 10/2011 | McCash et al. |
| 8,039,206 B1 | 10/2011 | Keenan |
| 8,057,608 B1 | 11/2011 | Saaski et al. |
| 8,069,690 B2 | 12/2011 | Desantolo et al. |
| 8,110,112 B2 | 2/2012 | Alburty et al. |
| 8,142,570 B1 | 3/2012 | Saaski et al. |
| 8,268,634 B2 | 9/2012 | Wu et al. |
| 8,272,255 B2 | 9/2012 | Halverson et al. |
| 8,278,091 B2 | 10/2012 | Rutter et al. |
| 8,281,937 B2 | 10/2012 | Collins et al. |
| 8,287,809 B2 | 10/2012 | Gould et al. |
| 8,322,539 B1 | 12/2012 | Ellis et al. |
| 8,343,726 B2 | 1/2013 | Boone et al. |
| 8,404,479 B2 | 3/2013 | Shimizu et al. |
| 8,475,739 B2 | 7/2013 | Holmes et al. |
| 8,541,242 B2 | 9/2013 | Boone et al. |
| 8,546,100 B2 | 10/2013 | Kshirsagar et al. |
| 8,562,572 B2 | 10/2013 | Proulx et al. |
| 8,563,264 B2 | 10/2013 | Halverson et al. |
| 8,569,072 B2 | 10/2013 | Halverson et al. |
| 8,584,535 B2 | 11/2013 | Page et al. |
| 8,597,878 B2 | 12/2013 | Hillebrand et al. |
| 8,603,008 B2 | 12/2013 | Libby et al. |
| 8,640,882 B2 | 2/2014 | Collins et al. |
| 8,647,508 B2 | 2/2014 | Halverson |
| 8,647,574 B2 | 2/2014 | Halverson et al. |
| 8,647,890 B2 | 2/2014 | Aberl et al. |
| 8,664,001 B2 | 3/2014 | Niskanen et al. |
| 8,685,746 B2 | 4/2014 | Halverson et al. |
| 8,709,796 B2 | 4/2014 | Faure et al. |
| 8,726,744 B2 | 5/2014 | Alburty et al. |
| 8,741,595 B2 | 6/2014 | Kshirsagar |
| 8,871,155 B2 | 10/2014 | Wu et al. |
| 8,898,069 B2 | 11/2014 | Hood et al. |
| 8,900,462 B2 | 12/2014 | Yamada et al. |
| 8,940,527 B2 | 1/2015 | Guirguis |
| 9,044,694 B2 | 6/2015 | Hacker et al. |
| 9,103,843 B2 | 8/2015 | Nieuwenhuis et al. |
| 9,113,850 B2 | 8/2015 | Skakoon |
| 9,115,382 B2 | 8/2015 | Bell |
| 9,295,453 B2 | 3/2016 | Katz |
| 9,297,804 B2 | 3/2016 | Palmon et al. |
| 9,314,570 B2 | 4/2016 | Kim |
| 9,327,284 B2 | 5/2016 | Rosman et al. |
| 9,328,325 B2 | 5/2016 | Kshirsagar et al. |
| 9,360,404 B2 | 6/2016 | Okanojo et al. |
| 9,381,000 B2 | 7/2016 | Morsey |
| 9,388,448 B2 | 7/2016 | Halverson |
| 9,470,612 B2 | 10/2016 | Rajagopal et al. |
| 9,482,351 B2 | 11/2016 | Proulx et al. |
| 9,546,391 B2 | 1/2017 | Rey et al. |
| 9,592,508 B2 | 3/2017 | Holmes et al. |
| 9,675,755 B2 | 6/2017 | Shick et al. |
| 9,709,468 B2 | 7/2017 | Ebi et al. |
| 9,719,125 B2 | 8/2017 | Kshirsagar et al. |
| 9,945,855 B2 | 4/2018 | Carrino et al. |
| 9,987,633 B2 | 6/2018 | Roscoe et al. |
| 10,106,830 B2 | 10/2018 | Maitra et al. |
| 10,376,878 B2 | 8/2019 | Calanca et al. |
| 10,612,258 B2 | 4/2020 | Coelho et al. |
| 10,993,705 B2 | 5/2021 | Katz et al. |
| 2002/0127630 A1 | 9/2002 | Diguiseppi et al. |
| 2003/0003441 A1 | 1/2003 | Colston et al. |
| 2003/0057147 A1 | 3/2003 | Sutcliffe |
| 2003/0092086 A1 | 5/2003 | Hirata et al. |
| 2003/0098271 A1 | 5/2003 | Somack et al. |
| 2003/0104507 A1 | 6/2003 | Wood et al. |
| 2003/0153021 A1 | 8/2003 | Lu et al. |
| 2004/0005246 A1 | 1/2004 | Efthimiadis et al. |
| 2004/0038425 A1 | 2/2004 | Ferguson et al. |
| 2004/0149636 A1 | 8/2004 | Backes et al. |
| 2004/0157971 A1 | 8/2004 | Kim |
| 2004/0161788 A1 | 8/2004 | Chen et al. |
| 2004/0197845 A1 | 10/2004 | Hassibi et al. |
| 2004/0220498 A1 | 11/2004 | Li et al. |
| 2005/0048592 A1 | 3/2005 | Wood et al. |
| 2005/0070701 A1 | 3/2005 | Hochstetler et al. |
| 2005/0142571 A1 | 6/2005 | Parthasarathy et al. |
| 2005/0152992 A1 | 7/2005 | Johnson, Jr. et al. |
| 2005/0153423 A1 | 7/2005 | Baba et al. |
| 2005/0181467 A1 | 8/2005 | Schrecengost et al. |
| 2005/0189290 A1 | 9/2005 | Maiden |
| 2005/0244943 A1 | 11/2005 | Ladisch et al. |

(56) References Cited

U.S. PATENT DOCUMENTS

| | | |
|---|---|---|
| 2005/0250138 A1 | 11/2005 | Young et al. |
| 2006/0062854 A1 | 3/2006 | Chandra et al. |
| 2006/0166347 A1 | 7/2006 | Faulstich et al. |
| 2006/0184085 A1 | 8/2006 | Kimura et al. |
| 2006/0273049 A1 | 12/2006 | Leach et al. |
| 2007/0062870 A1 | 3/2007 | Chen et al. |
| 2007/0148458 A1 | 6/2007 | Sahouani et al. |
| 2007/0212266 A1 | 9/2007 | Johnston et al. |
| 2007/0254320 A1 | 11/2007 | Olstein |
| 2007/0269341 A1 | 11/2007 | Halverson et al. |
| 2008/0023408 A1 | 1/2008 | Hansen |
| 2008/0064939 A1 | 3/2008 | Reynolds et al. |
| 2008/0078717 A1 | 4/2008 | Shigesada et al. |
| 2008/0153125 A1 | 6/2008 | Buttry et al. |
| 2008/0207794 A1 | 8/2008 | Wright et al. |
| 2009/0011403 A1 | 1/2009 | Smith et al. |
| 2009/0068065 A1 | 3/2009 | Pagoria et al. |
| 2009/0258411 A1 | 10/2009 | Petithory et al. |
| 2009/0281483 A1 | 11/2009 | Baker et al. |
| 2010/0190171 A1 | 7/2010 | Kshirsagar et al. |
| 2010/0209927 A1 | 8/2010 | Menon et al. |
| 2010/0209961 A1 | 8/2010 | Kshirsagar et al. |
| 2010/0248214 A1 | 9/2010 | Kshirsagar et al. |
| 2010/0248350 A1 | 9/2010 | Gazenko |
| 2010/0273177 A1 | 10/2010 | Piasio et al. |
| 2011/0315625 A1 | 12/2011 | Keenan et al. |
| 2011/0318814 A1 | 12/2011 | Kshirsagar et al. |
| 2012/0107799 A1 | 5/2012 | Daum |
| 2012/0156114 A1 | 6/2012 | Ziegmann et al. |
| 2012/0203167 A1 | 8/2012 | Johnson |
| 2012/0301907 A1 | 11/2012 | Sellappan et al. |
| 2013/0023443 A1 | 1/2013 | Shirai et al. |
| 2013/0059290 A1 | 3/2013 | Armes |
| 2013/0244225 A1 | 9/2013 | Kshirsagar et al. |
| 2013/0260370 A1 | 10/2013 | Kshirsagar et al. |
| 2014/0315221 A1 | 10/2014 | Morsey |
| 2015/0010918 A1 | 1/2015 | Ruvinsky |
| 2015/0031040 A1 | 1/2015 | Calanca et al. |
| 2015/0076069 A1 | 3/2015 | Ellis et al. |
| 2015/0093749 A1 | 4/2015 | Ling |
| 2015/0133574 A1 | 5/2015 | Kshirsagar et al. |
| 2016/0209305 A1 | 7/2016 | Kshirsagar et al. |
| 2016/0296927 A1 | 10/2016 | Kirschhoffer et al. |
| 2016/0341641 A1 | 11/2016 | Williams et al. |
| 2017/0043336 A1 | 2/2017 | Khattak et al. |
| 2017/0248503 A1 | 8/2017 | Kshirsagar et al. |
| 2017/0283792 A1 | 10/2017 | Benitez Porras et al. |
| 2018/0051313 A1 | 2/2018 | Rajagopal et al. |
| 2018/0339292 A1 | 11/2018 | Katz et al. |
| 2019/0381498 A1 | 12/2019 | Fruchter et al. |
| 2019/0383807 A1 | 12/2019 | Connelly et al. |
| 2020/0140251 A1 | 5/2020 | Katz et al. |
| 2022/0288583 A1 | 9/2022 | Katz et al. |

FOREIGN PATENT DOCUMENTS

| | | |
|---|---|---|
| EP | 0364173 | 4/1990 |
| EP | 0378353 | 7/1990 |
| EP | 0952209 | 10/1999 |
| EP | 1089800 | 11/2003 |
| EP | 1166078 | 9/2004 |
| EP | 1674867 | 7/2009 |
| EP | 2214830 | 9/2012 |
| EP | 2214829 | 12/2012 |
| EP | 2217378 | 2/2013 |
| EP | 2217377 | 9/2013 |
| EP | 1907527 | 2/2016 |
| EP | 3290920 | 3/2018 |
| EP | 2868742 | 8/2018 |
| GB | 2411668 | 7/2008 |
| JP | H05203649 | 8/1993 |
| JP | 2003215126 | 7/2003 |
| JP | 2004279113 | 10/2004 |
| JP | 2005257604 | 9/2005 |
| JP | 2006-167411 | 6/2006 |
| JP | 2013000107 | 1/2013 |
| WO | 89/09279 | 10/1989 |
| WO | 93/01271 | 1/1993 |
| WO | 96/04067 | 2/1996 |
| WO | 2000/021973 | 4/2000 |
| WO | 00/29112 | 5/2000 |
| WO | 01/14257 | 3/2001 |
| WO | 2002153297 | 5/2002 |
| WO | 2003038162 | 2/2003 |
| WO | 03/069301 | 8/2003 |
| WO | 2004/015413 | 2/2004 |
| WO | 2006/100452 | 9/2006 |
| WO | 2007/050072 | 5/2007 |
| WO | 2007/137257 | 11/2007 |
| WO | 2008/075044 | 6/2008 |
| WO | 2008/093329 | 8/2008 |
| WO | 2009/018544 | 2/2009 |
| WO | 2009/048743 | 4/2009 |
| WO | 2009/067498 | 5/2009 |
| WO | 2009/067503 | 5/2009 |
| WO | 2009/067513 | 5/2009 |
| WO | 2009/067518 | 5/2009 |
| WO | 2009/082667 | 7/2009 |
| WO | 2010/056128 | 5/2010 |
| WO | 2012/031156 | 3/2012 |
| WO | 2014/048263 | 4/2014 |
| WO | 2014/145810 | 9/2014 |
| WO | 2017/112911 | 6/2017 |
| WO | 2018/102783 | 6/2018 |
| WO | 2018/158768 | 9/2018 |
| WO | 2019/060950 | 4/2019 |
| WO | 2019/139901 | 7/2019 |
| WO | 2021/229564 | 11/2021 |

OTHER PUBLICATIONS

Covalciuc KA et al., "Comparison of Four Clinical Specimen Types for Detection of Influenza A and B Viruses by Optical Immunoassay (Flu OIA Test) and Cell Culture Methods," Journal of Clinical Microbiology, Dec. 1999, p. 3971-3974.

Bisno, Alan L., Michael A. Gerber, Jack M. Gwaltney Jr., Edward L. Kaplan, and Richard H. Schwartz. (2002). Practice Guidelines for the Diagnosis and Management of Group A Streptococcal Pharyngitis. Clinical Infectious Diseases. 35: 113-125.

Fox, James W et al., "Diagnosis of Streptococcal Pharyngitis by Detection of *Streptococcus pyogenes* in Posterior Pharyngeal versus Oral Cavity Specimens," Journal of Clinical Microbiology, Jul. 2006. p. 2593-2594.

Gao Y et al., "The Scl1 of M41-type group A *Streptococcus* binds the highdensity lipoprotein," FEMS Microbiol Lett. Aug. 1, 2010; 309(1).

Garbieri et al., "Human DNA extraction from whole saliva that was fresh or stored for 3, 6 or 12 months using five different protocols," J. Appl. Oral Sci. vol. 25 No. 2 Bauru Mar./Apr. 2017.

Hamburger, Morton Jr. (1944). Studies on the Transmission of Hemolytic Streptococcus Infections: II. Beta Hemolytic Streptococci in the Saliva of Persons with Positive Throat Cultures. The Journal of Infectious Diseases. 75(1): 71-78. https://www.jstor.org/stable/30089409.

Johnston DA & Bodey GP. (1970). Semiquantitative Oropharyngeal Culture Technique. Applied Microbiology. 20(2): 218-223.

Jordens JZ, et al. (2002). Detection of Meningococcal Carriage by Culture and PCR of Throat Swabs and Mouth Gargles. J Clin Microbiol. 40(1): 75-79.

Kaplan, Edward L., Robert Couser, Barbara Ballard Huwe, Carolyn Mckay, and Lewis W. Wannamaker. (1979). Significance of Quantitative Salivary Cultures for Group A and Non-group A Beta-Hemolytic Streptococci in Patients with Pharyngitis and in Their Family Contacts. Pediatrics. 64(6): 904-912.

Karaby O et al., "Efficacy of Throat Gargling for Detection of Group A Beta-Hemolytic *Streptococcus*," Jpn. J. Infect. Dis. 58, 39-40, 2005.

McKesson Strep_A_5003_insert_2015_12.

Spellberg, Barbara and Claudia Brandt. (2016). Laboratory Diagnosis of *Streptococcus pyogenes* (group A streptococci). In Ferretti JJ, Stevens DL, Fischetti VA (Ed). *Streptococcus pyogenes*: Basic

(56) References Cited

OTHER PUBLICATIONS

Biology to Clinical Manifestations [Internet]. Oklahoma City (OK): University of Oklahoma Health Sciences Center. 2016.
Thermo Scientific Titan3 and Target2 Syringe Filters Product Catalog 2016.
Yilmaz F et al. (Abstract) 2008, "Effectiveness of rapid antigen test with throat gargle in detecting group A beta-hemolytic streptococci," Kulak Burun Bogaz Ihtis Derg. Sep.-Oct. 2008;18(5):280-3.
Yilmaz, Fahrettin, et al.(2008). Boğaz gargarasi ile yapilan hizli antij en testinin grup A beta-hemolitik streptokoklari saptamadaki etkinliği. Kulak Burun Bogaz Ihtis Derg. 18(5): 280-283. Klinik Çalişma. Turkish.
Yilmaz,Fahrettin, et al. (2008). Effectiveness of rapid antigen test with throat gargle in detecting group A beta-hemolytic streptococci. Journal of Ear Nose and Throat. 18(5): 280-283. Clinical Study. Google Translation.
An International Search Report and a Written Opinion both dated Jun. 29, 2020, which issued during the prosecution of Applicant's PCT/IL2019/050997.
An International Search Report and a Written Opinion both dated Dec. 31, 2019, which issued during the prosecution of Applicant's PCT/IL2019/050994.
An International Search Report and a Written Opinion both dated Aug. 23, 2018, which issued during the prosecution of Applicant's PCT/IL2018/050225.
An Office Action dated Jul. 21, 2017, which issued during the prosecution of UK Patent Application No. 1703383.8.
An Invitation to pay additional fees dated Jun. 12, 2018, which issued during the prosecution of Applicant's PCT/IL2018/050225.
An International Search Report and a Written Opinion both dated Dec. 3, 2020, which issued during the prosecution of Applicant's PCT/IL2020/050957.
An Office Action dated Mar. 25, 2021, which issued during the prosecution of U.S. Appl. No. 16/489,853.
An International Search Report and a Written Opinion both dated Jun. 22, 2021, which issued during the prosecution of Applicant's PCT/IB2021/052055.
An International Search Report and a Written Opinion both dated Jun. 22, 2021, which issued during the prosecution of Applicant's PCT/IB2021/052056.
Ek, Peter, et al."A combination of naso-and oropharyngeal swabs improves the diagnostic yield of respiratory viruses in adult emergency department patients." Infectious Diseases 51.4 (2019): 241-248.
Kim, Curi, et al."Comparison of nasopharyngeal and oropharyngeal swabs for the diagnosis of eight respiratory viruses by real-time reverse transcription—PCR assays." PloS one 6.6 (2011): e21610.
Black, W. D., et al. "Reverse transcriptase-polymerase chain reaction for the detection equine rhinitis B viruses and cell culture isolation of the virus." Archives of virology 152.1 (2007): 137-149.
Dou, Maowei, et al. "A low-cost microfluidic platform for rapid and instrument-free detection of whooping cough." Analytica chimica acta 1065 (2019): 71-78.
Duverlie, Gilles, et al. "A nylon membrane enzyme immunoassay for rapid diagnosis of influenza A infection." Journal of virological methods 40.1 (1992): 77-84.
An Invitation to pay additional fees dated Mar. 3, 2020, which issued during the prosecution of Applicant's PCT/IL2019/050997.
Oil filter. (Jul. 14, 2021). In Wikipedia. https://en.wikipedia.org/w/index.php?title=Oil_filter.
U.S. Appl. No. 62/727,268, filed Sep. 5, 2018.
An International Search Report and a Written Opinion both dated Jan. 10, 2022, which issued during the prosecution of Applicant's PCT/IL2021/051035.
An International Search Report and a Written Opinion both dated Aug. 4, 2021, which issued during the prosecution of Applicant's PCT/IL2021/050519.
An Office Action dated Aug. 24, 2021, which issued during the prosecution of U.S. Appl. No. 16/489,853.
DNA extraction from water: 50-50-50 buffer-chloroform/phenol method, Oct. 1, 2004 (Oct. 1, 2004), pp. 1-5, XP055936619. Retrieved from the Internet: URL: http: //www.eeescience.utoledo.edu/faculty/sigler/Von_Sigler/LEPR_Protocols_files/DNA%20extraction%20-%20water.pdf.
An Office Action dated Jul. 8, 2022, which issued during the prosecution of European Patent Application No. 19769600.8.
An Invitation to pay additional fees dated May 25, 2022, which issued during the prosecution of Applicant's PCT/IL2022/050024.
An Office Action together with the English machine translation dated Apr. 15, 2020 which issued during the prosecution of Chinese Patent Application No. 201880028401.4.
An Office Action together with the English machine translation dated Apr. 13, 2022 which issued during the prosecution of Chinese Patent Application No. 201980064434.9.
An Office Action dated Apr. 1, 2022, which issued during the prosecution of U.S. Appl. No. 16/489,853.
An Office Action together with the English machine translation dated Oct. 15, 2021 which issued during the prosecution of Chinese Patent Application No. 201880028401.4.
An Office Action dated Oct. 24, 2022, which issued during the prosecution of U.S. Appl. No. 17/122,594.
An International Search Report and a Written Opinion both dated Jul. 21, 2022, which issued during the prosecution of Applicant's PCT/IL2022/050024.
An Office Action dated Jul. 15, 2022, which issued during the prosecution of U.S. Appl. No. 17/122,594.

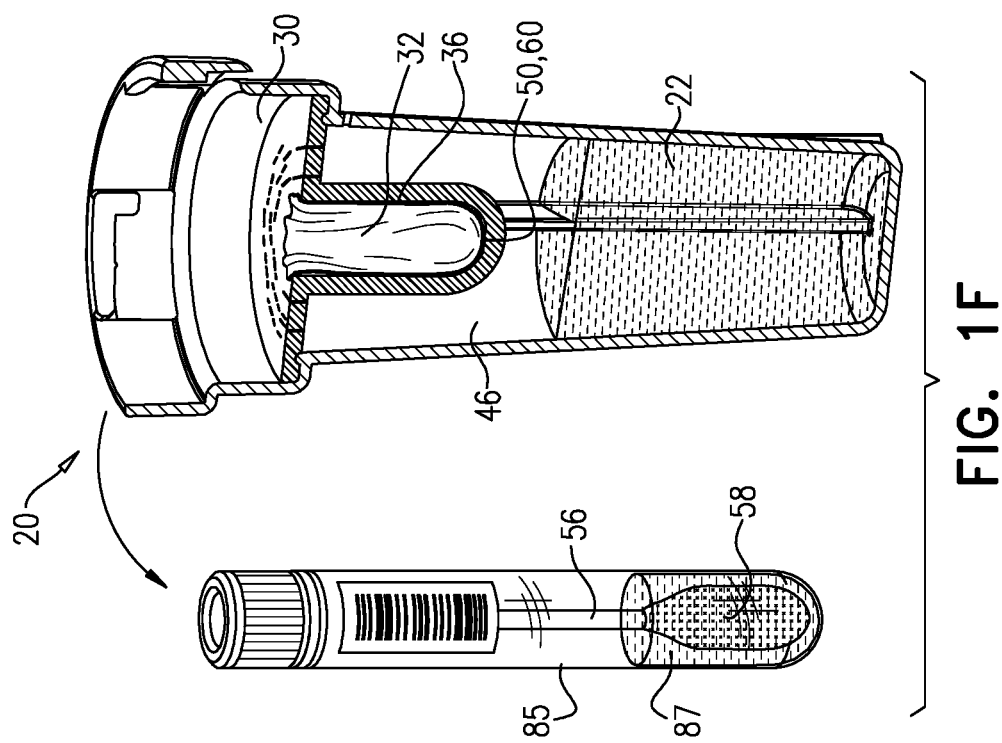
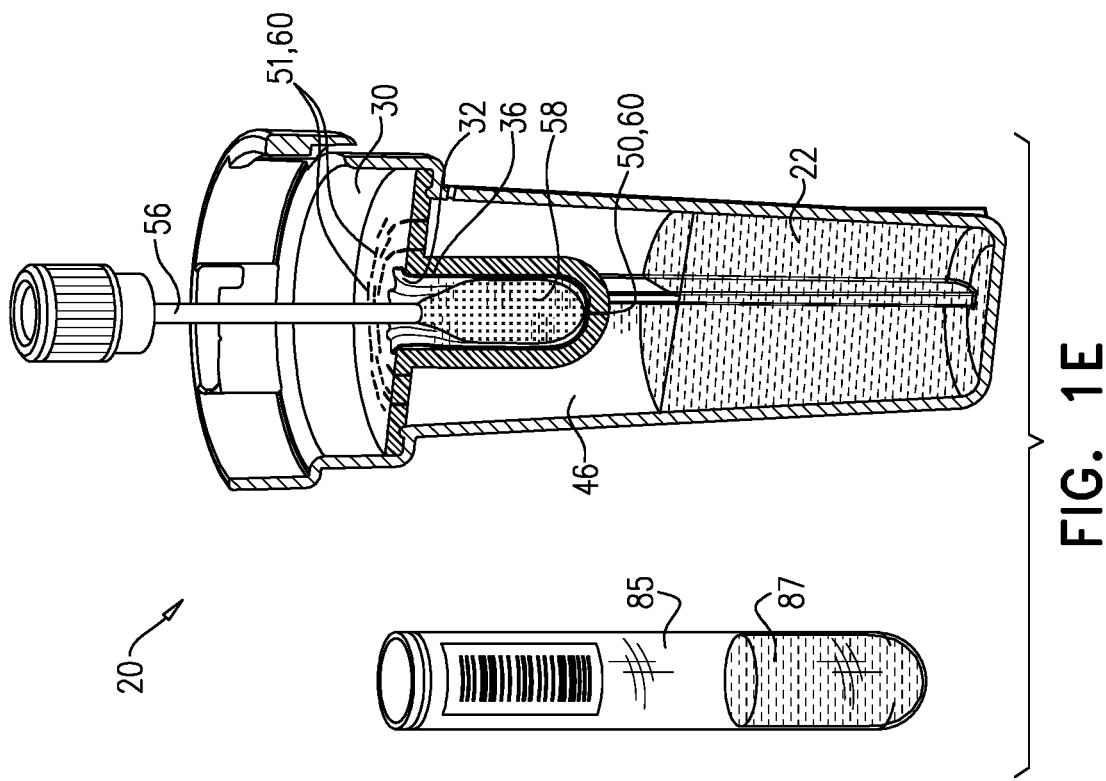
FIG. 1E
FIG. 1F

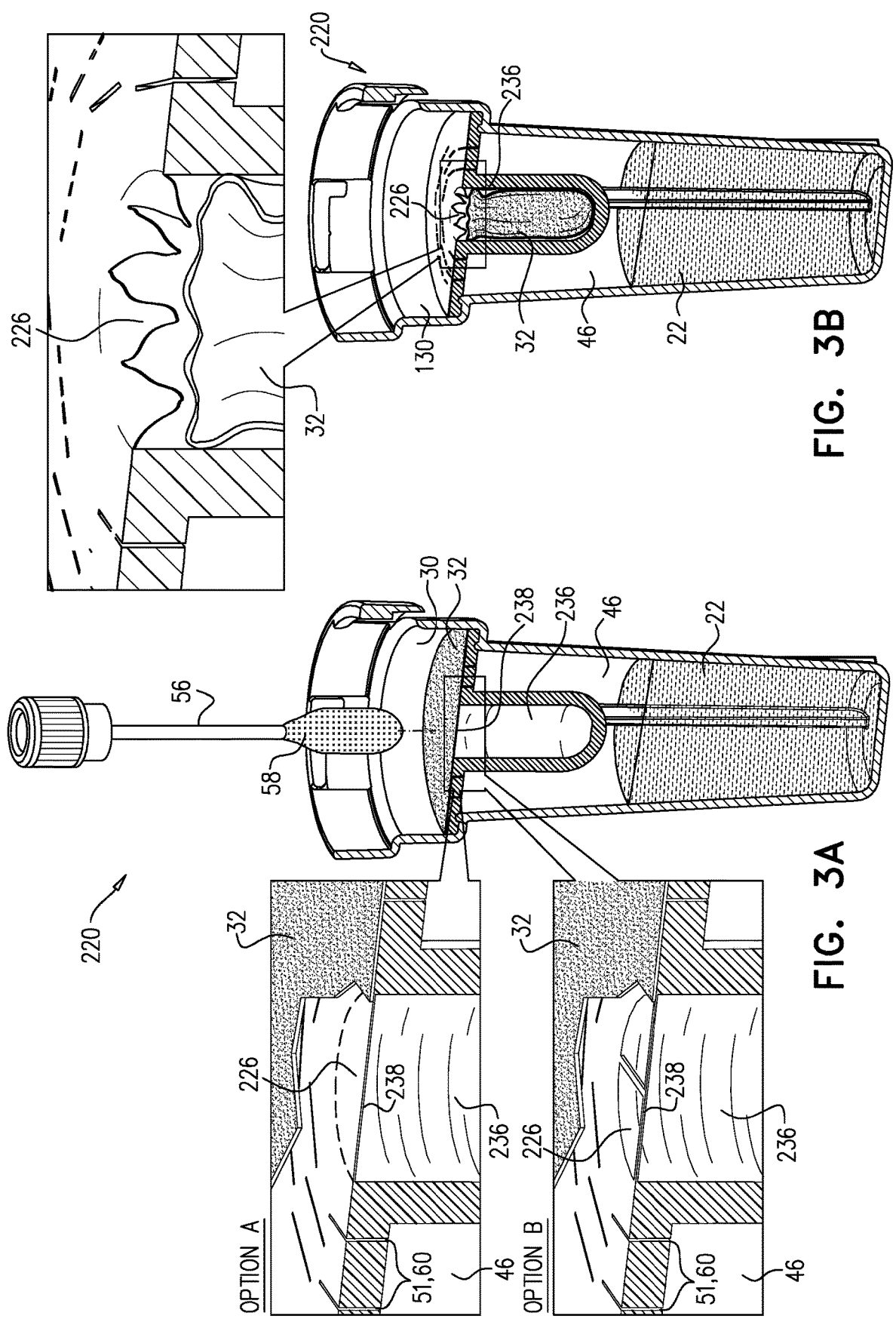

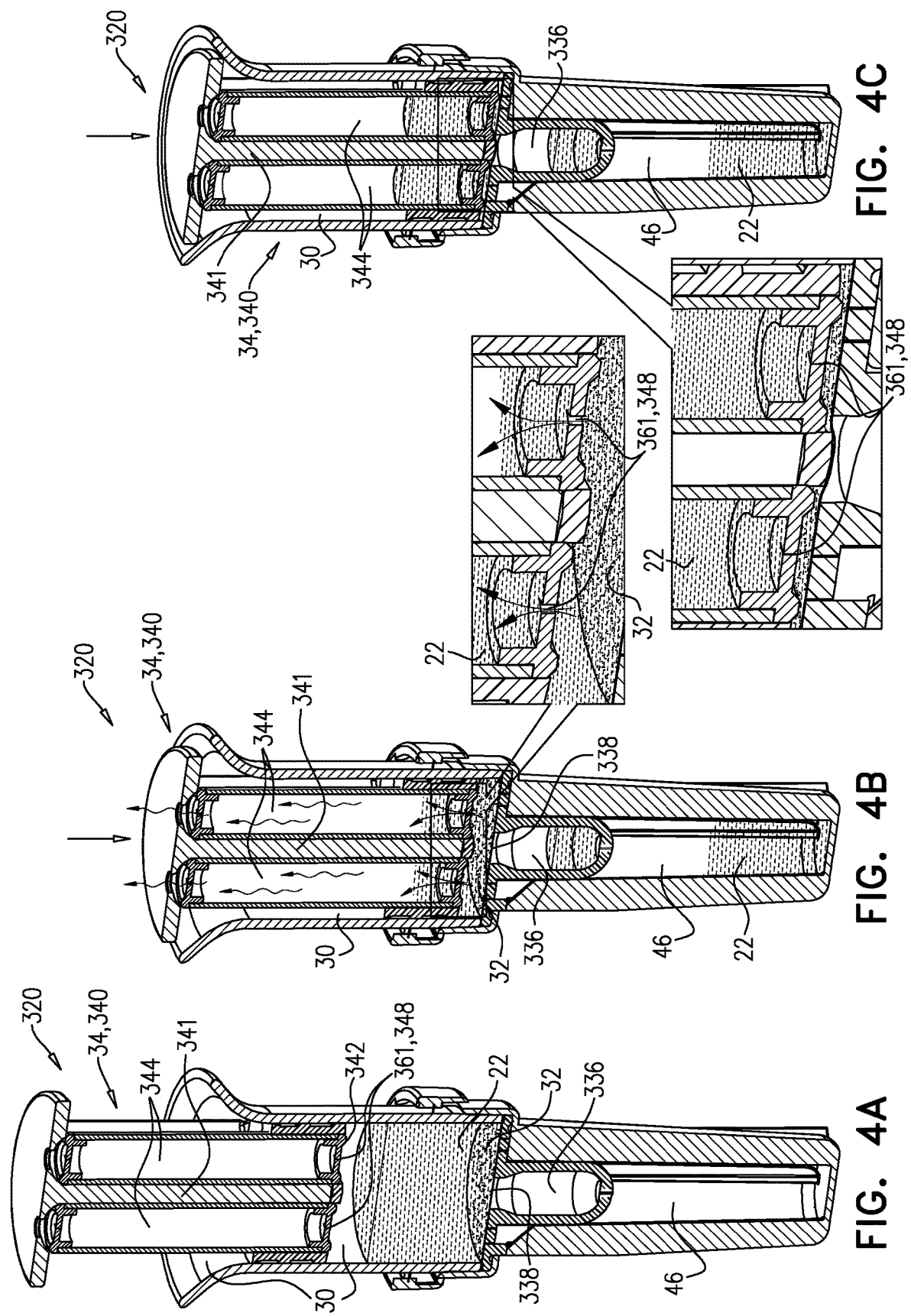

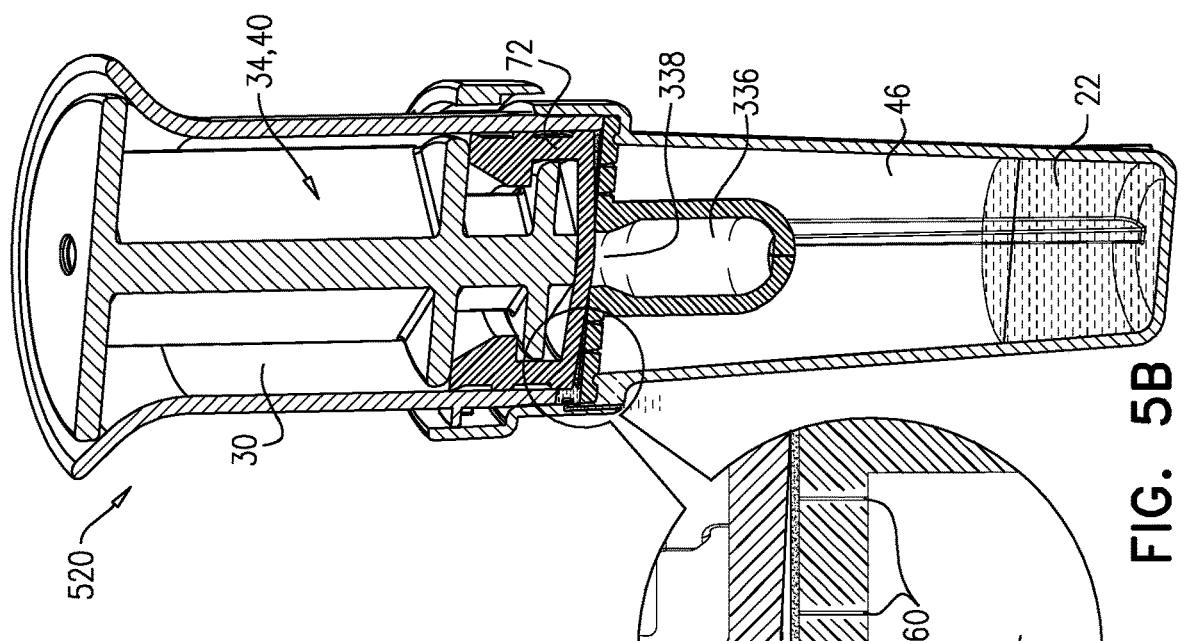
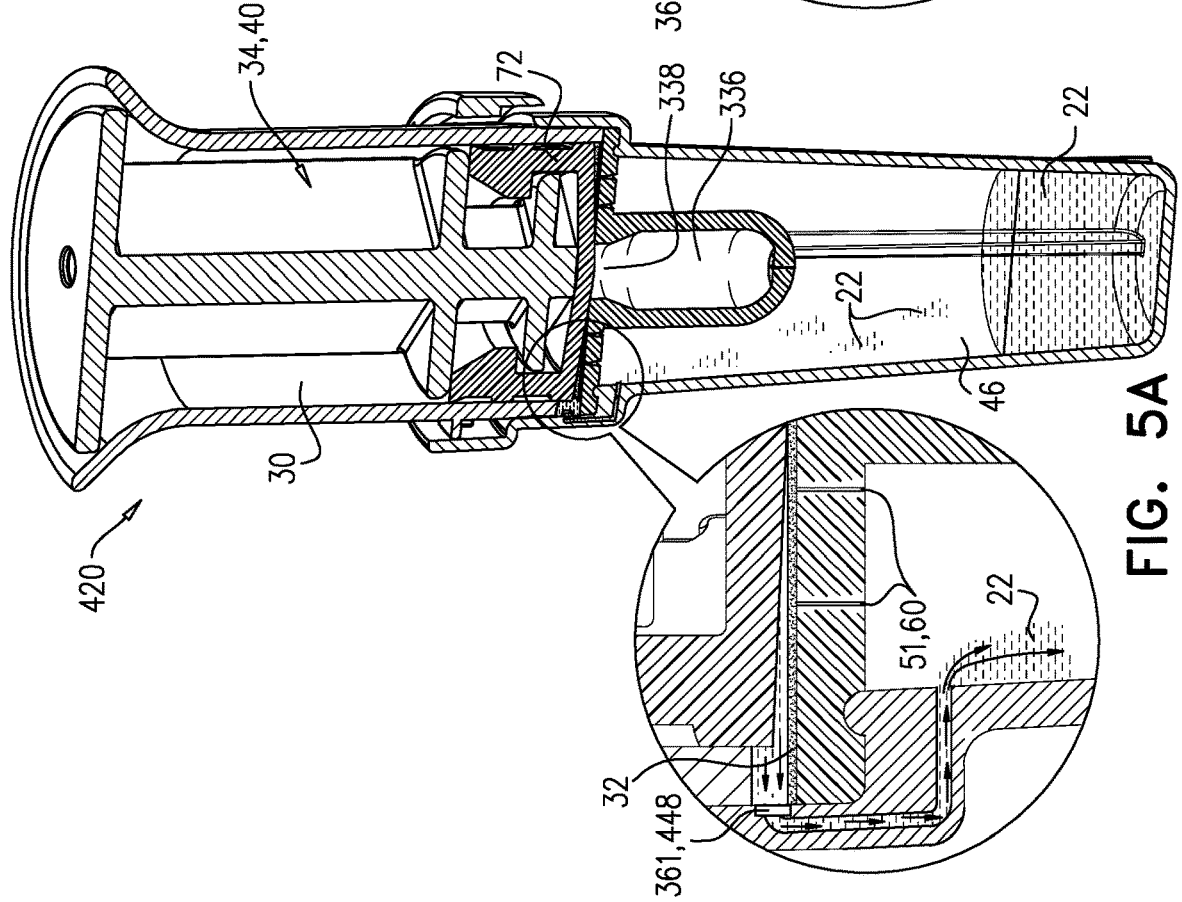
FIG. 5B
FIG. 5A

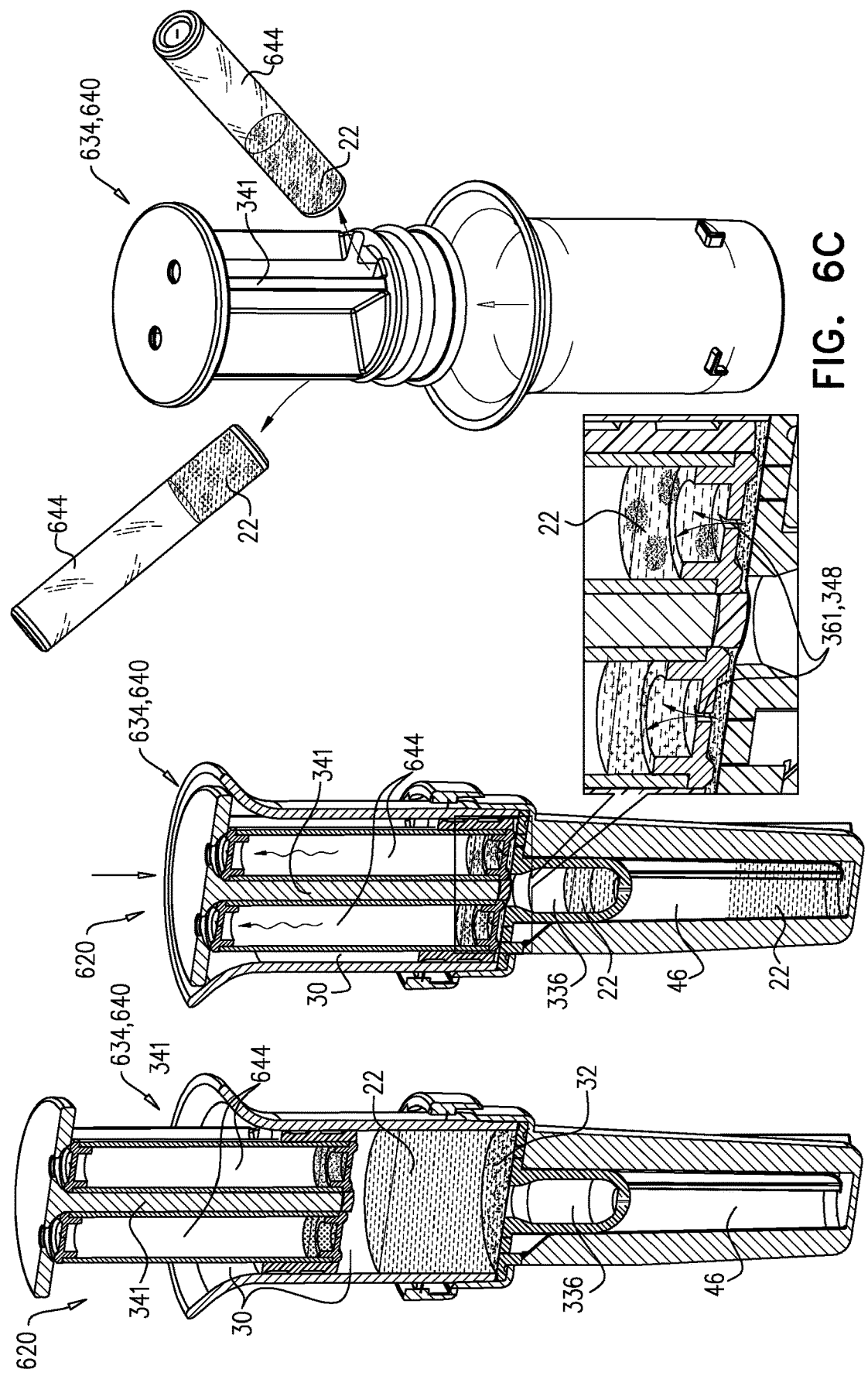

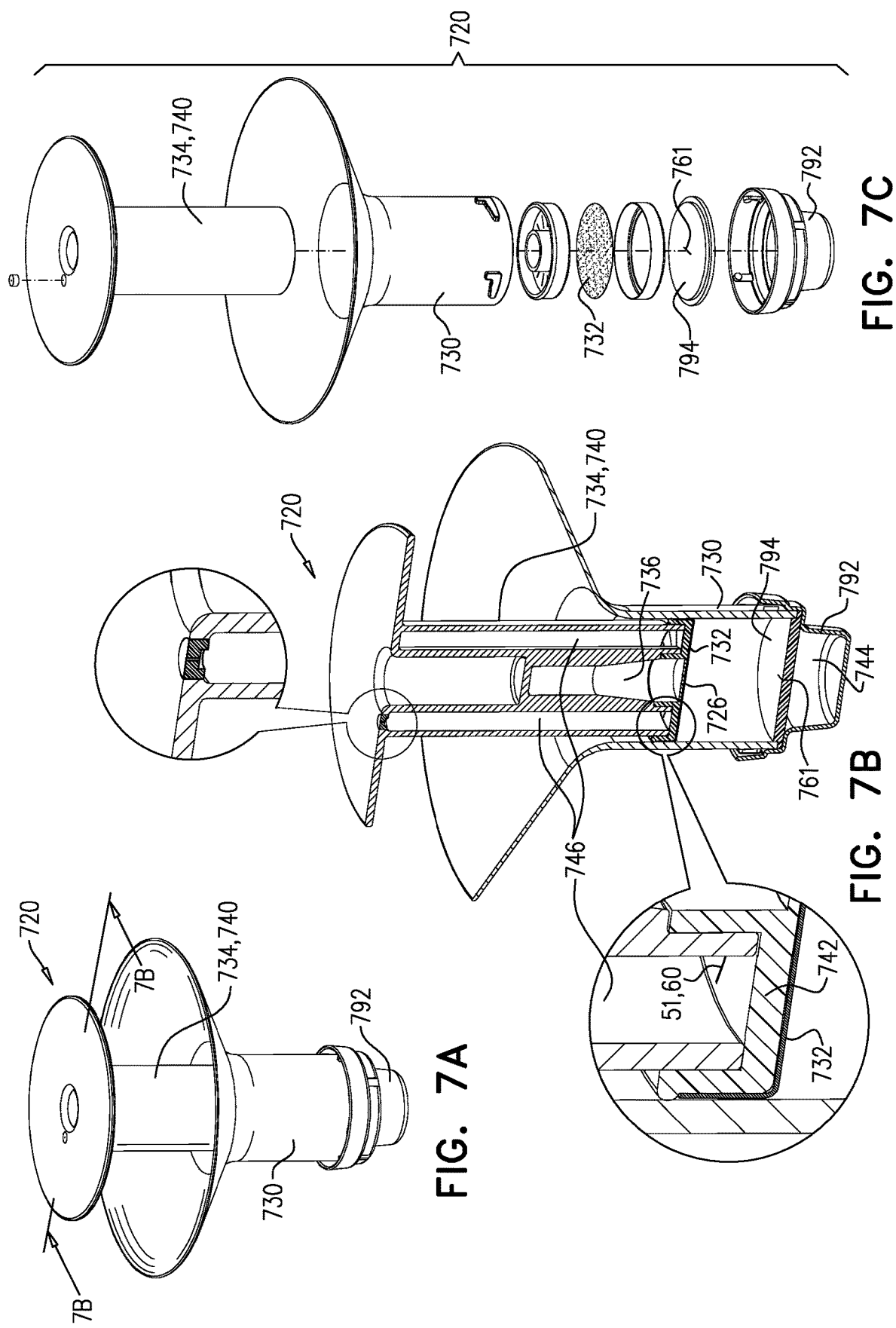

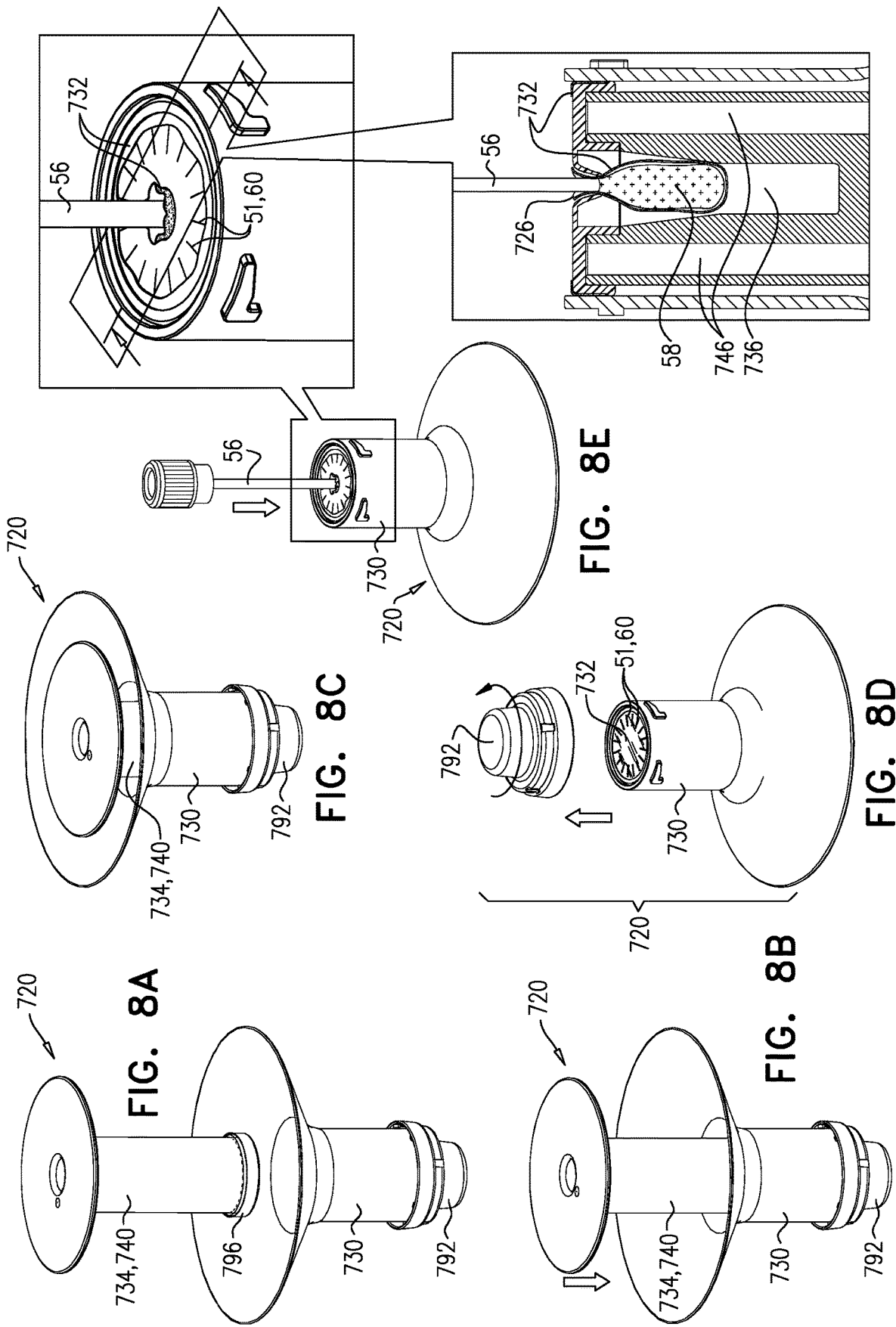

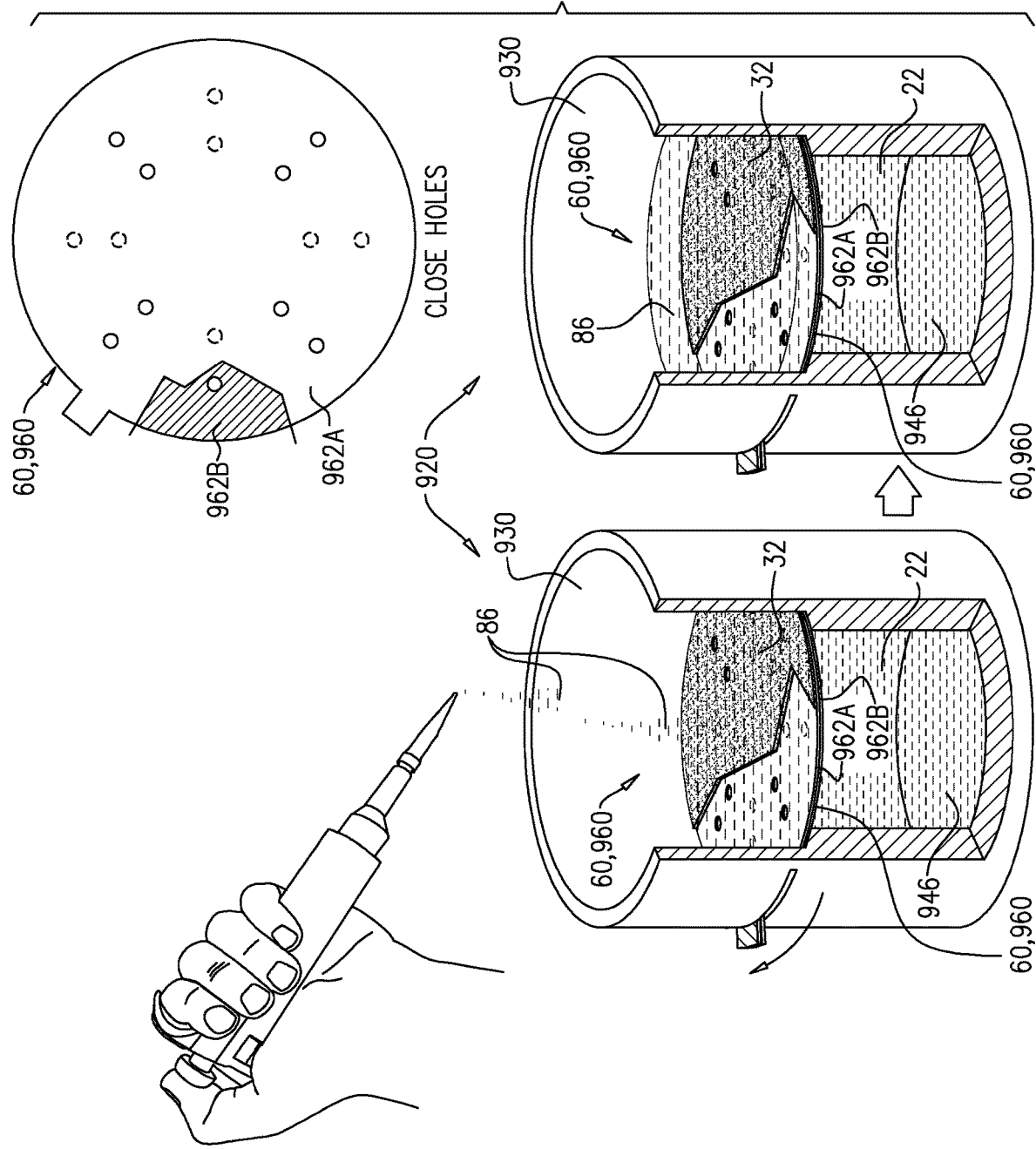

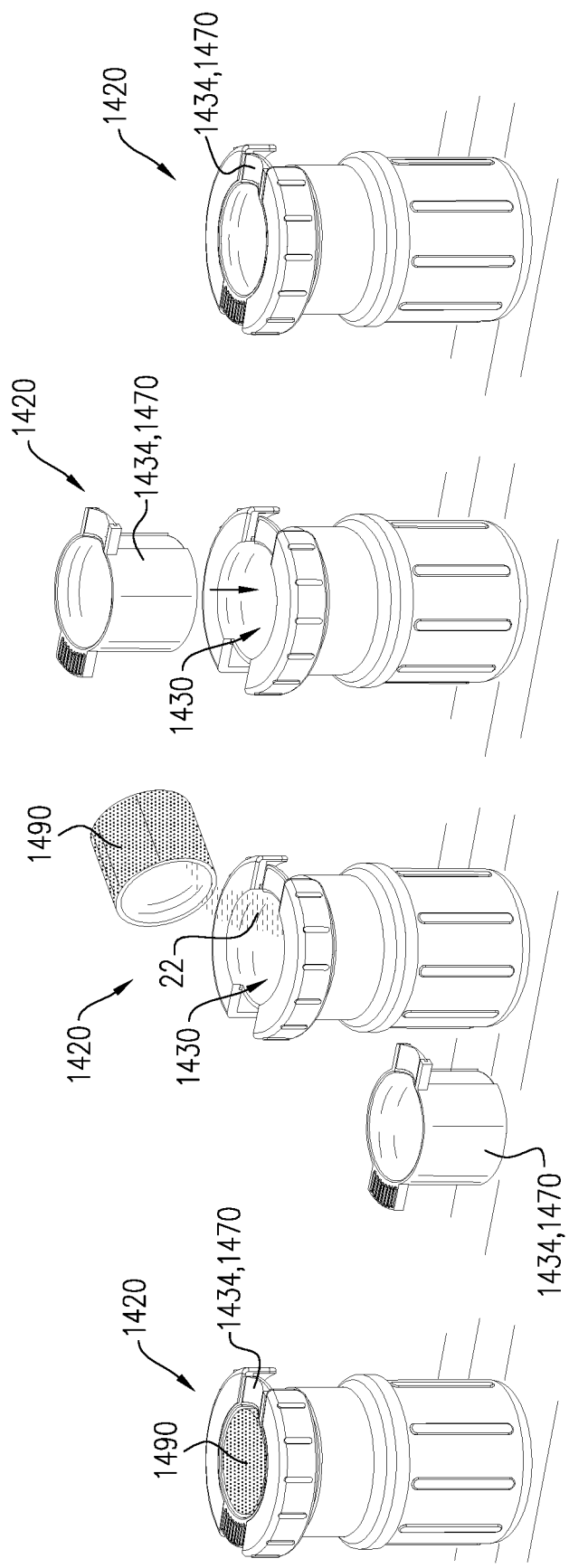

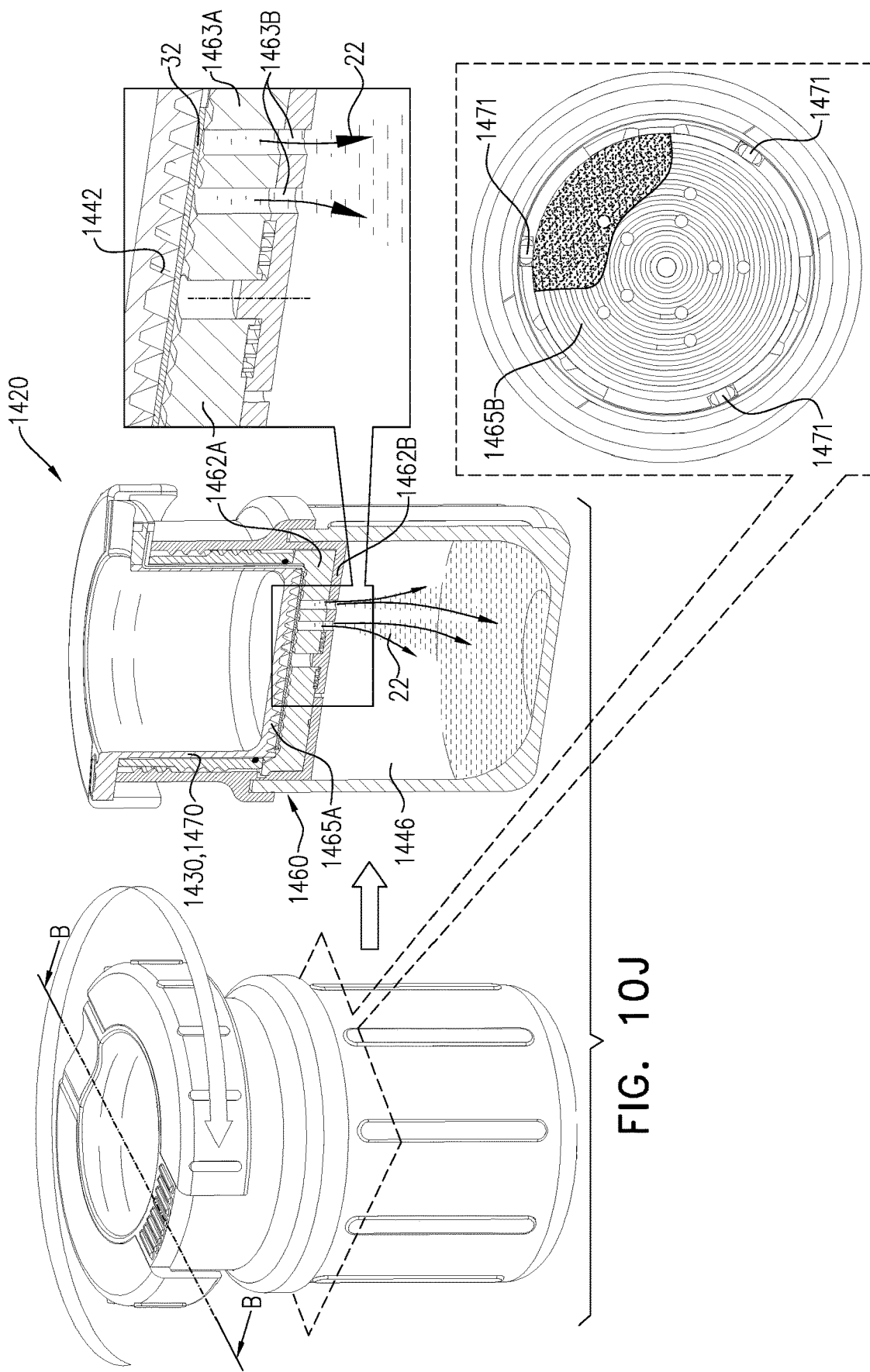

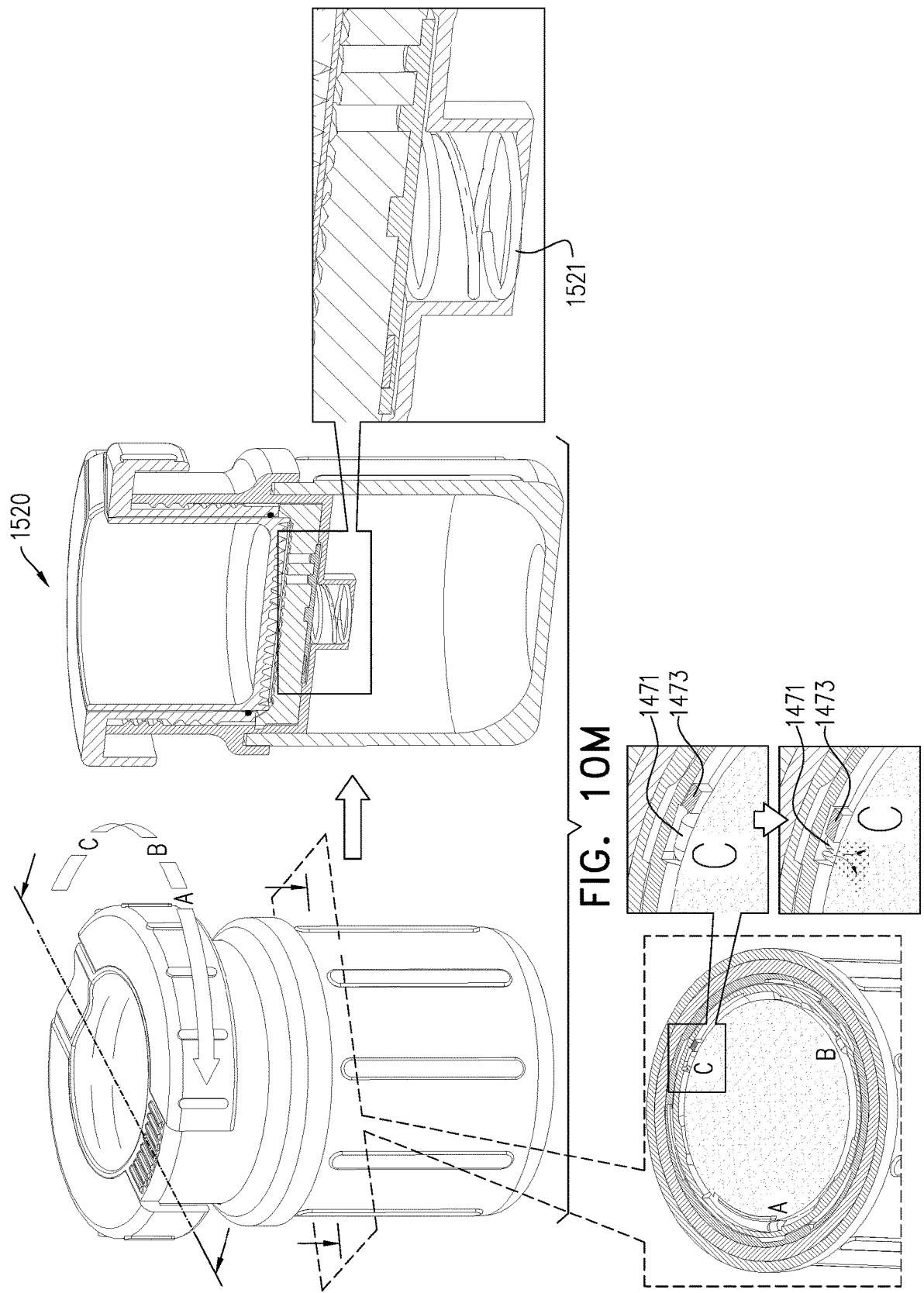

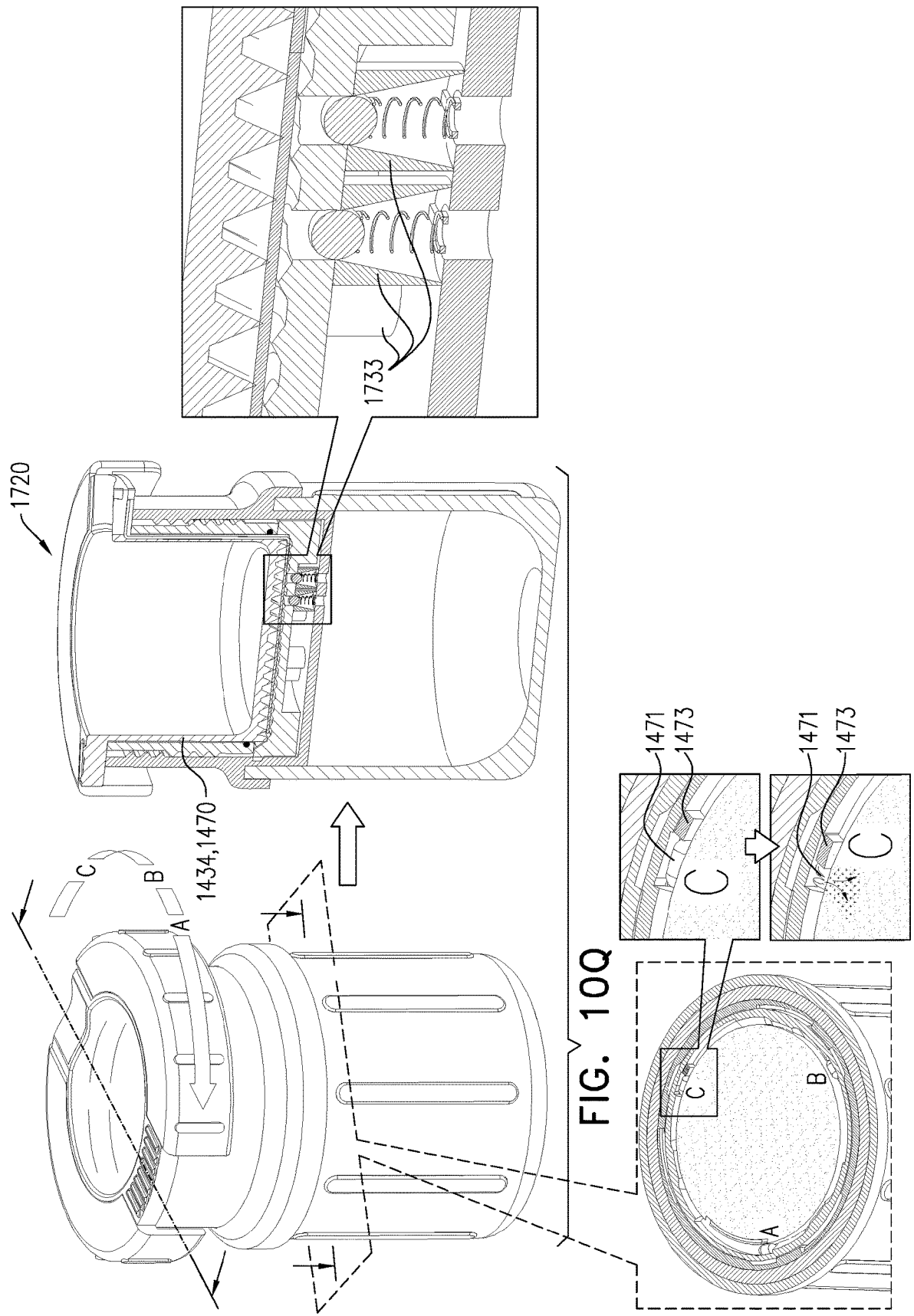

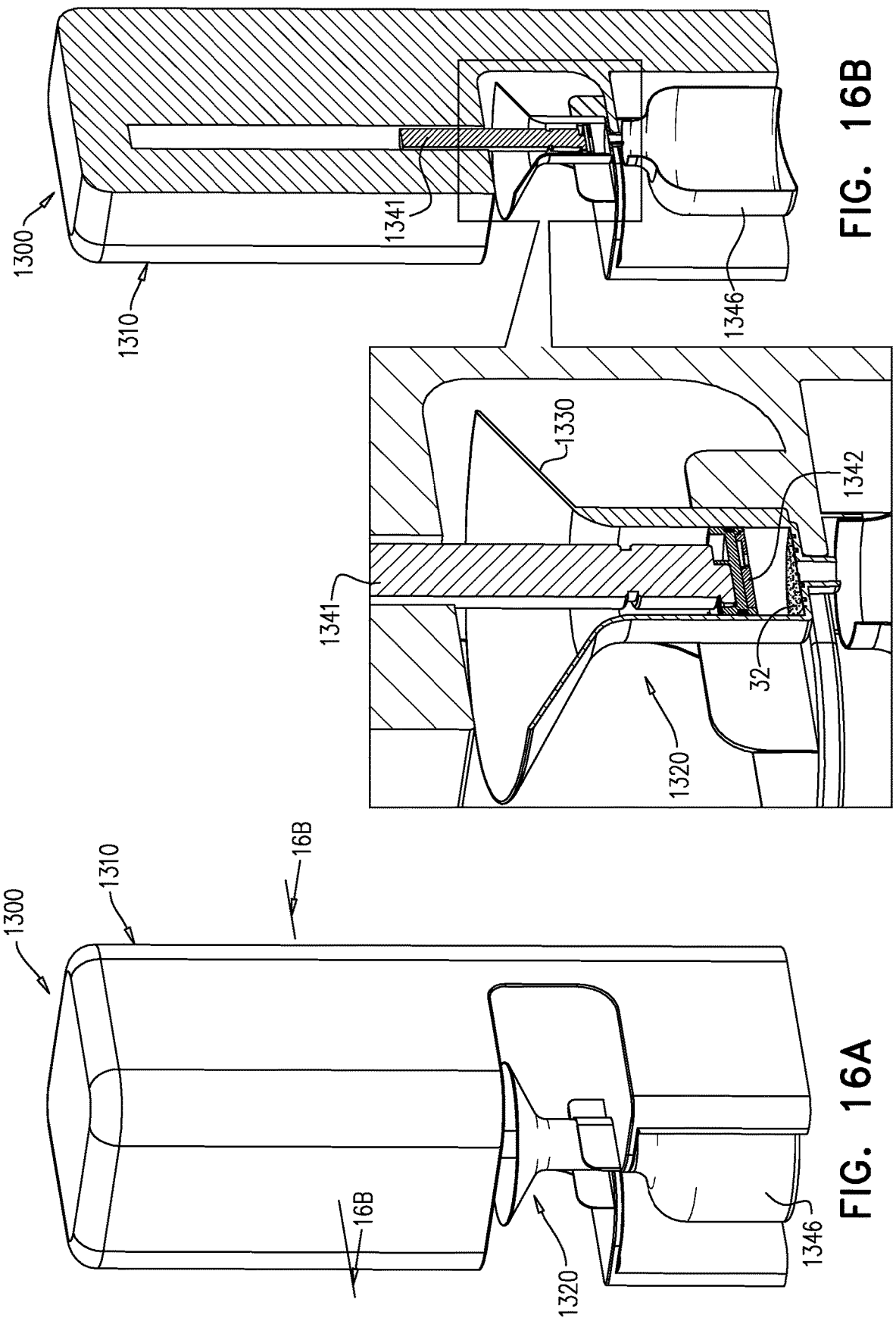

TABLE 1A

| Date | CT pt. ID #[1] | Clinical Result [2] | GAS Strain: WT#[3] | RST Method: T/F[5] | Calculated # of GAS Added to System[4] (CFUs) | Backup RST Result | Strength of Backup RST Result (0-4)[6] |
|---|---|---|---|---|---|---|---|
| 25.06.18 | 006.XMH | pos | WT1 | T | 80,400 | pos | 4 |
| 02.07.18 | 007.IMX | pos | WT2 | T | 38 | pos | 3 |
| 03.07.18 | 008.ZNT | pos | WT3 | T | 4,033 | Pos | 3 |
| 09.07.18 | 009.OSA | pos | WT4 | T | 22,867 | Pos | 4 |
|  |  |  |  | F | 22,867 | pos | 4 |
| 12.07.18 | 010.OIV | neg | - | T | 0 | neg | 0 |
|  |  |  |  | F | 0 | neg | 0 |
|  | 011.BPF | pos | WT5 | T | 6,800 | pos | 3 |
|  |  |  |  | F | 6,800 | pos | 4 |
|  | 012.IGD | pos | WT6 | T | 1,343 | pos | 2 |
|  |  |  |  | F | 1,343 | Pos | 3 |
| 17.07.18 | 013.SDJ | pos | WT7 | T | 67 | Pos | 1 |
|  |  |  |  | F | 67 | Pos | 2 |
|  | 014.EAY | pos | WT8 | T | 52 | Pos | 1 |
|  |  |  |  | F | 52 | pos | 2 |

Table 1

[1] CT pt. ID # = clinical trial patient ID number. [2] Blind clinical diagnosis based on standard throat swab culture. [3] WT = wildtype. [4] Calculated # of GAS added = based on limiting dilutions to determine amount of GAS in total gargle, then dividing by total volume of gargle (mL), and then dividing by 5 (to factor 0.2 mL inoculate volume). System = a single tube containing culture media and inoculated sample that is incubated as a unit for the purpose of Backup RST. [5] T = whole tube RST, F = filter RST. [6] 0 = neg, 1 = weak pos, 2 = moderate pos, 3 = strong pos, 4 = very strong pos. [7] Clinical diagnosis differed from standard throat swab culture result.

FIG. 19A/1

TABLE 1A

| Date | CT pt. ID #[1] | Clinical Result [2] | GAS Strain: WT#[3] | RST Method: T/F[5] | Calculated # of GAS Added to System[4] (CFUs) | Backup RST Result | Strength of Backup RST Result (0-4)[6] |
|---|---|---|---|---|---|---|---|
| 23.07.18 | 015.ZKL | pos | WT9 | T | 13,933 | pos | 4 |
| 15.10.18 | 017.PZF | pos | WT11 | F | 13,933 | pos | 4 |
| | | | | T | 1,723 | pos | 4 |
| 22.10.18 | 018.MWE | pos | WT12 | F | 1,723 | pos | 4 |
| | | | | T | 28,667 | pos | 4 |
| 24.10.18 | 019.PUC | pos | WT13 | F | 28,667 | pos | 3 |
| | | | | T | 417 | pos | 4 |
| 29.10.18 | 020.TFX | neg | - | F | 417 | pos | 4 |
| | | | | T | 0 | neg | 0 |
| 31.10.18 | 021.JDY | neg | - | F | 0 | neg | 0 |
| | | | | T | 0 | neg | 0 |
| | 022.TCC | neg | - | F | 0 | neg | 0 |
| | | | | T | 0 | neg | 0 |
| | | | | F | 0 | neg | 0 |

FIG. 19A/2

Table 1
[1] CT pt. ID # = clinical trial patient ID number. [2] Blind clinical diagnosis based on standard throat swab culture. [3] WT = wildtype. [4] Calculated # of GAS added = based on limiting dilutions to determine amount of GAS in total gargle, then dividing by total volume of gargle (mL), and then dividing by 5 (to factor 0.2 mL inoculate volume). System = a single tube containing culture media and inoculated sample that is incubated as a unit for the purpose of Backup RST. [5] T = whole tube RST, F = filter RST. [6] 0 = neg, 1 = weak pos, 2 = moderate pos, 3 = strong pos, 4 = very strong pos. [7] Clinical diagnosis differed from standard throat swab culture result.

TABLE 1A

| Date | CT pt. ID #[1] | Clinical Result [2] | GAS Strain: WT#[3] | RST Method: T/F[5] | Calculated # of GAS Added to System[4] (CFUs) | Backup RST Result | Strength of Backup RST Result (0-4)[6] |
|---|---|---|---|---|---|---|---|
| 05.12.18 | 031.ERY | neg | - | T | 0 | neg | 0 |
|  |  |  |  | F | 0 | neg | 0 |
| 12.12.18 | 032.OJS | pos | WT18 | T | 1,317 | pos | 4 |
|  |  |  |  | F | 1,317 | pos | 4 |
| 30.01.19 | 033.VEN | pos | WT19 | T | 36 | neg | 0 |
|  |  |  |  | F | 36 | pos | 1 |
| 16.02.19 | 034.JNO | pos | WT20 | T | 49,060 | pos | 4 |
|  |  |  |  | F | 49,060 | pos | 4 |

Table 1

[1] CT pt. ID # = clinical trial patient ID number. [2] Blind clinical diagnosis based on standard throat swab culture. [3] WT = wildtype. [4] Calculated # of GAS added = based on limiting dilutions to determine amount of GAS in total gargle, then dividing by total volume of gargle (mL), and then dividing by 5 (to factor 0.2 mL inoculate volume). System = a single tube containing culture media and inoculated sample that is incubated as a unit for the purpose of Backup RST. [5] T = whole tube RST, F = filter RST. [6] 0 = neg, 1 = weak pos, 2 = moderate pos, 3 = strong pos, 4 = very strong pos. [7] Clinical diagnosis differed from standard throat swab culture result.

FIG. 19A/3

TABLE 1A

| Date | CT pt. ID #[1] | Clinical Result [2] | GAS Strain: WT#[3] | RST Method: T/F[5] | Calculated # of GAS Added to System[4] (CFUs) | Backup RST Result | Strength of Backup RST Result (0-4)[6] |
|---|---|---|---|---|---|---|---|
| 12.11.18 | 023.GGJ | neg | - | T | 0 | neg | 0 |
|  |  |  |  | F | 0 | neg | 0 |
| 19.11.18 | 024.DPK | pos[7] | WT14 | T | 771 | pos | 4 |
|  |  |  |  | F | 771 | pos | 4 |
|  | 025.FCJ | pos | WT15 | T | 15,467 | pos | 4 |
|  |  |  |  | F | 15,467 | pos | 4 |
| 21.11.18 | 026.SWM | neg | - | T | 0 | neg | 0 |
|  |  |  |  | F | 0 | neg | 0 |
| 26.11.18 | 027.DPZ | pos | WT16 | T | 2,690 | pos | 4 |
|  |  |  |  | F | 2,690 | pos | 4 |
|  | 028.SCV | pos | WT17 | T | 254 | pos | 4 |
|  |  |  |  | F | 254 | pos | 4 |
|  | 029.ZGR | neg | - | T | 0 | neg | 0 |
|  |  |  |  | F | 0 | neg | 0 |
| 28.11.18 | 030.HPM | neg | - | T | 0 | neg | 0 |
|  |  |  |  | F | 0 | neg | 0 |

Table 1

[1] CT pt. ID # = clinical trial patient ID number. [2] Blind clinical diagnosis based on standard throat swab culture. [3] WT = wildtype. [4] Calculated # of GAS added = based on limiting dilutions to determine amount of GAS in total gargle, then dividing by total volume of gargle (mL), and then dividing by 5 (to factor 0.2 mL inoculate volume). System = a single tube containing culture media and inoculated sample that is incubated as a unit for the purpose of Backup RST. [5] T = whole tube RST, F = filter RST. [6] 0 = neg, 1 = weak pos, 2 = moderate pos, 3 = strong pos, 4 = very strong pos. [7] Clinical diagnosis differed from standard throat swab culture result.

FIG. 19A/4

TABLE 1B

| Gargle RST Backup (Both Methods) | | | | |
|---|---|---|---|---|
| Sensitivity = 100% (19/19) Specificity = 100% (9/9) | | Clinical Result | | |
| | | pos | neg | total |
| Gargle Backup RST Result | pos | 19 | 0 | 19 |
| | neg | 0 | 9 | 9 |
| | total | 19 | 9 | 28 |

FIG. 19B

Table 1

[1] CT pt. ID # = clinical trial patient ID number. [2] Blind clinical diagnosis based on standard throat swab culture. [3] WT = wildtype. [4] Calculated # of GAS added = based on limiting dilutions to determine amount of GAS in total gargle, then dividing by total volume of gargle (mL), and then dividing by 5 (to factor 0.2 mL inoculate volume). System = a single tube containing culture media and inoculated sample that is incubated as a unit for the purpose of Backup RST. [5] T = whole tube RST, F = filter RST. [6] 0 = neg, 1 = weak pos, 2 = moderate pos, 3 = strong pos, 4 = very strong pos. [7] Clinical diagnosis differed from standard throat swab culture result.

TABLE 1C

| Gargle Filter RST Backup Method | | | |
|---|---|---|---|
| Sensitivity = 100% (16/16) Specificity = 100% (9/9) | | Clinical Result | |
| | | pos | neg | total |
| Filter RST Result | pos | 16 | 0 | 16 |
| | neg | 0 | 9 | 9 |
| | total | 16 | 9 | 25 |

Table 1

[1] CT pt. ID # = clinical trial patient ID number. [2] Blind clinical diagnosis based on standard throat swab culture. [3] WT = wildtype. [4] Calculated # of GAS added = based on limiting dilutions to determine amount of GAS in total gargle, then dividing by total volume of gargle (mL), and then dividing by 5 (to factor 0.2 mL inoculate volume). System = a single tube containing culture media and inoculated sample that is incubated as a unit for the purpose of Backup RST. [5] T = whole tube RST, F = filter RST. [6] 0 = neg, 1 = weak pos, 2 = moderate pos, 3 = strong pos, 4 = very strong pos. [7] Clinical diagnosis differed from standard throat swab culture result.

FIG. 19C

TABLE 1D

| Gargle Whole Tube RST Backup Method | | | | |
|---|---|---|---|---|
| Sensitivity = 95% (18/19) Specificity = 100% (9/9) | | Clinical Result | | |
| | | pos | neg | total |
| Whole Tube RST Result | pos | 18 | 0 | 18 |
| | neg | 1 | 9 | 10 |
| | total | 19 | 9 | 28 |

FIG. 19D

Table 1

[1] CT pt. ID # = clinical trial patient ID number. [2] Blind clinical diagnosis based on standard throat swab culture. [3] WT = wildtype. [4] Calculated # of GAS added = based on limiting dilutions to determine amount of GAS in total gargle, then dividing by total volume of gargle (mL), and then dividing by 5 (to factor 0.2 mL inoculate volume). System = a single tube containing culture media and inoculated sample that is incubated as a unit for the purpose of Backup RST. [5] T = whole tube RST, F = filter RST. [6] 0 = neg, 1 = weak pos, 2 = moderate pos, 3 = strong pos, 4 = very strong pos. [7] Clinical diagnosis differed from standard throat swab culture result.

TABLE 2

| Date 2018 | sample type: G/P[1] | media type [2] | strain: AT/WT[3] | GAS added to system [4] (CFUs) | # of systems assayed | inoculate vol. (mL) | media vol. (mL) | RST: S/T/F [5] | inc.[6] time (h) |
|---|---|---|---|---|---|---|---|---|---|
| 18.06 | P | TSB | AT | 18 - 18,500 | 4 | 0.05 | 0.4 | S | 22 |
|  | P | TH | AT | 18 - 18,500 | 4 | 0.05 | 0.4 | S | 22 |
| 24.06 | P | TH | AT | 460 | 3 | 0.05 | 0.4 | S | 21 |
|  | P | TH | AT | 460 | 3 | 0.05 | 0.9 | S | 21 |
| 28.06 | P | TH | AT | 148 | 3 | 0.05 | 0.9 | S | 25.3 |
|  | G | TH | AT | 148 | 3 | 0.05 | 0.9 | S | 25.3 |
| 05.07 | G | TH | AT, WT1, WT3 | 24 - 35,6667 | 15 | 0.1 | 0.9 | S | 22 |
| 05.08 | G | TH | AT | 5,670 | 1 | 0.2 | 0.9 | S, T | 23.5 |
|  | G | TH | AT | 567,000 | 1 | 0.2 | 0.9 | S, T | 23.5 |
| 14.08 | G | TH | AT | 124 | 3 | 0.2 | 0.9 | S, T | 22.7 |
| 20.08 | G | TH | AT | 168 | 2 | 0.2 | 0.9 | F, S | 16 |
|  | G | TH | AT | 168 | 2 | 0.2 | 0.9 | F, S, T | 18 |
|  | G | TH | AT | 168 | 2 | 0.2 | 0.9 | S, T | 24 |
| 23.08 | P | TH | AT | 44 | 1 | 0.2 | 0.9 | F | 14 |
|  | P | TH | AT | 44 | 1 | 0.2 | 0.9 | F | 16 |
|  | P | TH | AT | 44 | 1 | 0.2 | 0.9 | S | 65 |
| 27.08 | G | TH | AT | 43 | 2 | 0.2 | 0.9 | S, F | 12 |
|  | P | TH | AT | 33 | 1 | 0.2 | 0.9 | S, F | 12 |
|  | G | TH | AT | 43 | 2 | 0.2 | 0.9 | S, F | 24 |
|  | P | TH | AT | 43 | 1 | 0.2 | 0.9 | S, F | 24 |
|  | G | TH | AT | 33 | 2 | 0.2 | 0.9 | S | 75 |
|  | P | TH | AT | 33 | 1 | 0.2 | 0.9 | S | 75 |
| 28.08 | G | TH | AT, WT1 - WT9 | 260 - 10,650 | 10 | 0.2 | 0.9 | S | 24 |
|  | G | TH | AT, WT1 - WT9 | 780 - 31,950 | 10 | 0.6 | 3 | S | 24 |

Table 2

[1] G = gargle spiked with GAS, P = pure GAS suspension in PBS. [2] TH = Todd Hewitt, TSB = tryptic soy broth. [3] AT = ATCC 19615, WT = wildtype. [4] System = a single tube containing culture media and inoculated sample that is incubated as a unit. [5] S = 0.1 mL sample RST, T = whole tube RST, F = filter RST. [6] incubation at 37°C.

FIG. 20

TABLE 3

| inc.[1] time (h) | sample type: G/P[2] | aprox# of GAS in total system (CFUs) | # of systems assayed | RST results: pos/neg |
|---|---|---|---|---|
| 0 | G | 43 | - | - |
|   | P | 33 | - | - |
| 4 | G | 534 | 2 | neg |
|   | P | 154 | 1 | neg |
| 8 | G | 3,460 | 2 | neg |
|   | P | 2,255 | 1 | neg |
| 12 | G | 202,400 | 2 | pos |
|   | P | 7,150 | 1 | pos |

Table 3
[1] incubation at 37°C
[2] G = gargle spiked with GAS, P = pure GAS suspension

FIG. 21

TABLE 4

| Date 2018 | CT pt. ID #[1] | sample type: G/P[2] | GAS added to system (CFUs) | RST method: S/T/F[3] | # of systems tested with method | strength of RST result[4] (0-4) |
|---|---|---|---|---|---|---|
| 12.07 | 011.BPF | G | 6,800 | T | 1 | 3 |
|  | 011.BPF | G | 6,800 | F | 1 | 4 |
| 17.02 | 012.IGD | G | 1,343 | T | 1 | 2 |
|  | 012.IGD | G | 1,343 | F | 1 | 3 |
|  | 013.SDJ | G | 67 | T | 1 | 1 |
|  | 013.SDJ | G | 67 | F | 1 | 2 |
|  | 014.EAY | G | 52 | T | 1 | 1 |
|  | 014.EAY | G | 52 | F | 1 | 2 |
| 27.08 | - | G | 43 | S | 2 | 1 |
|  | - | G | 43 | F | 2 | 3 |
|  | - | P | 33 | S | 1 | 0 |
|  | - | P | 33 | F | 1 | 1 |

Table 4
[1] CT pt. ID # = clinical trial patient ID number
[2] G = gargle spiked with GAS, P = pure GAS suspension in PBS
[3] S = 0.1 mL sample RST, T = whole tube RST, F = filter RST
[4] 0 = neg, 1 = weak pos, 2 = moderate pos, 3 = strong pos, 4 = very strong pos

FIG. 22

TABLE 5

| Date | CT pt. ID #[1] | clinical result[2] (pos/neg) | GAS count on saliva swab blood plate (CFUs) |
|---|---|---|---|
| 25.06.18 | 006.XMH | pos | TNTC [3] |
| 02.07.18 | 007.IMX | pos | 45 |
| 03.07.18 | 008.ZNT | pos | TNTC |
| 09.07.18 | 009.OSA | pos | TNTC |
| 12.07.18 | 010.OIV | neg | 0 |
| 12.07.18 | 011.BPF | pos | 28 |
| 17.07.18 | 012.IGD | pos | 4 |
| 17.07.18 | 013.SDJ | pos | 125 |
| 17.07.18 | 014.EAY | pos | 75 |
| 23.07.18 | 015.ZKL | pos | 25 |
| 15.10.18 | 017.PZF | pos | 200 |
| 22.10.18 | 018.MWE | pos | TNTC |
| 24.10.18 | 019.PUC | pos | TNTC |
| 29.10.18 | 020.TFX | neg | 0 |
| 29.10.18 | 021.JDY | neg | 0 |
| 31.10.18 | 022.TCC | neg | 0 |
| 12.11.18 | 023.GGJ | neg | 0 |
| 19.11.18 | 024.DPK | pos[4] | 10 |
| 19.11.18 | 025.FCJ | pos | 600 |
| 21.11.18 | 026.SWM | neg | 0 |
| 26.11.18 | 027.DPZ | pos | TNTC |
| 26.11.18 | 028.SCV | pos | 150 |
| 28.11.18 | 029.ZGR | neg | 0 |
| 28.11.18 | 030.HPM | neg | 0 |
| 05.12.18 | 031.ERY | neg | 0 |
| 12.12.18 | 032.OJS | pos | TNTC |
| 30.01.19 | 033.VEN | pos | 0 |
| 16.02.19 | 034.JNO | pos | TNTC |

Table 5
[1] CT pt. ID # = clinical trial patient ID number
[2] Blind clinical diagnosis using standard throat swab culture
[3] TNTC = too numerous to count (>1000)
[4] Clinical diagnosis differed from standard throat swab culture

FIG. 23

TABLE 6

| Date (2018) | CT pt. ID #[1] | GAS count on saliva swab blood plate (CFUs) | inc.[2] time (h) | RST Method: Sw/T/F[3] | Strength of RST result[4] (0-4) |
|---|---|---|---|---|---|
| 17.07 | 012.IGD | 4 | 21.5 | Sw | 1 |
| 17.07 | 012.IGD | 4 | 21.5 | T | 0 |
| 17.07 | 013.SDJ | 125 | 21.5 | Sw | 0 |
| 17.07 | 013.SDJ | 125 | 21.5 | T | 0 |
| 17.07 | 014.EAY | 75 | 21.5 | Sw | 0 |
| 17.07 | 014.EAY | 75 | 21.5 | T | 0 |
| 23.07 | 015.ZKL | 25 | 21 | Sw | 2 |
| 23.07 | 015.ZKL | 25 | 21 | F | 4 |

Table 6
[1] CT pt. ID # = clinical trial patient ID number
[2] Sw = swab RST, T = whole tube RST, F = filter RST
[4] 0 = neg, 1 = weak pos, 2 = moderate pos, 3 = strong pos, 4 = very strong pos

FIG. 24

TABLE 7

| swab type | aprox concentration of GAS (CFUs/100uL) | GAS count on swab plate (CFUs) | % recovery of GAS from 100uL |
|---|---|---|---|
| Cotton | 8,533 | 167 | 1.91% |
| Polyester | 8,533 | 110 | 1.29% |
| Flocked | 8,533 | ~750 | 8.79% |
| Cotton | 2,560 | 49 | 1.91% |
| Polyester | 2,560 | 59 | 2.3% |
| Flocked | 2,560 | 170 | 6.64% |
| Cotton | 1,280 | 26 | 2.03% |
| Polyester | 1,280 | 28 | 2.19% |
| Flocked | 1,280 | 96 | 7.5% |

FIG. 25

TABLE 8

| inoculation method: 0.2/FL1/FL2 [1] | aprox. # of GAS added to system [2] during inoculation | culture media vol. (mL) | RST method: Sw/S/T/F [4] | strength of RST result [5] (0 - 4) |
|---|---|---|---|---|
| 0.2 | 5,670 | 0.9 | S | 3 |
| FL1 | ~2,835 [3] | 0.9 | S | 3 |
| FL2 | ~5,670 [3] | 0.9 | S | 3 |

Table 8

[1] 0.2 = 0.2 mL of bacterial suspension added to culture media, FL1 = flocked swab dipped 5x in bacterial suspension and then dipped 5x in culture media, FL2 = same as FL1 but repeated with a second flocked swab
[2] System = a single tube containing culture media and inoculated sample that is incubated as a unit
[3] These numbers are based on an estimate that the liquid media inoculation volume of flocked swab is at least 0.1 mL. This estimate is based on flocked swab uptake measurements by weighing before and after dipping in liquid. Uptake = 0.135 mL. Since flocked swabs are specifically designed for efficient elution, we assume that at least 75% of flocked swab uptake is eluted.
[4] Sw = swab RST, S = 0.1 mL sample RST, T = whole tube RST, F = filter RST
[5] 0 = neg, 1 = weak pos, 2 = moderate pos, 3 = strong pos, 4 = very strong pos

FIG. 26

TABLE 9

| CT pt. ID #[1] | clinical result[2] | SwRST result[3] | F RST result[4] |
|---|---|---|---|
| 017.PZF | 1 | 1 | 1 |
| 018.MWE | 1 | 1 | 1 |
| 019.PUC | 1 | 1 | 1 |
| 020.TFX | 0 | 0 | 0 |
| 021.JDY | 0 | 0 | 0 |
| 022.TCC | 0 | 0 | 0 |
| 023.GGJ | 0 | 0 | 0 |
| 024.DPK | 1[5] | 1 | 1 |
| 025.FCJ | 1 | 1 | 0 |
| 026.SWM | 0 | 0 | 0 |
| 027.DPZ | 1 | 1 | 1 |
| 028.SCV | 1 | 1 | 1 |
| 029.ZGR | 0 | 0 | 0 |
| 030.HPM | 0 | 0 | 0 |
| 031.ERY | 0 | 0 | 0 |
| 032.OJS | 1 | 1 | 1 |
| 033.VEN | 1 | 0 | 0 |
| 034.JNO | 1 | 1 | 1 |

Saliva Filter RST Backup Method

Sensitivity = 90% (9/10)
Specificity = 100% (8/8)

| | | Clinical Result | | |
|---|---|---|---|---|
| | | 1 | 0 | total |
| F RST Result | 1 | 9 | 0 | 9 |
| | 0 | 1 | 8 | 9 |
| | total | 10 | 8 | 18 |

Saliva Swab RST Backup Method

Sensitivity = 80% (8/10)
Specificity = 100% (8/8)

| | | Clinical Result | | |
|---|---|---|---|---|
| | | 1 | 0 | total |
| SwRST Result | 1 | 8 | 0 | 8 |
| | 0 | 2 | 8 | 10 |
| | total | 10 | 8 | 18 |

Table 9
[1] CT pt. ID # = clinical trial patient ID number
[2] Blind clinical diagnosis based on standard throat swab culture
[3] Sw RST = swab RST method
[4] F RST = filter RST method
[5] Clinical diagnosis differed from standard throat swab culture

FIG. 27

TESTING FOR PARTICULATES

CROSS-REFERENCE TO RELATED APPLICATIONS

The present application is the U.S. national stage of International Application PCT/IL2019/050997, filed Sep. 5, 2019, which published as PCT Publication WO 2020/049569, and which claims priority from U.S. Provisional Application 62/727,268, filed Sep. 5, 2018, which is assigned to the assignee of the present application and incorporated herein by reference.

FIELD OF THE APPLICATION

Applications of the present invention relate to testing for the presence of particulates, such as bacteria, in fluids.

BACKGROUND OF THE APPLICATION

Streptococcal pharyngitis, streptococcal tonsillitis, or streptococcal sore throat (known colloquially as strep throat) is a type of pharyngitis caused by group A beta hemolytic streptococcus bacteria. Common symptoms include fever, sore throat, and enlarged cervical lymph nodes.

The rapid strep test is commonly used to test for the presence of group A streptococcus bacteria. In this test, a swab is streaked across the throat to collect bacteria, and is subsequently inserted into an extraction solution, e.g., a mixture of 2M sodium nitrite (hereinbelow, "solution A"), and 0.2M acetic acid (hereinbelow, "solution B"). (Hereinbelow, this mixture is sometimes referred to as "A and B solution.") The extraction solution extracts strep A carbohydrate antigen from the bacteria. A dipstick containing an antibody specific to strep A carbohydrate antigen is inserted into the mixture containing the antigen. The mixture migrates up the dipstick and reacts with the antibody, thus generating a line on the dipstick. The presence of this line indicates a positive test result.

Other clinical situations also call for testing for presence of a particulate. For example, a physician may wish to test a patient's blood for the presence of a virus, or a stool specimen for the presence of a pathogen.

SUMMARY OF THE APPLICATION

In some applications of the present invention, a testing device is provided for testing for presence of particulate in a liquid, such as group A streptococcus bacteria. The testing device typically comprises a liquid container for containing the liquid; a filter, disposed in or downstream of the liquid container; and a liquid-pressure source, such as a plunger, which is arranged to apply pressure to drive the liquid contained in the liquid container through the filter. For some applications, the liquid comprises gargled fluid, i.e., a gargle fluid that the patient has gargled in his or her mouth and spit out, perhaps along with some saliva. Alternatively, for some applications, the liquid comprises saliva not swabbed from the throat of a patient.

There is therefore provided, in accordance with an Inventive Concept 1 of the present invention, apparatus including a testing device for testing for the presence of particulate in a liquid, the testing device including:
 a liquid container for containing the liquid;
 a filter, disposed in or downstream of the liquid container;
 a liquid-pressure source, which is arranged to apply pressure to drive the liquid contained in the liquid container through the filter; and
 a filter chamber that is (a) disposed downstream of the liquid container, (b) shaped so as to define an inlet, and (c) in fluid communication with the filter.

Inventive Concept 2. The apparatus according to Inventive Concept 1, wherein the inlet of the filter chamber has an inlet area that equals between 4% and 40% of a filter area of the filter.

Inventive Concept 3. The apparatus according to Inventive Concept 1, wherein the inlet of the filter chamber has an inlet area that is less than a greatest cross-sectional area of the filter chamber, the inlet area and the greatest cross-sectional area measured in respective planes parallel to each other.

Inventive Concept 4. The apparatus according to Inventive Concept 1, wherein the filter chamber has an internal volume of between 0.5 and 12 ml.

Inventive Concept 5. The apparatus according to Inventive Concept 4, wherein the internal volume is between 0.5 and 4 ml.

Inventive Concept 6. The apparatus according to Inventive Concept 4, wherein the internal volume is between 1 and 5 ml.

Inventive Concept 7. The apparatus according to Inventive Concept 1, wherein the filter chamber has an internal surface area that equals between 10% and 150% of a filter surface area of an upstream side of the filter.

Inventive Concept 8. The apparatus according to Inventive Concept 1, wherein the filter chamber has an internal length of between 0.5 and 10 cm.

Inventive Concept 9. The apparatus according to Inventive Concept 1, wherein the filter chamber has an internal length equal to between 50% and 2000% of a greatest internal width of the filter chamber.

Inventive Concept 10. The apparatus according to Inventive Concept 1, wherein the filter chamber is nipple-shaped.

Inventive Concept 11. The apparatus according to Inventive Concept 1, wherein the filter chamber includes one or more pressure-activated valves, not disposed at the inlet of the filter chamber.

Inventive Concept 12. The apparatus according to Inventive Concept 1, wherein the liquid-pressure source includes a vacuum pump disposed downstream of filter.

Inventive Concept 13. The apparatus according to Inventive Concept 1, wherein the liquid-pressure source includes a positive-pressure pump disposed upstream of the filter.

Inventive Concept 14. The apparatus according to Inventive Concept 1, wherein the filter has a filter surface area of an upstream side of the filter that equals between 0.3 and 100 cm2.

Inventive Concept 15. The apparatus according to Inventive Concept 14, wherein the filter surface area equals between 0.3 and 30 cm2.

Inventive Concept 16. The apparatus according to Inventive Concept 1, wherein the filter is configured to trap at least 40% of group A streptococcus bacteria and allow passage of the liquid.

Inventive Concept 17. The apparatus according to Inventive Concept 1, wherein the filter is configured to trap at least 40% of the particulate to be tested and allow passage of the liquid.

Inventive Concept 18. The apparatus according to any one of Inventive Concepts 1-17, wherein the testing device further includes a waste liquid receptacle, which is coupled to the liquid container downstream of the filter, and wherein the liquid-pressure source is arranged to apply pressure to drive the liquid contained in the liquid container through the filter and then into the waste liquid receptacle.

Inventive Concept 19. The apparatus according to Inventive Concept 18,
wherein the liquid-pressure source includes a plunger, which includes a plunger head that is shaped so as to be insertable into the liquid container, and
wherein the plunger is shaped so as to define the waste liquid receptacle.

Inventive Concept 20. The apparatus according to Inventive Concept 18, wherein the waste liquid receptacle contains an antibacterial agent.

Inventive Concept 21. The apparatus according to Inventive Concept 18, wherein the filter chamber is laterally surrounded by at least a portion of the waste liquid receptacle.

Inventive Concept 22. The apparatus according to Inventive Concept 18, wherein the filter chamber is disposed within the waste liquid receptacle.

Inventive Concept 23. The apparatus according to any one of Inventive Concepts 1-17, wherein the filter is removably disposed upstream of the filter chamber with the filter partially covering the inlet of the filter chamber.

Inventive Concept 24. The apparatus according to Inventive Concept 23, wherein the inlet of the filter chamber has an inlet centroid that is disposed within a distance of a filter centroid, the distance equal to 50% of a greatest dimension of the filter, when the filter is removably disposed upstream of the filter chamber with the filter partially covering the inlet of the filter chamber.

Inventive Concept 25. The apparatus according to Inventive Concept 23, wherein the testing device further includes a support for the filter, disposed at least partially between the inlet of the filter chamber and the filter.

Inventive Concept 26. The apparatus according to Inventive Concept 23, wherein the apparatus further includes an elongate member configured to push at least a portion of the filter into the filter chamber.

Inventive Concept 27. The apparatus according to Inventive Concept 23,
wherein the liquid-pressure source includes a plunger, which includes a plunger head that is shaped so as to be insertable into the liquid container, and
wherein the plunger head is configured to push at least a portion of the filter into the filter chamber.

Inventive Concept 28. The apparatus according to Inventive Concept 23, wherein the testing device further includes a frangible seal that removably blocks liquid flow into the inlet of the filter chamber.

Inventive Concept 29. The apparatus according to Inventive Concept 23, wherein the filter chamber includes one or more valves, not disposed at the inlet of the filter chamber.

Inventive Concept 30. The apparatus according to Inventive Concept 29, wherein the one or more valves include one or more pressure-activated valves.

Inventive Concept 31. The apparatus according to Inventive Concept 30, wherein the one or more valves include one or more non-pressure-activated valves.

32. The apparatus according to Inventive Concept 29,
wherein the liquid container is shaped so as to define one or more openings through a wall of the liquid container,
wherein the one or more openings are downstream of the filter when the filter is removably disposed upstream of the filter chamber with the filter partially covering the inlet of the filter chamber, and
wherein the filter chamber is not disposed so as to receive the liquid that is driven through the one or more openings.

Inventive Concept 33. The apparatus according to any one of Inventive Concepts 1-17, wherein the filter is disposed at least partially within the filter chamber.

Inventive Concept 34. The apparatus according to Inventive Concept 33, wherein the filter is disposed entirely within the filter chamber.

Inventive Concept 35. The apparatus according to Inventive Concept 33, wherein the filter is shaped as a receptacle.

Inventive Concept 36. The apparatus according to any one of Inventive Concepts 1-17, wherein the liquid-pressure source includes a plunger, which includes a plunger head that is shaped so as to be insertable into the liquid container.

Inventive Concept 37. The apparatus according to Inventive Concept 36, wherein the plunger is shaped so as to define the filter chamber.

Inventive Concept 38. The apparatus according to any one of Inventive Concepts 1-17, wherein the testing device further includes one or more heating elements which are configured to heat the filter at a generally constant temperature, the temperature in the range of 20 and 50 degrees C.

Inventive Concept 39. The apparatus according to Inventive Concept 38, wherein the temperature is in the range of 30 to 40 degrees C.

Inventive Concept 40. The apparatus according to Inventive Concept 38, wherein the liquid container includes, upstream of the filter, a frangible dividing waterproof or water-resistant membrane that isolates the filter from the liquid in the liquid container.

Inventive Concept 41. The apparatus according to Inventive Concept 38,
wherein the liquid-pressure source includes a plunger, which includes a plunger head that is shaped so as to be insertable into the liquid container, and
wherein the one or more heating elements are disposed in the plunger.

Inventive Concept 42. The apparatus according to any one of Inventive Concepts 1-17, wherein the liquid container is shaped so as to define upstream and downstream openings, and wherein an area of the upstream opening is greater than the area of the downstream opening.

Inventive Concept 43. The apparatus according to Inventive Concept 42, wherein the liquid container includes an upstream end portion that includes the upstream opening, and wherein the upstream end portion is conical.

Inventive Concept 44. The apparatus according to Inventive Concept 43, wherein a diameter of the upstream opening is at least 20% greater than a diameter of the downstream opening.

Inventive Concept 45. The apparatus according to any one of Inventive Concepts 1-17, wherein the apparatus further includes sterile packaging, in which at least the liquid container, the filter chamber, and the filter are removably disposed.

Inventive Concept 46. The apparatus according to any one of Inventive Concepts 1-17, wherein the apparatus further includes at least one container including an extraction reagent.

Inventive Concept 47. The apparatus according to Inventive Concept 46, wherein the apparatus further includes a test strip.

There is further provided, in accordance with an Inventive Concept 48 of the present invention, a method including:
applying pressure to drive liquid contained in a liquid container of a testing device through a filter of the testing device, wherein the filter is disposed in or downstream of the liquid container, and wherein the liquid includes at least one substance selected from the group of substances consisting of gargled fluid, saliva not swabbed from a throat of a patient, and an incubated culture medium containing a biological sample; and thereafter, testing, within a filter chamber of the testing device, for the presence of particulate trapped by the filter while the filter is disposed at least partially in the filter chamber, wherein the filter chamber is (a) disposed downstream of the liquid container, (b) shaped so as to define an inlet, and (c) in fluid communication with the filter.

Inventive Concept 49. The method according to Inventive Concept 48, wherein testing includes applying an extraction reagent to the filter while the filter is in the filter chamber.

Inventive Concept 50. The method according to Inventive Concept 49, wherein testing further includes after applying the extraction reagent, inserting a test strip into the filter chamber and examining the test strip to test for the presence of the particulate.

Inventive Concept 51. The method according to Inventive Concept 48, further including taking a sample from the filter, and testing the sample, outside the testing device, for the presence of the particulate.

Inventive Concept 52. The method according to Inventive Concept 51, wherein testing the sample outside the testing device includes testing the sample outside the testing device without first incubating the sample.

Inventive Concept 53. The method according to Inventive Concept 52, wherein testing the sample outside the testing device includes performing a technique selected from the group consisting of: a nucleic acid amplification rapid strep test (RST) technique and real-time quantitative polymerase chain reaction (qPCR) assaying.

Inventive Concept 54. The method according to Inventive Concept 51, wherein testing the sample outside the testing device includes incubating the sample outside the testing device and subsequently testing the sample outside the testing device.

Inventive Concept 55. The method according to Inventive Concept 54, wherein testing the sample outside the testing device includes performing a technique selected from the group consisting of: lateral flow immunoassaying, an ELISA-based rapid strep test (RST), an antibody-coated-beads-based RST, a nucleic-acid-based RST, and a fluorescent immunoassaying (FIA).

Inventive Concept 56. The method according to Inventive Concept 48, wherein the liquid includes the gargled fluid.

Inventive Concept 57. The method according to Inventive Concept 48, wherein the liquid includes the saliva not swabbed from the throat of the patient.

Inventive Concept 58. The method according to Inventive Concept 57, wherein the saliva not swabbed from the throat of the patient is saliva spit by the patient.

Inventive Concept 59. The method according to Inventive Concept 48, wherein the liquid includes the incubated culture medium containing the biological sample.

Inventive Concept 60. The method according to Inventive Concept 48, wherein applying the pressure includes pushing a plunger including a plunger head inserted into the liquid container.

Inventive Concept 61. The method according to Inventive Concept 60, wherein the plunger is shaped so as to define the filter chamber.

Inventive Concept 62. The method according to Inventive Concept 48, wherein applying the pressure includes applying positive pressure using a positive-pressure pump disposed upstream of the filter.

Inventive Concept 63. The method according to Inventive Concept 48, wherein applying the pressure includes applying negative pressure using a vacuum pump disposed downstream of the filter.

Inventive Concept 64. The method according to Inventive Concept 48, wherein applying the pressure includes applying the pressure while the filter is removably disposed upstream of the filter chamber with the filter partially covering the inlet of the filter chamber, and wherein testing includes pushing at least a portion of the filter into the filter chamber.

Inventive Concept 65. The method according to Inventive Concept 64, wherein pushing includes pushing the at least a portion of the filter into the filter chamber using an elongate member.

Inventive Concept 66. The method according to Inventive Concept 65, wherein pushing the at least a portion of the filter into the filter chamber includes taking a sample from the filter using the elongate member, and testing the sample, outside the testing device, for the presence of the particulate.

Inventive Concept 67. The method according to Inventive Concept 64, wherein the testing device further includes a frangible seal that removably blocks liquid flow into the inlet of the filter chamber, and wherein the method further includes, after applying the pressure and before testing for the presence of the particulate trapped by the filter, breaking the frangible seal.

Inventive Concept 68. The method according to Inventive Concept 64, wherein the filter chamber includes one or more valves, not disposed at the inlet of the filter chamber.

Inventive Concept 69. The method according to Inventive Concept 68, wherein the one or more valves include one or more pressure-activated valves.

Inventive Concept 70. The method according to Inventive Concept 69, wherein the one or more valves include one or more non-pressure-activated valves.

Inventive Concept 71. The method according to Inventive Concept 48, wherein applying the pressure includes applying the pressure while the filter is disposed at least partially within the filter chamber.

Inventive Concept 72. The method according to Inventive Concept 71, wherein applying the pressure includes applying the pressure while the filter is disposed entirely within the filter chamber.

Inventive Concept 73. The method according to Inventive Concept 71, wherein the filter is shaped as a receptacle.

Inventive Concept 74. The method according to Inventive Concept 48, further including, before applying the pressure, taking a sample of the liquid, and testing the sample, outside the testing device, for the presence of the particulate.

There is still further provided, in accordance with an Inventive Concept 75 of the present invention, a method including:

applying pressure to drive liquid contained in a liquid container of a testing device (a) through a filter of the testing device and (b) then through one or more valves of the testing device, wherein the filter is disposed in or downstream of the liquid container, wherein the one or more valves are disposed downstream of the filter, and wherein the liquid includes at least one substance selected from the group of substances consisting of gargled fluid, saliva not swabbed from a throat of a patient, and an incubated culture medium containing a biological sample; and thereafter, testing, within the testing device, for the presence of particulate trapped by the filter while the one or more valves are closed and the filter is disposed in the testing device.

Inventive Concept 76. The method according to Inventive Concept 75, wherein testing includes applying an extraction reagent to the filter.

Inventive Concept 77. The method according to Inventive Concept 76, wherein testing further includes after applying the extraction reagent, inserting a test strip into the testing device and examining the test strip to test for the presence of the particulate.

Inventive Concept 78. The method according to Inventive Concept 75, wherein the liquid includes the gargled fluid.

Inventive Concept 79. The method according to Inventive Concept 75, wherein the liquid includes the saliva not swabbed from the throat of the patient.

Inventive Concept 80. The method according to Inventive Concept 79, wherein the saliva not swabbed from the throat of the patient is saliva spit by the patient.

Inventive Concept 81. The method according to Inventive Concept 75, wherein the liquid includes the incubated culture medium containing the biological sample.

Inventive Concept 82. The method according to Inventive Concept 75, wherein the liquid container has an internal volume of between 0.5 and 500 ml.

Inventive Concept 83. The method according to Inventive Concept 75, wherein applying the pressure includes pushing a plunger including a plunger head inserted into the liquid container.

Inventive Concept 84. The method according to Inventive Concept 75, wherein applying the pressure includes applying positive pressure using a positive-pressure pump disposed upstream of the filter.

Inventive Concept 85. The method according to Inventive Concept 75, wherein applying the pressure includes applying negative pressure using a vacuum pump disposed downstream of the one or more valves.

Inventive Concept 86. The method according to Inventive Concept 75, wherein the one or more valves include one or more pressure-activated valves.

Inventive Concept 87. The method according to Inventive Concept 75, wherein the one or more valves include one or more non-pressure-activated valves.

Inventive Concept 88. The method according to Inventive Concept 87, wherein the testing device is configured to automatically close the one or more non-pressure-activated valves after the pressure is applied to drive the liquid through the filter and then through the one or more non-pressure-activated valves.

Inventive Concept 89. The method according to Inventive Concept 87, wherein the one or more non-pressure-activated valves include two discs that are shaped so as to define respective sets of openings, and wherein the one or more non-pressure-activated valves are configured to assume open and closed states when the two sets of openings are aligned and non-aligned with each other.

Inventive Concept 90. The method according to Inventive Concept 87,
wherein applying the pressure includes pushing a plunger including a plunger head inserted into the liquid container, and
wherein the testing device is configured to automatically close the one or more non-pressure-activated valves after the plunger applies the pressure to drive the liquid contained in the liquid container through the filter and then through the one or more non-pressure-activated valves.

Inventive Concept 91. The method according to Inventive Concept 90, wherein the testing device is configured such that motion of the plunger automatically closes the one or more non-pressure-activated valves after the plunger applies the pressure to drive the liquid contained in the liquid container through the filter and then through the one or more non-pressure-activated valves.

Inventive Concept 92. The method according to Inventive Concept 91,
wherein pushing the plunger include rotating the plunger, and
wherein the testing device is configured such that rotational motion of the plunger automatically closes the one or more non-pressure-activated valves after the plunger applies the pressure to drive the liquid contained in the liquid container through the filter and then through the one or more non-pressure-activated valves.

Inventive Concept 93. The method according to Inventive Concept 92, wherein the plunger is shaped so as to define one or more plunger threads, and wherein an internal wall of the liquid container is shaped so as to define one or more liquid-container threads that engage the one or more plunger threads such that rotation of the plunger advances the plunger in a downstream direction within the liquid container.

Inventive Concept 94. The method according to Inventive Concept 92,
wherein the one or more non-pressure-activated valves include two discs that are shaped so as to define respective sets of openings, and wherein the one or more non-pressure-activated valves are configured to assume open and closed states when the two sets of openings are aligned and non-aligned with each other,
wherein pushing the plunger include rotating the plunger, and
wherein the testing device is configured such that rotational motion of the plunger automatically closes the one or more non-pressure-activated valves by rotating at least one of the two discs with respect to the other of the discs, after the plunger applies the pressure to drive the liquid contained in the liquid container through the filter and then through the one or more non-pressure-activated valves.

Inventive Concept 95. The method according to Inventive Concept 75, wherein applying the pressure includes applying the pressure to drive the liquid contained in the liquid container through the filter, then through the one or more valves, and then into a waste liquid receptacle of the testing device, wherein the waste liquid receptacle is coupled to the liquid container downstream of the one or more valves.

Inventive Concept 96. The method according to Inventive Concept 95,
wherein applying the pressure includes pushing a plunger including a plunger head inserted into the liquid container, and
wherein the plunger is shaped so as to define the waste liquid receptacle.

Inventive Concept 97. The method according to Inventive Concept 95, wherein the waste liquid receptacle contains an antibacterial agent.

Inventive Concept 98. The method according to Inventive Concept 75, wherein the testing device further includes a filter chamber that is (a) disposed downstream of the liquid container, (b) shaped so as to define an inlet, and (c) in fluid communication with filter.

Inventive Concept 99. The method according to Inventive Concept 98, wherein applying the pressure includes pushing a plunger including a plunger head inserted into the liquid container, and wherein the plunger is shaped so as to define the filter chamber.

Inventive Concept 100. The method according to Inventive Concept 98, wherein the liquid-pressure source is arranged to apply pressure to drive the liquid contained in the liquid container through the filter, then through the one or more valves, and then into a waste liquid receptacle of the testing device, wherein the waste liquid receptacle is coupled to the liquid container downstream of the one or more valves, and wherein the filter chamber is laterally surrounded by at least a portion of the waste liquid receptacle.

Inventive Concept 101. The method according to Inventive Concept 98, wherein the liquid-pressure source is arranged to apply pressure to drive the liquid contained in the liquid container through the filter, then through the one or more valves, and then into a waste liquid receptacle of the testing device, wherein the waste liquid receptacle is coupled to the liquid container downstream of the one or more valves, and wherein the filter chamber is disposed within the waste liquid receptacle.

Inventive Concept 102. The method according to Inventive Concept 98, wherein the inlet of the filter chamber has an inlet area that is less than a greatest cross-sectional area of the filter chamber, the inlet area and the greatest cross-sectional area measured in respective planes parallel to each other.

Inventive Concept 103. The method according to Inventive Concept 98, wherein the filter chamber is nipple-shaped.

Inventive Concept 104. The method according to Inventive Concept 98, wherein the filter chamber includes at least one of the one or more valves, not disposed at the inlet of the filter chamber.

Inventive Concept 105. The method according to Inventive Concept 98, wherein applying the pressure includes applying the pressure while the filter is removably disposed upstream of the filter chamber with the filter partially covering the inlet of the filter chamber.

Inventive Concept 106. The method according to Inventive Concept 105, wherein the method further includes, after applying the pressure and before testing for the presence of the particulate trapped by the filter, pushing at least a portion of the filter into the filter chamber.

Inventive Concept 107. The method according to Inventive Concept 106, wherein applying the pressure includes pushing a plunger including a plunger head inserted into the liquid container, and wherein pushing the at least a portion of the filter into the filter chamber includes pushing the at least a portion of the filter into the filter chamber using the plunger head.

Inventive Concept 108. The method according to Inventive Concept 106, wherein pushing includes pushing the at least a portion of the filter into the filter chamber using an elongate member.

Inventive Concept 109. The method according to Inventive Concept 108, wherein pushing the at least a portion of the filter into the filter chamber includes taking a sample from the filter using the elongate member, and testing the sample, outside the testing device, for the presence of the particulate.

Inventive Concept 110. The method according to Inventive Concept 105, wherein the inlet of the filter chamber has an inlet centroid that is disposed less than a distance from a filter centroid, the distance equal to 50% of a greatest dimension of the filter.

Inventive Concept 111. The method according to Inventive Concept 105, wherein the testing device further includes a frangible seal that removably blocks liquid flow into the inlet of the filter chamber, and wherein the method further includes, after applying the pressure and before testing for the presence of the particulate trapped by the filter, breaking the frangible seal.

Inventive Concept 112. The method according to Inventive Concept 98, wherein the filter chamber is not disposed so as to receive the liquid that is driven through at least one of the one or more valves.

Inventive Concept 113. The method according to Inventive Concept 98, wherein the filter chamber includes at least one of the one or more valves, not disposed at the inlet of the filter chamber.

Inventive Concept 114. The method according to Inventive Concept 113, wherein the liquid container is shaped so as to define one or more openings through a wall of the liquid container, wherein the one or more openings are downstream of the filter when the filter is removably disposed upstream of the filter chamber with the filter partially covering the inlet of the filter chamber, wherein the filter chamber is not disposed so as to receive the liquid that is driven through the one or more openings, and wherein applying the pressure includes applying the pressure to drive the liquid (i) partially through (a) the filter and (b) one or more of the one or more valves of the testing device and (ii) partially through the one or more openings.

Inventive Concept 115. The method according to Inventive Concept 98, wherein the filter is disposed at least partially within the filter chamber.

Inventive Concept 116. The method according to Inventive Concept 115, wherein the filter is disposed entirely within the filter chamber.

Inventive Concept 117. The method according to Inventive Concept 115, wherein the filter is shaped as a receptacle.

Inventive Concept 118. The method according to Inventive Concept 75, wherein the filter is configured to trap at least 40% of group A streptococcus bacteria and allow passage of the liquid.

Inventive Concept 119. The method according to Inventive Concept 75, wherein the filter is configured to trap at least 40% of the particulate.

Inventive Concept 120. The method according to Inventive Concept 75, wherein the method further includes, before testing for the presence of the particulate trapped by the filter, activating one or more heating elements which are configured to heat the filter at a generally constant temperature, the temperature in the range of 20 and 50 degrees C.

Inventive Concept 121. The method according to Inventive Concept 120, wherein the temperature is in the range of 30 to 40 degrees C.

Inventive Concept 122. The method according to Inventive Concept 120, wherein the one or more heating elements are disposed within the testing device.

Inventive Concept 123. The method according to Inventive Concept 122,
wherein applying the pressure includes pushing a plunger including a plunger head inserted into the liquid container, and
wherein the one or more heating elements are disposed in the plunger.

Inventive Concept 124. The method according to Inventive Concept 75, wherein the method further includes, before most of the liquid initially contained in the testing device has been driven through the filter, activating one or more heating elements which are configured to heat the filter at a generally constant temperature, the temperature in the range of 20 and 50 degrees C.

Inventive Concept 125. The method according to Inventive Concept 124, wherein the temperature is in the range of 30 to 40 degrees C.

Inventive Concept 126. The method according to Inventive Concept 124, wherein activating the one or more heating elements includes activating the one or more heating elements before any of the liquid initially contained in the testing device has been driven through the filter.

Inventive Concept 127. The method according to Inventive Concept 126,
wherein the liquid container includes, upstream of the filter, a frangible dividing waterproof or water-resistant membrane that isolates the filter from the liquid in the liquid container, and
wherein the method further includes breaking the frangible dividing waterproof or water-resistant membrane before driving the liquid through the filter.

Inventive Concept 128. The method according to Inventive Concept 126, wherein activating the one or more heating elements includes orienting the testing device with the filter above the liquid, such that the liquid is not in contact with the filter during heating.

Inventive Concept 129. The method according to Inventive Concept 124, wherein the one or more heating elements are disposed within the testing device.

Inventive Concept 130. The method according to Inventive Concept 75,
wherein the one or more valves are one or more first valves, and
wherein the testing device further includes one or more second pressure relief valves, which are in fluid communication with the liquid container and are disposed upstream of the filter.

Inventive Concept 131. The method according to Inventive Concept 130,
wherein the liquid-pressure source is arranged to apply pressure to drive the liquid contained in the liquid container through the filter, then through the one or more valves, and then into a waste liquid receptacle of the testing device, wherein the waste liquid receptacle is coupled to the liquid container downstream of the one or more valves, and
wherein the one or more second pressure relief valves are in fluid communication with the waste liquid receptacle not via the filter.

Inventive Concept 132. The method according to Inventive Concept 130,
wherein the liquid-pressure source includes a plunger, which includes (a) a plunger shaft and (b) a plunger head that is disposed at a downstream end portion of the plunger shaft and shaped so as to be insertable into the liquid container,
wherein the testing device includes one or more unfiltered liquid receptacles,
wherein the one or more second pressure relief valves are in fluid communication with the one or more unfiltered liquid receptacles, and
wherein the method further includes, after applying the pressure, taking a sample of the liquid in the one or more unfiltered liquid receptacles, and testing the sample, outside the testing device, for the presence of the particulate.

Inventive Concept 133. The method according to Inventive Concept 132, wherein the one or more unfiltered liquid receptacles are disposed along the plunger shaft.

Inventive Concept 134. The method according to Inventive Concept 133, wherein the one or more unfiltered liquid receptacles are removably coupled to the plunger.

Inventive Concept 135. The method according to Inventive Concept 130,
wherein the one or more first valves include one or more first pressure-activated valves configured to open upon exposure to a first pressure gradient across the one or more first pressure-activated valves, and
wherein the one or more second pressure relief valves are configured to open upon exposure to a second pressure gradient across the one or more second pressure relief valves, the second pressure gradient greater than the first pressure gradient.

Inventive Concept 136. The method according to Inventive Concept 75, wherein the method further includes, before applying the pressure, removing the liquid container, the one or more valves, and the filter from sterile packaging.

Inventive Concept 137. The method according to Inventive Concept 75, wherein the particulate includes biological particulate.

Inventive Concept 138. The method according to Inventive Concept 137, wherein the biological particulate is selected from the group consisting of: a microorganism, a fungus, a bacterium, a spore, a virus, a mite, a biological cell, a biological antigen, a protein, a protein antigen, and a carbohydrate antigen.

Inventive Concept 139. The method according to Inventive Concept 75, wherein testing for the presence of the particulate includes applying an extraction reagent to the filter after applying the pressure.

Inventive Concept 140. The method according to Inventive Concept 139, wherein testing for the presence of the particulate includes using a test strip.

Inventive Concept 141. The method according to Inventive Concept 75, further including, after applying the pressure, taking a sample from the filter, and testing the sample, outside the testing device, for the presence of the particulate trapped by the filter.

Inventive Concept 142. The method according to Inventive Concept 75, further including, before applying the pressure, taking a sample of the liquid, and testing the sample, outside the testing device, for the presence of the particulate.

Inventive Concept 143. The method according to Inventive Concept 75, further including taking a sample from the filter, and testing the sample, outside the testing device, for the presence of the particulate.

Inventive Concept 144. The method according to Inventive Concept 143, wherein testing the sample outside the testing device includes testing the sample outside the testing device without first incubating the sample.

Inventive Concept 145. The method according to Inventive Concept 144, wherein testing the sample outside the testing device includes performing a technique selected from the group consisting of: a nucleic acid amplification rapid strep test (RST) technique and real-time quantitative polymerase chain reaction (qPCR) assaying.

Inventive Concept 146. The method according to Inventive Concept 143, wherein testing the sample outside the testing device includes incubating the sample outside the testing device and subsequently testing the sample outside the testing device.

Inventive Concept 147. The method according to Inventive Concept 146, wherein testing the sample outside the testing device includes performing a technique selected from the group consisting of: lateral flow immunoassaying, an ELISA-based rapid strep test (RST), an antibody-coated-beads-based RST, a nucleic-acid-based RST, and a fluorescent immunoassaying (FIA).

There is additionally provided, in accordance with an Inventive Concept 148 of the present invention, apparatus including a testing device for testing for the presence of particulate in a liquid, the testing device including:

a liquid container for containing the liquid, the liquid container shaped so as to define upstream and downstream openings;

a filter, removably disposed in the liquid container; and a plunger head that (a) is shaped so as to be insertable into the liquid container so as to form a movable seal with a wall of the liquid container, and (b) is arranged such that when pushed, the plunger head applies pressure to drive the liquid contained in the liquid container through the filter and then through the downstream opening, wherein the testing device is configured such that rotation of the plunger head radially compresses the filter toward a central longitudinal axis of the plunger head.

Inventive Concept 149. The apparatus according to Inventive Concept 148, wherein the testing device is configured such that the rotation of the plunger head crushes the filter.

Inventive Concept 150. The apparatus according to Inventive Concept 149, wherein the plunger head includes a protrusion, and wherein the testing device is configured such that the rotation of the plunger head causes the protrusion to move radially toward the central longitudinal axis of the plunger head.

Inventive Concept 151. The apparatus according to Inventive Concept 150, wherein the liquid container is shaped so as to define a filter-support surface surrounding the downstream opening, wherein the filter-support surface supports a radial portion of the filter excluding a central portion of the filter, wherein the filter-support surface is shaped so as to define a spiral groove, wherein the protrusion is configured to engage the spiral groove through the filter, and wherein the testing device is configured such that the rotation of the plunger head causes the spiral groove to guide the protrusion radially toward the central longitudinal axis of the plunger head.

There is yet additionally provided, in accordance with an Inventive Concept 152 of the present invention, a method including:

inserting a plunger head into a liquid container of a testing device so as to form a movable seal with a wall of the liquid container;

pushing the plunger head to apply pressure to drive liquid contained in the liquid container through a filter of the testing device and then through a downstream opening of the liquid container, which also has an upstream opening, wherein the filter is removably disposed in the liquid container; and rotating the plunger head to radially crush the filter toward a central longitudinal axis of the plunger head.

Inventive Concept 153. The method according to Inventive Concept 152, further including, after rotating the plunger head, testing the filter for the presence of particulate trapped by the filter.

Inventive Concept 154. The method according to Inventive Concept 152, wherein rotating the plunger head crushes the filter.

Inventive Concept 155. The method according to Inventive Concept 154, wherein the plunger head includes a protrusion, and wherein rotating the plunger head causes the protrusion to move radially toward the central longitudinal axis of the plunger head.

Inventive Concept 156. The method according to Inventive Concept 155, wherein the liquid container is shaped so as to define a filter-support surface surrounding the downstream opening, wherein the filter-support surface supports a radial portion of the filter excluding a central portion of the filter, wherein the filter-support surface is shaped so as to define a spiral groove, wherein the protrusion is configured to engage the spiral groove through the filter, and wherein rotating the plunger head causes the spiral groove to guide the protrusion radially toward the central longitudinal axis of the plunger head.

Inventive Concept There is further provided, in accordance with an Inventive Concept 157 of the present invention, apparatus including a testing device for testing for the presence of particulate in a liquid, the testing device including:

a liquid container for containing the liquid, wherein the liquid container has an internal volume of between 0.5 and 500 ml;

one or more valves;

a filter, disposed in or downstream of the liquid container and upstream of the one or more valves; and a plunger, which (a) includes a plunger head that is shaped so as to be insertable into the liquid container, and (b) is arranged to apply pressure to drive the liquid contained in the liquid container through the filter and then through the one or more valves.

Inventive Concept 158. The apparatus according to Inventive Concept 157, wherein the one or more valves include one or more pressure-activated valves.

Inventive Concept 159. The apparatus according to Inventive Concept 157, wherein the one or more valves include one or more non-pressure-activated valves.

Inventive Concept 160. The apparatus according to Inventive Concept 159, wherein the one or more non-pressure-activated valves include two discs that are shaped so as to define respective sets of openings, and wherein the one or more non-pressure-activated valves are configured to assume open and closed states when the two sets of openings are aligned and non-aligned with each other.

Inventive Concept 161. The apparatus according to Inventive Concept 159, wherein the testing device is configured to automatically close the one or more non-pressure-activated valves after the plunger applies the pressure to drive the liquid contained in the liquid container through the filter and then through the one or more non-pressure-activated valves.

Inventive Concept 162. The apparatus according to Inventive Concept 161, wherein the testing device is configured such that motion of the plunger automatically closes the one or more non-pressure-activated valves after the plunger applies the pressure to drive the liquid contained in the liquid container through the filter and then through the one or more non-pressure-activated valves.

Inventive Concept 163. The apparatus according to Inventive Concept 162, wherein the testing device is configured such that rotational motion of the plunger automatically closes the one or more non-pressure-activated valves after the plunger applies the pressure to drive the liquid contained in the liquid container through the filter and then through the one or more non-pressure-activated valves.
Inventive Concept 164. The apparatus according to Inventive Concept 163, wherein the plunger is shaped so as to define one or more plunger threads, and wherein an internal wall of the liquid container is shaped so as to define one or more liquid-container threads that engage the one or more plunger threads such that rotation of the plunger advances the plunger in a downstream direction within the liquid container.
Inventive Concept 165. The apparatus according to Inventive Concept 163,
wherein the one or more non-pressure-activated valves include two discs that are shaped so as to define respective sets of openings, and wherein the one or more non-pressure-activated valves are configured to assume open and closed states when the two sets of openings are aligned and non-aligned with each other, and
wherein the testing device is configured such that rotational motion of the plunger automatically closes the one or more non-pressure-activated valves by rotating at least one of the two discs with respect to the other of the discs, after the plunger applies the pressure to drive the liquid contained in the liquid container through the filter and then through the one or more non-pressure-activated valves.
Inventive Concept 166. The apparatus according to Inventive Concept 157, wherein the filter has a filter surface area of an upstream side of the filter that equals between 0.3 and 100 cm2.
Inventive Concept 167. The apparatus according to Inventive Concept 166, wherein the filter surface area equals between 0.3 and 30 cm2.
Inventive Concept 168. The apparatus according to Inventive Concept 157, wherein the filter is configured to trap at least 40% of group A streptococcus bacteria and allow passage of the liquid.
Inventive Concept 169. The apparatus according to Inventive Concept 157, wherein the filter is configured to trap at least 40% of the particulate to be tested and allow passage of the liquid.
Inventive Concept 170. The apparatus according to any one of Inventive Concepts 157-169, wherein the testing device further includes a waste liquid receptacle, which is coupled to the liquid container downstream of the one or more valves, and wherein the plunger is arranged to apply pressure to drive the liquid contained in the liquid container through the filter, then through the one or more valves, and then into the waste liquid receptacle.
Inventive Concept 171. The apparatus according to Inventive Concept 170, wherein the plunger is shaped so as to define the waste liquid receptacle.
Inventive Concept 172. The apparatus according to Inventive Concept 170, wherein the waste liquid receptacle contains an antibacterial agent.
Inventive Concept 173. The apparatus according to any one of Inventive Concepts 157-169, wherein the testing device further includes a filter chamber that is (a) disposed downstream of the liquid container, (b) shaped so as to define an inlet, and (c) in fluid communication with the filter.
Inventive Concept 174. The apparatus according to Inventive Concept 173, wherein the plunger is shaped so as to define the filter chamber.
Inventive Concept 175. The apparatus according to Inventive Concept 173,
wherein the testing device further includes a waste liquid receptacle, which is coupled to the liquid container downstream of the filter,
wherein the plunger is arranged to apply pressure to drive the liquid contained in the liquid container through the filter and then into the waste liquid receptacle, and
wherein the filter chamber is laterally surrounded by at least a portion of the waste liquid receptacle.
Inventive Concept 176. The apparatus according to Inventive Concept 173,
wherein the testing device further includes a waste liquid receptacle, which is coupled to the liquid container downstream of the filter,
wherein the plunger is arranged to apply pressure to drive the liquid contained in the liquid container through the filter and then into the waste liquid receptacle, and
wherein the filter chamber is disposed within the waste liquid receptacle.
Inventive Concept 177. The apparatus according to Inventive Concept 173, wherein the inlet of the filter chamber has an inlet area that equals between 4% and 40% of a filter surface area of an upstream side of the filter.
Inventive Concept 178. The apparatus according to Inventive Concept 173, wherein the inlet of the filter chamber has an inlet area that is less than a greatest cross-sectional area of the filter chamber, the inlet area and the greatest cross-sectional area measured in respective planes parallel to each other.
Inventive Concept 179. The apparatus according to Inventive Concept 173, wherein the filter chamber has an internal volume of between 0.5 and 12 ml.
Inventive Concept 180. The apparatus according to Inventive Concept 179, wherein the internal volume is between 0.5 and 4 ml.
Inventive Concept 181. The apparatus according to Inventive Concept 179, wherein the internal volume is between 1 and 5 ml.
Inventive Concept 182. The apparatus according to Inventive Concept 173, wherein the filter chamber has an internal surface area that equals between 10% and 150% of a filter surface area of an upstream side of the filter.
Inventive Concept 183. The apparatus according to Inventive Concept 173, wherein the filter chamber has an internal length of between 0.5 and 10 cm.
Inventive Concept 184. The apparatus according to Inventive Concept 173, wherein the filter chamber has an internal length equal to between 50% and 2000% of a greatest internal width of the filter chamber.
Inventive Concept 185. The apparatus according to Inventive Concept 173, wherein the filter chamber is nipple-shaped.
Inventive Concept 186. The apparatus according to Inventive Concept 173, wherein the filter chamber includes at least one of the one or more valves, not disposed at the inlet of the filter chamber.
Inventive Concept 187. The apparatus according to Inventive Concept 173, wherein the filter is removably disposed upstream of the filter chamber with the filter partially covering the inlet of the filter chamber.
Inventive Concept 188. The apparatus according to Inventive Concept 187, wherein the inlet of the filter chamber has an inlet centroid that is disposed less than a distance from a filter centroid, the distance equal to 50% of a greatest dimension of the filter, when the filter is removably disposed upstream of the filter chamber with the filter partially covering the inlet of the filter chamber.

Inventive Concept 189. The apparatus according to Inventive Concept 187, wherein the testing device further includes a support for the filter, disposed at least partially between the inlet of the filter chamber and the filter.

Inventive Concept 190. The apparatus according to Inventive Concept 187, wherein the apparatus further includes an elongate member configured to push at least a portion of the filter into the filter chamber.

Inventive Concept 191. The apparatus according to Inventive Concept 187, wherein the plunger head is configured to push at least a portion of the filter into the filter chamber.

Inventive Concept 192. The apparatus according to Inventive Concept 187, wherein the testing device further includes a frangible seal that removably blocks liquid flow into the inlet of the filter chamber.

Inventive Concept 193. The apparatus according to Inventive Concept 187, wherein the filter chamber is not disposed so as to receive the liquid that is driven through at least one of the one or more valves.

Inventive Concept 194. The apparatus according to Inventive Concept 187, wherein the filter chamber includes at least one of the one or more valves, not disposed at the inlet of the filter chamber.

Inventive Concept 195. The apparatus according to Inventive Concept 194,
wherein the liquid container is shaped so as to define one or more openings through a wall of the liquid container,
wherein the one or more openings are downstream of the filter when the filter is removably disposed upstream of the filter chamber with the filter partially covering the inlet of the filter chamber, and
wherein the filter chamber is not disposed so as to receive the liquid that is driven through the one or more openings.

Inventive Concept 196. The apparatus according to Inventive Concept 173, wherein the filter is disposed at least partially within the filter chamber.

Inventive Concept 197. The apparatus according to Inventive Concept 196, wherein the filter is disposed entirely within the filter chamber.

Inventive Concept 198. The apparatus according to Inventive Concept 196, wherein the filter is shaped as a receptacle.

Inventive Concept 199. The apparatus according to any one of Inventive Concepts 157-169, wherein the testing device further includes one or more heating elements which are configured to heat the filter at a generally constant temperature, the temperature in the range of 20 and 50 degrees C.

Inventive Concept 200. The apparatus according to Inventive Concept 199, wherein the temperature is in the range of 30 to 40 degrees C.

Inventive Concept 201. The apparatus according to Inventive Concept 199, wherein the liquid container includes, upstream of the filter, a frangible dividing waterproof or water-resistant membrane that isolates the filter from the liquid in the liquid container.

Inventive Concept 202. The apparatus according to Inventive Concept 199, wherein the one or more heating elements are disposed in the plunger.

Inventive Concept 203. The apparatus according to any one of Inventive Concepts 157-169,
wherein the one or more valves are one or more first valves, and
wherein the testing device further includes one or more second pressure relief valves, which are in fluid communication with the liquid container and are disposed upstream of the filter.

Inventive Concept 204. The apparatus according to Inventive Concept 203,
wherein the testing device further includes a waste liquid receptacle, which is coupled to the liquid container downstream of the filter,
wherein the plunger is arranged to apply pressure to drive the liquid contained in the liquid container through the filter and then into the waste liquid receptacle, and
wherein the one or more second pressure relief valves are in fluid communication with the waste liquid receptacle not via the filter.

Inventive Concept 205. The apparatus according to Inventive Concept 203,
wherein the plunger includes a plunger shaft, and the plunger head is disposed at a downstream end portion of the plunger shaft,
wherein the testing device includes one or more unfiltered liquid receptacles, and
wherein the one or more second pressure relief valves are in fluid communication with the one or more unfiltered liquid receptacles.

Inventive Concept 206. The apparatus according to Inventive Concept 205, wherein the one or more unfiltered liquid receptacles are disposed along the plunger shaft.

Inventive Concept 207. The apparatus according to Inventive Concept 206, wherein the one or more unfiltered liquid receptacles are removably coupled to the plunger.

Inventive Concept 208. The apparatus according to Inventive Concept 203,
wherein the one or more first valves include one or more first pressure-activated valves configured to open upon exposure to a first pressure gradient across the one or more first pressure-activated valves, and
wherein the one or more second pressure relief valves are configured to open upon exposure to a second pressure gradient across the one or more second pressure relief valves, the second pressure gradient greater than the first pressure gradient.

Inventive Concept 209. The apparatus according to any one of Inventive Concepts 157-169, wherein the liquid container is shaped so as to define upstream and downstream openings, and wherein an area of the upstream opening is greater than the area of the downstream opening.

Inventive Concept 210. The apparatus according to Inventive Concept 209, wherein the liquid container includes an upstream end portion that includes the upstream opening, and wherein the upstream end portion is conical.

Inventive Concept 211. The apparatus according to Inventive Concept 210, wherein a diameter of the upstream opening is at least 10% greater than a diameter of the downstream opening.

Inventive Concept 212. The apparatus according to any one of Inventive Concepts 157-169, wherein the apparatus further includes sterile packaging, in which at least the at least the liquid container, the one or more valves, and the filter are removably disposed.

Inventive Concept 213. The apparatus according to any one of Inventive Concepts 157-169, wherein the apparatus further includes at least one container containing an extraction reagent.

Inventive Concept 214. The apparatus according to Inventive Concept 213, wherein the apparatus further includes a test strip.

Inventive Concept 215. The apparatus according to any one of Inventive Concepts 157-169, wherein the apparatus further includes a container containing a solution for use in a detecting a pathogen.

There is further provided, in accordance with an Inventive Concept 216 of the present invention, apparatus including a testing device for testing for the presence of particulate in a liquid, the testing device including:

a liquid container for containing the liquid, wherein the liquid container has an internal volume of between 0.5 and 500 ml;

one or more non-pressure-activated valves;

a filter, disposed in or downstream of the liquid container and upstream of the one or more valves; and a liquid-pressure source, which is arranged to apply pressure to drive the liquid contained in the liquid container through the filter and then through the one or more valves, wherein the testing device is configured to automatically close the one or more non-pressure-activated valves after the liquid-pressure source applies the pressure to drive the liquid contained in the liquid container through the filter and then through the one or more non-pressure-activated valves.

Inventive Concept 217. The apparatus according to Inventive Concept 216, wherein the testing device is configured such that motion of the liquid-pressure source automatically closes the one or more non-pressure-activated valves after the liquid-pressure source applies the pressure to drive the liquid contained in the liquid container through the filter and then through the one or more non-pressure-activated valves.

Inventive Concept 218. The apparatus according to Inventive Concept 217, wherein the testing device is configured such that rotational motion of the liquid-pressure source automatically closes the one or more non-pressure-activated valves after the liquid-pressure source applies the pressure to drive the liquid contained in the liquid container through the filter and then through the one or more non-pressure-activated valves.

Inventive Concept 219. The apparatus according to Inventive Concept 218, wherein the one or more non-pressure-activated valves include two discs that are shaped so as to define respective sets of openings, and wherein the one or more non-pressure-activated valves are configured to assume open and closed states when the two sets of openings are aligned and non-aligned with each other, and wherein the testing device is configured such that rotational motion of the liquid-pressure source automatically closes the one or more non-pressure-activated valves by rotating at least one of the two discs with respect to the other of the discs, after the liquid-pressure source applies the pressure to drive the liquid contained in the liquid container through the filter and then through the one or more non-pressure-activated valves.

There is further provided, in accordance with an Inventive Concept 220 of the present invention, a method including:

incubating gargled fluid for between 12 and 75 hours in a container that contains a liquid growth medium, a dehydrated growth medium, or a gel growth medium; and thereafter, performing a strep test using a rapid strep test (RST) technique on the gargled fluid and growth medium.

Inventive Concept 221. The method according to Inventive Concept 220, wherein performing the strep test using the RST technique includes performing a lateral flow test.

Inventive Concept 222. The method according to Inventive Concept 220, wherein performing the strep test using the RST technique includes performing an RST technique selected from the group consisting of: an ELISA-based RST, an antibody-coated-beads-based RST, a nucleic-acid-based RST, and a fluorescent immunoassaying (FIA) RST.

Inventive Concept 223. The method according to Inventive Concept 220, wherein performing the strep test using the RST technique includes performing the RST technique on the gargled fluid and the growth medium while the gargled fluid and the growth medium are in the container.

Inventive Concept 224. The method according to Inventive Concept 220, wherein performing the strep test using the RST technique includes transferring at least a portion of the gargled fluid and the growth medium to another container and performing the RST technique while the at least a portion of the gargled fluid and the growth medium are in the other container.

Inventive Concept 225. The method according to Inventive Concept 224, wherein transferring the at least a portion of the gargled fluid and the growth medium to the other container includes:

inserting an absorbent element into the gargled fluid and growth medium; and thereafter, placing the absorbent element into the other container.

Inventive Concept 226. The method according to Inventive Concept 225, wherein the absorbent element is a swab.

Inventive Concept 227. The method according to Inventive Concept 226, wherein the swab is a flocked swab.

Inventive Concept 228. The method according to Inventive Concept 224, wherein transferring the at least a portion of the gargled fluid and the growth medium includes transferring at least 0.05 ml of the gargled fluid and the growth medium.

Inventive Concept 229. The method according to Inventive Concept 220, wherein performing the strep test using the RST technique further includes filtering the gargled fluid and the growth medium after incubating, and performing the strep test using the RST technique on the filter.

Inventive Concept 230. The method according to Inventive Concept 229, wherein filtering the gargled fluid and the growth medium after incubating includes:

placing the gargled fluid and the growth medium in a liquid container of a testing device; and applying pressure to drive the gargled fluid and the growth medium contained in the liquid container (a) through a filter of the testing device and (b) then through one or more valves of the testing device, wherein the filter is disposed in or downstream of the liquid container, and wherein the one or more valves are disposed downstream of the filter.

Inventive Concept 231. The method according to Inventive Concept 229, wherein filtering the gargled fluid and the growth medium after incubating includes:

placing the gargled fluid and the growth medium in a liquid container of a testing device;

applying pressure to drive the gargled fluid and the growth medium contained in the liquid container through a filter of the testing device, wherein the filter is disposed in or downstream of the liquid container; and thereafter, testing, within a filter chamber of the testing device, for the presence of particulate trapped by the filter while the filter is disposed at least partially in the filter chamber, wherein the filter chamber is (a) disposed downstream of the liquid container, (b) shaped so as to define an inlet, and (c) in fluid communication with the filter.

There is further provided, in accordance with an Inventive Concept 232 of the present invention, a method for testing for the presence of particulate in gargled fluid, the method including:

incubating the gargled fluid for between 12 and 75 hours in a container that contains a liquid growth medium, a dehydrated growth medium, or a gel growth medium; and thereafter, performing a test for the particulate using a rapid test technique on the gargled fluid and growth medium.

Inventive Concept 233. The method according to Inventive Concept 232, wherein performing the test using the rapid test technique includes performing a lateral flow test.

Inventive Concept 234. The method according to Inventive Concept 232, wherein performing the test using the rapid test technique includes performing a rapid test technique selected from the group consisting of: an ELISA-based rapid test, an antibody-coated-beads-based rapid test, a nucleic-acid-based rapid test, and a fluorescent immunoassaying (FIA) rapid test.

There is further provided, in accordance with an Inventive Concept 235 of the present invention, a method for testing for the presence of particulate in gargled fluid, the method including:

incubating the gargled fluid for between 12 and 75 hours in a container that contains a liquid growth medium, a dehydrated growth medium, or a gel growth medium; and thereafter, performing a lateral flow test for the particulate on the gargled fluid and growth medium.

Inventive Concept 236. The method according to Inventive Concept 235, wherein the particulate is strep, and wherein performing the lateral flow test includes performing the lateral flow test for the strep.

Inventive Concept 237. The method according to any one of Inventive Concepts 232 and 235, wherein performing the test includes performing the test on the gargled fluid and the growth medium while the gargled fluid and the growth medium are in the container.

Inventive Concept 238. The method according to any one of Inventive Concepts 232 and 235, wherein performing the test includes transferring at least a portion of the gargled fluid and the growth medium to another container and performing the test while the at least a portion of the gargled fluid and the growth medium are in the other container.

Inventive Concept 239. The method according to any one of Inventive Concepts 220, 232, and 235, wherein the container does not contain agar.

Inventive Concept 240. The method according to any one of Inventive Concepts 220, 232, and 235, further including mixing the gargled fluid with the growth medium before incubating.

There is further provided, in accordance with an Inventive Concept 241 of the present invention, a method including:

incubating saliva not swabbed from a patient's throat for between 12 and 75 hours in a container that contains a liquid growth medium, a dehydrated growth medium, or a gel growth medium; and thereafter, performing a strep test using a rapid strep test (RST) technique on the saliva and growth medium.

Inventive Concept 242. The method according to Inventive Concept 241, wherein the saliva not swabbed from the throat of the patient is saliva spit by the patient.

Inventive Concept 243. The method according to Inventive Concept 241, wherein the container does not contain agar.

Inventive Concept 244. The method according to Inventive Concept 241, further including mixing the saliva with the growth medium before incubating.

Inventive Concept 245. The method according to Inventive Concept 241, wherein performing the strep test using the RST technique includes performing a lateral flow test.

Inventive Concept 246. The method according to Inventive Concept 241, wherein performing the strep test using the RST technique includes performing an RST technique selected from the group consisting of: an ELISA-based RST, an antibody-coated-beads-based RST, a nucleic-acid-based RST, and a fluorescent immunoassaying (FIA) RST.

Inventive Concept 247. The method according to Inventive Concept 241, wherein incubating includes:

receiving, on an absorbent element, saliva from the patient's mouth; and thereafter, placing the absorbent element into the container that contains the liquid growth medium, dehydrated growth medium, or gel growth medium.

Inventive Concept 248. The method according to Inventive Concept 247, wherein the absorbent element is a swab.

Inventive Concept 249. The method according to Inventive Concept 248, wherein the swab is a flocked swab.

Inventive Concept 250. The method according to Inventive Concept 247, wherein performing the strep test using the RST technique includes performing the RST technique on the saliva and the growth medium while the saliva and the growth medium are in the container.

Inventive Concept 251. The method according to Inventive Concept 247, wherein performing the strep test using the RST technique includes transferring at least a portion of the saliva and the growth medium to another container and performing the RST technique while the at least a portion of the saliva and the growth medium are in the other container.

Inventive Concept 252. The method according to Inventive Concept 251, wherein transferring the at least a portion of the saliva and the growth medium to the other container includes:

removing the swab from the container that contains the liquid growth medium, dehydrated growth medium, or gel growth medium; and thereafter, placing the swab into the other container.

Inventive Concept 253. The method according to Inventive Concept 251, wherein transferring the at least a portion of the saliva and the growth medium includes transferring at least 0.05 ml of the saliva and the growth medium.

Inventive Concept 254. The method according to Inventive Concept 247, wherein performing the strep test using the RST technique further includes filtering the at least a portion of the saliva and the growth medium after incubating, and performing the strep test using the RST technique on the filter.

Inventive Concept 255. The method according to Inventive Concept 254, wherein filtering the saliva and the growth medium after incubating includes:

placing the saliva and the growth medium in a liquid container of a testing device; and applying pressure to drive the saliva and the growth medium contained in the liquid container (a) through a filter of the testing device and (b) then through one or more valves of the testing device, wherein the filter is disposed in or downstream of the liquid container, and wherein the one or more valves are disposed downstream of the filter.

Inventive Concept 256. The method according to Inventive Concept 254, wherein filtering the saliva and the growth medium after incubating includes:

placing the saliva and the growth medium in a liquid container of a testing device;

applying pressure to drive the saliva and the growth medium contained in the liquid container through a filter of the testing device, wherein the filter is disposed in or downstream of the liquid container; and thereafter, testing, within a filter chamber of the testing device, for the presence of particulate trapped by the filter while the filter is disposed at least partially in the filter chamber, wherein the filter chamber is (a) disposed downstream of the liquid container, (b) shaped so as to define an inlet, and (c) in fluid communication with the filter.

There is further provided, in accordance with an Inventive Concept 257 of the present invention, a system including:
(a) a liquid including at least one substance selected from the group of substances consisting of gargled fluid, saliva not swabbed from a throat of a patient, and an incubated culture medium containing a biological sample; and
(b) a testing device, which includes:
a liquid container containing the liquid;
one or more valves;
a filter, disposed in or downstream of the liquid container and upstream of the one or more valves; and
a liquid-pressure source, which is arranged to apply pressure to drive the liquid contained in the liquid container through the filter and then through the one or more valves.

Inventive Concept 258. The system according to Inventive Concept 257, wherein the liquid includes the gargled fluid.

Inventive Concept 259. The system according to Inventive Concept 257, wherein the liquid includes the saliva not swabbed from the throat of the patient.

Inventive Concept 260. The system according to Inventive Concept 257, wherein the liquid includes the incubated culture medium containing the biological sample.

Inventive Concept 261. The system according to Inventive Concept 257, wherein the liquid container has an internal volume of between 0.5 and 500 ml.

Inventive Concept 262. The system according to Inventive Concept 257, wherein the liquid-pressure source includes a plunger, which includes a plunger head that is shaped so as to be insertable into the liquid container.

Inventive Concept 263. The system according to Inventive Concept 257, wherein the liquid-pressure source includes a vacuum pump disposed downstream of the one or more valves.

Inventive Concept 264. The system according to Inventive Concept 257, wherein the liquid-pressure source includes a positive-pressure pump disposed upstream of the filter.

Inventive Concept 265. The system according to Inventive Concept 257, wherein the one or more valves include one or more pressure-activated valves.

Inventive Concept 266. The system according to Inventive Concept 257, wherein the one or more valves include one or more non-pressure-activated valves.

Inventive Concept 267. The system according to Inventive Concept 257, wherein the testing device further includes a waste liquid receptacle, which is coupled to the liquid container downstream of the one or more valves, and wherein the liquid-pressure source is arranged to apply pressure to drive the liquid contained in the liquid container through the filter, then through the one or more valves, and then into the waste liquid receptacle.

Inventive Concept 268. The system according to Inventive Concept 257, wherein the testing device further includes a filter chamber that is (a) disposed downstream of the liquid container, (b) shaped so as to define an inlet, and (c) in fluid communication with the filter.

There is further provided, in accordance with an Inventive Concept 268 of the present invention, apparatus including a testing device for testing for the presence of particulate in a liquid, the testing device including:
(a) an upstream component, which includes:
(i) a plunger housing, which is shaped so as to define upstream and downstream openings; and
(ii) a plunger, which includes a downstream plunger head that is shaped so as to be insertable into the plunger housing so as to form a movable seal with a wall of the plunger housing, wherein an area of a downstream surface of the downstream plunger head equals between 80% and 100% of an area of the downstream opening; and
(b) a downstream component, which includes:
(i) a filter, which has a filter surface area of an upstream side of the filter equal to at least 80% of the area of the downstream surface of the downstream plunger head; and
(ii) a waste liquid receptacle, disposed downstream of the filter,
wherein the testing device is shaped so as to define a liquid container for containing the liquid, and
wherein the upstream component and the downstream component are configured to be removably coupled together so as to form a liquid-impermeable seal.

Inventive Concept 270. The apparatus according to Inventive Concept 269, wherein the upstream component and the downstream component are configured to be removably coupled together so as to form the liquid-impermeable seal, such that the upstream component and the downstream component partially overlap each other at an axial overlap region that at least partially defines the liquid container.

Inventive Concept 271. The apparatus according to Inventive Concept 269, wherein the testing device is configured such that at least 80% of the surface area of an upstream side of the filter is exposed to outside the testing device when the upstream component and the downstream component are decoupled from each other.

Inventive Concept 272. The apparatus according to Inventive Concept 269, wherein the upstream component and the downstream component are configured to be removably coupled together by click-fitting together.

Inventive Concept 273. The apparatus according to Inventive Concept 269, wherein the upstream component and the downstream component are configured to be removably coupled together by friction-fitting together.

Inventive Concept 274. The apparatus according to Inventive Concept 269, wherein the upstream component and the downstream component are configured to be removably coupled together by twist-and-lock fitting together.

Inventive Concept 275. The apparatus according to any one of Inventive Concepts 269-274, wherein an area of the upstream opening is greater than the area of the downstream opening.

Inventive Concept 276. The apparatus according to Inventive Concept 275, wherein the plunger housing includes an upstream end portion that includes the upstream opening, and wherein the upstream end portion is conical.

Inventive Concept 277. The apparatus according to Inventive Concept 276, wherein a diameter of the upstream opening is at least 10% greater than a diameter of the downstream opening.

There is further provided, in accordance with an Inventive Concept 278 of the present invention, a method including:
decoupling an upstream component of a testing device from a downstream component of the testing device so as to expose a filter of the testing device; and
testing for particulate trapped in the filter,
wherein the upstream component includes:
(i) a plunger housing, which is shaped so as to define upstream and downstream openings; and
(ii) a plunger, which includes a downstream plunger head that is shaped so as to be insertable into the plunger housing so as to form a movable seal with a wall of the plunger housing, wherein an area of a downstream surface of the downstream plunger head equals between 80% and 100% of an area of the downstream opening, wherein the downstream component includes:
(i) the filter, wherein the filter has a filter surface area of an upstream side of the filter equal to at least 80% of the area of the downstream surface of the downstream plunger head; and
(ii) a waste liquid receptacle, disposed downstream of the filter, wherein the testing device is shaped so as to define a liquid container for containing a liquid that includes at least one substance selected from the group of substances consisting of gargled fluid, saliva not swabbed from a throat of a patient, and an incubated culture medium containing a biological sample, and wherein the upstream component and the downstream component are configured to be removably coupled together so as to form a liquid-impermeable seal.

Inventive Concept 279. The method according to Inventive Concept 278, wherein the upstream component and the downstream component are configured to be removably coupled together so as to form the liquid-impermeable seal, such that the upstream component and the downstream component partially overlap each other at an axial overlap region that at least partially defines the liquid container.

Inventive Concept 280. The method according to Inventive Concept 278, wherein the testing device is configured such that at least 80% of the surface area of an upstream side of the filter is exposed to outside the testing device when the upstream component and the downstream component are decoupled from each other.

Inventive Concept 281. The method according to Inventive Concept 278, wherein an area of the upstream opening is greater than the area of the downstream opening.

Inventive Concept 282. The method according to Inventive Concept 281, wherein the plunger housing includes an upstream end portion that includes the upstream opening, and wherein the upstream end portion is conical.

Inventive Concept 283. The method according to Inventive Concept 282, wherein a diameter of the upstream opening is at least 10% greater than a diameter of the downstream opening.

Inventive Concept 284. The method according to Inventive Concept 278, wherein the upstream component and the downstream component are configured to be removably coupled together by click-fitting together.

Inventive Concept 285. The method according to Inventive Concept 278, wherein the upstream component and the downstream component are configured to be removably coupled together by friction-fitting together.

Inventive Concept 286. The method according to Inventive Concept 278, wherein the upstream component and the downstream component are configured to be removably coupled together by twist-and-lock fitting together.

There is further provided, in accordance with an Inventive Concept 286 of the present invention, apparatus including a testing device for testing for the presence of particulate in a liquid, the testing device including:
a liquid container for containing the liquid;
a filter, disposed in or downstream of the liquid container; and
a plunger head, which (a) is shaped so as to be insertable into the liquid container, (b) is configured to apply pressure to drive the liquid from the liquid container through the filter, and (c) has a downstream surface that is at least partially coated with a solid or semi-solid growth medium.

Inventive Concept 288. The apparatus according to Inventive Concept 287, wherein an area of the downstream surface of the plunger head is between 0.3 and 100 cm2.

Inventive Concept 289. The apparatus according to Inventive Concept 287, wherein the plunger head is shaped so as to be insertable into the liquid container so as to form a movable seal with a wall of the liquid container.

Inventive Concept 290. The apparatus according to Inventive Concept 287, wherein the testing device further includes a plunger shaft, and the plunger head is disposed at a downstream end portion of the plunger shaft.

Inventive Concept 291. The apparatus according to Inventive Concept 287, wherein the testing device further includes a waste liquid receptacle, coupled to the liquid container downstream of the filter.

Inventive Concept 292. The apparatus according to any one of Inventive Concepts 287-291, wherein the growth medium includes agar.

Inventive Concept 293. The apparatus according to any one of Inventive Concepts 287-291, wherein the growth medium is solid.

Inventive Concept 294. The apparatus according to Inventive Concept 293, wherein the solid growth medium is dehydrated.

Inventive Concept 295. The apparatus according to Inventive Concept 293, wherein the solid growth medium includes powdered solid growth medium.

Inventive Concept 296. The apparatus according to any one of Inventive Concepts 287-291, further including a cap that is configured to be coupled to and fully cover the growth medium on the downstream surface of the plunger head.

Inventive Concept 297. The apparatus according to Inventive Concept 296, wherein the cap is transparent.

There is further provided, in accordance with an Inventive Concept 297 of the present invention, a method including:
pushing a plunger head to apply pressure to drive liquid from a liquid container of a testing device through a filter of the testing device, wherein the plunger head has a downstream surface that is at least partially coated with a solid or semi-solid growth medium;
touching the downstream surface of the plunger head to the filter; and
assessing the downstream surface of the plunger head for biological growth.

Inventive Concept 299. The method according to Inventive Concept 298, wherein the liquid includes at least one substance selected from the group of substances consisting of gargled fluid, saliva not swabbed from a throat of a patient, and an incubated culture medium containing a biological sample.

Inventive Concept 300. The method according to Inventive Concept 298, wherein assessing includes assessing the downstream surface of the plunger head for biological growth of a biological particulate selected from the group consisting of: a microorganism, a fungus, a bacterium, a spore, a virus, a mite, a biological cell, a biological antigen, a protein, a protein antigen, and a carbohydrate antigen.

Inventive Concept 301. The method according to Inventive Concept 298, wherein the growth medium includes agar.

Inventive Concept 302. The method according to Inventive Concept 298, wherein the method further includes heating the plunger head before assessing the downstream surface of the plunger head for biological growth.

Inventive Concept 303. The method according to Inventive Concept 298, wherein the growth medium is solid.

Inventive Concept 304. The method according to Inventive Concept 303, wherein the solid growth medium is dehydrated.

Inventive Concept 305. The method according to Inventive Concept 303, wherein the solid growth medium includes powdered solid growth medium.

Inventive Concept 306. The method according to Inventive Concept 298, further including coupling a cap the plunger head such that the cap fully covers the growth medium on the downstream surface of the plunger head.

Inventive Concept 307. The method according to Inventive Concept 306, wherein the cap is transparent.

There is further provided, in accordance with an Inventive Concept 307 of the present invention, a method including:

pushing a plunger head to apply pressure to drive liquid from a liquid container of a testing device through a filter of the testing device;

touching a downstream surface of the plunger head to the filter;

thereafter, touching the downstream surface of the plunger head to culture medium contained in a culture-medium container;

heating the culture-medium container; and assessing the culture-medium container for biological growth.

Inventive Concept 309. The method according to Inventive Concept 308, wherein the culture medium includes agar.

Inventive Concept 310. The method according to Inventive Concept 308, wherein the liquid includes at least one substance selected from the group of substances consisting of gargled fluid, saliva not swabbed from a throat of a patient, and an incubated culture medium containing a biological sample.

Inventive Concept 311. The method according to Inventive Concept 308, wherein assessing includes assessing the culture-medium container for biological growth of a biological particulate selected from the group consisting of: a microorganism, a fungus, a bacterium, a spore, a virus, a mite, a biological cell, a biological antigen, a protein, a protein antigen, and a carbohydrate antigen.

Inventive Concept 312. The method according to Inventive Concept 308, wherein the downstream surface of the plunger head is rough.

Inventive Concept 313. The method according to Inventive Concept 312, wherein touching the downstream surface of the plunger head to the filter includes grinding the filter with the rough downstream surface.

Inventive Concept 314. The method according to Inventive Concept 308, further including testing, within the testing device, for the presence of a biological particulate trapped by the filter.

There is further provided, in accordance with an Inventive Concept 314 of the present invention, a testing kit for testing for the presence of particulate in a liquid, the testing kit including:

a liquid container for containing the liquid, the liquid container shaped so as to define upstream and downstream openings;

a filter, disposed in or downstream of the liquid container; and a plunger head that (a) is shaped so as to be insertable into the liquid container so as to form a movable seal with a wall of the liquid container, and (b) is arranged such that when pushed, the plunger head applies pressure to drive the liquid contained in the liquid container through the filter and then through the downstream opening, wherein the testing kit does not include a plunger shaft.

Inventive Concept 316. The testing kit according to Inventive Concept 315, wherein the filter is configured to trap at least 40% of group A streptococcus bacteria and allow passage of the liquid.

Inventive Concept 317. The testing kit according to Inventive Concept 315, wherein the filter is configured to trap at least 40% of a particulate to be tested and allow passage of the liquid.

Inventive Concept 318. The testing kit according to Inventive Concept 315, further including sterile packaging, in which at least the liquid container, plunger head, and the filter are removably disposed.

Inventive Concept 319. The testing kit according to Inventive Concept 315, wherein the liquid container includes a liquid-tight seal disposed downstream of the filter, and wherein the testing kit is arranged such that when the plunger head is pushed, the plunger head applies the pressure to break or open the seal and drive the liquid through the filter and then through the downstream opening.

There is further provided, in accordance with an Inventive Concept 319 of the present invention, a method including:

receiving a testing kit including (a) a liquid container, the liquid container shaped so as to define upstream and downstream openings, (b) a filter, disposed in or downstream of the liquid container, (c) and a plunger head;

coupling the plunger head to a plunger shaft;

receiving a liquid in the liquid container;

inserting the plunger head into the liquid container so as to form a movable seal with a wall of the liquid container; and using the plunger shaft, pushing the plunger head to apply pressure to drive the liquid contained in the liquid container through the filter and then through the downstream opening, wherein the testing kit does not include the plunger shaft.

Inventive Concept 321. The method according to Inventive Concept 320, further including, after pushing the plunger head, testing for the presence of particulate trapped by the filter.

There is further provided, in accordance with an Inventive Concept 322 of the present invention, a method for testing for the presence of group A streptococcus bacteria in a sample of oral fluid obtained from a patient, the method including:

generating a biological product by incubating the sample of oral fluid for between 12 and 50 hours in a container that contains a liquid growth medium, the liquid growth medium having (a) a total nitrogen source concentration between 75 and 300 g/L and (b) a total solids concentration between 92.5 and 370 g/L; and thereafter, performing a strep test using a rapid strep test (RST) technique on the biological product.

Inventive Concept 323. The method according to Inventive Concept 322, wherein incubating includes incubating for between 16 and 50 hours.

Inventive Concept 324. The method according to Inventive Concept 322, wherein the container does not contain agar.

Inventive Concept 325. The method according to Inventive Concept 322, wherein performing the strep test using the RST technique includes performing a lateral flow test.

Inventive Concept 326. The method according to Inventive Concept 322, wherein performing the strep test using the RST technique includes performing an RST technique selected from the group consisting of: an ELISA-based RST, an antibody-coated-beads-based RST, a nucleic-acid-based RST, and a fluorescent immunoassaying (FIA) RST.

Inventive Concept 327. The method according to Inventive Concept 322, wherein the liquid growth medium has a pH of between 6 and 8.3.

Inventive Concept 328. The method according to Inventive Concept 322, wherein incubating includes incubating for between 12 and 36 hours.

Inventive Concept 329. The method according to any one of Inventive Concepts 322-328, wherein the sample of oral fluid is selected from the group consisting of: gargled fluid gargled by the patient, and saliva not swabbed from a throat of the patient.

Inventive Concept 330. The method according to Inventive Concept 329, wherein the sample of oral fluid is the gargled fluid.

Inventive Concept 331. The method according to Inventive Concept 329, wherein the sample of oral fluid is the saliva not swabbed from the throat of the patient.

Inventive Concept 332. The method according to Inventive Concept 331, wherein the saliva not swabbed from the throat of the patient is saliva spit by the patient.

Inventive Concept 333. The method according to any one of Inventive Concepts 322-328, wherein the sample of oral fluid is saliva swabbed from a tonsil of the patient.

Inventive Concept 334. The method according to any one of Inventive Concepts 322-328, wherein the liquid growth medium has a total sugar concentration of between 7 g/L and 20 g/L.

Inventive Concept 335. The method according to Inventive Concept 334, wherein the total sugar concentration is between 7 g/L and 14 g/L.

Inventive Concept 336. The method according to Inventive Concept 334, wherein the liquid growth medium has a glucose concentration of between 8 g/L and 12 g/L.

Inventive Concept 337. The method according to Inventive Concept 336, wherein the glucose concentration is between 8.5 g/L and 9.5 g/L.

Inventive Concept 338. The method according to any one of Inventive Concepts 322-328, wherein the total nitrogen source concentration is between 105 and 180 g/L.

Inventive Concept 339. The method according to Inventive Concept 338, wherein the total nitrogen source concentration is between 120 and 160 g/L.

Inventive Concept 340. The method according to any one of Inventive Concepts 322-328, wherein the total solids concentration is between 130 and 222 g/L.

Inventive Concept 341. The method according to Inventive Concept 340, wherein the total solids concentration is between 148 and 193 g/L.

Inventive Concept 342. The method according to any one of Inventive Concepts 322-328, wherein performing the strep test includes applying one or more extraction reagents to the biological product.

Inventive Concept 343. The method according to any one of Inventive Concepts 322-328, wherein generating the biological product further includes filtering the sample of oral fluid and the liquid growth medium after incubating.

Inventive Concept 344. The method according to Inventive Concept 343, wherein performing the strep test using the RST technique includes performing the strep test using the RST technique on the filter.

Inventive Concept 345. The method according to Inventive Concept 343, wherein performing the strep test includes applying one or more extraction reagents to the filtered biological product.

There is further provided, in accordance with an Inventive Concept 345 of the present invention, a liquid growth medium having (a) a total nitrogen source concentration between 75 and 300 g/L and (b) a total solids concentration between 92.5 and 370 g/L.

Inventive Concept 347. The liquid growth medium according to Inventive Concept 346, wherein the liquid growth medium has a pH of between 6 and 8.3.

Inventive Concept 348. The liquid growth medium according to Inventive Concept 346, wherein the liquid growth medium has a total sugar concentration of between 7 g/L and 20 g/L.

Inventive Concept 349. The liquid growth medium according to Inventive Concept 348, wherein the total sugar concentration is between 7 g/L and 14 g/L.

Inventive Concept 350. The liquid growth medium according to Inventive Concept 348, wherein the liquid growth medium has a glucose concentration of between 8 g/L and 12 g/L.

Inventive Concept 351. The liquid growth medium according to Inventive Concept 350, wherein the glucose concentration is between 8.5 g/L and 9.5 g/L 352. The liquid growth medium according to Inventive Concept 346, wherein the total nitrogen source concentration is between 105 and 180 g/L.

Inventive Concept 353. The liquid growth medium according to Inventive Concept 352, wherein the total nitrogen source concentration is between 120 and 160 g/L.

Inventive Concept 354. The liquid growth medium according to Inventive Concept 346, wherein the total solids concentration is between 130 and 222 g/L.

Inventive Concept 355. The liquid growth medium according to Inventive Concept 354, wherein the total solids concentration is between 148 and 193 g/L.

Inventive Concept 356. An assembly including the liquid growth medium according to any one of Inventive Concepts 346-355, the assembly further including a sealed sterile container that contains the liquid growth medium.

Inventive Concept 357. An assembly including the liquid growth medium according to any one of Inventive Concepts 346-355, the assembly further including a container that contains the liquid growth medium and a sample of oral fluid obtained from a patient.

Inventive Concept 358. A kit including the liquid growth medium according to any one of Inventive Concepts 346-355, the kit further including a lateral flow strep test strip.

Inventive Concept 359. A kit including the liquid growth medium according to any one of Inventive Concepts 346-355, the kit further including one or more extraction reagents.

Inventive Concept 360. A kit including the liquid growth medium according to any one of Inventive Concepts 346-355, the kit further including a filter.

There is further provided, in accordance with an Inventive Concept 361 of the present invention, a method of preparing a liquid growth medium, the method including:

adding a quantity of powdered growth medium to a volume of distilled water; and stirring until the powdered growth medium is dissolved in the distilled water to produce the liquid growth medium, wherein the quantity of powdered growth medium and the volume of the distilled water are selected such that the liquid growth medium has (a) a total nitrogen source concentration between 75 and 300 g/L and (b) a total solids concentration between 92.5 and 370 g/L.

Inventive Concept 362. The method according to Inventive Concept 361, wherein the liquid growth medium has a pH of between 6 and 8.3.

Inventive Concept 363. The method according to Inventive Concept 361, wherein the quantity of powdered growth medium and the volume of the distilled water are selected such that the liquid growth medium has a total sugar concentration of between 7 g/L and 20 g/L.

Inventive Concept 364. The method according to Inventive Concept 363, wherein the quantity of powdered growth medium and the volume of the distilled water are selected such that the total sugar concentration is between 7 g/L and 14 g.

Inventive Concept 365. The method according to Inventive Concept 363, wherein the quantity of powdered growth medium and the volume of the distilled water are selected such that the liquid growth medium has a glucose concentration of between 8 g/L and 12 g/L.

Inventive Concept 366. The method according to Inventive Concept 365, wherein the quantity of powdered growth medium and the volume of the distilled water are selected such that the glucose concentration is between 8.5 g/L and 9.5 g/L.

Inventive Concept 367. The method according to Inventive Concept 361, wherein the quantity of powdered growth medium and the volume of the distilled water are selected such that the total nitrogen source concentration is between 105 and 180 g/L.

Inventive Concept 368. The method according to Inventive Concept 367, wherein the quantity of powdered growth medium and the volume of the distilled water are selected such that the total nitrogen source concentration is between 120 and 160 g/L.

Inventive Concept 369. The method according to Inventive Concept 361, wherein the quantity of powdered growth medium and the volume of the distilled water are selected such that the total solids concentration is between 130 and 222 g/L.

Inventive Concept 370. The method according to Inventive Concept 369, wherein the quantity of powdered growth medium and the volume of the distilled water are selected such that the total solids concentration is between 148 and 193 g/L.

The present invention will be more fully understood from the following detailed description of embodiments thereof, taken together with the drawings, in which:

BRIEF DESCRIPTION OF THE DRAWINGS

FIGS. 1A-H are schematic illustrations of a testing device for testing for presence of particulate in a liquid, in accordance with an application of the present invention;

FIGS. 3A-B are schematic illustrations of yet another testing device for testing for presence of particulate in a liquid, in accordance with an application of the present invention;

FIGS. 4A-C are schematic illustrations of another testing device for testing for presence of particulate in a liquid, in accordance with an application of the present invention;

FIGS. 5A-B are schematic illustrations of additional testing devices for testing for presence of particulate in a liquid, in accordance with respective applications of the present invention;

FIGS. 6A-C are schematic illustrations of yet another testing device for testing for presence of particulate in a liquid, in accordance with an application of the present invention;

FIGS. 7A-C and 8A-E are schematic illustrations of still another testing device for testing for presence of particulate in a liquid, in accordance with an application of the present invention;

FIGS. 10A-C are schematic illustrations of yet another testing device for testing for presence of particulate in a liquid, in accordance with an application of the present invention;

FIGS. 10D-K are schematic illustrations of a testing device for testing for presence of particulate in a liquid, in accordance with an application of the present invention;

FIGS. 10L-M are schematic illustrations of a testing device for testing for presence of particulate in a liquid, in accordance with an application of the present invention;

FIGS. 10N-O are schematic illustrations of a testing device for testing for presence of particulate in a liquid, in accordance with an application of the present invention;

FIGS. 10P-Q are schematic illustrations of a testing device for testing for presence of particulate in a liquid, in accordance with an application of the present invention;

FIGS. 16A-B are schematic illustrations of a testing system, in accordance with an application of the present invention;

FIGS. 19A-D, 20, 21, and 22 are tables that present results of an experiment conducted in accordance with an application of the present invention;

FIGS. 23, 24, 25, 26, and 27 are tables that present results of another experiment conducted in accordance with an application of the present invention.

DETAILED DESCRIPTION OF APPLICATIONS

Figure 1A:
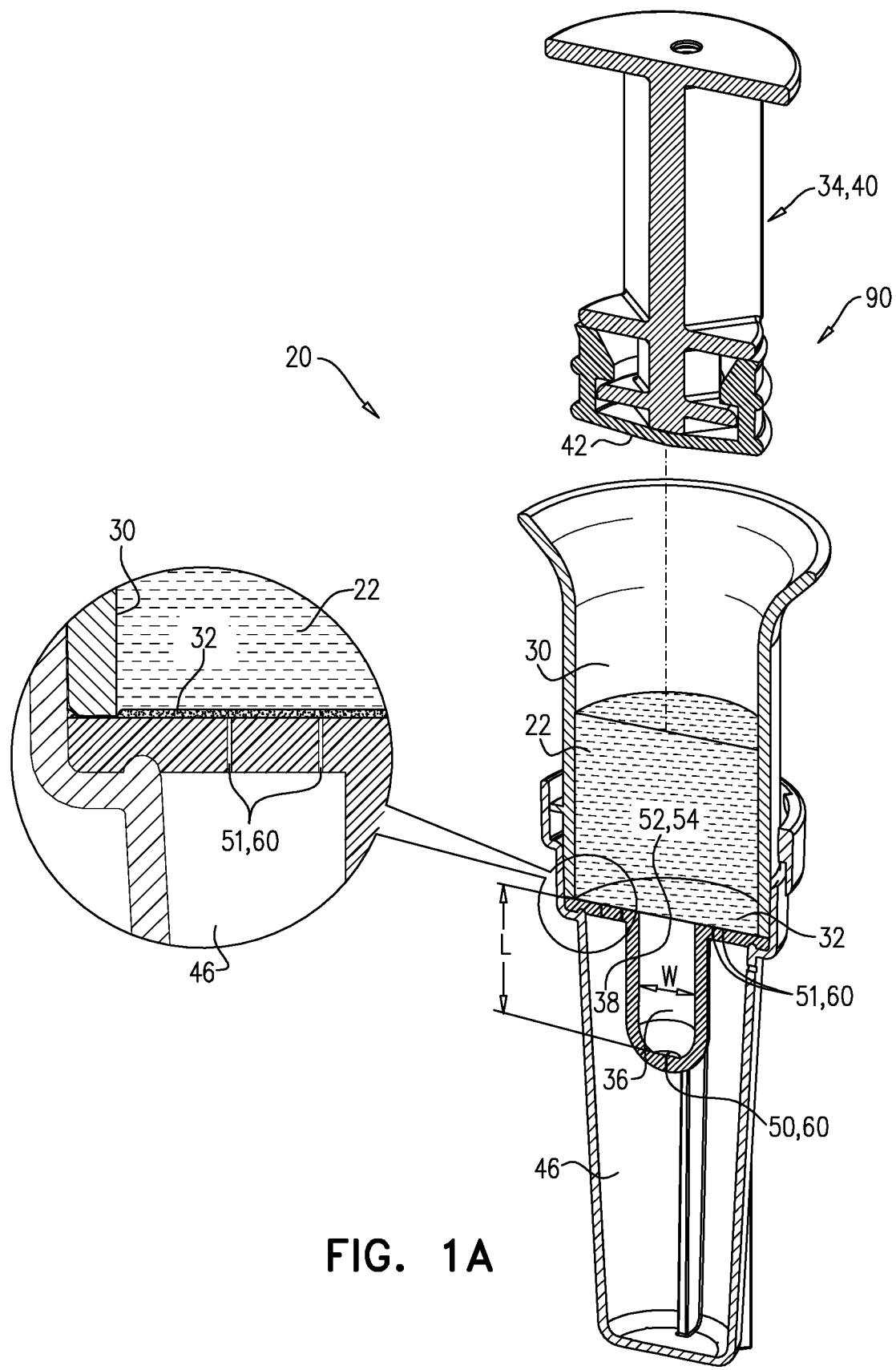

FIGS. 1A-H are schematic illustrations of a testing device 20 for testing for presence of particulate in a liquid 22, in accordance with an application of the present invention. For some applications, the particulate comprises biological particulate, for example, a microorganism, a fungus, a bacterium (e.g., a group A streptococcus bacterium), a spore, a virus, a mite, a biological cell, a biological antigen, a protein, a protein antigen, and a carbohydrate antigen. Alternatively, testing device 20 is used for testing a non-particulate substance of interest, whether a biological or chemical substance, soluble, immiscible or an emulsion, an atom, a molecule, a polymer or a mixture of substances.

Testing device 20 typically comprises:
- a liquid container 30 for containing liquid 22; typically, liquid container 30 has an internal volume of at least 0.5 ml (e.g., at least 1 ml, such as at least 5 ml), no more than 500 ml (e.g., no more than 70 ml), and/or between 0.5 ml (e.g., 1 ml or 5 ml) and 500 ml (e.g., 70 ml);
- a filter 32, disposed in or downstream of liquid container 30; and
- a liquid-pressure source 34, which is arranged to apply pressure to drive liquid 22 contained in liquid container 30 through filter 32.

As used in the present application, including in the claims, "upstream" and "downstream" refer to the direction of fluid flow through testing device 20, and not the orientation of the device with respect to the Earth. For example, filter chamber 736, described hereinbelow with reference to FIGS. 7A-8E, is downstream of liquid container 730, even though the filter chamber is physically above the liquid container when the testing device is oriented as shown in the figures.

Typically, liquid container 30 does not comprise a Luer lock or any other type of needle-coupling mechanism.

Filter 32 comprises synthetic or natural materials formed, for example, as a matrix, membrane, fabric, beads, or other configuration. For example, the inventors have tested the following filters manufactured by Sterlitech (Washington, USA):
- Grade C glass microfiber filter media (Cat. No. C2500 & C3700)
- GC-50 glass fiber membrane filters (Cat. No. GC5037100)
- polyethersulfone (PES) membrane filters (Cat. No. PES0825100, PES0837100, PES1225100, PES1237100, PES06525100, PES4525100, PES4525100)
- polycarbonate membrane filters (Cat. No. PCT0613100, PCT2025100, PCT0625100, PCT1025100, PCT0825100)
- cellulose acetate membrane filters (Cat. No. CA0825100)
- polyester membrane filters (Cat. No. PET0125100, PET0825100)

Typically, filter 32 is configured to trap at least 40% (such as at least 95%, e.g., at least 99%) of the particulate to be tested and allow passage of liquid 22. For example, for applications in which the particulate is group A streptococcus bacteria, the filter may be configured to trap at least 40% (such as at least 95%, e.g., at least 99%) of the group A streptococcus bacteria and allow passage of liquid 22. For some applications, filter 32 has a filter surface area of an upstream side of the filter equal to at least 0.3 cm2, no more than 100 cm2 (e.g., no more than 30 cm2), and/or between 0.3 cm2 and 100 cm2, such as between 0.3 and 30 cm2.

For some applications, liquid-pressure source 34 comprises at least one of the following:
- a plunger 40, which comprises a plunger head 42 that is shaped so as to be insertable into liquid container 30 so as to form a movable seal with a wall of a plunger housing (optionally, all or a portion of liquid container 30 defines the wall of the plunger housing);
- a positive-pressure pump (e.g., a hydraulic pump, a syringe, or a motorized and/or electrical pump) disposed upstream of filter 32 (configuration not shown); optionally, for some application, the positive-pressure pump comprises a chamber with one or more flexible walls, the squeezing of which pumps air and/or liquid 22 itself out of the chamber; or
- a vacuum pump disposed downstream of filter 32 (and, if provided, of the one or more valves 60, described hereinbelow) (configuration not shown).

For some applications, plunger 40 further comprises a plunger shaft, and plunger head 42 is disposed at a downstream end portion of the plunger shaft. Typically, but not necessarily, plunger 40 has one of the following configurations:
- the plunger head comprises a separate piece of material (e.g., comprising a polymer) that is coupled to the plunger shaft and is shaped so as to define the downstream surface of plunger head 42 and optionally a lateral sealing surface, or
- the distal surface of plunger head 42 is defined by the end of the plunger shaft, and, for example, a separate sealing ring (e.g., comprising a polymer) may be provided to provide a lateral sealing surface.

For some applications, testing device 20 further comprises a waste liquid receptacle 46, which is coupled to liquid container 30 downstream of filter 32 (and, if provided, of the one or more valves 60, described hereinbelow). Liquid-pressure source 34 is arranged to apply pressure to drive liquid 22 contained in liquid container 30 through filter 32 and then into waste liquid receptacle 46.

For some applications, testing device 20 further comprises a filter chamber 36 that is (a) disposed downstream of liquid container 30, (b) shaped so as to define an inlet 38, and (c) in fluid communication with filter 32. Filter chamber 36 is shaped such that when filter 32 is pushed into the filter chamber, such as described hereinbelow with reference to FIGS. 1D-E, the filter chamber collects filter 32 into a relatively small volume, thereby increasing the consolidated sensitivity of rapid and backup tests for particulate trapped by filter 32. If, by contrast, filter 32 were flat in liquid container 30, it would be difficult to collect a sample from a high percentage of the surface of the filter. In addition, filter chamber 36 readily hosts at least one extraction reagent 86 and a test strip 88, as described hereinbelow with reference to FIGS. 1G-H.

Optionally, filter chamber 36 is nipple-shaped. For some applications in which testing device 20 comprises waste liquid receptacle 46, filter chamber 36 is laterally surrounded by at least a portion of waste liquid receptacle 46, such as shown in FIGS. 1A-H. Alternatively or additionally, for some applications, filter chamber 36 is disposed within waste liquid receptacle 46, such as shown in FIGS. 1A-H.

For some applications, inlet 38 of filter chamber 36 has an inlet area that equals at least 4%, no more than 40%, and/or between 4% and 40% of a filter surface area of an upstream side of filter 32, such as between 10% and 20%. Alternatively or additionally, for some applications, filter chamber 36 has:
- an internal volume of at least 0.5 ml, no more than 12 ml (e.g., no more than 4 ml), and/or between 0.5 and 12 ml (such as between 0.5 and 4 ml), such as at least 1 ml (e.g., at least 2 ml), no more than 5 ml, and/or between 1 and 5 ml, such as between 2 and 5 ml,
- an internal surface area that equals at least 10%, no more than 150%, and/or between 10% and 150% of a filter surface area of an upstream side of filter 32, such as between 70% and 130%,
- an internal length L equal to between 0.5 and 10 cm, such as between 1.5 and 5 cm,
- an internal width W equal to between 0.3 and 3 cm, such as between 0.5 and 1.5 cm,
- an internal length L of at least 0.5 cm, no more than 10 cm (e.g., no more than 5 cm), and/or between 0.5 and 10 cm, such as between 0.5 cm and 5 cm, e.g., between 1 and 5 cm, and/or
- an internal length L equal to at least 50%, no more than 2000%, and/or between 50% and 2000% of a greatest internal width W of filter chamber 36, such as between 200% and 600%.

For some applications, such as shown in FIGS. 1A-H, filter chamber 36 comprises one or more pressure-activated valves 50, not disposed at inlet 38. For applications in which testing device 20 comprises waste liquid receptacle 46, the one or more pressure-activated valves 50 are typically disposed in fluid communication between filter chamber 36 and waste liquid receptacle 46. For some applications, liquid container 30 is shaped so as to define one or more openings 51 (typically, non-valved openings) through a wall of liquid container 30, the one or more openings 51 are downstream of filter 32 when filter 32 is removably disposed upstream of filter chamber 36 with filter 32 partially covering inlet 38, and filter chamber 36 is not disposed so as to receive liquid 22 that is driven through the one or more openings 51. The one or more openings 51 allow liquid 22 to pass, thereby drawing the liquid through filter 32. (As described hereinabove with reference to FIGS. 1A-B, testing device 20 may comprise an upstream component 70 and a downstream component 72 that are removably coupled together; in such configurations, the one or more openings 51 defined by liquid container 30 may optionally be defined by the portion of downstream component 72 that helps define liquid container 30.)

For some applications, such as shown in FIGS. 1A-D, filter 32 is removably disposed upstream of filter chamber 36 with filter 32 partially covering inlet 38. For some applications, inlet 38 has an inlet centroid 52 that is disposed within a distance of a filter centroid 54, the distance equal to 50% of a greatest dimension of filter 32, when filter 32 is removably disposed upstream of filter chamber 36 with filter 32 partially covering inlet 38. For example, filter 32 may be centered upstream of inlet 38.

For some applications, an elongate member 56 is provided that configured to push at least a portion of filter 32 into filter chamber 36. Optionally, elongate member 56 comprises a swab 58 at a distal end of the elongate member. In applications in which filter chamber 36 comprises one or more pressure-activated valves 50, inserting elongate member 56 into filter chamber may squeeze any liquid 22 remaining in filter chamber 36 through one or more pressure-activated valves 50 and out of filter chamber 36. For other applications in which liquid-pressure source 34 comprises plunger 40, plunger head 42 is configured to push at least a portion of filter 32 into filter chamber 36 (configuration not shown). In applications in which filter chamber 36 comprises one or more pressure-activated valves 50, inserting plunger head 42 into filter chamber may squeeze any liquid 22 remaining in filter chamber 36 through one or more pressure-activated valves 50 and out of filter chamber 36.

Reference is still made to FIGS. 1A-H. In an application of the present invention, testing device 20 further comprises one or more valves 60. For these applications, filter 32 is typically disposed in or downstream of liquid container 30 and upstream of the one or more valves 60. Liquid-pressure source 34 is arranged to apply pressure to drive liquid 22 contained in liquid container 30 through filter 32 and then through the one or more valves 60. For applications in which testing device 20 comprises waste liquid receptacle 46, waste liquid receptacle 46 is typically coupled (removably or permanently) to liquid container 30 downstream of the one or more valves 60, and liquid-pressure source 34 is arranged to apply pressure to drive liquid 22 contained in liquid container 30 through filter 32, then through the one or more valves 60, and then into waste liquid receptacle 46. Typically filter chamber 36 is not disposed so as to receive liquid 22 that is driven through at least one of the one or more valves 60.

For some applications, the one or more valves 60 comprise one or more pressure-activated valves. For example, as mentioned above, filter chamber 36 may comprise one or more pressure-activated valves 50, not disposed at inlet 38. For example, the pressure-activated valves may be formed from slits or flaps in an elastic material (such as silicone), or may comprise any small valves known in the valve art. The one or more pressure-activated valves are configured to open at the higher pressure applied by liquid-pressure source 34, so as to allow liquid 22 to pass through filter 32, and to remain closed at the much lower pressure applied by at least one extraction reagent 86, as described hereinbelow with reference to FIGS. 1G-H. Preventing the leakage of the at least one extraction reagent 86 causes the at least one extraction reagent 86 to bathe filter 32, which is beneficial for optimal testing for particulate trapped by filter 32 using a test strip 88, also as described hereinbelow with reference to FIGS. 1G-H.

Alternatively or additionally, for some applications, the one or more valves 60 comprise one or more non-pressure-activated valves, such as described hereinbelow with reference to FIGS. 10A-C, 10D-K, 10L-M, 10N-O, and/or 10P-Q.

For some applications, sterile packaging is provided, in which at least liquid container 30, filter chamber 36, the one or more valves 60, and/or filter 32 are removably disposed. The sterile packaging comprises one or more sterile packages; for example, each element may be removably disposed in a separate one of the packages, and/or more than one the elements may be disposed in a single one of the packages.

For some applications, at least one container comprising the at least one extraction reagent 86 is provided. For example, the at least one extraction reagent 86 may comprise 2M sodium nitrite and/or 0.2M acetic acid, and/or a releasing agent, which, upon contacting a microorganism, releases an antigen from the microorganism. For applications in which more than one extraction reagent 86 is provided, and/or extraction reagent 86 comprises a plurality of substances, each of the extraction reagents 86 and/or substances may be provided in a separate container, and the extraction reagents 86 and/or substances are combined prior to (e.g., immediately prior to) performing the assay. Alternatively or additionally, for some applications, a test strip 88 is provided. Typically, test strip 88 is a lateral flow test strip, such as a lateral flow immunoassay (e.g., chromatographic immunoassay) test strip, as is known in the art. For example, test strip 88 may contain an antibody specific to strep A carbohydrate antigen, and the mixture migrates up the test strip and reacts with the antibody, thus generating a line on the test strip; the presence of this line indicates a positive test result. Alternatively or additionally, for some applications, a container is provided containing a solution for use in a detecting a pathogen.

Reference is still made to FIGS. 1A-H. In an application of the present invention, testing device 20 comprises an upstream component 70 and a downstream component 72 (labeled in FIGS. 1B and 1C).

Upstream component 70 typically comprises:
  a plunger housing 74, which is shaped so as to define an upstream opening 76 (labeled in FIG. 1B) and a downstream opening 78 (labeled in FIG. 1C); and
  plunger 40, which comprises a downstream plunger head 42 that is shaped so as to be insertable into plunger housing 74 so as to form a movable seal with a wall of plunger housing 74; typically, an area of a downstream surface 80 of downstream plunger head 42 equals between 80% and 100% of an area of downstream opening 78 (unlike in conventional syringes, in which the downstream surface of the plunger head is typically much larger than the narrow downstream opening of the syringe barrel).

Typically, plunger housing 74 does not comprise a Luer lock or any other type of needle-coupling mechanism.

Downstream component 72 typically comprises:
  filter 32, which has a filter surface area if an upstream side of the filter equal to at least 80% of the area of downstream surface 80 of the downstream plunger head 42;
  waste liquid receptacle 46, disposed downstream of filter 32; and
  for applications in which it is provide, filter chamber 36.

Figure 1B:
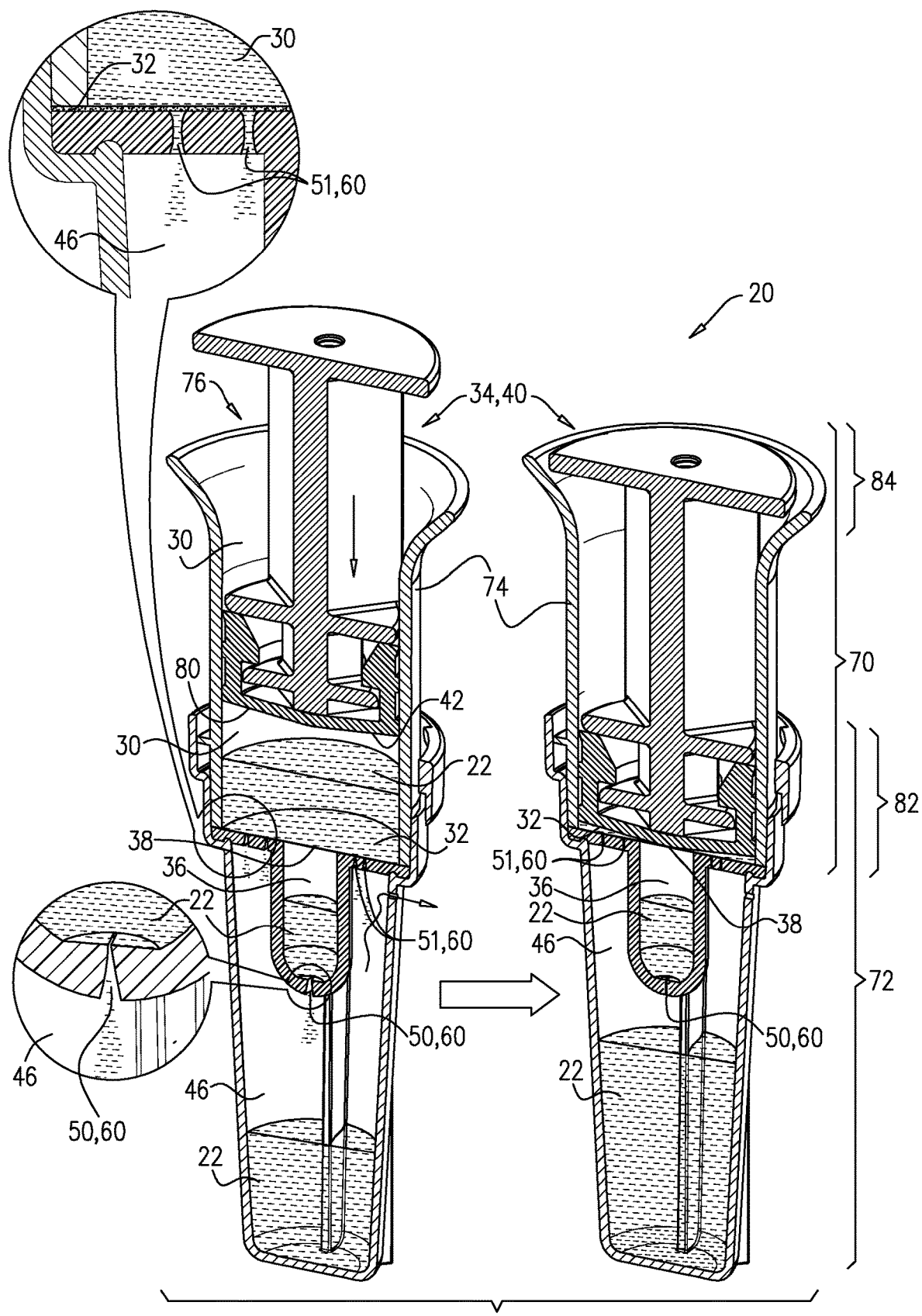
Figure 1C:
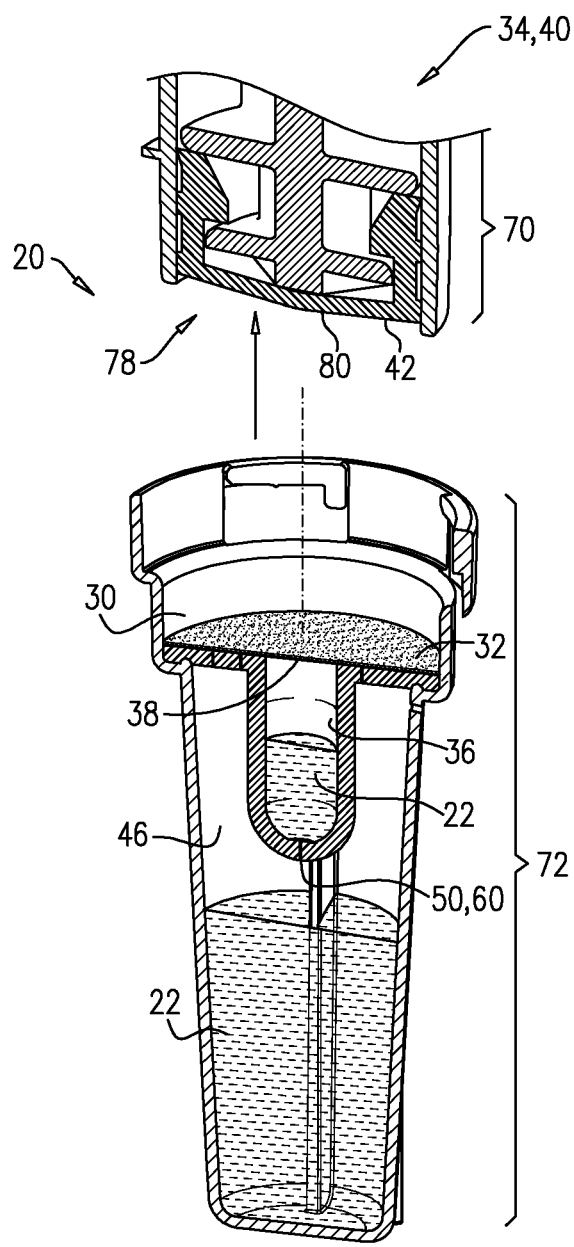

Testing device 20 is shaped so as to define liquid container 30 for containing liquid 22. Upstream component 70 and downstream component 72 are configured to be removably coupled together so as to form a liquid-impermeable seal, as shown in FIGS. 1A and 1B. FIG. 1C shows upstream component 70 and downstream component 72 after they have been decoupled from each other. For example, upstream component 70 and downstream component 72 may be configured to be removably coupled together by click-fitting together, by friction-fitting together, by twist-and-lock fitting together, or by magnetic coupling together.

For some applications, such as shown in FIGS. 1A-B, upstream component 70 and downstream component 72 are configured to be removably coupled together so as to form the liquid-impermeable seal, such that upstream component 70 and downstream component 72 partially overlap each other at an axial overlap region 82 (labeled in FIG. 1B) that at least partially defines liquid container 30. For other applications, upstream component 70 and downstream component 72 do not axially overlap (configuration not shown); in these other applications, liquid container 30 is optionally defined only by downstream component 72 and not by upstream component 70. For some applications, as perhaps best shown in the blow-up in FIG. 1A, an outer edge of filter 32 is squeezed directly or indirectly between upstream component 70 and downstream component 72 to hold the filter in place until upstream component 70 is decoupled from downstream component 72.

In general, in all of the configurations of testing devices described herein that comprise upstream and downstream components that are removably coupled together, the liquid container may be defined in part by the upstream component and in part by the downstream component. For example, a distal downstream wall of the liquid container that supports the filter may be defined by the downstream component, while the lateral wall of the liquid container may be defined by the upstream component or by the upstream and downstream components in combination.

Figure 1D:
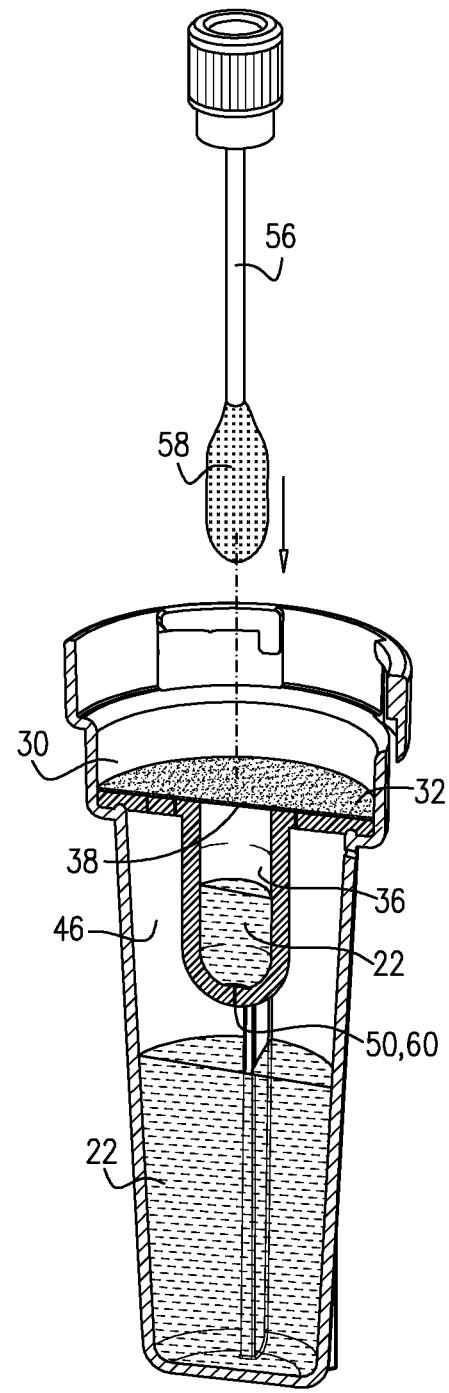

For some applications, such as shown in FIGS. 1C-D, testing device 20 is configured such that at least 80% of the surface area of an upstream side of filter 32 is exposed to outside testing device 20 when upstream component 70 and downstream component 72 are decoupled from each other.

For some applications, an area of upstream opening 76 is greater than the area of downstream opening 78. For example, a diameter of upstream opening 76 may be at least 10% (e.g., 20%, such as 30%) greater than a diameter of downstream opening 78. For some of these applications, plunger housing 74 includes an upstream end portion 84 (labeled in FIG. 1B) that includes upstream opening 76, and upstream end portion 84 is conical and/or funnel-shaped.

Reference is still made to FIGS. 1A-H. In an application of the present invention, a method is provided for testing liquid 22 for the presence of the particulate. For some applications, the particulate comprises biological particulate, for example, a microorganism, a fungus, a bacterium, a spore, a virus, a mite, a biological cell, a biological antigen, a protein, a protein antigen, and a carbohydrate antigen.

For applications in which one or more components of testing device 20 are removably disposed in sterile packing, the one or more components are removed from the sterile packaging.

As shown in FIG. 1A, the method comprises receiving, in liquid container 30, liquid 22 from a patient's mouth. For some applications, liquid 22 comprises gargled fluid, i.e., a gargle fluid that the patient has gargled in his or her mouth and spit out, perhaps along with some saliva. In the present application, including in the claims, "gargled fluid" means "gargle fluid" that has been gargled by a patient. Typically, the gargle fluid includes water, carbonated water, saline (e.g., phosphate buffered saline), *Pelargonium sidoides* extract, tannic acid, balloon flower *Platycodon grandiflorus*, berberine sulfate, S-carboxymethylcysteine, curcumin, coloring, flavoring, a detergent (such as Polysorbate 20 (e.g., Tween® 20)), or any combination thereof. In some applications, the gargle fluid is carbonated. Alternatively or additionally, for some applications, a detergent, such as Polysorbate 20 (e.g., Tween® 20) is added to the gargled fluid after being gargled by the patient. Alternatively, liquid 22 may comprise another type of biological fluid, such as blood (e.g., diluted blood), urine, stool (e.g., diluted stool), gastrointestinal (GI) fluid, or bronchoalveolar lavage fluid.

Alternatively, liquid 22 comprises saliva not swabbed from the throat of a patient (i.e., the saliva was collected without swabbing the patient's throat). (The distinction between "swab" as a verb and as a noun is noted. A "swab" (as a noun) may be used to obtain saliva without "swabbing" (as a verb) the patient's throat. For example, the patient may suck on a swab, or a swab may be dipped in a container into which gargle fluid or saliva has been placed.) By contrast, in commonly-practiced techniques for testing for strep, the tonsils are swabbed. Further alternatively, liquid 22 comprises liquid from a cultured medium containing a biological sample which had been incubated within the liquid container 30 or incubated separately from the device and then added to liquid container 30, for example for performing a backup test (e.g., a backup strep test) using rapid testing techniques, e.g., rapid strep testing techniques. As used in the present application, including in the claims, in the context of backup testing, "rapid" testing techniques (such as "rapid" strep testing techniques) refer to the type of test, rather than implying that the test is performed and provides results soon after the sample is obtained from the patient; indeed, for performing backup testing, the rapid testing techniques are typically performed well after the sample has been obtained from the patients, such as a number of hours thereafter, and typically include incubation of the sample.

Liquid 22 (e.g., saliva) may be spit directly by the patient into liquid container 30 or transferred by a healthcare worker from another container into which the patient spit. Alternatively, in the case of saliva, the saliva may be collected from the patient's mouth by having the patient suck on a swab or other absorbent collecting element, such as flocked swabs or cotton rolls.

For applications in which testing device 20 comprises plunger 40 and plunger housing 74, such as described above, liquid 22 is typically received in liquid container 30 before plunger 40 has been inserted into plunger housing 74 (or liquid container 30).

As shown in FIG. 1B, pressure is applied to drive liquid 22 contained in liquid container 30 of testing device 20 through filter 32, such as using one or more of the techniques for applying pressure described hereinabove. For applications in which testing device 20 comprises the one or more valves 60, the pressure also drives liquid 22 through the one or more valves 60 after the liquid is driven through filter 32. For applications in which liquid container 30 is shaped so as to define the one or more openings 51, as described hereinabove, the pressure drives liquid 22 through the one or more openings 51. Typically, toward the end of the application of the pressure, some air trapped in liquid container 30 is blown through filter 32, helping to expel most of liquid 22 remaining in filter chamber 36 and generally dry the filter chamber. For applications in which testing device 20 comprises waste liquid receptacle 46, applying the pressure drives liquid 22 contained in liquid container 30 through filter 32, then through the one or more valves 60, and then into waste liquid receptacle 46. For some applications in which testing device 20 comprises filter chamber 36, applying the pressure also drives some of liquid 22 into filter chamber 36. For some applications, testing device 20 further comprises a release button that pushes on filter chamber 36 to extract any remaining gargled fluid upon completion of application of the pressure (configuration not shown).

As shown in FIG. 1C, for applications in which testing device 20 comprises upstream component 70 and downstream component 72, upstream component 70 is decoupled from downstream component 72, in order to expose and provide access to filter 32. Instead removing plunger 40 from liquid container 30 might cause some of liquid 22 to spray out of liquid container.

As shown in FIG. 1A-D, for some application in which testing device 20 comprises filter chamber 36, the pressure is applied while filter 32 is removably disposed upstream of filter chamber 36 with filter 32 partially covering inlet 38. For some of these applications, after applying the pressure and before testing for the presence of the particulate trapped by filter 32, at least a portion of filter 32 is pushed into filter chamber 36, such as shown in FIGS. 1D-F. For example, the at least a portion of filter 32 may be pushed into filter chamber 36 using an elongate member 56, such as shown in FIG. 1D-E, using plunger head 42 (configuration not shown), or using gas pressure and/or suction (configuration not shown). For applications in which filter chamber 36 comprises one or more pressure-activated valves 50, such as described hereinabove, the elongate member 56 (e.g., swab 58 thereof) drives liquid 22 in filter chamber 36 out of filter chamber 36 through the one or more pressure-activated valves 50, into waste liquid receptacle 46 if provided, such as shown in FIG. 1E.

As shown in FIGS. 1E-F, for some applications, a sample is taken from filter 32 (either from a surface of the filter or of the filter itself, such as a small part of the filter) using elongate member 56 (e.g., swab 58 thereof), and the sample is tested, outside testing device 20, for the presence of the particulate. This testing may, for example, be an overnight backup test, e.g., an overnight backup strep test. The backup test may be performed by placing the sample (optionally while still on swab 58) into a test tube 85 containing growth medium 87 (e.g., Todd Hewitt broth, tryptic soy broth, Columbia Broth, Nutrient Broth, or Thioglycollate broth), capping the test tube, and incubating the test tube, as is known in the art. Optionally, growth medium 87 has the properties of the high-concentration liquid growth medium described in detail hereinbelow.

Alternatively, for some applications, the entire filter 32 is removed from testing device 20 and tested, outside testing device 20, for the presence of the particulate. If such testing is a rapid strep test, the method may conclude with this test, and not continue with the performance of a test in testing device 20, as described hereinbelow with reference to FIGS. 1G-H. For example, the rapid strep test may use any of the testing techniques described hereinbelow with reference to FIG. 12 regarding external analysis device 1010, with or without first culturing.

Figure 1G:
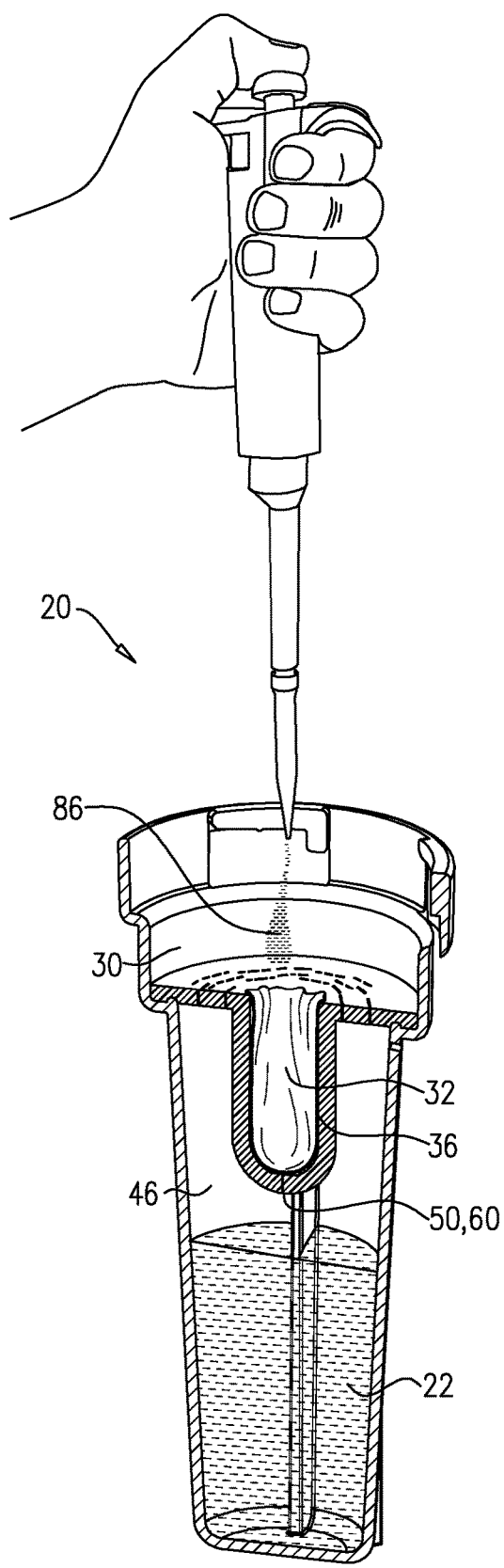
Figure 1H:
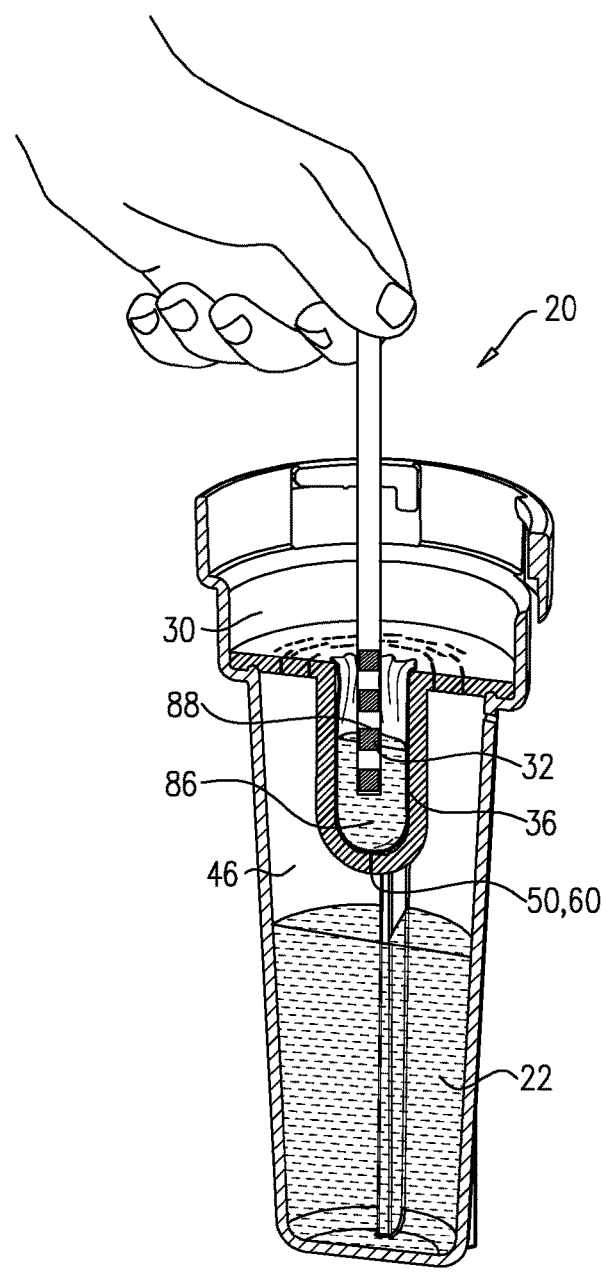

As shown in FIGS. 1G-H, the method further comprises testing, within testing device 20, for the presence of particulate trapped by filter 32 while filter 32 is disposed in testing device 20. For applications in which testing device 20 comprises the one or more valves 60, the testing is performed while the one or more valves 60 are closed. Alternatively or additionally, for applications in which testing device 20 comprises filter chamber 36, the testing is performed within filter chamber 36 while filter 32 is disposed at least partially in the filter chamber.

For some applications, the testing is performed by:
applying an extraction reagent 86 to filter 32, such as shown in FIG. 1G; for applications in which testing device 20 comprises filter chamber 36, the extraction reagent 86 is typically applied to filter 32 while filter 32 is in filter chamber 36; as mentioned above, for applications in which testing device 20 comprises the one or more valves 60, the testing is performed while the one or more valves 60 are closed so that extraction reagent 86 is retained by filter 32 rather than passing through the filter, and after applying extraction reagent 86, inserting a test strip 88 into testing device 20 (e.g., into filter chamber 36) and examining the test strip to test for the presence of the particulate, such as shown in FIG. 1H; optionally, filter 32 is mixed after application of extraction reagent 86 but before insertion of test strip 88.

Reference is still made to FIGS. 1A-H. In an application of the present invention, a system 90 (labeled in FIG. 1A) is provided that comprises:

a liquid 22 including at least one substance selected from the group of substances consisting of gargled fluid, saliva not swabbed from the throat of a patient, and an incubated culture medium containing a biological sample; and testing device 20, which comprises (a) liquid container 30 containing the liquid 22, (b) the one or more valves 60, (c) filter 32, disposed in or downstream of liquid container 30 and upstream of the one or more valves 60, and (d) liquid-pressure source 34, which is arranged to apply pressure to drive liquid 22 contained in liquid container 30 through filter 32 and then through the one or more valves 60.

Figure 2:
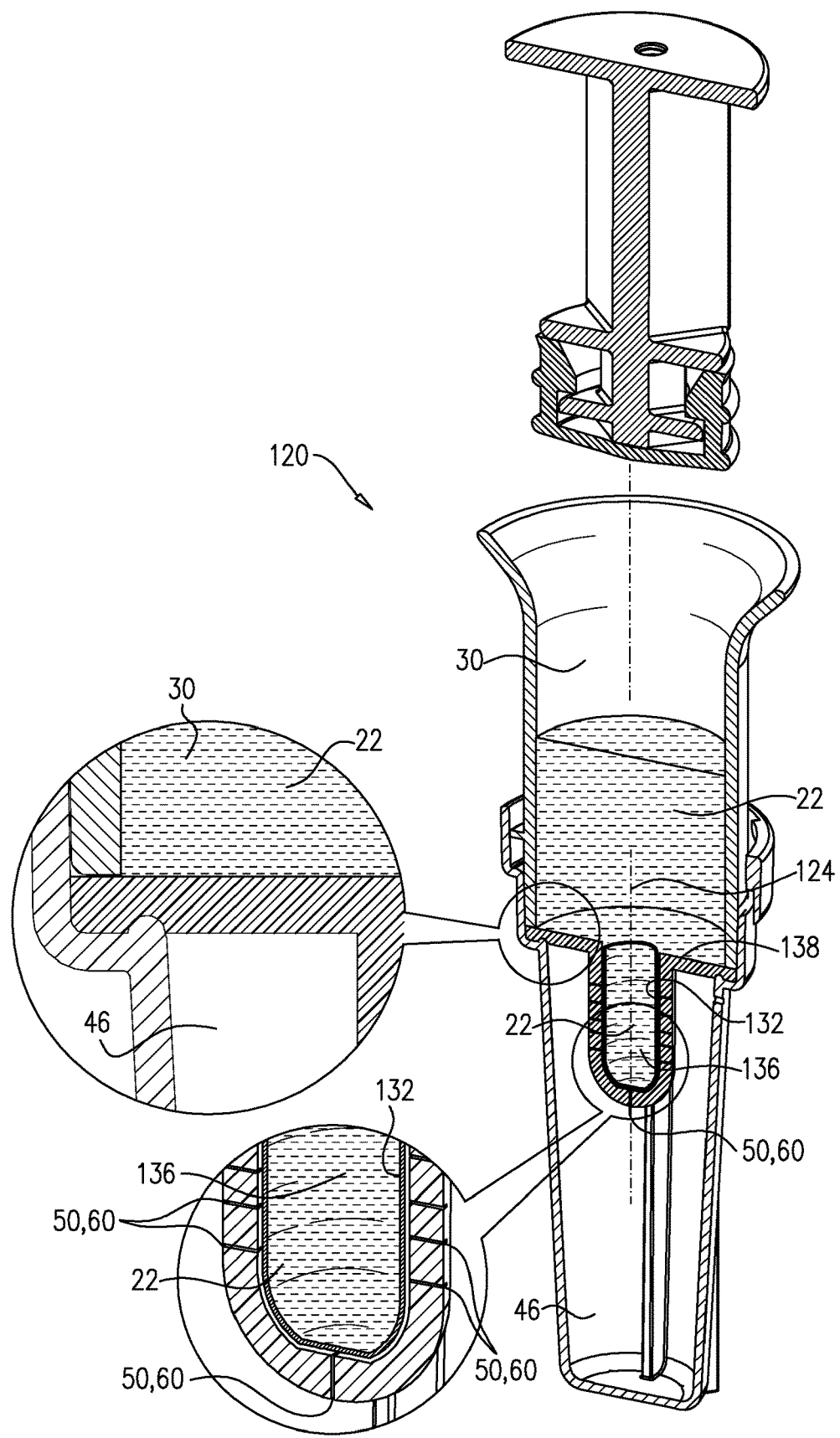
FIG. 2 is a schematic illustration of another testing device for testing for presence of particulate in a liquid, in accordance with an application of the present invention.

Reference is now made to FIG. 2, which is a schematic illustration of a testing device 120 for testing for presence of particulate in liquid 22, in accordance with an application of the present invention. Other than as described below, testing device 120 is similar to testing device 20, described hereinabove with reference to FIGS. 1A-H, and may implement any of the features thereof.

Testing device 120 comprises a filter 132 that is disposed at least partially, e.g., entirely, within a filter chamber 136. By contrast, filter 32 of testing device 20 is removably disposed upstream of filter chamber 36 with filter 32 partially covering inlet 38. Other than this feature, filter 132 may have any of the features of filter 32 described hereinabove with reference to FIGS. 1A-H, including material properties and dimensions.

Filter chamber 136 may implement any of the features of filter chamber 36, described hereinabove with reference to FIGS. 1A-H. Typically, filter chamber 136 comprises one or more pressure-activated valves 50 (such as a plurality, as shown in FIG. 2), not disposed at an inlet 138. Inlet 138 may implement any of the features of inlet 38 described hereinabove with reference to FIGS. 1A-H. In applications in which a plurality of pressure-activated valves 50 are provided, the bottom-most valve may serve to allow the flushing of the remaining liquid 22.

Testing device 120 may be used as described hereinabove with reference to FIGS. 1A-H. The pressure described hereinabove with reference to FIG. 1B is applied while filter 132 is disposed at least partially (e.g., entirely) within filter chamber 136. The pressure drives liquid 22 from liquid container 30 to filter chamber 136, then through filter 132, and then through the one or more pressure-activated valves 50, and optionally into waste liquid receptacle 46, if provided. Typically, liquid container 30 is not shaped so as to define the one or more openings 51 described hereinabove with reference to FIGS. 1A-H.

For some applications, filter 132 is disposed surrounding at least 270 degrees, typically 360 degrees, of a central longitudinal axis 124 of filter chamber 136, such that all or substantially all of liquid 22 that passes out of filter chamber 136 must pass through filter 132. For some applications, filter 132 covers all of the one or more pressure-activated valves 50. For some applications, filter 132 covers at least 80%, such as 100%, of the internal surface of filter chamber 136. For some applications, such as shown in FIG. 2, filter 132 is shaped as a receptacle.

Reference is now made to FIGS. 3A-B, which are schematic illustrations of a testing device 220 for testing for presence of particulate in liquid 22, in accordance with an application of the present invention. Other than as described below, testing device 220 is similar to testing device 20, described hereinabove with reference to FIGS. 1A-H, and may implement any of the features thereof.

Testing device 220 further comprises a frangible seal 226 that removably blocks liquid flow into an inlet 238 of a filter chamber 236. For example, frangible seal 226 may comprise a pliable material (such as silicone) that is easily torn, such as shown in Option A in FIG. 3A, or a rigid material that is easily broken (e.g., shaped so as define slits to aid in breaking), such as shown in Option B in FIG. 3A. Typically, filter 32 of testing device 220, like filter 32 of testing device 20, is removably disposed upstream of filter chamber 236 with filter 32 partially covering inlet 238 of filter chamber 236. When pressure is applied, as described hereinabove with reference to FIG. 1B, substantially all of liquid 22 is driven out of liquid container 30, either the one or more openings 51 or valves 60 described herein. Thereafter, before testing for the presence of the particulate trapped by filter 32, frangible seal 226 is broken, such as using elongate member 56 (e.g., swab 58 thereof), as shown in FIG. 3A, or using plunger head 42 (configuration not shown), and at least a portion of (e.g., the entirely of) filter 32 is pushed into filter chamber 236. Because liquid container 30 is substantially empty of liquid 22, only a minimal amount of liquid 22 enters filter chamber 236. Therefore, filter chamber 236 typically does not comprise any pressure-activated valves 50 not disposed at an inlet 238, because drainage of liquid is not required.

For some applications, filter chamber 236, before frangible seal 226 is broken, contains a material, such as a rapid test solution (e.g., a rapid strep test) in liquid or solid (e.g., powdered) form. This may simplify the use of the testing device because the material is not flushed during the application of pressure, and thus does not need to be added during use after applying the pressure.

For some applications, testing device 20 further comprises a support for filter 32 (e.g., the configuration of frangible seal 226 shown in Option B in FIG. 3A), disposed at least partially between inlet 38 and filter 32. During application of pressure, as described hereinbelow with reference to FIG. 1B, the support helps prevent filter 32 from entering filter chamber 36, which might occur if inlet 38 is relative wide. The support is easily breakable or flexible such that filter 32 can still readily be pushed into filter chamber 36. For example, the support may comprise a very thin plastic sheet (like a plastic bag) that has holes such that the support provides enough support for the filter to rest on and not puncture, and also very flexible so that it can easily be pushed into filter chamber 36 together with filter 32. Alternatively, the support may comprise a harder or firmer material that is easily breakable, e.g., may comprise slits to enable easy breaking. Optionally, plunger head 42 is configured to break the support (configuration not shown). The support may comprise an elastomer and/or be perforated with openings, e.g., having an average diameter of between 0.2 and 5 mm.

Figure 3C:
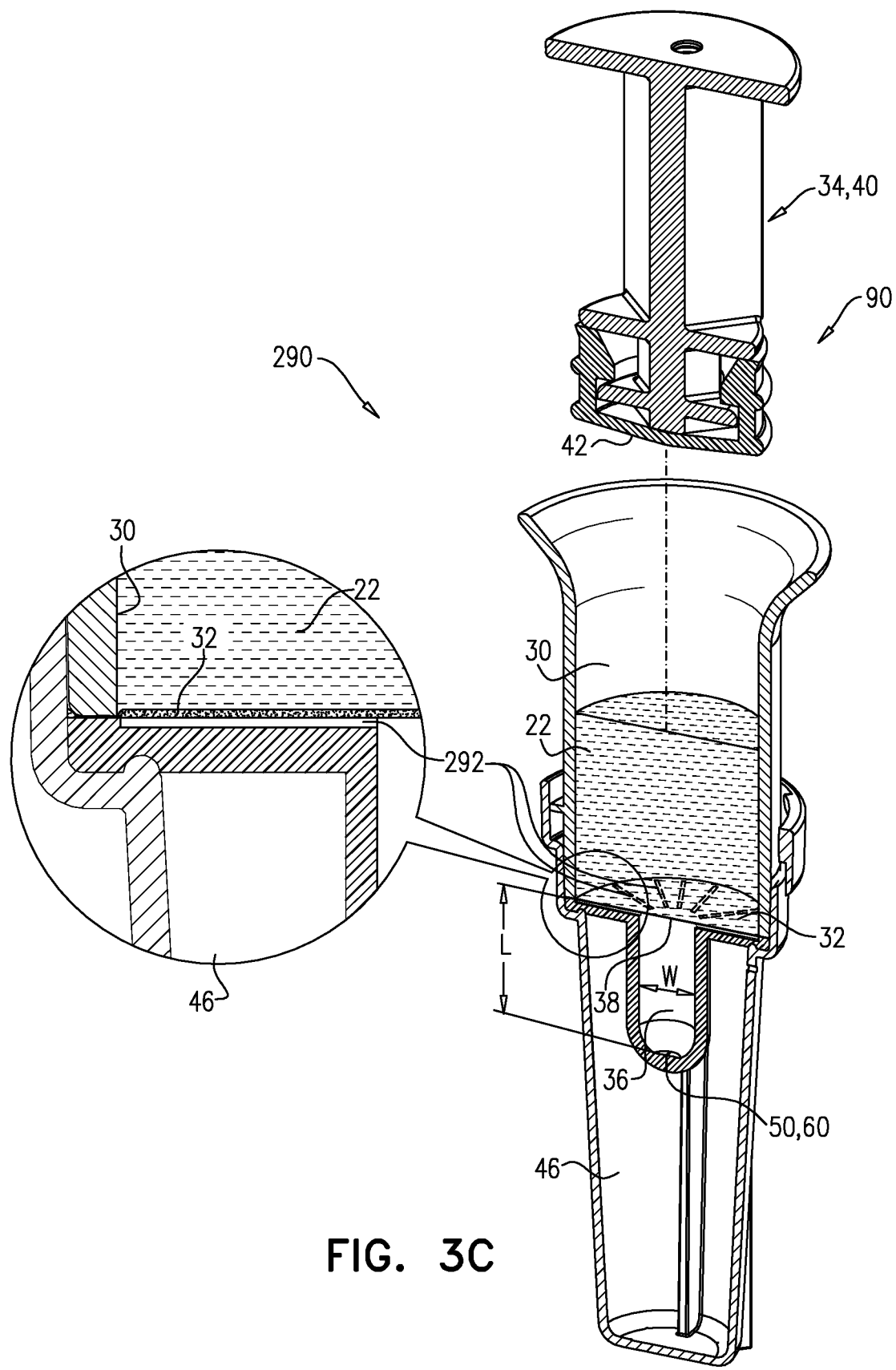
FIG. 3C is a schematic illustration of still another testing device for testing for presence of particulate in a liquid, in accordance with an application of the present invention.

Reference is now made to FIG. 3C, which is a schematic illustration of a testing device 290 for testing for presence of particulate in liquid 22, in accordance with an application of the present invention. Other than as described below, testing device 290 is similar to testing device 20, described hereinabove with reference to FIGS. 1A-H, and may implement any of the features thereof. Liquid container 30 is not shaped so as to define the one or more openings 51 or the one or more valves 60 described hereinabove with reference to FIGS. 1A-H. Instead, in order to allow liquid 22 to pass through the peripheral portion of filter 32 not disposed over inlet 38, the downstream surface of liquid container 30 is shaped so as define a plurality of elongate indentations 292 that extend radially inward to the edge of inlet 38. The liquid 22 that is driven through the peripheral portion of filter 32 enters the indentations and drains from the indentations into filter chamber 36. This configuration allows for the entire filter upstream surface area to be utilized while allowing the air trapped in liquid container 30 to blow out most of remaining liquid 22 from filter chamber 36 to leave the filter chamber generally dry.

Reference is now made to FIGS. 4A-C, which are schematic illustrations of a testing device 320 for testing for presence of particulate in liquid 22, in accordance with an application of the present invention. Reference is also made to FIGS. 5A-B, which are schematic illustrations of a testing device 420 and a testing device 520, respectively, for testing for presence of particulate in liquid 22, in accordance with respective applications of the present invention. Other than as described below, testing devices 320, 420, and 520 are similar to testing device 20, described hereinabove with reference to FIGS. 1A-H, and may implement any of the features thereof.

For applications in which the one or more valves 60 are provided, such as shown in FIGS. 4A-C and 5A-B, the one or more valves 60 are one or more first valves 60, and testing devices 320, 420, and 520 further comprise one or more second pressure relief valves 361, which are in fluid communication with liquid container 30 and are disposed upstream of filter 32. For some applications, the one or more first valves 60 comprise one or more first pressure-activated valves 60 configured to open upon exposure to a first pressure gradient across the one or more first pressure-activated valves 60, and the one or more second pressure relief valves 361 are configured to open upon exposure to a second pressure gradient across the one or more second pressure relief valves 361, the second pressure gradient greater than the first pressure gradient. Alternatively, the one or more valves 60 are not provided; for example, the wall of liquid container 30 may be shaped so as to define the one or more openings 51 described hereinabove with reference to FIGS. 1A-H.

The one or more second pressure relief valves 361 allow drainage of liquid 22 if excess pressure occurs in liquid container 30, such as if filter 32 becomes clogged during the application of pressure described hereinabove with reference to FIG. 1B.

Reference is made to FIGS. 4A-C. For some applications, liquid-pressure source 34 comprises a plunger 340, which comprises (a) a plunger shaft 341 and (b) a plunger head 342 disposed at a downstream end portion of plunger shaft 341 and shaped so as to be insertable into liquid container 30. Plunger 340 (including plunger head 342 and plunger shaft 341) may implement any of the configures of plunger 40 described hereinabove with reference to FIGS. 1A-H. Testing device 320 comprises one or more unfiltered liquid receptacles 344 (e.g., vials). The one or more second pressure relief valves 361 comprise one or more second pressure relief valves 348 that are in fluid communication with the one or more unfiltered liquid receptacles 344. For some applications, the one or more unfiltered liquid receptacles 344 are disposed along plunger shaft 341, such as shown. Optionally, the one or more unfiltered liquid receptacles 344 are removably coupled to plunger 340. Typically, the one or more unfiltered liquid receptacles 344 are shaped so as to define vents to allow the escape of air as liquid 22 enters. Optionally, the one or more unfiltered liquid receptacles 344 contain an antibacterial agent, such as described hereinbelow with reference to FIG. 9 regarding waste liquid receptacle 46.

Reference is made to FIG. 5A. For some applications, testing device 420 further comprises waste liquid receptacle 46, which is coupled to liquid container 30 downstream of filter 32 (and of the one or more valves 60, if provided). Liquid-pressure source 34 is arranged to apply pressure to drive liquid 22 contained in liquid container 30 through filter 32, then through the one or more openings 51 or the one or more valves 60, if provided, and then into waste liquid receptacle 46. The one or more second pressure relief valves 361 comprise one or more second pressure relief valves 448 that are in fluid communication with waste liquid receptacle 46 not via filter 32.

Reference is made to FIG. 5B. For some applications, the one or more second pressure relief valves 361 comprise one or more second pressure relief valves 548 that are in fluid communication with outside testing device 520.

Reference is made to FIGS. 6A-C, which are schematic illustrations of a testing device 620 for testing for presence of particulate in liquid 22, in accordance with an application of the present invention. Other than as described below, testing device 620 is similar to testing device 320, described hereinabove with reference to FIGS. 4A-C and may implement any of the features thereof. In addition, other than as described below, testing device 620 is similar to testing device 20, described hereinabove with reference to FIGS. 1A-H, and may implement any of the features thereof.

Testing device 620 comprises one or more unfiltered liquid receptacles 644 (e.g., vials). The one or more second pressure relief valves 361, 348 are in fluid communication with the one or more unfiltered liquid receptacles 644, such that when pressure is applied, as described hereinabove with reference to FIG. 1B, a portion of the unfiltered liquid 22 is driven into the one or more unfiltered liquid receptacles 644. After applying the pressure, a sample of liquid 22 in the one or more unfiltered liquid receptacles 644 is taken, and the sample is tested, outside testing device 20, for the presence of the particulate, using any overnight or rapid test (e.g., rapid strep test) including or not including incubation. This may simplify the process of taking a sample for backup test, e.g., a backup strep test (and may even get a better sample of bacteria). Optionally, the one or more unfiltered liquid receptacles 644 contain culture media, e.g., including red blood cells.

Reference is now made to FIGS. 7A-C and 8A-E, which are schematic illustrations of a testing device 720 for testing for presence of particulate in liquid 22, in accordance with an application of the present invention. Other than as described below, testing device 720 is similar to the testing devices described hereinabove with reference to FIGS. 1A-6C, and may implement any of the features thereof; testing device is particularly similar to testing device 220, described hereinabove with reference to FIGS. 3A-B. Unless otherwise described, reference numerals in FIGS. 7A-C and 8A-E refer to like parts as reference numerals in FIGS. 1A-H based on the last two digits.

Testing device 720 comprises a liquid-pressure source 734, which comprises a plunger 740, which comprises a plunger head 742 that is shaped so as to be insertable into a liquid container 730. Plunger 740 is shaped so as to define a waste liquid receptacle 746.

Plunger 740 is also shaped so as to define a filter chamber 736. Filter chamber 736 typically does not comprise any pressure-activated valves 50. Testing device 720 further comprises a frangible seal 726 that removably blocks liquid flow into an inlet 738 of filter chamber 736. Frangible seal 726 may implement any of the features of frangible seal 226 described hereinabove with reference to FIGS. 3A-B.

For some applications, testing device 720 comprises a cap 792, which is removably coupled to a distal end of liquid container 730 (i.e., to the end opposite the end into which plunger 740 is inserted). A proximal wall 794 of cap 792 defines a distal wall of liquid container 730. For some applications, cap 792 is shaped so as to define an unfiltered liquid receptacle 744, and proximal wall 794 of cap 792 comprises one or more second pressure relief valves 761 that (a) are in fluid communication with unfiltered liquid receptacle 744 and, when cap 792 is coupled to liquid container 730, with liquid container 730, and (b) are disposed upstream of filter 732.

Before use (e.g., during manufacture), cap 792 is removably coupled to liquid container 730, such as by twisting the cap onto liquid container 730, as shown in FIG. 8A. Also before use, plunger 740 is not coupled to liquid container 730. Optionally, plunger 740 has a distal protective cover 796, which is removed before use.

Liquid 22 (such as gargled fluid, saliva not swabbed from the throat of a patient, or an incubated culture medium containing a biological sample) is received in liquid container 730.

As shown in FIG. 8B, plunger 740 is inserted into liquid container 730 after removing cap 792.

As shown in FIG. 8C, plunger 740 is pushed until the distal end of the plunger reaches proximal wall 794 of cap 792. This pushing applies pressure to liquid 22, such as described hereinabove with reference to FIG. 1B.

As shown in FIG. 8D, cap 792 is removed from liquid container 730, such as by twisting the cap, and, optionally, further pushing the plunger until the plunger pushes off the cap, in order to expose a filter 732. The cap is disposed.

As shown in FIG. 8E, at least a portion (e.g., the entirely) of filter 732 is pushed into filter chamber 736, such as using elongate member 56, which also breaks frangible seal 726. (The filter may tear, as shown, leaving a portion of the filter outside filter chamber 736, e.g., connected at a periphery of the filter to liquid container 730, as shown.)

The use of testing device 720 may continue as described hereinabove with reference to FIGS. 1E-H, mutatis mutandis.

Figure 9:
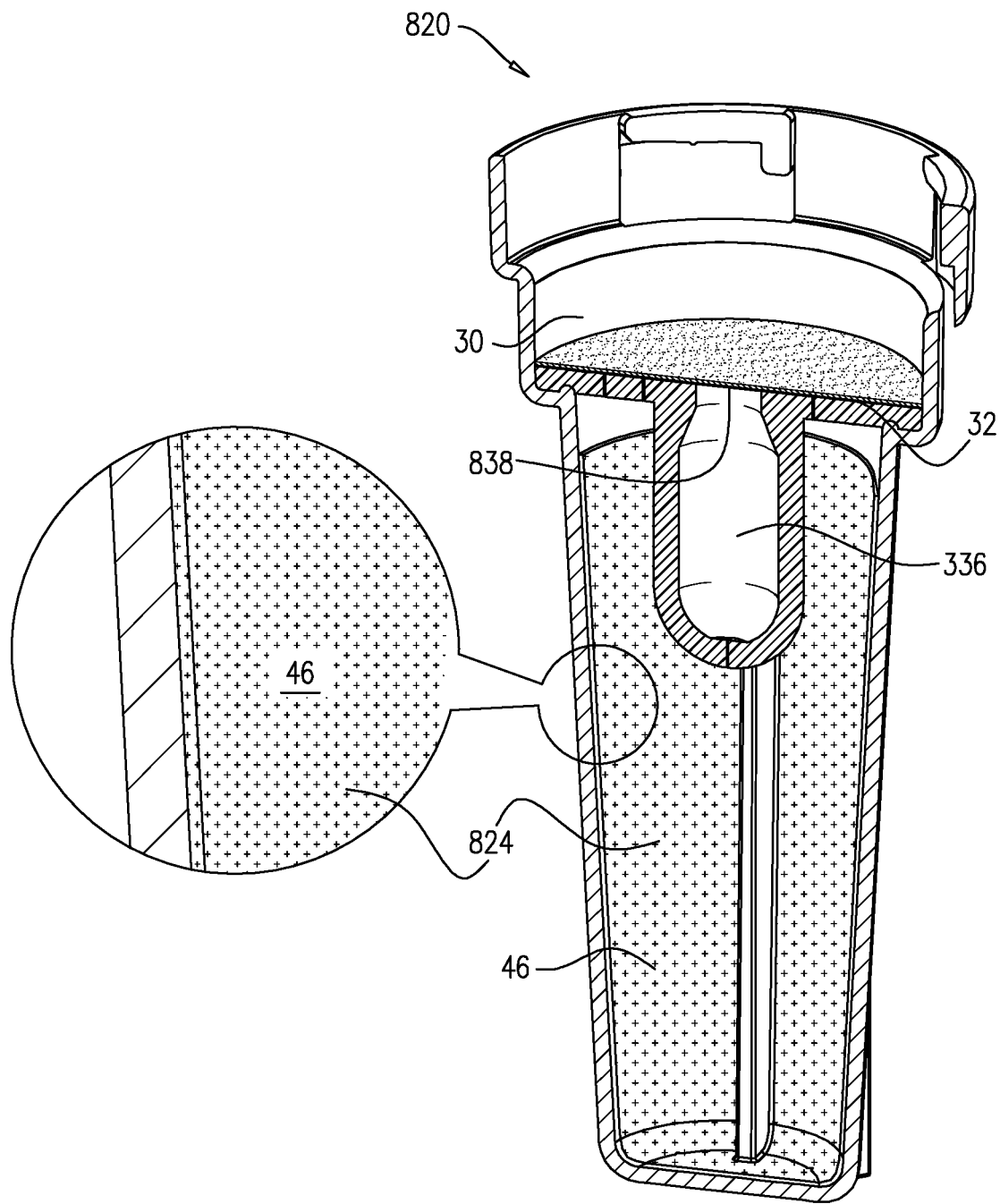
FIG. 9 is a schematic illustration of another testing device for testing for presence of particulate in a liquid, in accordance with an application of the present invention.

Reference is now made to FIG. 9, which is a schematic illustration of a testing device 820 for testing for presence of particulate in liquid 22, in accordance with an application of the present invention. Other than as described below, testing device 820 is similar to the testing devices described hereinabove with reference to FIGS. 1A-8E, and may implement any of the features thereof. Similarly, any of testing devices described herein may implement the features of FIG. 9, mutatis mutandis.

Testing device 820 comprises waste liquid receptacle 46, which contains an antibacterial agent 824, such as a detergent, thiomersal, bleach, or iodine (I/KI) to kill any bacteria that passes through filter 32, to reduce the risk of contamination upon accidental exposure to the liquid in waste liquid receptacle 46.

For some applications, an inlet 838 of a filter chamber 336 of testing device 820 has an inlet area that is less than a greatest cross-sectional area of filter chamber 336, the inlet area and the greatest cross-sectional area measured in respective planes parallel to each other. For example, the inlet area may be no more than 95%, such as no more than 90%, e.g., no more than 80% of the greatest cross-sectional area of filter chamber 336. Providing this narrowing of filter chamber 336 at inlet 838 may help retain filter 32 in filter chamber 336 during withdrawal of elongate member 56, as described hereinabove with reference to FIG. 1F. Testing devices 320, 420, 520, 620, 1020, and 1120, described herein with reference to FIGS. 4A-C, 5A, 5B, 6A-C, 14B, and 15B, respectively, are also shown comprising filter chamber 336; these testing devices may alternatively comprise filter chambers 36, 136, 236, or 736, mutatis mutandis.

Figure 10A:
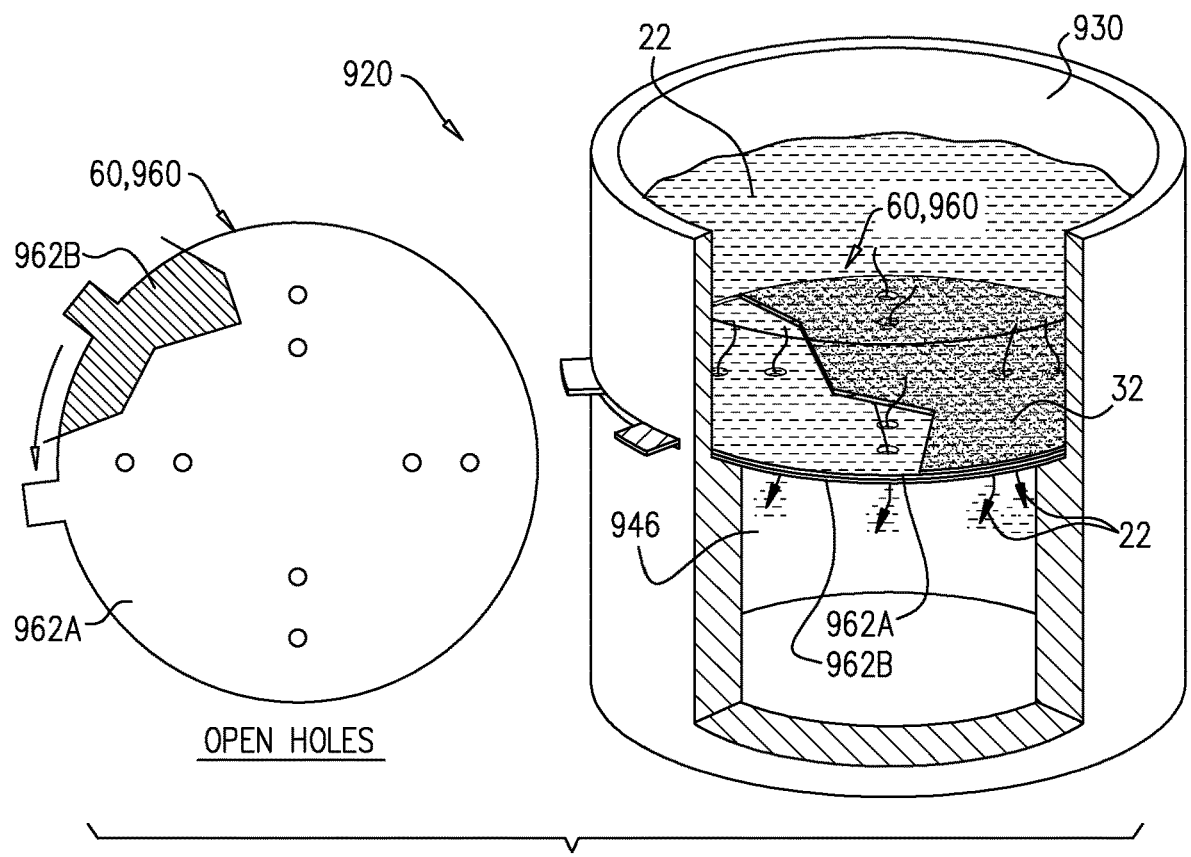
Figure 10B:
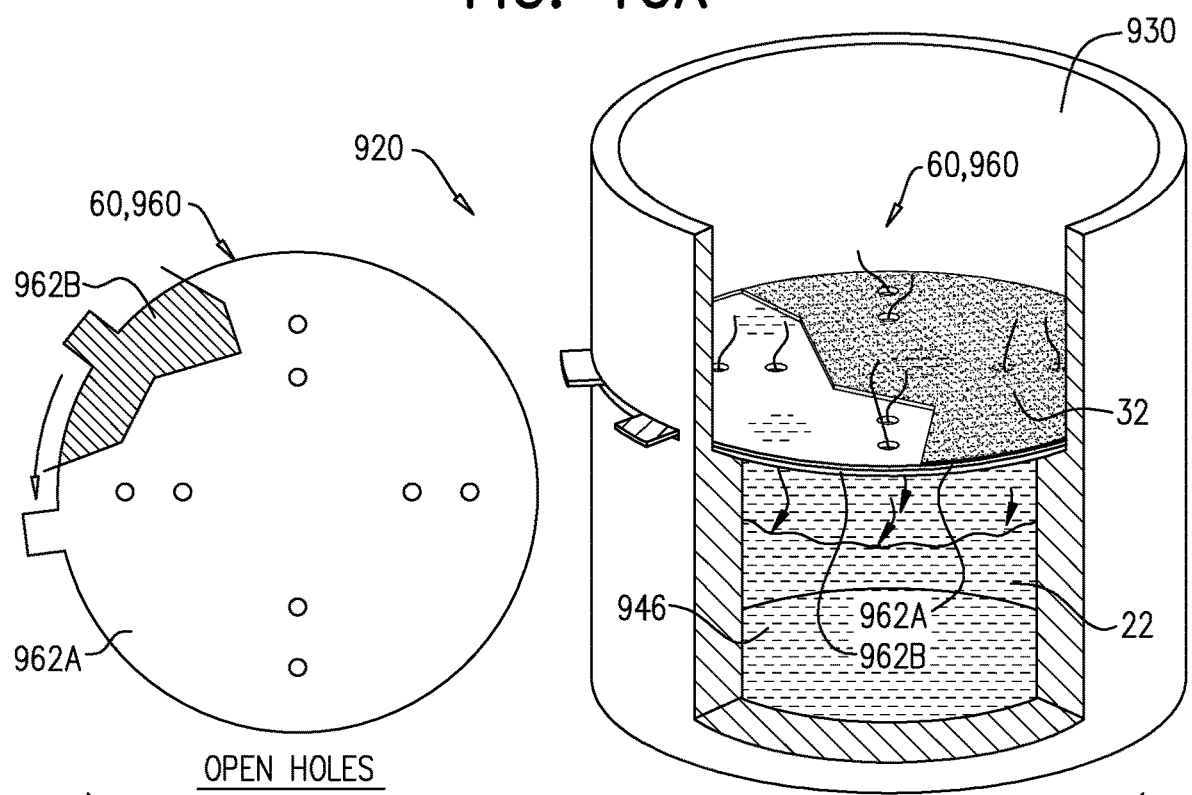
Figure 10H:
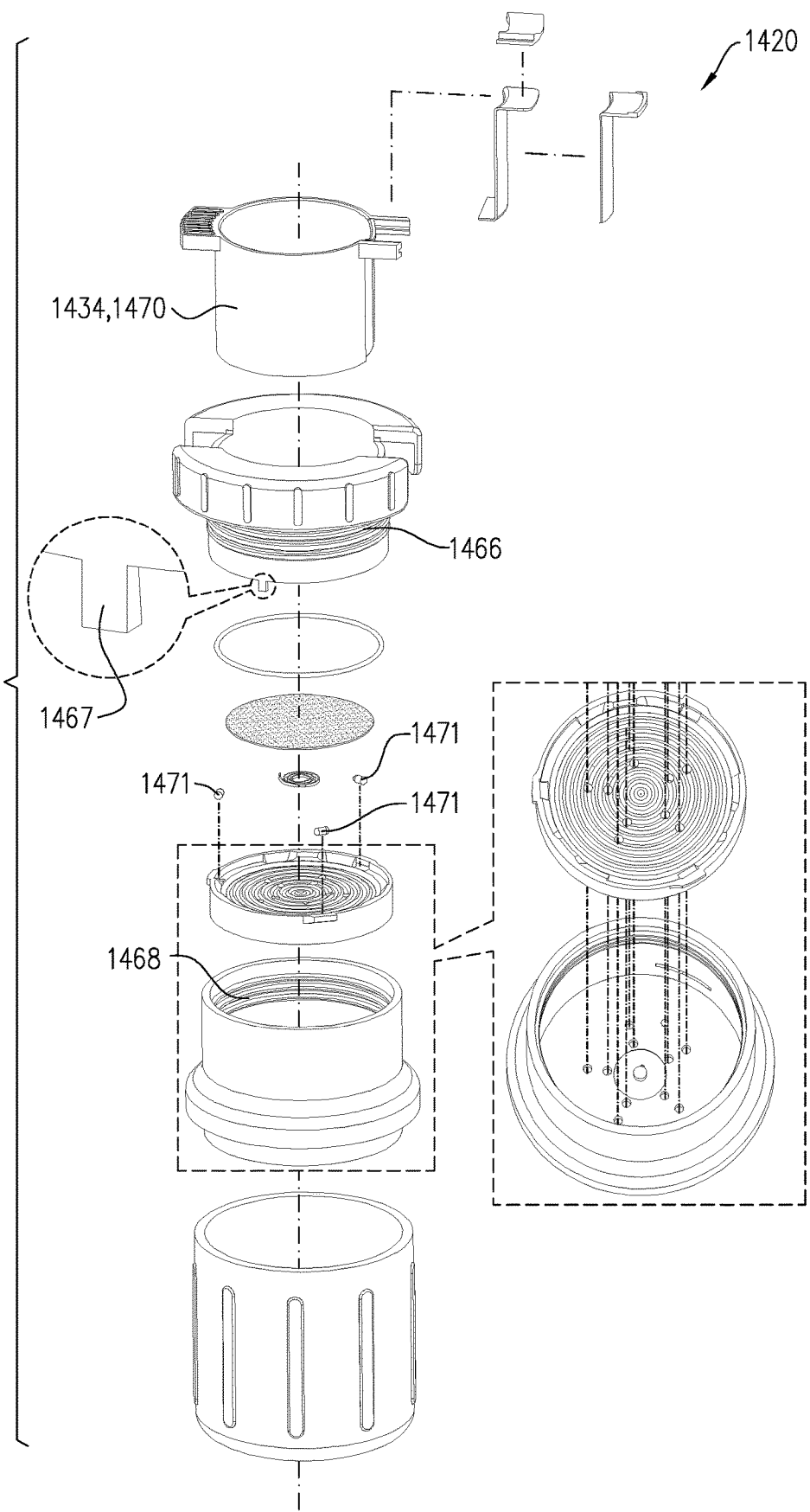

Reference is now made to FIGS. 10A-C, which are schematic illustrations of a testing device 920 for testing for presence of particulate in liquid 22, in accordance with an application of the present invention. (Filter 32 is shown in partial cut-away view to show the one or more non-pressure-activated valves 960 described below.) Other than as described below, testing device 920 is similar to the testing devices described hereinabove with reference to FIGS. 1A-9, and may implement any of the features thereof.

The one or more valves 60 of testing device 920 comprise one or more non-pressure-activated valves 960. For example, the one or more non-pressure-activated valves 960 may be opened and closed by aligning and non-aligning, respectively, sets of openings in two discs 962A and 962B of the one or more non-pressure-activated valves 960, either manually or automatically by the testing device, such as described hereinbelow. Other manual and automated configurations will be readily apparent to those skilled in the art who have read the present application.

During use, liquid 22 is received in a liquid container 930, as shown in FIG. 10A, typically while the one or more non-pressure-activated valves 960 are in an opened state (e.g., with the openings in disc 962A aligned with the openings in disc 962B), thereby allowing liquid 22 to pass through the one or more valves and the filter, optionally into a waste liquid receptacle 946 if provided, as shown in FIGS. 10A-B. Typically, while the one or more non-pressure-activated valves 960 are open, pressure is applied using a liquid-pressure source such as those described herein.

Thereafter, as partially shown in FIG. 10C, the one or more non-pressure-activated valves 960 are closed (e.g., by rotating at least one of discs 962A and 962B so that their respective openings are not aligned with one another) and filter 32 is tested for the presence of particulate trapped by filter 32, such as described hereinabove with reference to FIGS. 1G-H, mutatis mutandis. The closed one or more valves retain extraction reagent 86 in filter 32 by preventing the extraction agent from passing through the filter.

As described hereinabove, for some applications, the testing devices described herein comprise a liquid-pressure source that is arranged to apply pressure to drive liquid contained in the liquid container through the filter and, optionally, then into the waste liquid receptacle. For some of these applications, the testing device is configured to automatically (typically, non-electrically) close one or more non-pressure-activated valves of the testing device after the plunger applies the pressure to drive the liquid contained in the liquid container through the filter and then through the one or more non-pressure-activated valves. For some of these applications, the testing device is configured such that motion of the plunger automatically (typically, non-electrically) closes the one or more non-pressure-activated valves after the plunger applies the pressure to drive the liquid contained in the liquid container through the filter and then through the one or more non-pressure-activated valves. Although the testing device is described in this and the following configurations as non-electrically closing the one or more non-pressure-activated valves, the testing device may alternatively electrically close the one or more non-pressure-activated valves, such as using a motor.

Figure 10I:
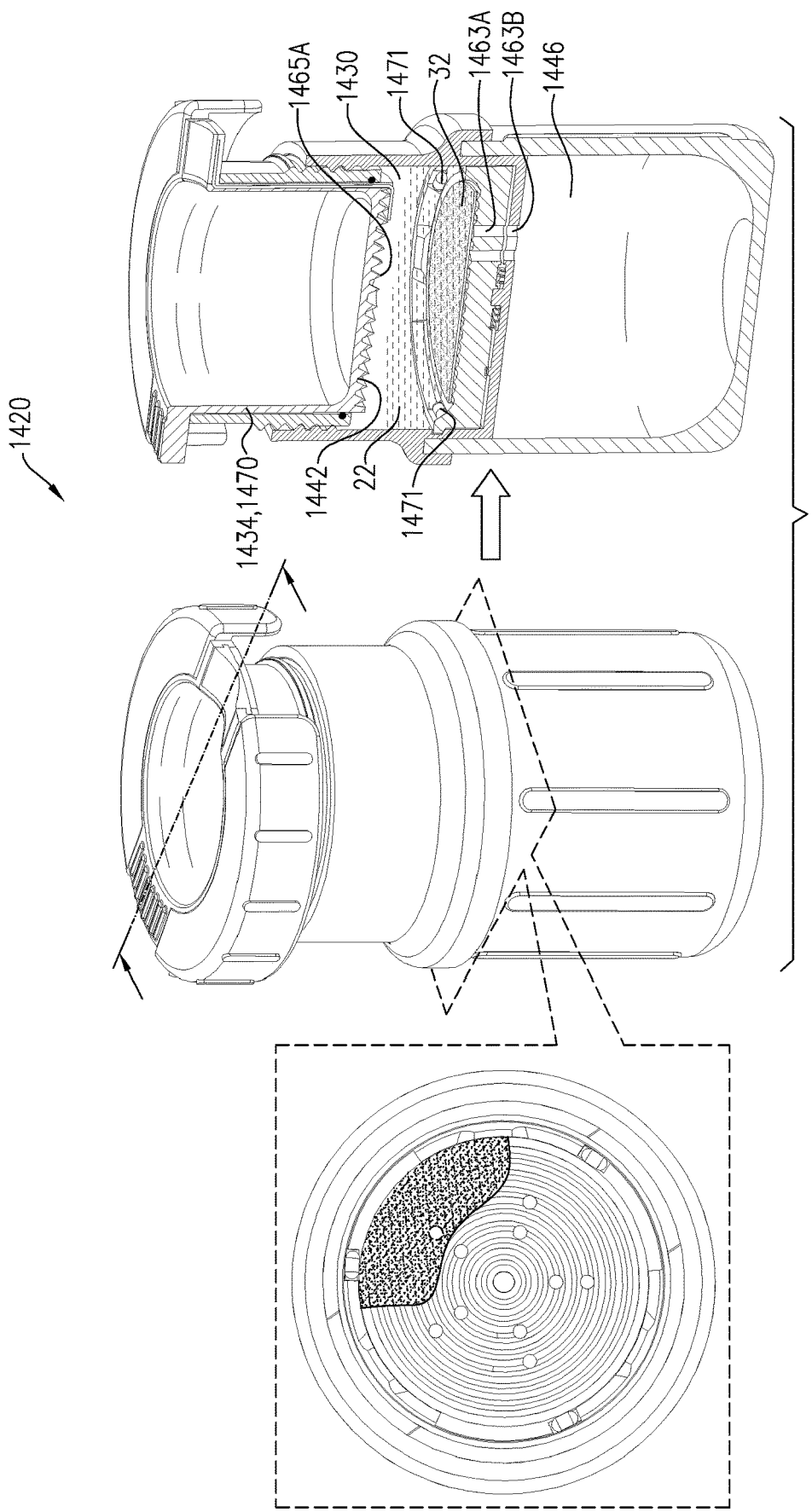

Reference is now made to FIGS. 10D-K, which are schematic illustrations of a testing device 1420 for testing for presence of particulate in liquid 22, in accordance with an application of the present invention. Other than as described below, testing device 1420 is similar to the testing devices described hereinabove with reference to FIGS. 1A-9 and 10A-C, and may implement any of the features thereof, mutatis mutandis. Testing device 1420 comprises a liquid-pressure source 1434, which comprises a plunger 1440, which comprises a plunger head 1442 that is shaped so as to be insertable into a liquid container 1430. Testing device 1420 typically further comprises a waste liquid receptacle 1446, which is coupled to liquid container 1430 downstream of filter 32. Plunger 1440 is arranged to apply pressure to drive liquid 22 contained in liquid container 1430 through filter 32 and then through one or more non-pressure-activated valves 1460 of testing device 1420, and into waste liquid receptacle 1446, if provided, as shown in FIGS. 10I-J.

Figure 10K:
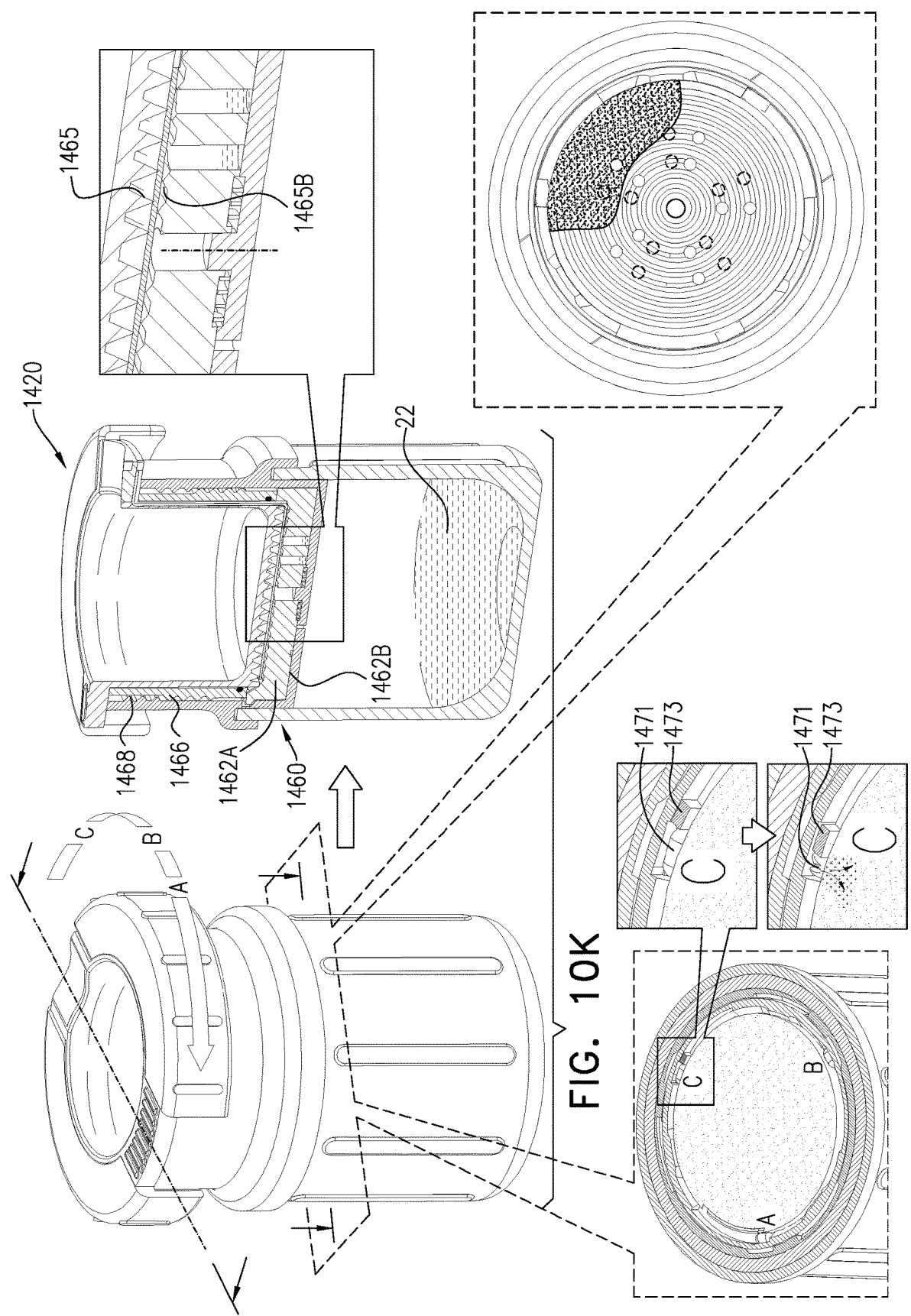

As shown in FIG. 10K, testing device 1420 is configured such that rotational motion of plunger 1440 automatically (typically, non-electrically) closes the one or more non-pressure-activated valves 1460 of testing device 1420 after plunger 1440 applies the pressure to drive liquid 22 contained in liquid container 1430 through filter 32 and then through the one or more non-pressure-activated valves 1460. For example, the last turn of plunger 1440, or a fraction of the last turn (which may or may not include the last portion of the last turn), may automatically close the one or more non-pressure-activated valves 1460.

For some applications, plunger 1440 is shaped so as to define one or more plunger threads 1466, and an internal wall of liquid container 1430 is shaped so as to define one or more liquid-container threads 1468 that engage the one or more plunger threads 1466 such that rotation of plunger 1440 advances plunger 1440 in a downstream direction within liquid container 1430. Advancing plunger 1440 helps control the speed of the advancement and helps maintain steady advancement against pressure in liquid container 1430.

For some applications, the one or more non-pressure-activated valves 1460 comprise two discs 1462A and 1462B, which are shaped so as to define respective sets of openings 1463A and 1463B, for example as described hereinabove with reference to FIGS. 10A-C. For these applications, testing device 1420 is configured such that rotational motion of plunger 1440 automatically closes the one or more non-pressure-activated valves 1460 by rotating at least one of the two discs 1462A and 1462B with respect to the other of the discs, after plunger 1440 applies the pressure to drive liquid 22 contained in liquid container 1430 through filter 32 and then through the one or more non-pressure-activated valves 1460. For example, the last turn of plunger 1440, or a fraction of the last turn (which may or may not include the last portion of the last turn), may automatically rotate the at least one of the discs. For example, ridges 1465A on plunger head 1442 may engage, via filter 32, corresponding ridges 1465B on an upstream surface of disc 1462A after plunger 1440 has been advanced in a downstream direction into contact with disc 1462A. Alternatively or additionally, for some applications, testing device 1420 comprises one or more tabs 1467 that rotate the upper disc and/or break the capsules described hereinbelow.

For some applications, testing device 1420 comprises one or more reagent containers 1471, such as capsules, that contain one or more extraction reagents 86 (either the same type of extraction reagents or differing extraction reagents). Reagent containers 1471 are disposed at least partially in liquid container 1430, such that upon opening of the containers, such as by crushing, tearing, or breaking, extraction reagents 86 are released into liquid container 1430, typically near filter 32. For example, testing device 1420 may configured such that rotational motion of plunger 1440 automatically opens reagents containers 1471, such as by bringing one or more respective protrusions 1473 into contact with the reagent containers. For example, a fraction of the last turn (or the last turn), may automatically open reagents containers 1471. Typically, a fraction of last turn (may or may not include the last portion of the last turn) opens reagents containers 1471, and the fraction occurs after the fraction of the last turn that closes the one or more non-pressure-activated valves 1460, such that the one or more valves are closed before the reagents are released.

Reference is made to FIGS. 10D-G, which illustrate a portion of a method for using testing device 1420 for testing liquid 22 for the presence of the particulate. This method is optional, and testing device 1420 is not necessarily used in this manner and thus does not necessarily comprise the elements necessary for use in this manner. These techniques may be also be practiced in combination with any of the testing devices described herein for which they are applicable, mutatis mutandis.

In this portion of the method, the user typically receives testing device 1420 with the elements thereof removably coupled together, as shown in FIG. 10D. The user removes plunger 1440 of liquid-pressure source 1434 and a container 1490 from the body of testing device 1420, as shown in FIG. 10E; for example, plunger 1440 may be removed from liquid container 1430 and container 1490 may be removed from a cavity defined by plunger 1440. Liquid 22 is received from the patient into container 1490 (step not shown). Liquid 22 is poured from container 1490 into liquid container 1430, as shown in FIG. 10E. Plunger 1440 is reinserted into liquid container 1430, as shown in FIG. 10G.

Figure 10L:
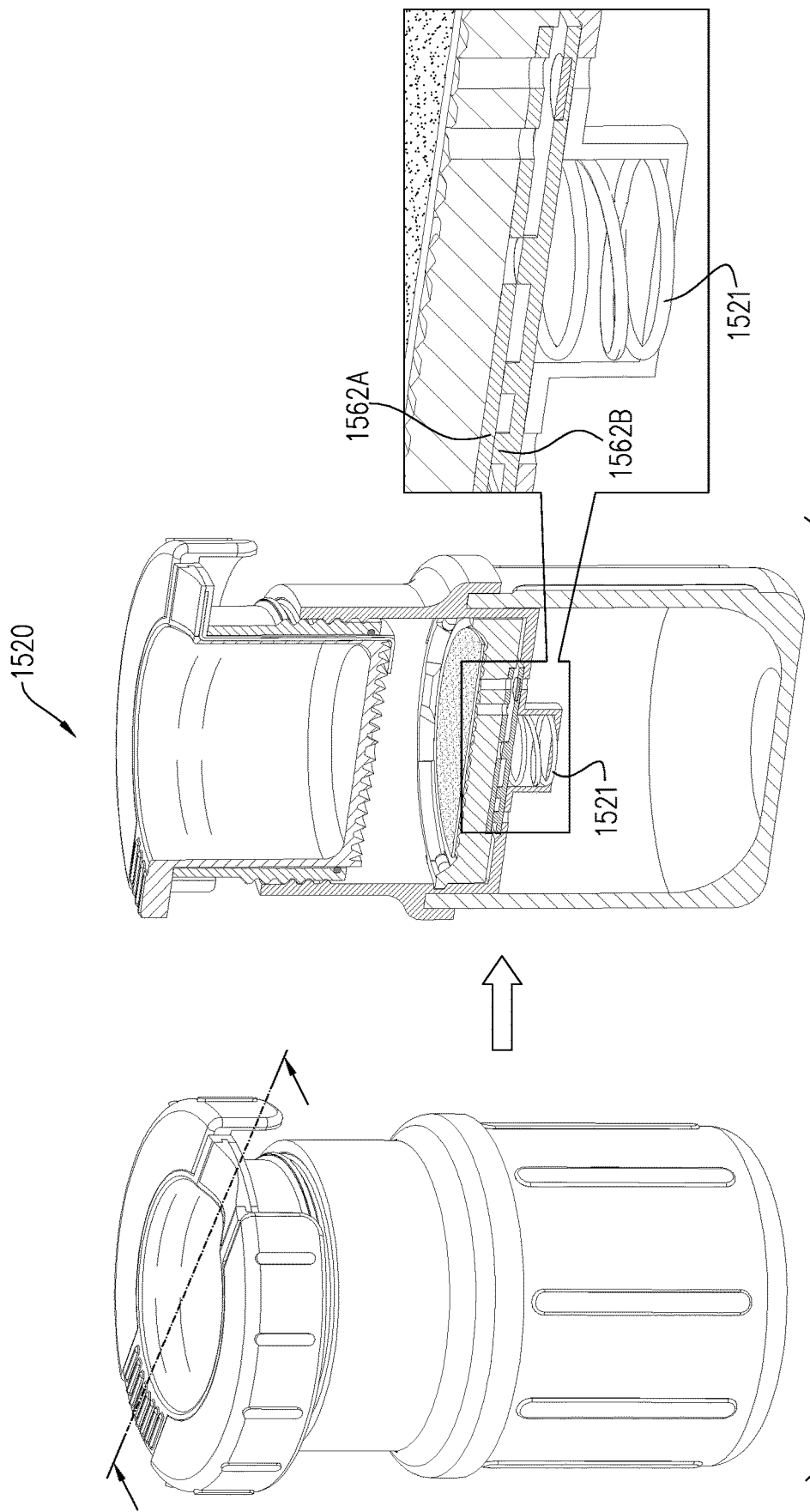

Reference is now made to FIGS. 10L-M, which are schematic illustrations of a testing device 1520 for testing for presence of particulate in liquid 22, in accordance with an application of the present invention. Other than as described below, testing device 1520 is similar to testing device 1420 described hereinabove with reference to FIGS. 10D-K. and may implement any of the features thereof, mutatis mutandis. Testing device 1520 comprises a spring 1521, which is biased to hold slightly separated discs 1562A and 1562B of one or more non-pressure-activated valves 1560 of testing device 1520, thereby creating a fluid flow path through the openings of the discs, as shown in FIG. 10L. The downstream advancing of the plunger pushes the upper disc 1562A downstream and thus the discs together (and compresses the spring), as shown in FIG. 10M, thereby blocking fluid flow through the openings. The discs typically do not rotate with respect to one another in this configuration.

Figure 10N:
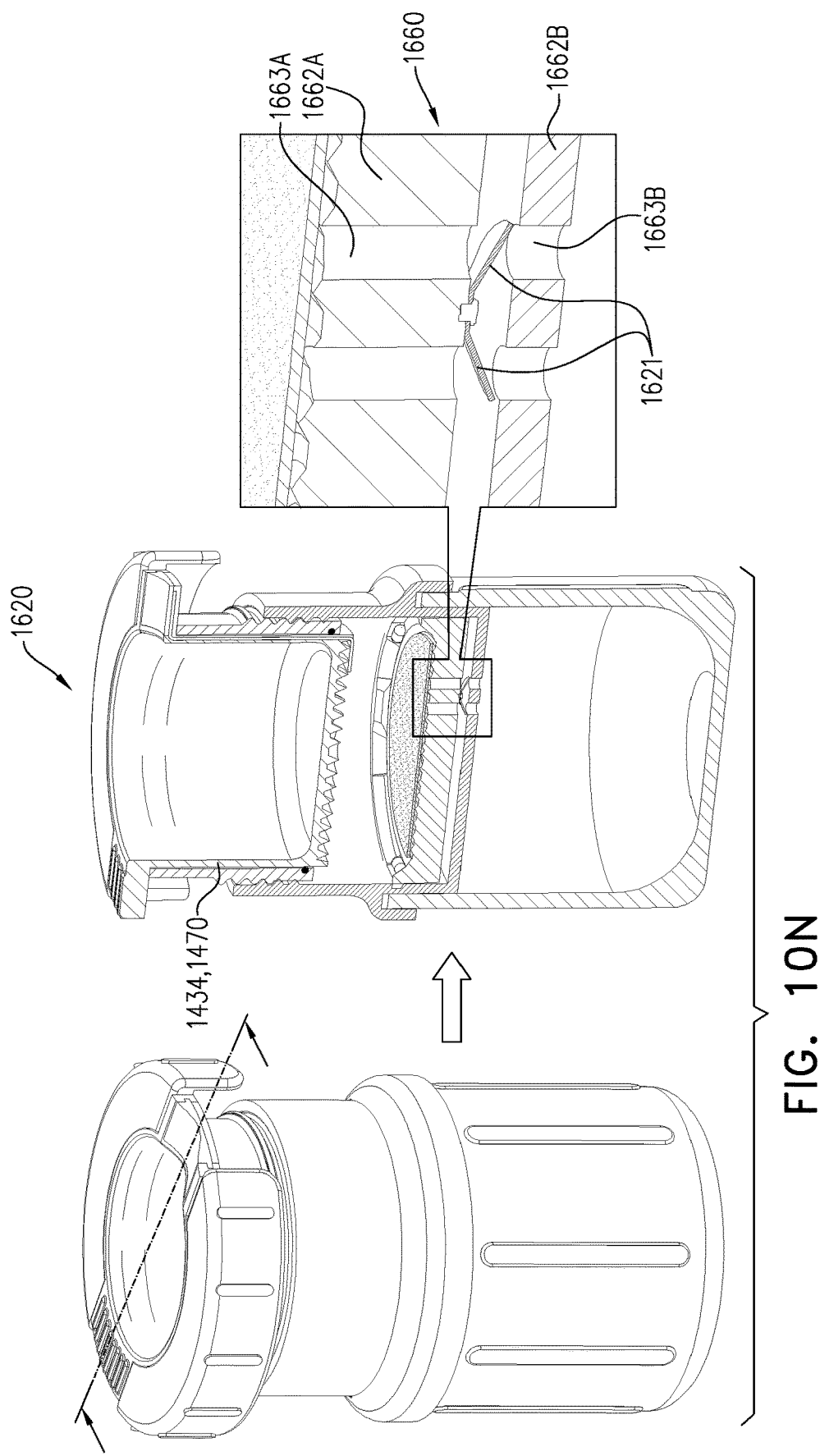
Figure 100:
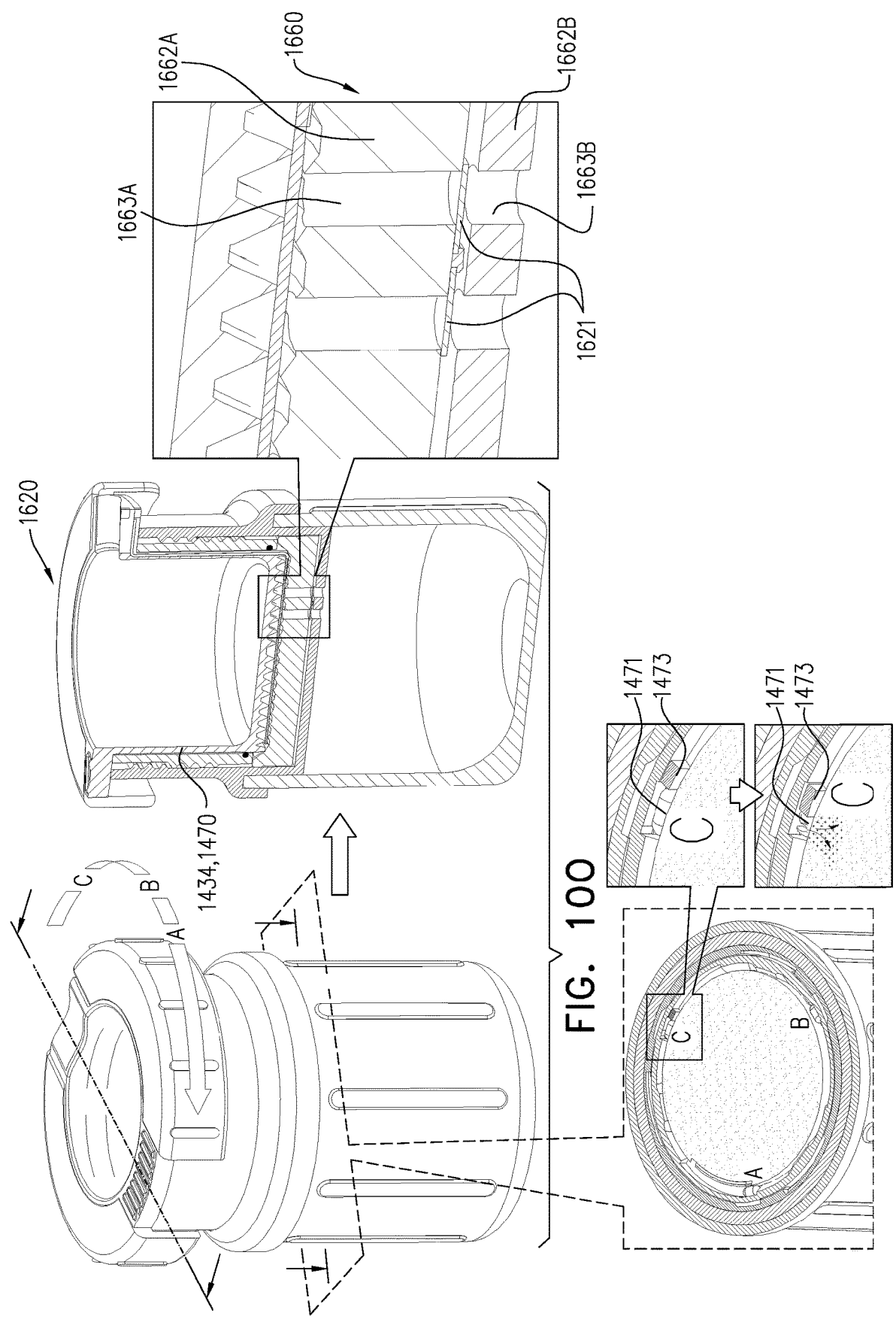

Reference is now made to FIGS. 10N-O, which are schematic illustrations of a testing device 1620 for testing for presence of particulate in liquid 22, in accordance with an application of the present invention. Other than as described below, testing device 1620 is similar to testing devices 1420 and 1520 described hereinabove with reference to FIGS. 10D-K and FIGS. 10L-M, respectively, and may implement any of the features thereof, mutatis mutandis. Testing device 1620 comprises one or more flaps 1621, which, in an initial configuration, do not block openings 1663A and 1663B defined by discs 1662A and 1662B, respectively, of one or more non-pressure-activated valves 1660 of testing device 1620, as shown in FIG. 10N. Typically, flaps 1621 are somewhat springy and biased to hold slightly separated discs 1562A and 1562B of one or more non-pressure-activated valves 1560 of testing device 1520. As shown in FIG. 10O, when plunger 1470 is advanced in a downstream direction into contact with disc 1662A, which in turn pushes upstream disc 1662A closer to downstream disc 1662B, thereby causing the one or more flaps 1621 to block openings 1663A and 1663B (such as by displacing or deforming the flaps). The discs typically do not rotate with respect to one another in this configuration.

Figure 10P:
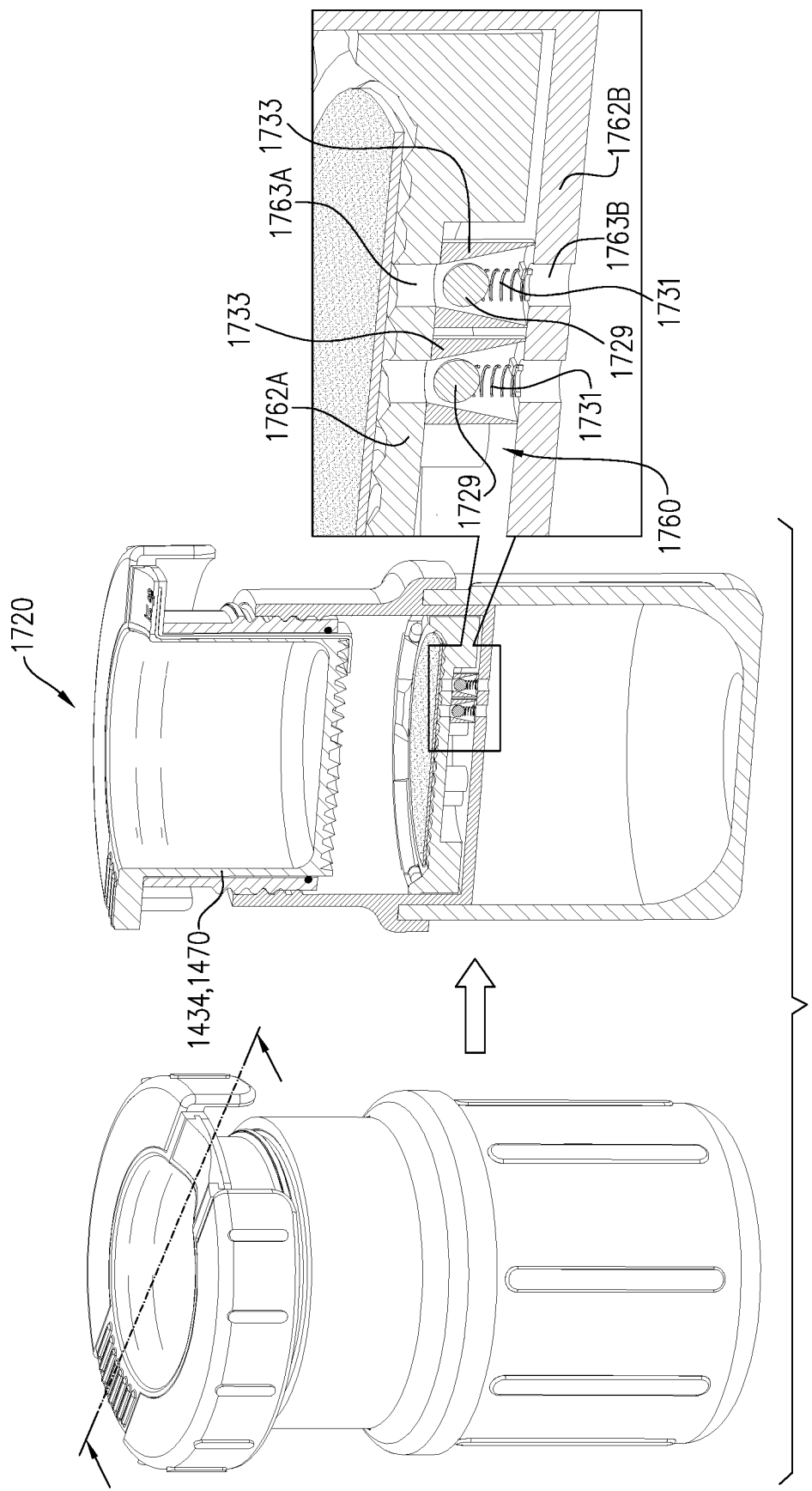

Reference is now made to FIGS. 10P-Q, which are schematic illustrations of a testing device 1720 for testing for presence of particulate in liquid 22, in accordance with an application of the present invention. Other than as described below, testing device 1720 is similar to testing devices 1420, 1520, and 1620 described hereinabove with reference to FIGS. 10D-K, FIGS. 10L-M, and FIGS. 10N-O, respectively, and may implement any of the features thereof, mutatis mutandis. Testing device 1720 comprises one or more compressible spacers 1733, which hold slightly separated discs 1762A and 1762B of one or more non-pressure-activated valves 1760 of testing device 1720, thereby creating a fluid flow path through the openings of the discs, as shown in FIG. 10P, by holding the discs at a sufficient distance from each other such that one or more plugs 1729 (e.g., spherical plugs) do not plug openings 1763A of upper disc 1762A. The downstream advancing of the plunger pushes upper disc 1762A downstream and thus the discs together (and compresses the compressible spacers 1733), as shown in FIG. 10Q, thereby causing the one or more plugs 1729 to block openings 1763A. One or more springs 1731 may be provided to push the one ore more plugs 1729 against openings 1763A. Alternatively, a spring similar to spring 1521 of testing device 1520 may be provided instead of or in addition to compressible spacers 1733. The discs typically do not rotate with respect to one another in this configuration.

Reference is now made to FIGS. 11A-E, which are schematic illustrations of testing device 20 further comprising one or more heating elements 1000, in accordance with respective applications of the present invention. Although these configurations are illustrated with respect to testing device 20, they may also be combined with the other testing devices described herein, mutatis mutandis. These configurations enable incubation of liquid 22 within testing device 20.

In these configurations, testing device 20 further comprises one or more heating elements 1000 that are configured to heat filter 32 and/or liquid 22 in liquid container 30 at a generally constant temperature, typically in the range of 20 and 50 degrees C., such as in the range of 30 to 40 degrees C. It is noted that the temperature is considered "generally constant" even if the temperature varies somewhat, such as because of cycling on and off of the one or more heating elements 1000.

Heating elements 1000 may comprise, for example, electrical heating elements or chemical heating elements (e.g., a heating bag). For applications in which heating elements 1000 are electrical, they are coupled in electrical communication with a power supply 1002, such as an external power supply (e.g., the power grid) or an external or internal battery. For example, the coupling may be done using a conventional electrical plug or USB interface. For some applications, testing device comprises control circuitry 1004 and a heat sensor 1006 (e.g., a thermocouple or other thermostat), and control circuitry 1004 is configured to drive heating elements 1000 responsively to a temperature sensed using heat sensor 1006 in order to maintain the generally constant temperature mentioned above.

Figure 11A:
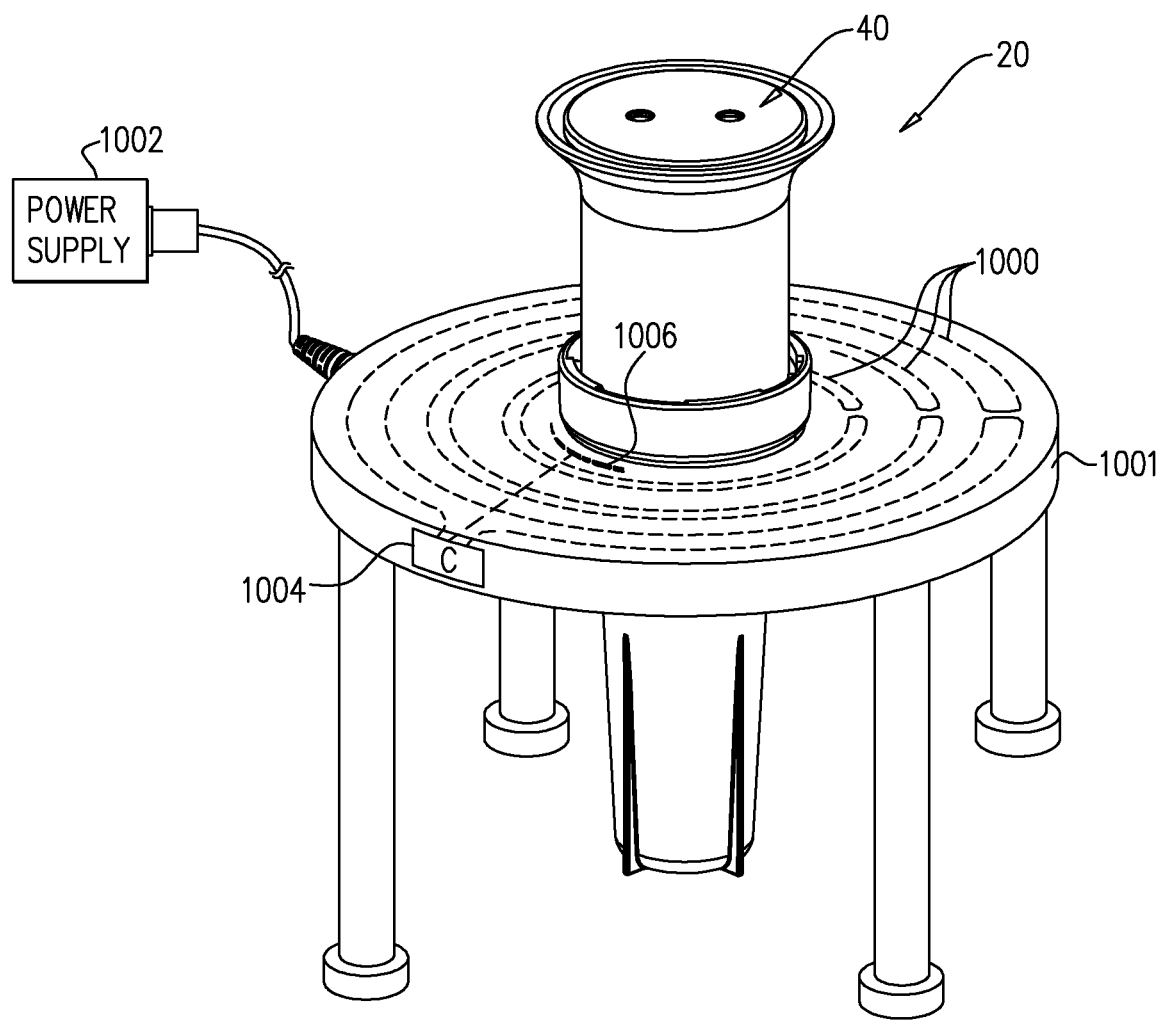
FIGS. 11A-E are schematic illustrations of the testing device of FIGS. 1A-H further comprising one or more heating elements, in accordance with respective applications of the present invention.

For some applications, heating elements 1000 are disposed external to main body of testing device 20, such as supported by a stand 1001, such as shown in FIG. 11A.

Figure 11B:
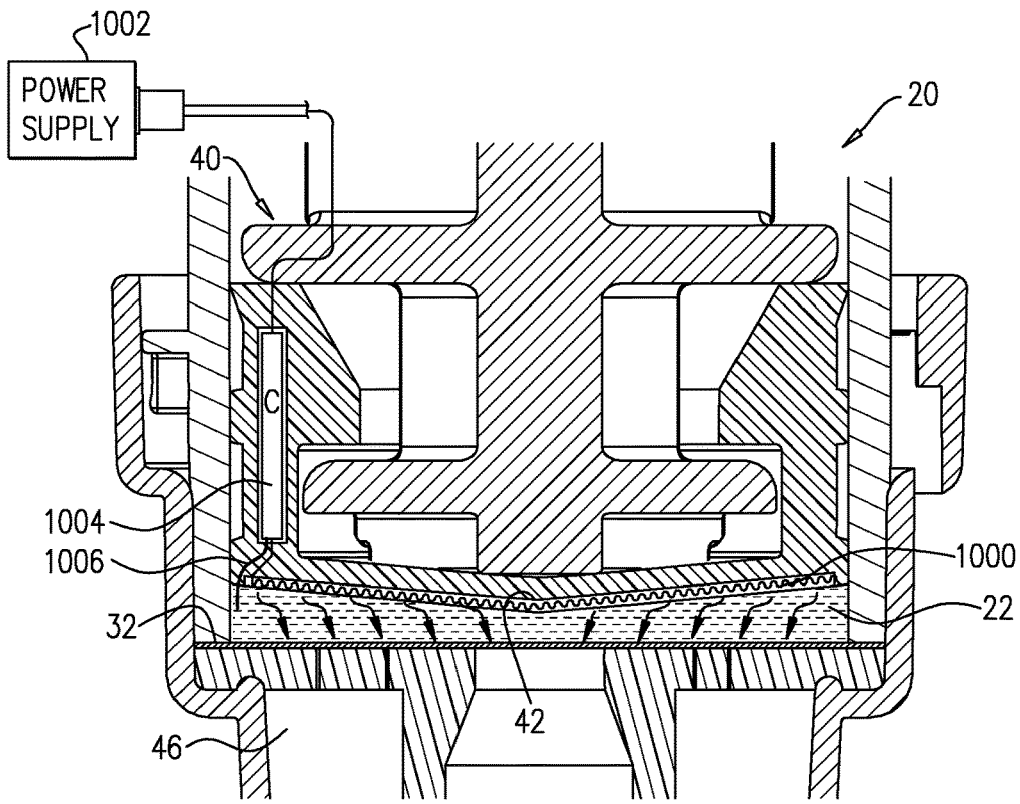

For other applications, such as shown in FIG. 11B, in which liquid-pressure source 34 comprises plunger 40 that comprises plunger head 42 that is shaped so as to be insertable into liquid container 30, such as described hereinabove, the one or more heating elements 1000 are disposed in the plunger 40, such as in plunger head 42, e.g., separated from the distal end of the plunger head by a layer of material such that liquid 22 does not interfere with the electrical current.

Figure 11C:
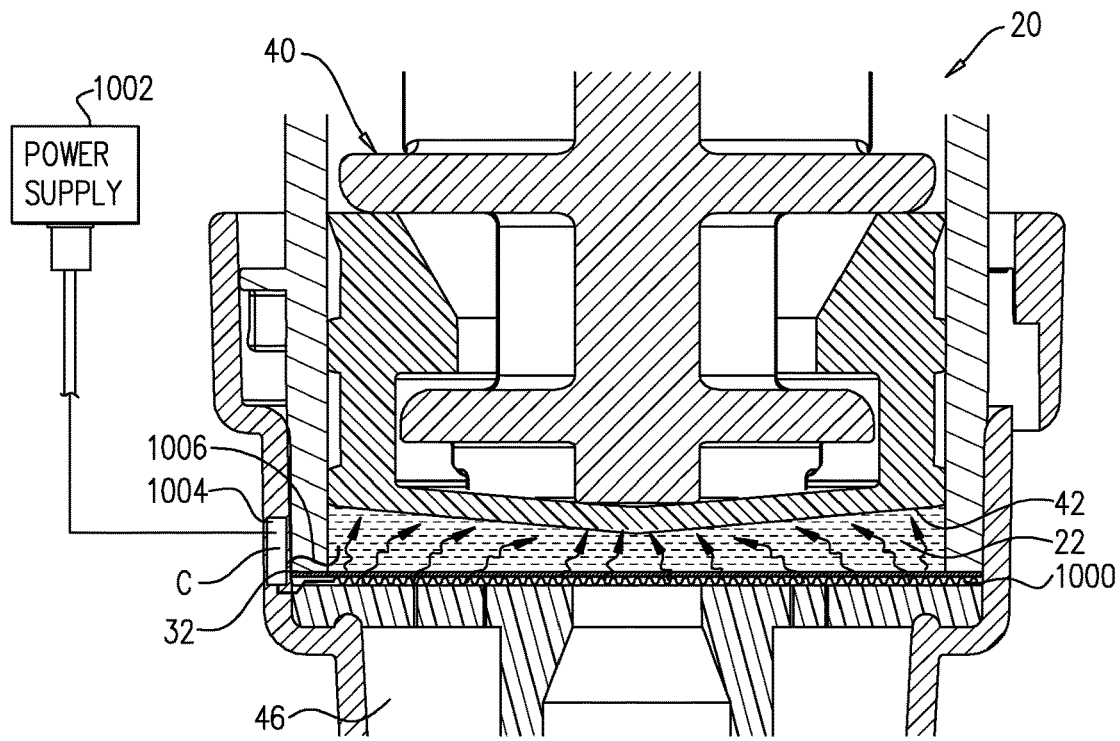

For still other applications, such as shown in FIG. 11C, the one or more heating elements 1000 are disposed downstream of filter 32 (as shown) or upstream of filter 32 (configuration not shown).

Figure 11D:
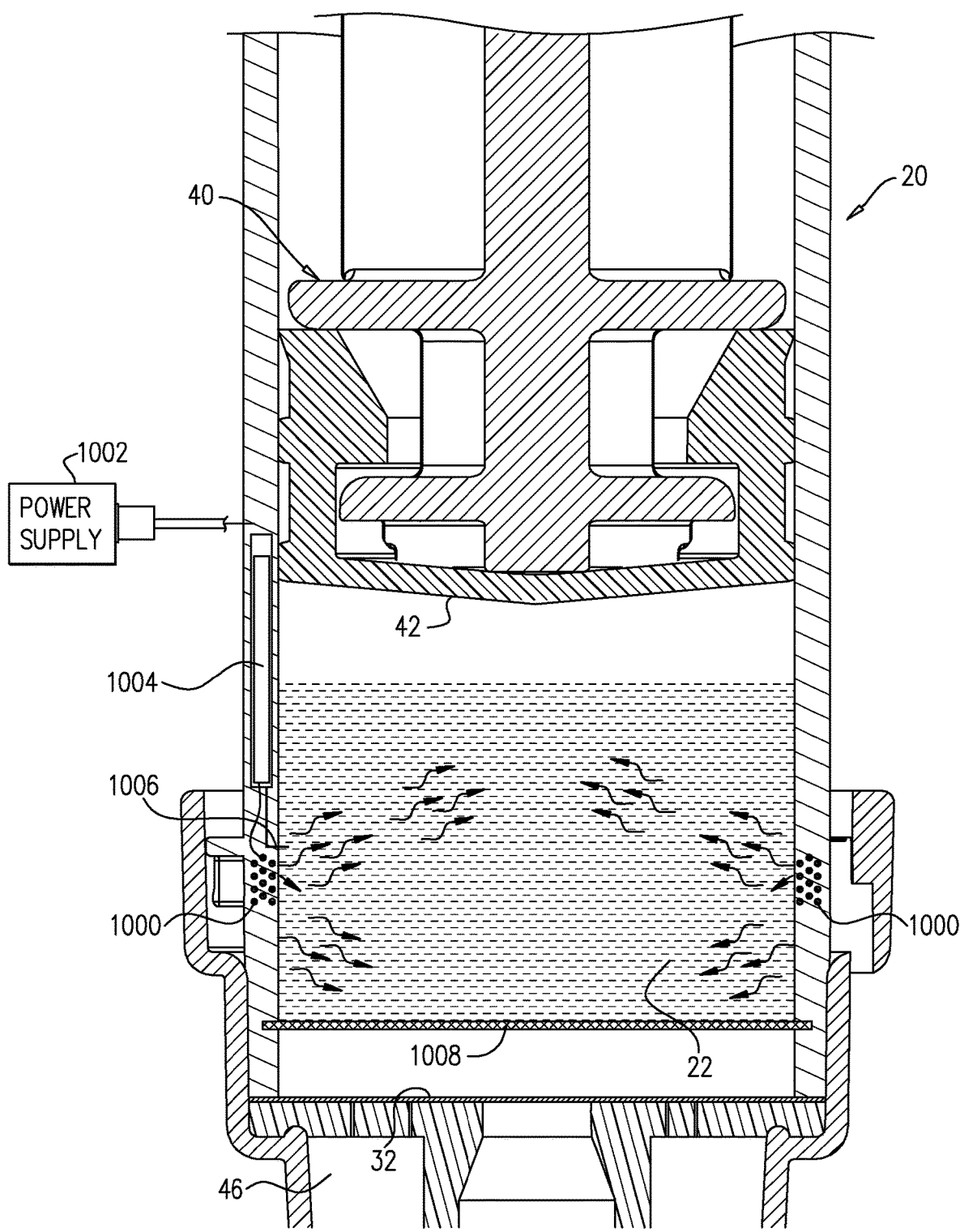
Figure 11E:
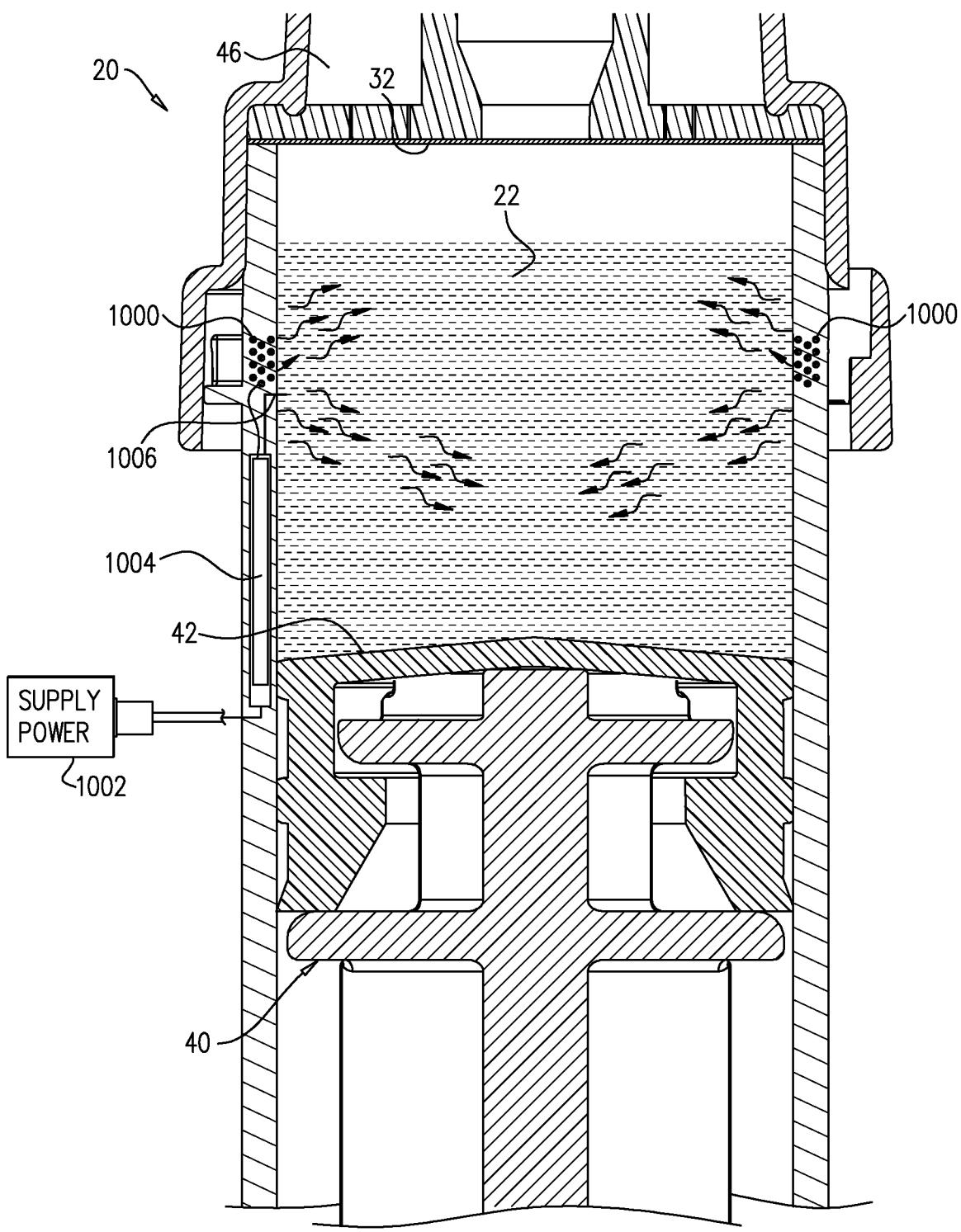

For other applications, such as shown in FIGS. 11D-E, the one or more heating elements 1000 are disposed around liquid container 30.

For some applications, the one or more heating elements 1000 are configured to heat filter 32 and/or liquid 22 in liquid container 30 after most or nearly all (e.g., at least 90%) of liquid 22 has been driven out of liquid container 30 and the particulate has been trapped by filter 32, such as shown in FIGS. 11B and 11C (the configuration shown in FIG. 11D can alternatively be used with the plunger pushed farther down than illustrated, and the configuration shown in FIG. 11A can also be used). Typically, growth medium 87 (e.g., Todd Hewitt broth or tryptic soy broth) is placed in testing device 20 (e.g., in liquid container 30, filter 32, or the distal downstream surface of plunger head 42) before the heating is performed, in order to incubate the particulate in liquid 22 and/or filter 32. For example, such heating may allow a rapid test (e.g., a rapid strep test) to be performed after incubation of the particulate trapped by the filter 32, for example for between 1 and 24 hours, in order to achieve more accurate results. Optionally, growth medium 87 has the properties of the high-concentration liquid growth medium described in detail hereinbelow.

For other applications, the one or more heating elements 1000 are configured to heat filter 32 and/or liquid 22 in liquid container 30 while most (e.g., at least 90%) or all of liquid 22 remains in liquid container 30 before being driven out of liquid container 30 and through filter 32, e.g., by pushing with plunger head 42, such as shown in FIGS. 11D and 11E (the configurations shown in FIGS. 11B and 11C can also be used with plunger pushed down less than illustrated, and the configuration shown in FIG. 11A can also be used). Typically, growth medium 87 (e.g., Todd Hewitt broth or tryptic soy broth) is placed in testing device 20 (e.g., in liquid container 30, filter 32, or the distal downstream surface of plunger head 42) before the heating is performed, in order to incubate the particulate in liquid 22. Thereafter, after waiting, for example for between 1 and 24 hours, liquid 22 is driven through filter 32, and the filter is tested for particulate, for example using a rapid test (e.g., a rapid strep test) performed within or outside of testing device 20. Such incubation may achieve more accurate results. Optionally, growth medium 87 has the properties of the high-concentration liquid growth medium described in detail hereinbelow.

Depending on the characteristics of the particular type of filter 32 used, the filter may be damaged (e.g., degraded) by immersion in heated liquid 22 for 1 to 24 hours. Therefore, in order to prevent such possible damage, testing device 20 may be oriented with filter 32 above liquid 22 and liquid-pressure source 34 (e.g., plunger 40) below filter 32, such that liquid 22 is not in contact with filter 32 during the heating, such as shown in FIG. 11E. Other configurations may also be used, such the configuration shown in FIG. 11A or FIG. 11B, mutatis mutandis.

Alternatively, in order to prevent the above-mentioned possible damage, for some applications, such as shown in FIG. 11D, liquid container 30 comprises a frangible dividing waterproof or water-resistant membrane 1008 upstream of filter 32 (e.g., spaced at least 1 mm, such as at least 3 mm, at least 5 mm, or at least 10 mm, from the filter), which isolates filter 32 from liquid 22 in liquid container 30. For some applications, membrane 1008 is elastic, which among other things, may allow insertion of plunger head 42 into liquid container 30. After completion of incubation, pushing plunger 40 causes the plunger to break (e.g., tear) membrane 1008 and allow liquid 22 to come in contact with filter 32 for passage therethrough. Other configurations may also be used, such the configuration shown in FIG. 11A, mutatis mutandis.

Figure 12:
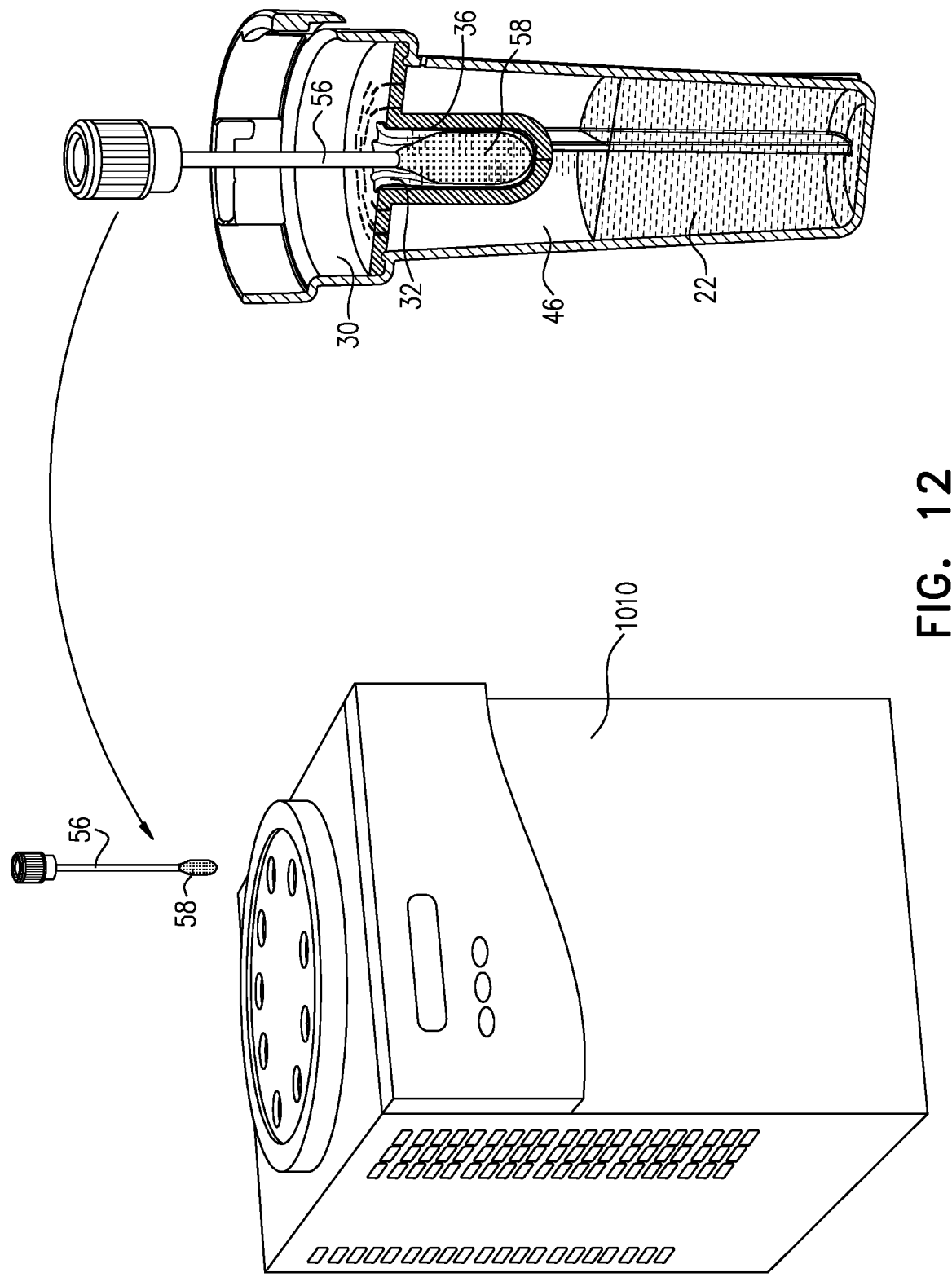
FIG. 12 is a schematic illustration of a method for performing a test, in accordance with an application of the present invention.

Reference is now made to FIG. 12, which is a schematic illustration of a method for performing a test, e.g., a backup strep test, in accordance with an application of the present invention. A sample is taken from filter 32 (either from a surface of the filter or of the filter itself, such as a small part of the filter), e.g., using elongate member 56 (e.g., swab 58 thereof), such as described hereinabove with reference to FIGS. 1E-F. The sample is analyzed using an external analysis device 1010, such as a nucleic acid amplification RST technique, such as isothermal amplification, e.g., using Alere™ i (Abbott Laboratories, Waltham, Mass., USA), or real-time quantitative polymerase chain reaction (qPCR) assaying, typically without first incubating the sample. Alternatively, the sample is incubated (either before placing the sample in external analysis device 1010 or inside device 1010 by device 1010) and external analysis device 1010 tests the sample using a technique such as lateral flow immunoassaying, an ELISA-based RST, an antibody-coated-beads-based RST, a nucleic-acid-based RST, or a fluorescent immunoassaying (FIA).

Figure 13A:
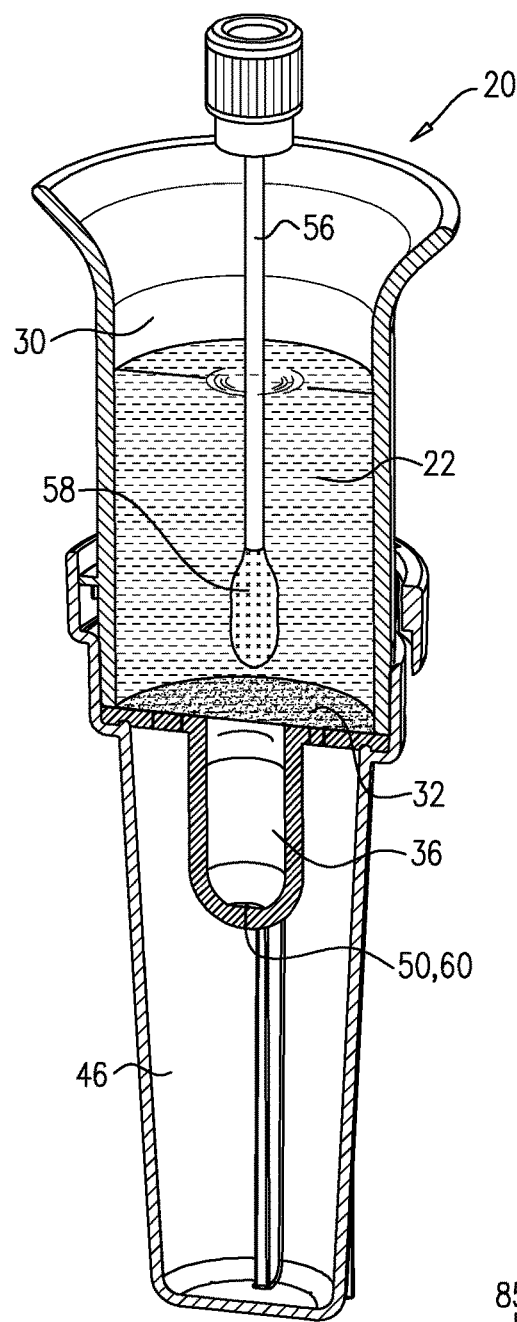
FIGS. 13A-B are schematic illustrations of a method for performing a backup test, in accordance with an application of the present invention.
Figure 13B:
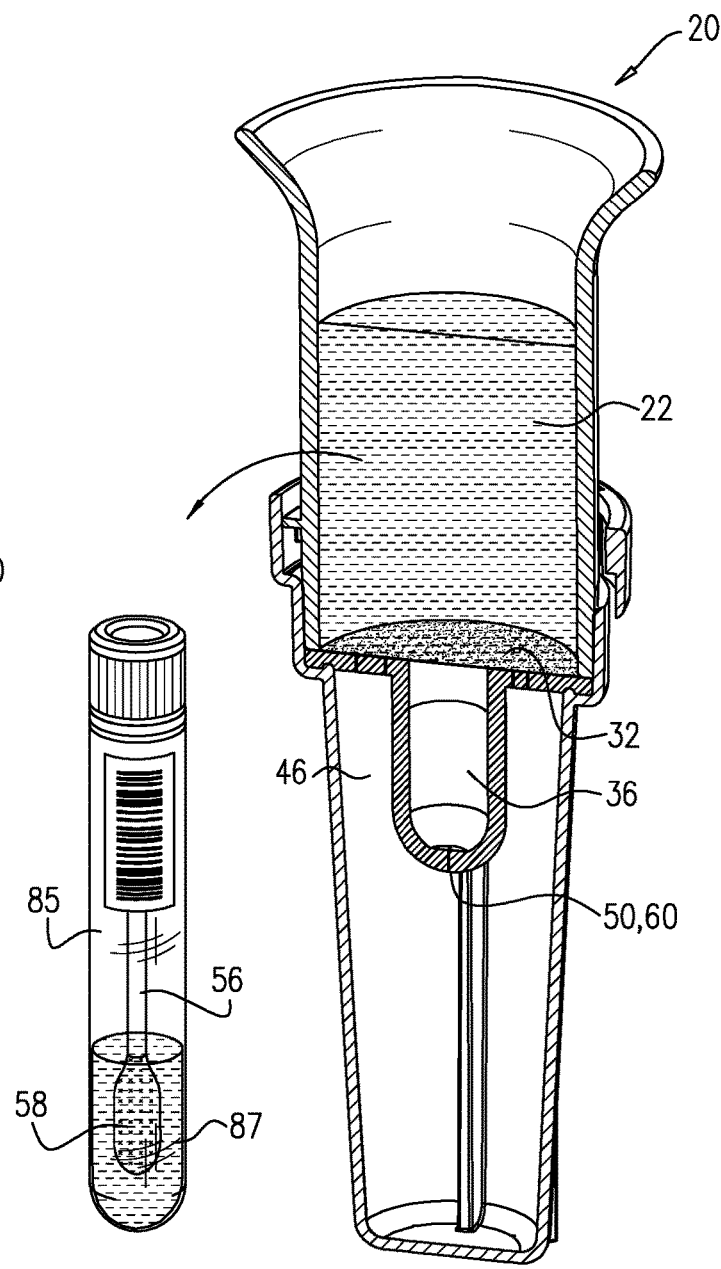
Figure 13C:
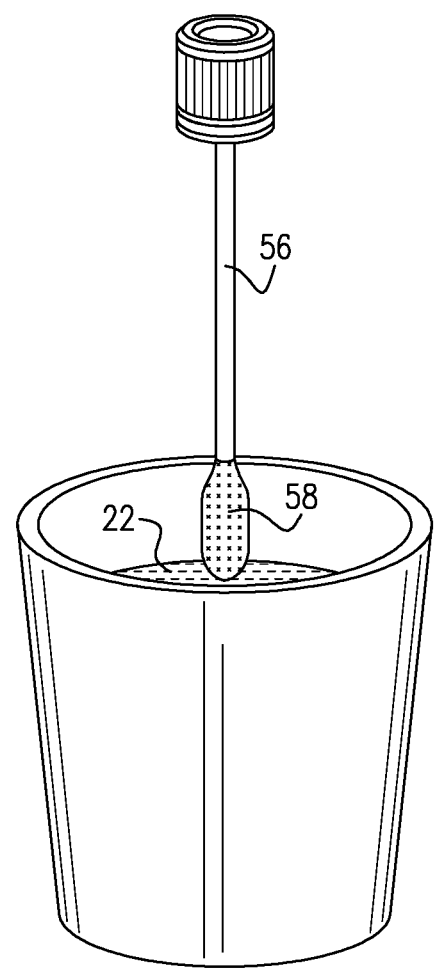
FIG. 13C is a schematic illustration of another method for performing a backup test, in accordance with an application of the present invention.

Reference is now made to FIGS. 13A-C, which are schematic illustrations of methods for performing a backup test, e.g., a backup strep test, in accordance with respective applications of the present invention. Although these configurations are illustrated with respect to testing device 20, they may also be combined with the other testing devices described herein, mutatis mutandis. Prior to liquid 22 being passed through filter 32, some of liquid 22, e.g., gargled fluid or saliva not swabbed from the patient's throat, is removed as a sample for a backup test. FIG. 13A shows an absorbent element, e.g., a swab 58, e.g., a flocked swab, a cotton swab, or a polyester swab, being inserted into liquid 22 and then placed into test tube 85 containing growth medium 87. For some applications, liquid 22, or a portion of liquid 22, is transferred into the container, e.g., test tube 85, by other means, such as for example, pouring, using a syringe, using a pipette, or a pump. Growth medium 87 may be a liquid growth medium, a dehydrated growth medium, or a gel growth medium. Optionally, growth medium 87 has the properties of the high-concentration liquid growth medium described in detail hereinbelow. Typically, test tube 85 does not contain agar.

Figure 13D:
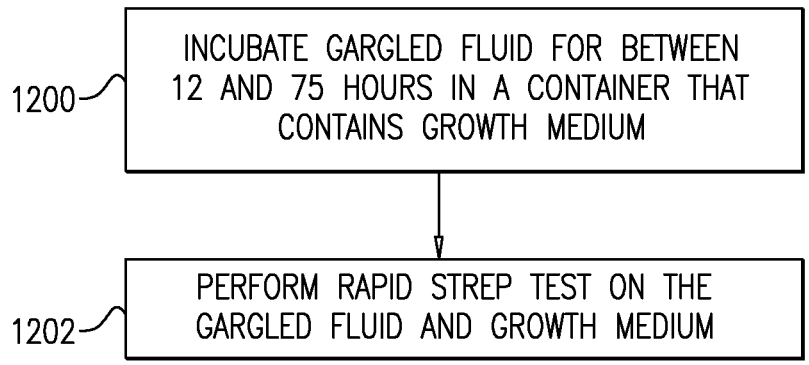
FIG. 13D is a flowchart depicting a method for performing a backup strep test using rapid strep test (RST) techniques on gargled fluid after incubation, in accordance with some applications of the present invention.

Reference is now made to FIG. 13D, which is a flowchart depicting a method for performing a backup strep test using rapid strep test (RST) techniques on gargled fluid after incubation, in accordance with some applications of the present invention. Examples of the method of FIG. 13D are provided in the experimental data set forth hereinbelow in the section entitled, "Measuring Group A Beta-Hemolytic Streptococcus Bacteria in Throat Gargle: Results of Overnight Growth in Liquid Media, Assayed by Rapid Strep Test." In step 1200 the gargled fluid is incubated for at least 12 hours and/or less than 75 hours in a container, e.g., test tube 85, that contains a liquid growth medium, a dehydrated growth medium, or a gel growth medium. As illustrated by the experimental data, the total volume of gargled fluid and growth medium is typically at least 0.45 ml and/or less than 3.6 ml. In some applications, the gargled fluid is mixed with the growth medium before incubation. Typically, the container containing the growth medium does not contain agar.

In step 1202, after incubation, an RST, e.g., a lateral flow test, is performed on the mixture of gargled fluid and growth medium. For some applications, the RST may be one of the following: an ELISA-based RST, an antibody-coated-beads-based RST, a nucleic-acid-based RST, and a fluorescent immunoassaying (FIA) RST. As supported by the experimental data set forth hereinbelow in the section entitled, "Measuring Group A Beta-Hemolytic Streptococcus Bacteria in Throat Gargle: Results of Overnight Growth in Liquid Media, Assayed by Rapid Strep Test,", a number of methods used for performing the RST yield usable results, as follows:

RST is performed on the mixture of gargled fluid and growth medium while the gargled fluid and growth medium are in the container. This method of RST is referred to as "whole tube RST" in the experimental data.

At least a portion, e.g., at least 0.05 ml, e.g., 0.1 ml, of the mixture of gargled fluid and growth medium is transferred to another container, and the RST is performed on the portion of the gargled fluid and growth medium in the other container. This method of RST is referred to as "sample RST" in the experimental data. For some applications, the portion of the mixture is transferred by inserting an absorbent element, e.g., a swab, e.g., a flocked, cotton, or polyester swab, into the mixture of gargled fluid and growth medium and then placing the swab into the other container. Alternatively, if an absorbent element, e.g., a swab, was used to transfer liquid 22, e.g., the gargled fluid, into the container with growth medium, then that same absorbent element, e.g., swab may be removed and used to transfer the portion of the mixture into the other container for "sample RST." For some applications, the portion of the mixture is transferred into the container, e.g., test tube 85, by other means, such as for example, pouring, using a syringe, using a pipette, or a pump.

At least a portion of the mixture of gargled fluid and growth medium, after incubation, is filtered, e.g., passed through a filtration membrane (optionally, using any of the filtering devices described herein), and the RST is performed on the filter. This method of RST is referred to as "filter RST" in the experimental data.

Results of a clinical trial performed by the inventors, including twenty-eight patients, are shown in Tables 1A-1D of FIGS. 19A-D, respectively, of the experimental data set forth hereinbelow in the section entitled, "Measuring Group A Beta-Hemolytic Streptococcus Bacteria in Throat Gargle: Results of Overnight Growth in Liquid Media, Assayed by Rapid Strep Test." Gargled fluid was collected from each of the 28 patients and tested using "whole tube RST" and/or "filter RST" after incubation for at least 21 hours and/or less than 25 hours (further details regarding parameters of the tested systems are set forth in the experimental data). As shown in Tables 1A-1D, 19 systems yielded true positive RST results, which corresponded to 19 of the patients who were clinically positive for GAS pharyngitis (true positive), and nine systems yielded true negative results, which corresponded to nine patients who were clinically negative for GAS pharyngitis (true negative). See Table 2 of FIG. 20 in the experimental data for parameters from 78 additional experimental systems that yielded true positive RST results. These additional experimental systems each contained either (a) gargled fluid which was spiked with Group A Streptococcal ("GAS") bacteria, or (b) a GAS bacteria suspension in a pure buffer.

Figure 13E:
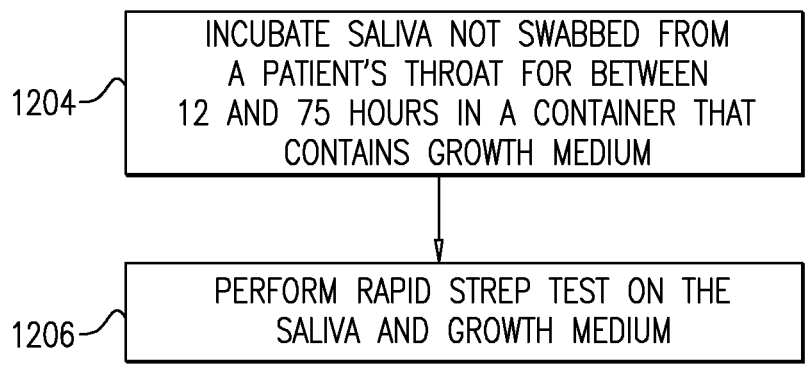
FIG. 13E is a flowchart depicting a method for performing a backup strep test using rapid strep test (RST) techniques on saliva not swabbed from a patient's throat after incubation, in accordance with some applications of the present invention.

Reference is now made to FIG. 13E, which is a flowchart depicting a method for performing a backup strep test using rapid strep test (RST) techniques on saliva not swabbed from a patient's throat after incubation, in accordance with some applications of the present invention. Examples of this method are provided in the experimental data set forth hereinbelow in the section entitled, "Measuring Group A Beta-Hemolytic Streptococcus Bacteria in Saliva Sample: Results of Overnight Growth in Liquid Media, Assayed by Rapid Strep Test." In step 1204 the saliva swab is incubated for at least 12 hours and/or less than 75 hours in a container, e.g., test tube 85, that contains a liquid growth medium, a dehydrated growth medium, or a gel growth medium. In some applications, the saliva is mixed with the growth medium before incubation. Typically, the container containing the growth medium does not contain agar. For some applications, the patient sucks on the swab, or the swab is rubbed on the patient's tongue and/or cheek. In this manner, the saliva is received on the swab, e.g., a flocked swab, a cotton swab, or a polyester swab, from the patient's mouth, and the swab is then placed directly into the container that contains the growth medium. Alternatively, the patient spits saliva into the container.

In step 1206, after incubation, an RST, e.g., a lateral flow test, is performed on the mixture of saliva and growth medium. For some applications, the RST may be one of the following: an ELISA-based RST, an antibody-coated-beads-based RST, a nucleic-acid-based RST, and a fluorescent immunoassaying (FIA) RST. As supported by the experimental data set forth hereinbelow in the section entitled, "Measuring Group A Beta-Hemolytic Streptococcus Bacteria in Saliva Sample: Results of Overnight Growth in Liquid Media, Assayed by Rapid Strep Test," and similarly to as described hereinabove with reference to FIG. 13D, a number of methods were used for performing the RST, as follows:

"Whole tube RST," as described hereinabove, mutatis mutandis.

"Sample RST," as described hereinabove, mutatis mutandis.

"Filter RST," as described hereinabove, mutatis mutandis.

After incubation, at least a portion of the mixture of saliva and growth medium is transferred to another container by removing the swab from the container containing the growth medium and placing the swab into the other container, and the RST is performed on the swab in the other container. This method of RST is referred to as "swab RST" in the experimental data.

In a clinical trial performed by the inventors, 28 patients were asked to suck on a flocked swab for about ten seconds. The saliva swabs were then inoculated onto blood plates, and beta-hemolytic colonies were counted using a light table. As illustrated by Table 5 of FIG. 23 in the experimental data set forth hereinbelow in the section entitled, "Measuring Group A Beta-Hemolytic Streptococcus Bacteria in Saliva Sample: Results of Overnight Growth in Liquid Media, Assayed by Rapid Strep Test," 18 out of 19 (94.7%) saliva swabs from subjects who were clinically positive for GAS pharyngitis were found to contain a number of colony-forming units (CFUs) of GAS ranging from four to "too numerous to count." A false negative was obtained for 1 of the 19 saliva swabs.

As illustrated by the experimental data, experiments were also carried out by the inventors using saliva swab simulations by dipping swabs into pure GAS bacteria suspensions (referred to as "saliva swab simulation 1" in the experimental data) or into gargled fluid that was spiked with GAS bacteria (referred to as "saliva swab simulation 2" in the experimental data). The data presented in Table 7 of FIG. 25 represent an experiment using "saliva swab simulation 1" which compared the total absorbance plus elution of GAS bacteria onto a plate from three different swab materials: cotton, polyester, and flocked. The flocked swabs appear to have the highest absorption plus elution efficiency, however the cotton and polyester swabs provide useful results as well. The data presented in Table 8 of FIG. 26 represent an experiment using "saliva swab simulation 2" showing that flocked swabs may be used as an efficient way of transferring liquid, e.g., saliva, or gargled fluid, into the culture medium.

Almost all saliva swab clinical samples which were inoculated into Todd Hewitt (TH) broth and assayed by backup methods using RST methods yielded either true positive or true negative results for all subjects enrolled in phase 2 of the Proof of Concept Clinical Trial, seen in Table 9 of FIG. 27. The data presented in Table 9 describe Clinical Trial saliva swabs that were incubated in TH culture broth and were then assayed using backup test methods performed using RST methods. The Filter RST method had a sensitivity of 90% and the Swab RST method had a sensitivity of 80%.

Figure 14A:
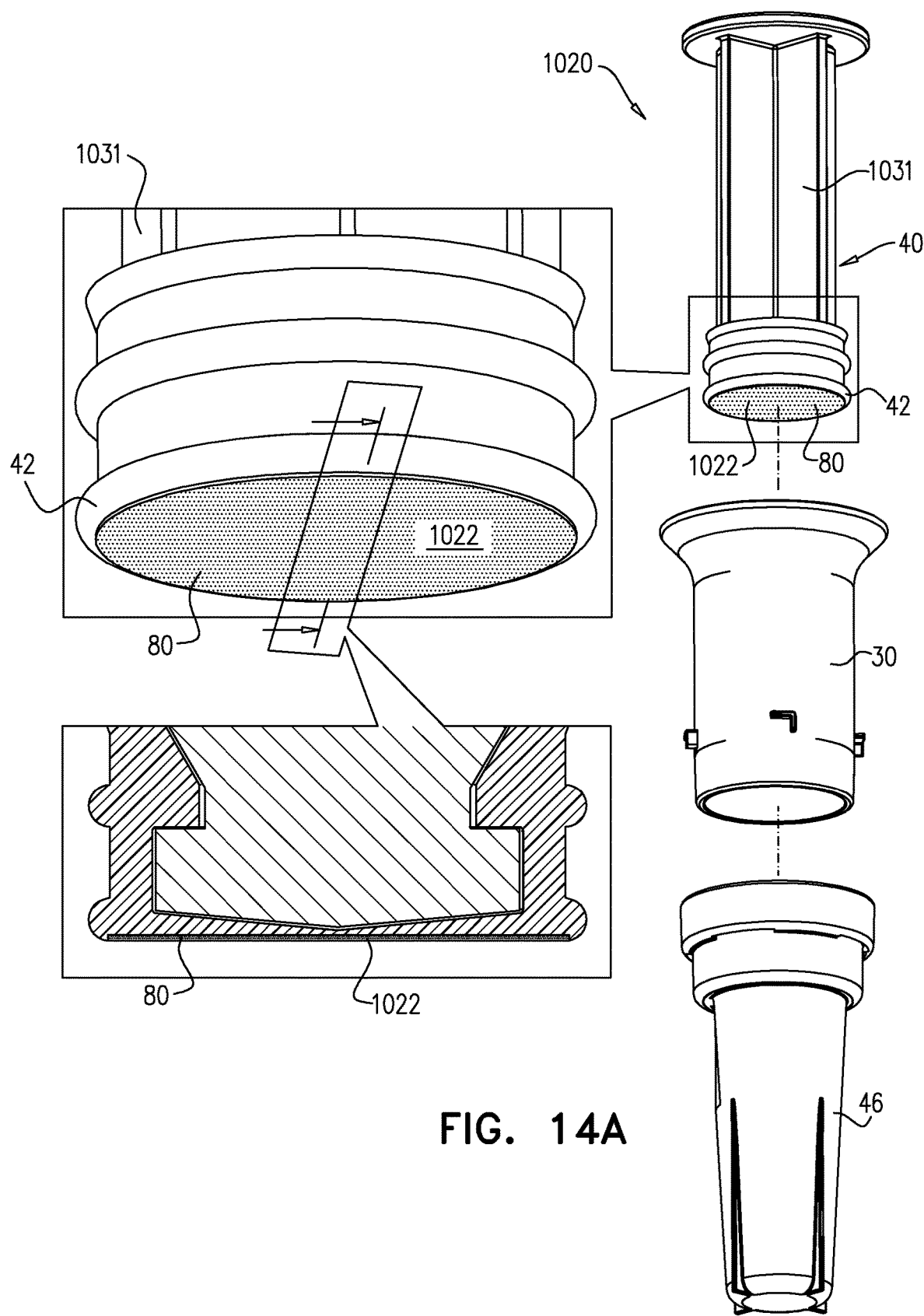
FIGS. 14A-C are schematic illustrations of another testing device for testing for presence of particulate in a liquid, in accordance with an application of the present invention.
Figure 14C:
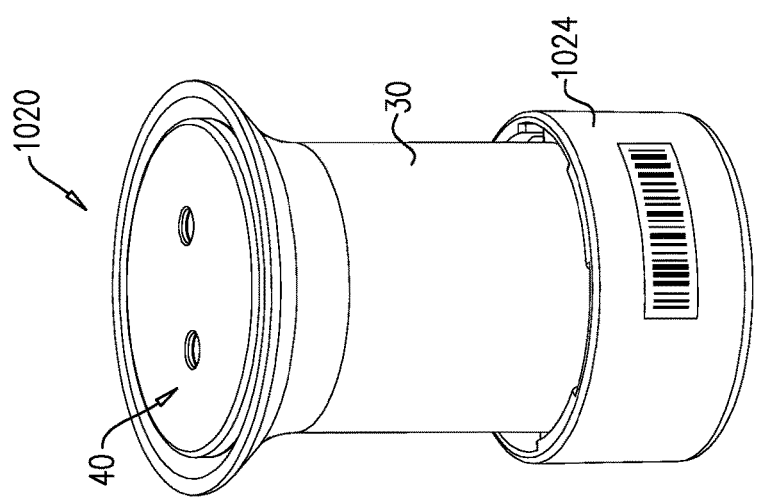
Figure 14B:
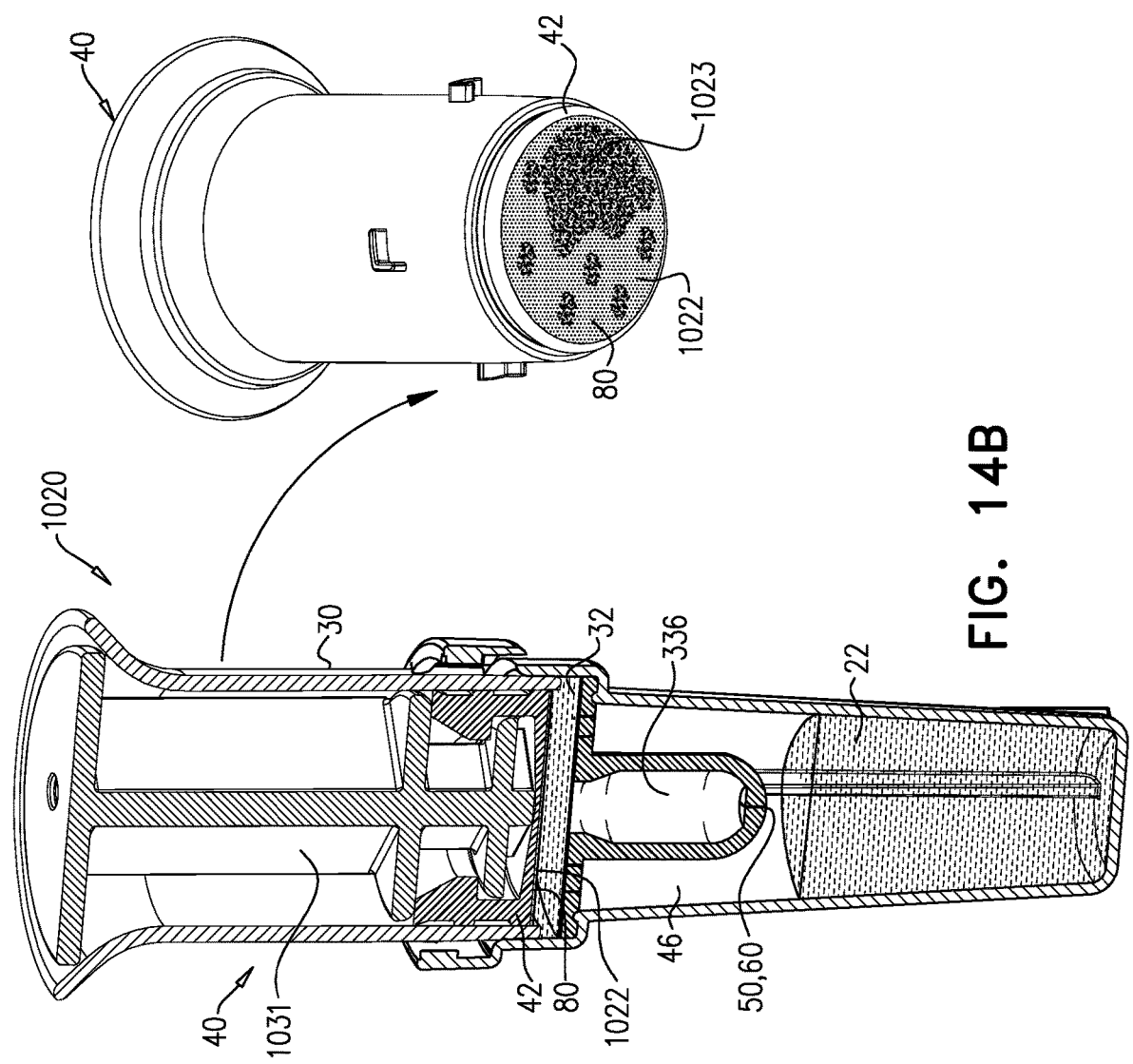

Reference is now made to FIGS. 14A-C, which are schematic illustrations of a testing device 1020 for testing for presence of particulate in liquid 22, in accordance with an application of the present invention. Although testing device 1020 is illustrated as being similar to testing device 20 described hereinabove with reference to FIGS. 1A-H, the techniques of testing device 1020 may also be combined with the other testing devices described herein, mutatis mutandis.

Testing device 1020 comprises:
liquid container 30 for containing liquid 22;
filter 32, disposed in or downstream of liquid container 30; and
plunger head 42, which (a) is shaped so as to be insertable into liquid container 30, (b) is configured to apply pressure to drive liquid 22 from liquid container 30 through filter 32, and (c) has downstream surface 80.

Downstream surface 80 is at least partially coated with a solid (e.g., dehydrated and/or powdered) or semi-solid (e.g., gel and/or paste) growth medium 1022. For example, growth medium 1022 may comprise agar.

For some applications, a cap 1024 is provided that is configured to be coupled to and fully cover growth medium 1022 on downstream surface 80 of plunger head 42. For example, cap 1024 may be transparent to enable observation of the culture on downstream surface 80 without removing the cap.

Typically, plunger head 42 is shaped so as to be insertable into liquid container 30 so as to form a movable seal with a wall of liquid container 30. For some applications, testing device 1020 further comprises a plunger shaft 1031, and plunger head 42 is disposed at a downstream end portion of plunger shaft 1031. Plunger 40 (including plunger head 42 and plunger shaft 1031) may implement any of the configures of plunger 40 described hereinabove with reference to FIGS. 1A-H. For some applications, an area of downstream surface 80 of plunger head 42 is between 0.3 and 100 cm2, such as between 0.3 and 30 cm2. For some applications, testing device 1020 further comprises waste liquid receptacle 46, coupled to liquid container 30 downstream of filter 32.

For some applications, a method for using testing device 1020 comprises:
- pushing plunger head 42 to apply pressure to drive liquid 22 from liquid container 30 through filter 32;
- touching downstream surface 80 of plunger head 42 to filter 32; particulate 1023, such as bacteria, on filter 32 are captured by growth medium 1022 on downstream surface 80; and
- assessing downstream surface 80 of plunger head 42 for biological growth.

Typically, downstream surface 80 is placed directly in an incubator before assessing, thereby obviating the need to use another device to take a backup sample and plate it onto agar. Downstream surface 80 is optionally accessed by decoupling upstream component 70 from downstream component 72, such as described hereinabove with reference to FIGS. 1B-C.

For some applications, liquid 22 includes at least one substance selected from the group of substances consisting of gargled fluid, saliva not swabbed from the throat of a patient, and an incubated culture medium containing a biological sample.

For some applications, downstream surface 80 of plunger head 42 is assessed for biological growth of a biological particulate selected from the group consisting of: a microorganism, a fungus, a bacterium, a spore, a virus, a mite, a biological cell, a biological antigen, a protein, a protein antigen, and a carbohydrate antigen. For some applications, plunger head 42 is heated before downstream surface 80 of plunger head 42 is assessed for biological growth.

Figure 15A:
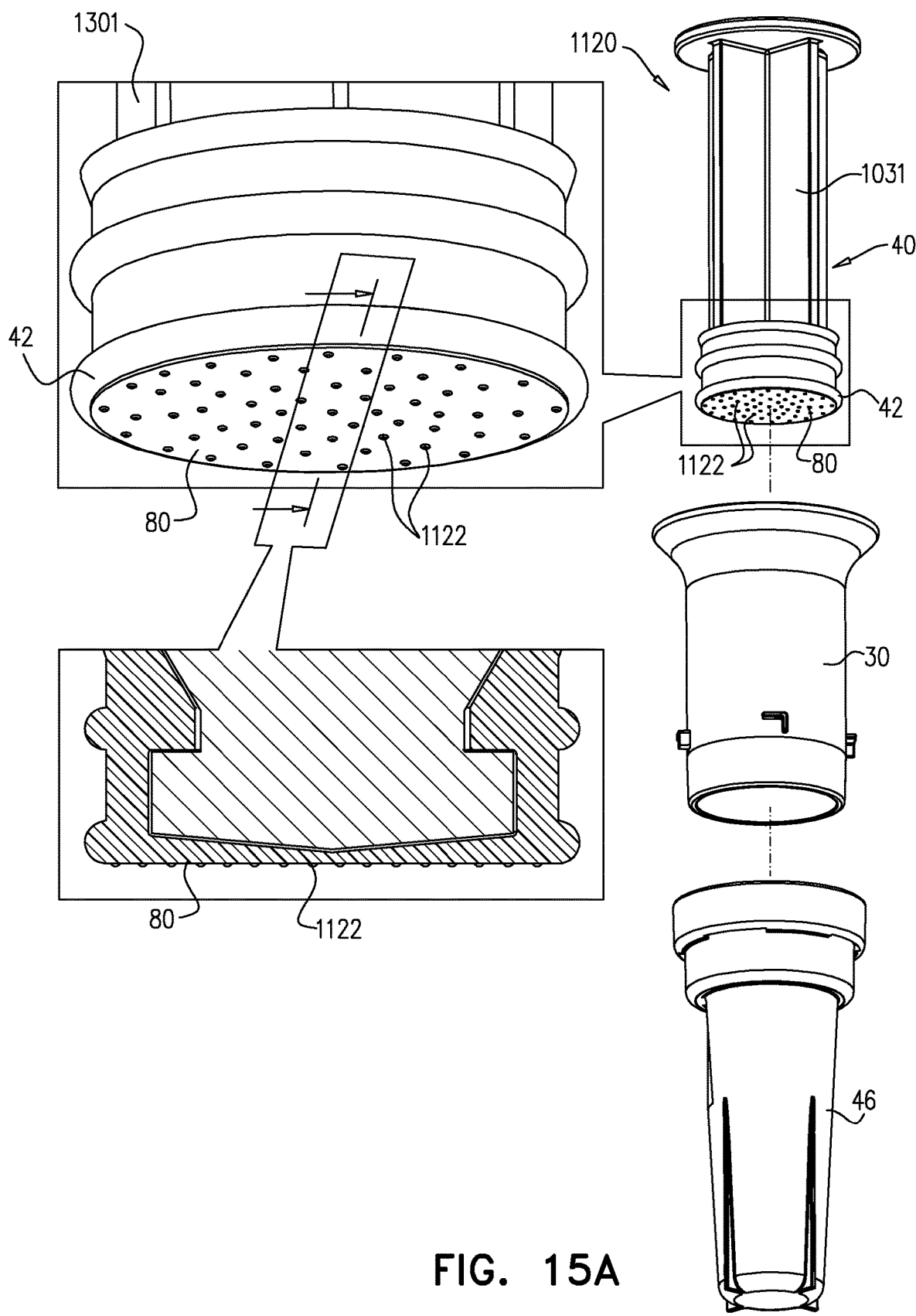
FIGS. 15A-C are schematic illustrations of a method for using the testing device of FIGS. 14A-C for testing for presence of particulate in a liquid, in accordance with an application of the present invention.
Figure 15B:
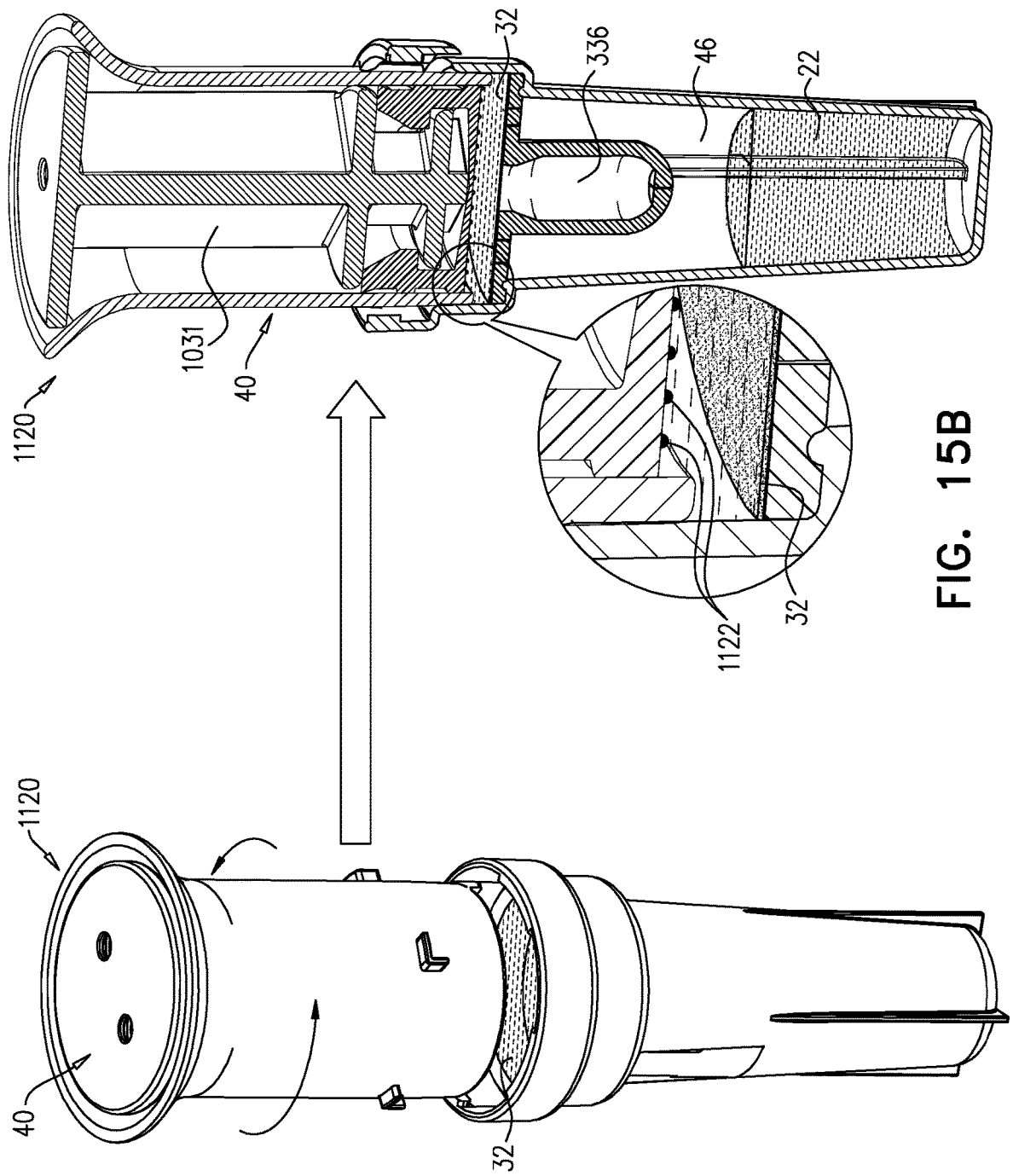
Figure 15C:
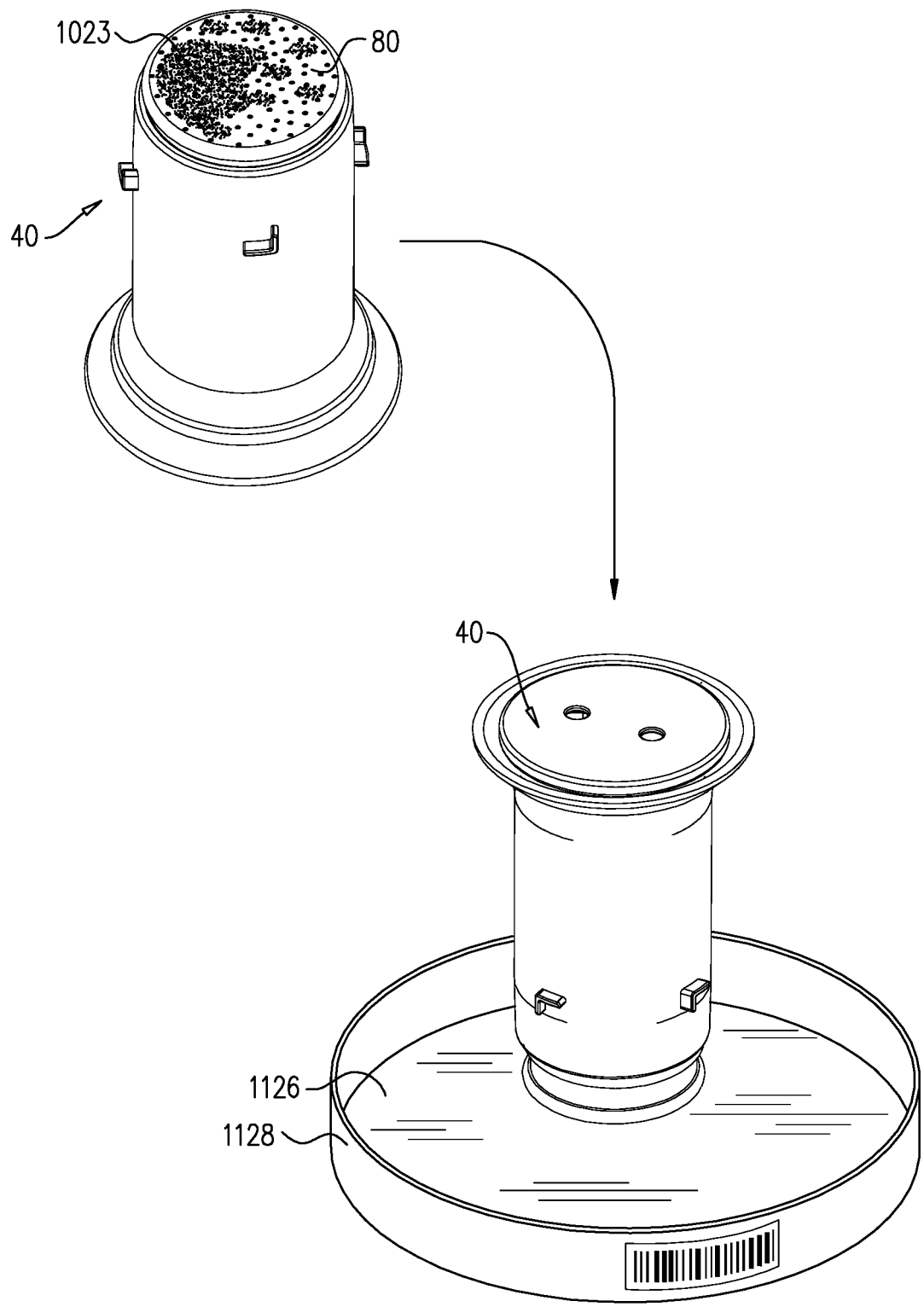

Reference is now made to FIGS. 15A-C, which are schematic illustrations of a method for using a testing device 1120 for testing for presence of particulate in liquid 22, in accordance with an application of the present invention. Although testing device 1120 is illustrated as being similar to testing device 20 described hereinabove with reference to FIGS. 1A-H, the method described with reference to testing device 1120 may also be combined with the other testing devices described herein, mutatis mutandis.

The method comprises:
- pushing plunger head 42 to apply pressure to drive liquid 22 from liquid container 30 of testing device 1120 through filter 32;
- touching downstream surface 80 of plunger head 42 to filter 32;
- thereafter, touching downstream surface 80 of plunger head 42 to culture medium 1126 contained in a culture-medium container 1128, such as a petri dish; for example, culture medium 1126 may include agar;
- heating culture-medium container 1128; and
- assessing culture-medium container 1128 for biological growth.

For some applications, liquid 22 includes at least one substance selected from the group of substances consisting of gargled fluid, saliva not swabbed from the throat of a patient, and an incubated culture medium containing a biological sample.

For some applications, culture-medium container 1128 is assessed for biological growth of a biological particulate 1023 selected from the group consisting of: a microorganism, a fungus, a bacterium, a spore, a virus, a mite, a biological cell, a biological antigen, a protein, a protein antigen, and a carbohydrate antigen.

Downstream surface 80 is optionally accessed by decoupling upstream component 70 from downstream component 72, such as described hereinabove with reference to FIGS. 1B-C.

For some applications, plunger head 42 is rotated while touching downstream surface 80 of plunger head 42 to filter 32 to increase the sample taken from filter 32, such as by macerating or grinding the filter. For applications in which downstream surface 80 is decoupled from upstream component 70 by rotation, this rotation may itself increase the sample taken from filter 32.

For some applications, downstream surface 80 of plunger head 42 is rough, i.e., is shaped so as to define many small protrusions 1122, such as like sandpaper, or with plastic protrusions, in order to collect a better sample of particulate 1023 by macerating or grinding the filter.

For some applications, touching downstream surface 80 of plunger head 42 to filter 32 comprises grinding filter 32 with rough downstream surface 80.

For some applications, the method further comprising testing, within testing device 1120, for the presence of biological particulate 1023 trapped by filter 32, such as described hereinabove. In these applications, the sample taken from downstream surface 80 of plunger head 42 is used to perform a backup test, e.g., a backup strep test, for the rapid test performed inside testing device 1120, as described hereinabove.

Reference is now made to FIGS. 16A-B, which are schematic illustrations of a testing system 1300, in accordance with an application of the present invention. Testing system 1300 comprises a testing machine 1310 and a testing device 1320 for testing for the presence of particulate in a liquid 22 (shown in FIGS. 18B-F). Testing device 1320 is configured to be removably inserted into testing machine 1310 for performing a test. Testing device 1320 may be disposable, while testing machine 1310 is typically reused many times with separate testing devices 1320. Testing device may optionally implement any of the features of the other testing devices described herein, mutatis mutandis.

Figure 17:
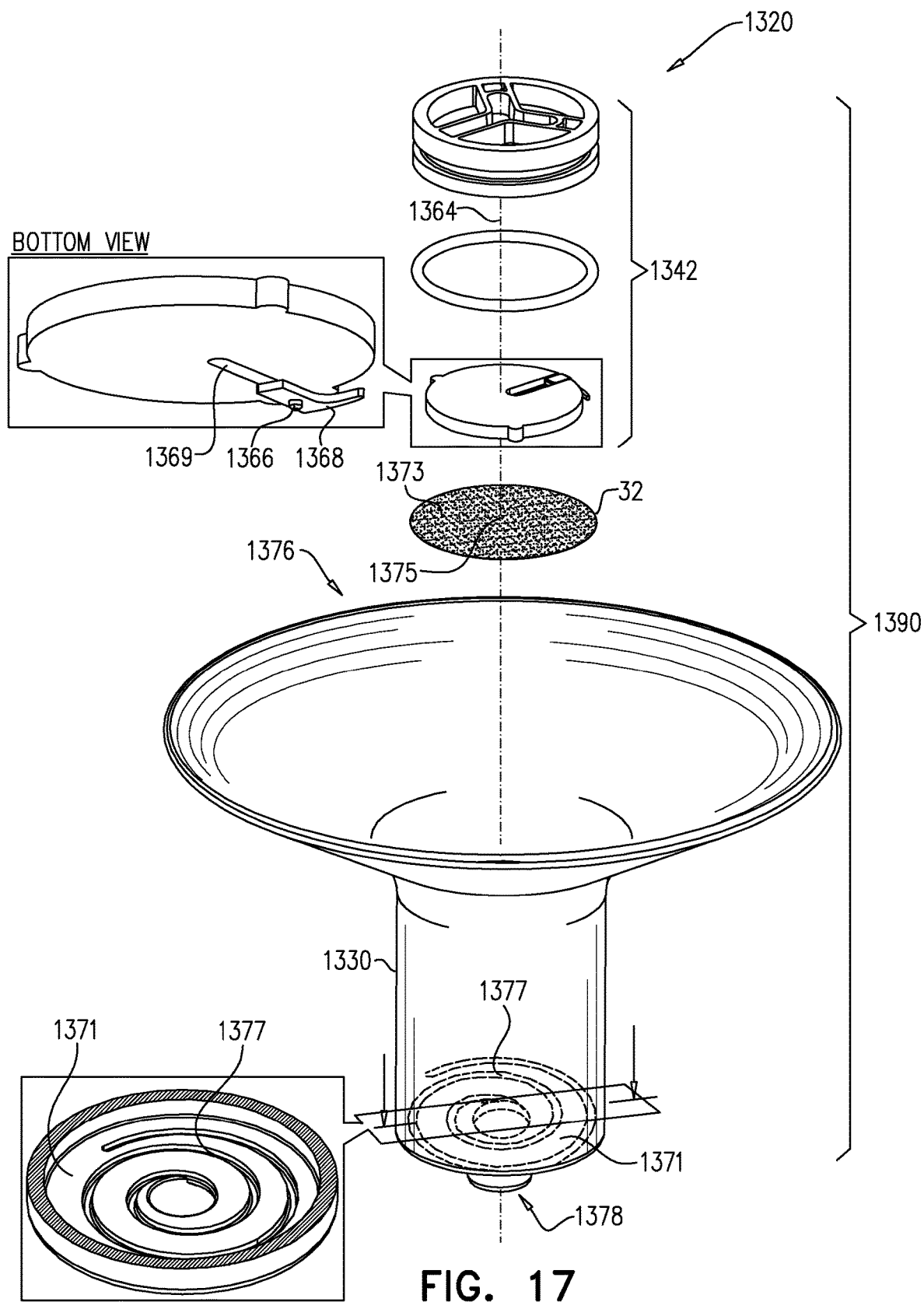
FIG. 17 is a schematic exploded view of a testing device of the testing system of FIG. 16A-B, in accordance with an application of the present invention.

Reference is also made to FIG. 17, which is a schematic exploded view of testing device 1320, in accordance with an application of the present invention. Testing device 1320 comprises:
- a liquid container 1330 for containing liquid 22, liquid container 1330 shaped so as to define an upstream opening 1376 and a downstream opening 1378;
- a filter 32, removably disposed in liquid container 1330; and
- a plunger head 1342 that (a) is shaped so as to be insertable into liquid container 1330 so as to form a movable seal with a wall of liquid container 1330, and (b) is arranged such that when pushed, plunger head 1342 applies pressure to drive liquid 22 contained in liquid container 1330 through filter 32 and then through downstream opening 1378.

Figure 18A:
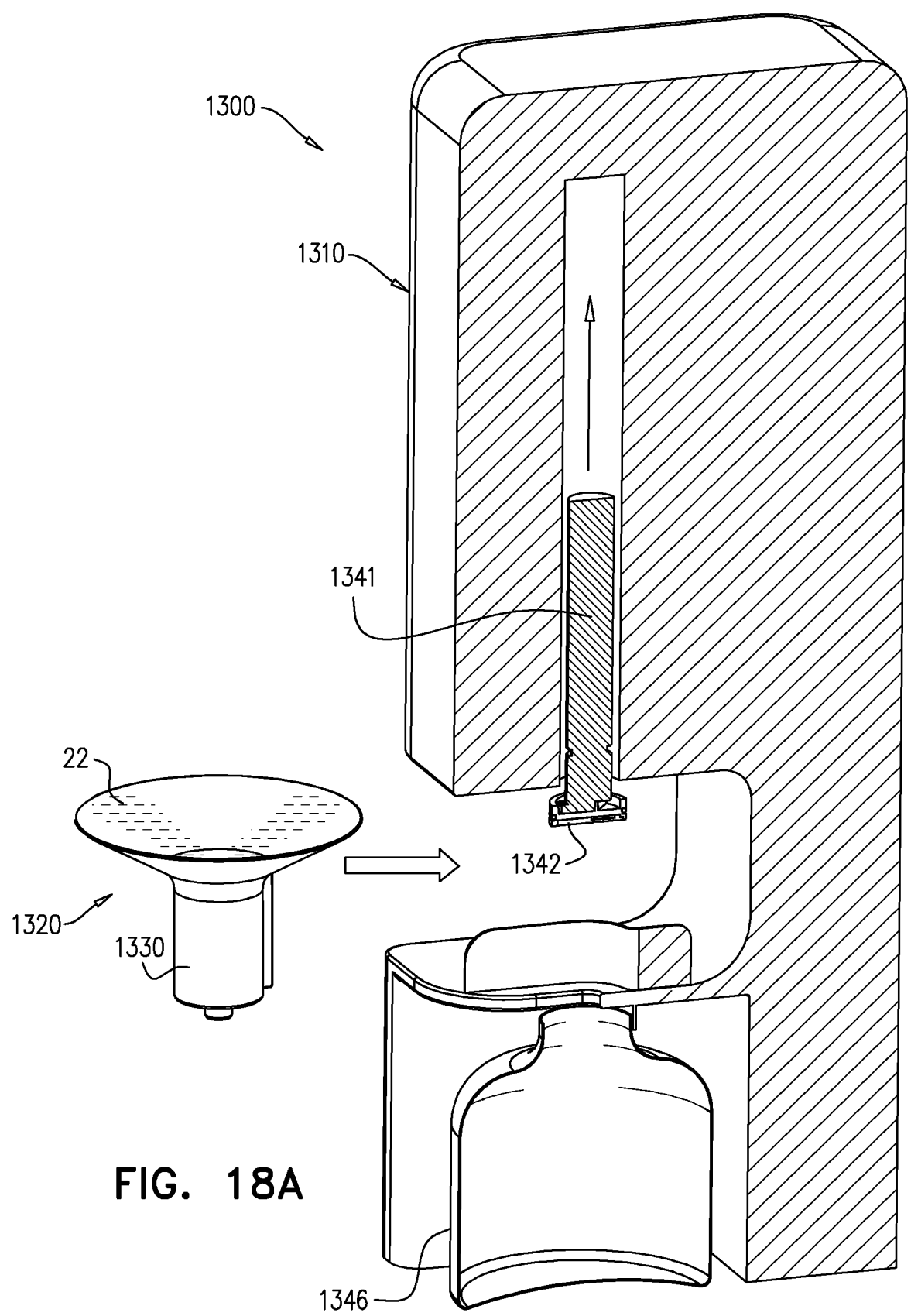
FIGS. 18A-F are schematic illustrations of a method for using the testing system of FIGS. 16A-B to test for the presence of the particulate in a liquid, in accordance with an application of the present invention.
Figure 18B:
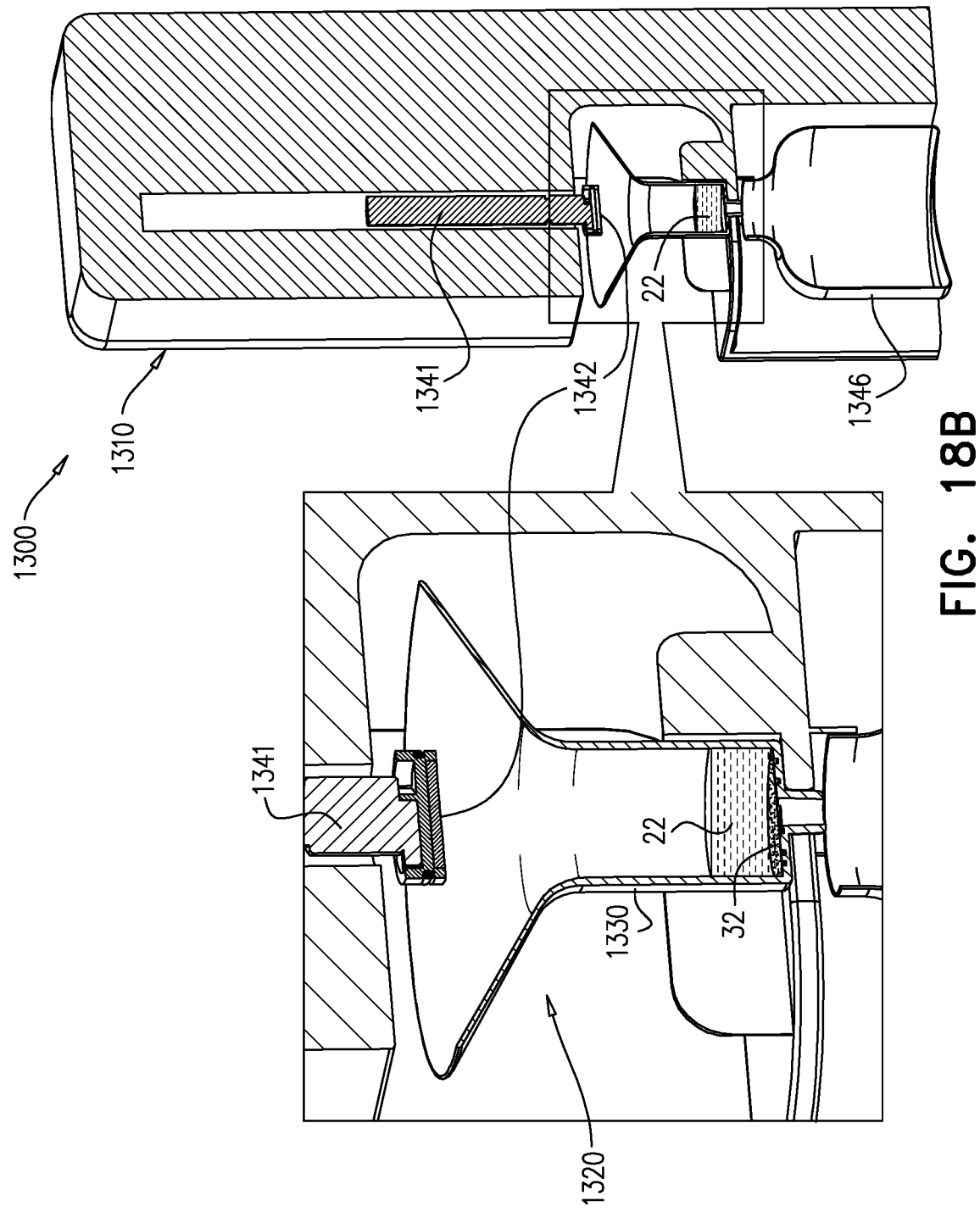
Figure 18C:
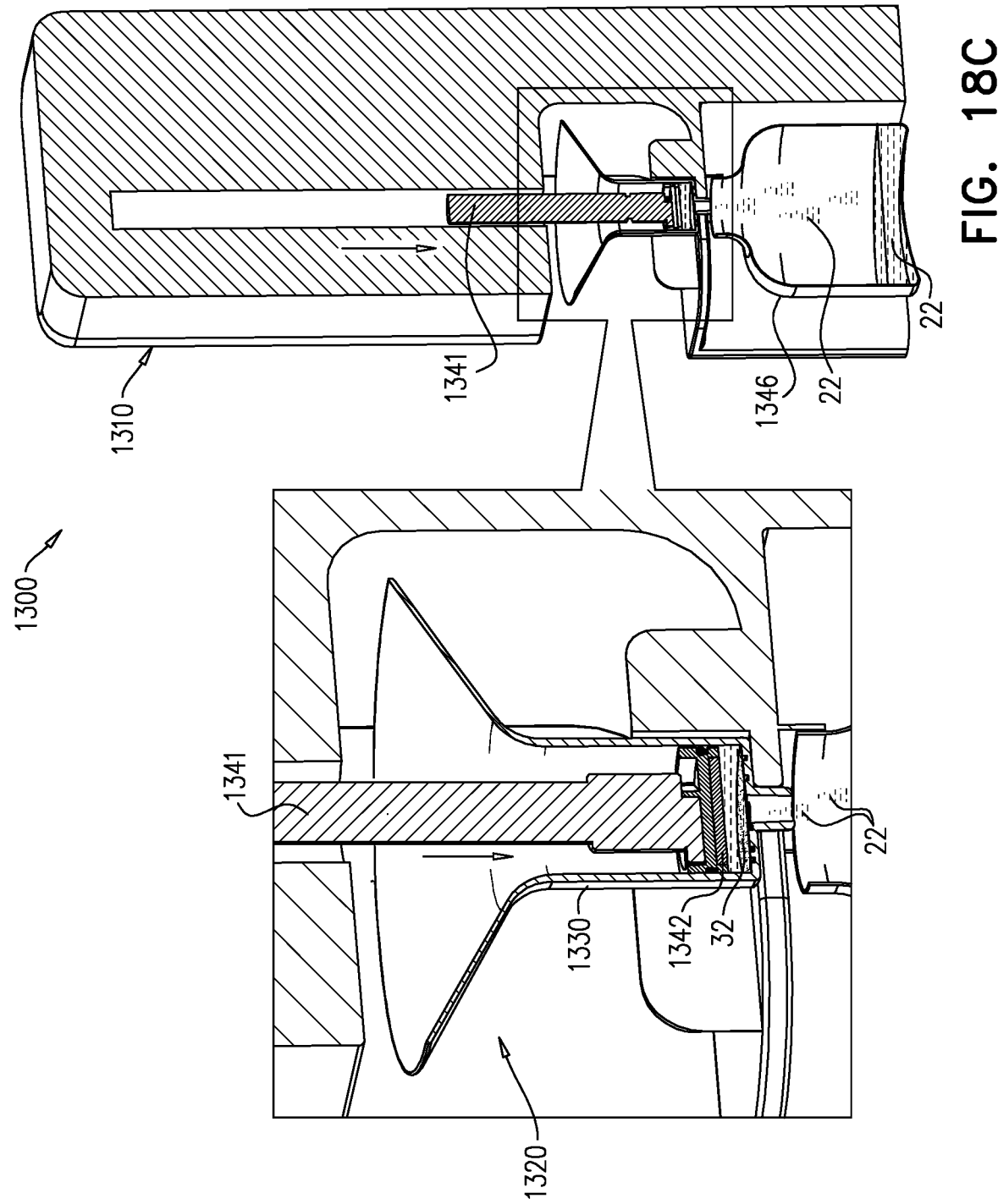
Figure 18D:
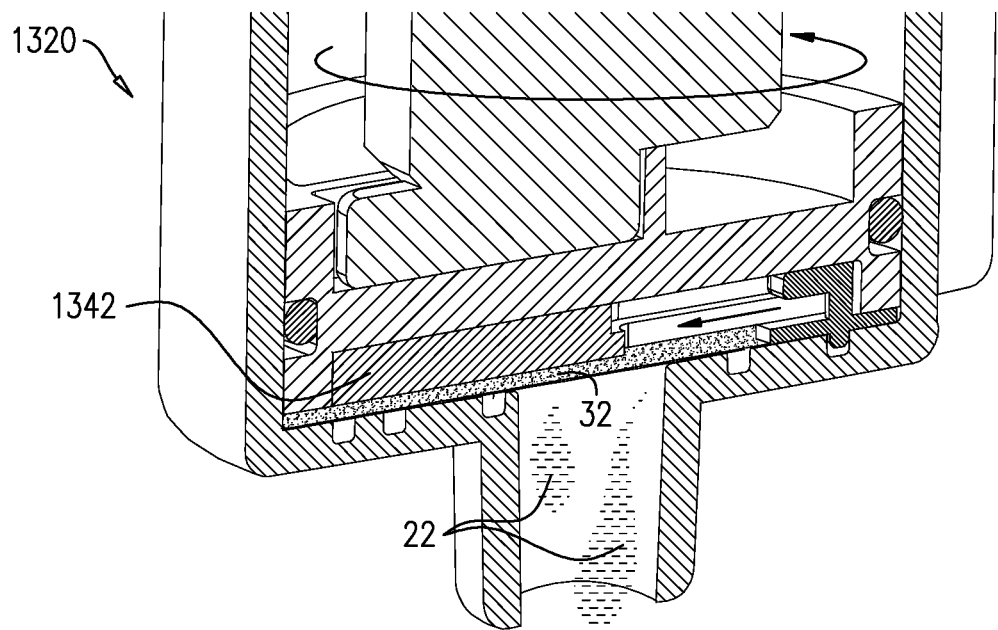
Figure 18E:
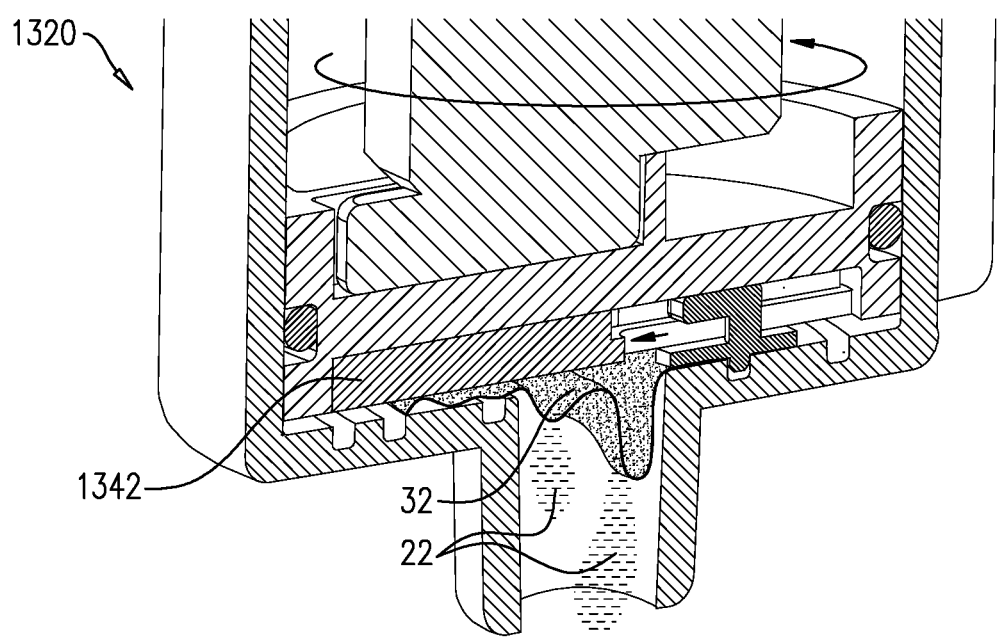
Figure 18F:
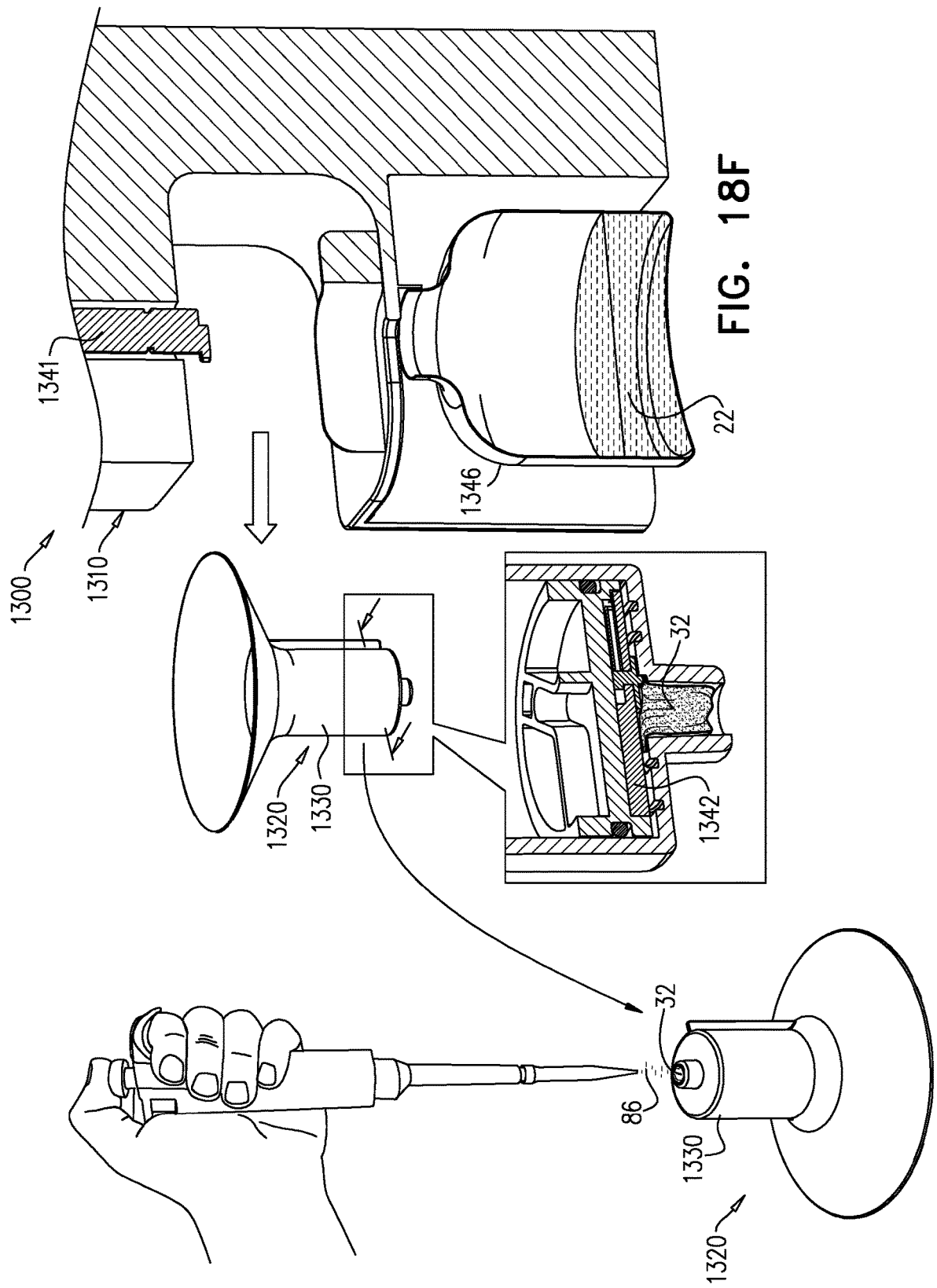

Testing device 1320 is configured such that rotation of plunger head 1342 radially compresses filter 32 toward a central longitudinal axis 1364 of plunger head 1342, as shown in FIG. 18F, described hereinbelow. This concentrates filter 32 in a more compact volume to better enable the performance of a test for the particulate, as described hereinbelow with reference to FIG. 18F. For some applications, testing device 1320 is configured such that the rotation of plunger head 1342 crushes filter 32, which may improve the sensitivity of the subsequent testing.

For some applications, plunger head 1342 comprises a protrusion 1366 (best seen in FIG. 17), and testing device 1320 is configured such that the rotation of plunger head 1342 causes protrusion 1366 to move radially toward central longitudinal axis 1364 of plunger head 1342. For example, protrusion 1366 may be coupled to a base 1368 that can slide radially within a track 1369, such as shown in the bottom view in FIG. 17, or protrusion 1366 may be directly slidable within a track.

For some applications, liquid container 1330 is shaped so as to define a filter-support surface 1371 surrounding downstream opening 1378. Filter-support surface 1371 supports a radial portion 1373 of filter 32 excluding a central portion 1375 of filter 32 (the central portion 1375 is typically removably disposed over downstream opening 1378). Filter-support surface 1371 is shaped so as to define a spiral groove 1377. Protrusion 1366 is configured to engage spiral groove 1377 through filter 32. Testing device 1320 is configured such that the rotation of plunger head 1342 (such as by between one-third of a turn to 10 turns) causes spiral groove 1377 to guide protrusion 1366 radially toward central longitudinal axis 1364 of plunger head 1342.

Reference is now made to FIGS. 18A-F, which are schematic illustrations of a method for using testing system 1300 to test for the presence of the particulate in liquid 22, in accordance with an application of the present invention.

As shown in FIGS. 18A-B, plunger head 1342 of testing device 1320 is coupled to a plunger shaft 1341 of testing machine 1310. The other components of testing device 1320, including but not limited to liquid container 1330, are removably inserted into testing machine 1310, typically after liquid 22 is contained in liquid container 1330.

As shown in FIG. 18C, plunger shaft 1341 pushes plunger head 1342 applies pressure to drive liquid 22 contained in liquid container 1330 through filter 32 and then through downstream opening 1378.

As shown in FIGS. 18D-E, plunger shaft 1341 rotates plunger head 1342 to radially compress filter 32 toward central longitudinal axis 1364, shown in FIG. 18F. Optionally, liquid container 1330 includes a narrower outlet portion, and radially compresses the filter also deposits all or a portion of the filter in the narrower outlet portion.

As shown in FIG. 18F, filter 32 is tested for particulate trapped in filter 32, including, for example, applying extraction reagent 86, as described hereinabove.

For some applications, testing machine 1310 comprises a waste liquid receptacle 1346, into which liquid 22 is driven after passing through filter 32. Typically, waste liquid receptacle 1346 is large enough to accommodate tests performed using several testing devices 1320.

Reference is again made to FIG. 17. In an application of the present invention, a testing kit 1390 is provided for use with liquid 22. Testing kit 1390 comprises:

liquid container 1330 for containing liquid 22, liquid container 1330 shaped so as to define an upstream opening 1376 and a downstream opening 1378;

filter 32, disposed in or downstream of liquid container 1330; and plunger head 1342 that (a) is shaped so as to be insertable into liquid container 1330 so as to form a movable seal with a wall of liquid container 1330, and (b) is arranged such that when pushed, plunger head 1342 applies pressure to drive liquid 22 contained in liquid container 1330 through filter 32 and then through downstream opening 1378.

Testing kit 1390 does not comprise a plunger shaft. Instead, plunger head 1342 is removably coupled to plunger shaft 1341 of testing machine 1310, as described above with reference to FIGS. 18A-B.

Although testing kit 1390 has been described with reference to liquid container 1330 and plunger head 1342, testing kit 1390 may alternatively comprise any of the other liquid containers described herein or another liquid container known in the art, and/or plunger head 1342 may alternatively comprise any of the other plunger heads described herein or another plunger head known in the art.

For some applications, sterile packaging is provided, in which at least liquid container 1330, plunger head 1342, and filter 32 are removably disposed. The sterile packaging comprises one or more sterile packages; for example, each element may be removably disposed in a separate one of the packages, and/or more than one the elements may be disposed in a single one of the packages.

Although techniques for testing, including rapid testing, are generally described herein as being performed for detecting strep, they may also be used to detect other biological particulate, such as a virus. For example, for detecting a virus, the filters described herein may capture epithelial cells that include the virus.

Measuring Group a Beta-Hemolytic Streptococcus Bacteria in Throat Gargle:
Results of Overnight Growth in Liquid Media, Assayed by Rapid Strep Test In some applications of the present invention, group A streptococcus bacteria (GAS) can be detected in throat gargle by two primary method types: Direct ("Immediate") methods and Indirect ("Backup") methods. Immediate methods yield results faster than Backup methods (<20 minutes vs. 12-48 hours) but are not as sensitive (higher rate of false negatives).

In a clinical experiment performed by the inventors, Backup methods for GAS detection in throat gargle were tested. The experimental data is based on two types of GAS throat gargle simulations: pure GAS liquid suspension and throat gargle spiked with GAS. The Clinical Trial data is based on throat gargles obtained from patients with GAS pharyngitis who were enrolled in phase 2 of a Proof of Concept Clinical Trial (Protocol Number: STRP.P001, SNIH Clinical Trial Number: NCT03231098, Shaare Zedek Medical Center Helsinki IRB Number: SZMC-0181-17).

Materials and Methods

Bacterial Culture: 10 GAS strains were used: 1 standard control strain and 9 wildtype strains. The control GAS strain was American Type Culture Collection ("ATCC") 19615, a strain often used for quality control, and the wildtype GAS strains were isolated during Clinical Trials and labeled WT-1 through WT-9. All GAS bacteria used in experiments were taken from 1-7 days old cultures on blood agar plates stored at 4-8° C.

Growth conditions: The bacteria were routinely grown in a 37° C. incubator, without agitation. Liquid cultures were grown in 4 mL plastic test tubes, with liquid volumes of 0.45 mL, 0.6 mL, 1.0 mL, 1.1 mL, and 3.6 mL after inoculation. Cultures were incubated for 12-75 hours.

Growth media: Blood plate media: Standard 90 mm plate (Petri dishes) containing TSA+5% sheep blood. Blood plates were purchased from Hylabs (Rehovot, Israel, Cat. No. PD-049). Liquid media: Tryptic Soy Broth ("TSB"), which is a well-known general-purpose growth media. Sterile TSB tubes were purchased from Hylabs (Cat. No. TT139). Liquid media: Todd Hewitt broth ("TH"), which is a media specifically developed to grow Streptococci. TH powder was purchased from Sigma Aldrich (Missouri, USA, Cat. No. T1438-500g). The media was prepared and sterilized by filtration through 0.2 um filtration units. The liquid growth media was prepared with 4.5 times the concentration recommended in the instructions. At this higher concentration, the liquid growth media had the following concentrations: glucose: 9 g/L; nitrogen source: 135 g/L; inorganic molecules: 22.05 g/L; and total solids: 166.5 g/L (as shown in the 4.5 row of Table 11, described hereinbelow.

Bacterial suspensions: Pure GAS bacterial suspensions were made by transferring GAS colonies from culture into sterile Phosphate Buffer Saline ("PBS").

Bacterial counts: 0.05 mL or 0.1 mL samples of bacterial suspensions or throat gargles were inoculated onto blood plates without dilution and with using the appropriate limiting dilutions (dilutions of 10-fold to 8000-fold) and beta-hemolytic colonies were counted using a light table.

Throat gargle: Throat gargles were obtained by gargling 10-11 mL PBS for approximately 10 seconds.

Gargle spiked with GAS: Pure GAS liquid suspensions were added to gargle and diluted with gargle as necessary.

RST methods: Lateral flow immuno-assay RST kits were purchased from Moore Medical (Connecticut, USA, Cat. No. 82792). Standard RST: Conducted according to manufacturers' instructions. Swab containing specimen sample was placed into a tube containing 8 drops of RST solutions, agitated slightly, and removed after 1-3 minutes. RST dipstick was then added to tube and removed after 5 minutes. 0.1 mL Sample RST: Similar to standard RST. 0.1 mL of specimen sample was added to tube containing RST solutions instead of a swab. Whole tube RST: 8 drops of RST solutions were added directly into tubes containing liquid culture media (0.4 mL, 0.9 mL, or 3.0 mL) incubated with gargle or simulated gargle, and RST dipstick was added to tube 1-3 minutes after addition of RST solutions. Filter RST: Culture media incubated with gargle or simulated gargle was filtered, membrane filter containing concentrated specimen sample was placed into a tube, 8 drops of RST solutions were added, and tube contents were mixed by a blunt tip for 30-45 seconds. The RST dipstick was added to the filter mixture approximately 3 minutes after addition of RST solutions.

Summary of Results

Of the 28 patients enrolled in phase 2 of the Proof of Concept Clinical Trial, 19 patients had true positive results from Backup Test methods performed using RST methods and 9 patient had true negative results from Backup Test methods performed using RST methods, as displayed in Table 1A-1D of FIGS. 19A-D, respectively. The data in Table 1A of FIG. 19A presents the gargle Backup Test methods performed using RST results for 28 patient throat gargles. Each patient throat gargle was tested using one or two systems (total systems=53). Each system consisted of 0.2 mL inoculated gargle plus either 0.4 mL or 0.9 mL of TH culture media, for a total volume of either 0.6 mL or 1.1 mL. The calculated GAS within each inoculated gargle added to a system ranged from 36 CFU to 80,400 CFU. Systems were incubated for 21-25 hours at 37° C. and then processed using either the Filter RST method or Whole Tube RST method.

The data in Table 1B-1D of FIGS. 19B-D, respectively, present the sensitivity and specificity of the gargle Backup Test methods performed using RST results in general and separated by method. The data indicates that the Filter RST method has higher sensitivity (100%) than the Whole Tube RST method (95%).

Overall, 78 experimental systems containing simulated GAS gargles yielded true positive RST results, as detailed in Table 2 of FIG. 20. The data in Table 2 describes 78 systems which resulted in a positive lateral flow RST immunoassay after incubating a sample of simulated gargle containing GAS in culture media under a variety of conditions. Conditions include: incubating culture at 37° C. for 12 to 75 hours; using 2 different growth media; inoculation volumes of 0.05 mL, 0.1 mL, 0.2 mL, and 0.6 mL; overall volumes (inoculate+culture media) of 0.45 mL, 0.6 mL, 1.0 mL, 1.1 mL, and 3.6 mL; total number of starting GAS bacteria ranging between 18 to 567,000; and using 10 different GAS strains. All Backup method simulation tests using GAS bacteria suspension in a pure buffer, including tests which are not included in Table 2, consisted of at least 95% true positives. Backup method gargle simulation tests using gargle fluid spiked with GAS, including tests which are not included in Table 2, yielded a majority of true positive results, but were not as sensitive as pure GAS suspension due to inherent variability of the simulation and/or flaws in the model of spiking gargled fluid with GAS.

Minimum incubation time was 12 hours, as set forth in Table 3 of FIG. 21. The data in Table 3 describes an experiment where 9 systems were tested by lateral flow RST immunoassay after incubating a 0.2 mL sample of simulated gargle, either pure GAS suspension or gargle spiked with GAS, into 0.9 mL of Todd Hewitt culture media. Systems tested at 4 and 8 hours yielded negative RST, while systems tested at 12 hours yielded positive RST.

The data in Table 4 of FIG. 22 describe different lateral flow RST immunoassay methods and strength of RST results after incubating 0.2 mL of either a sample of simulated gargle containing GAS (four data points) or a sample of actual GAS pharyngitis patient gargle in 0.9 mL Todd Hewitt culture media (eight data points). The data suggest that of the three methods tested, the Filter RST method yields superior results and is the most sensitive method for detecting GAS using RST after incubation in culture media. The first eight rows of data from Table 4 (patient data) are also included in Table 1 (which also includes experimental collected performed after Table 4 was produced), while the last for rows of data (stimulations) are not included in Table 1 because the additional data in Table 1 rendered this data no longer relevant to support the conclusion because of the additional clinical data.

Conclusions

These experimental data support the Backup method for GAS detection in throat gargle that involves the incubation of a sample of unfiltered throat gargle in liquid culture media for 12 to 75 hours followed by lateral flow RST immunoassay. A total of 53 systems from 28 patients enrolled in phase 2 of the Proof of Concept Clinical Trial all yielded either true positive or true negative results. A total of 78 experimental systems yielded positive Backup Test methods performed using RST results in multiple conditions. The Filter RST Backup method is presented as the most sensitive Backup Test method performed using a RST method, but all Backup Test methods performed using RST methods were satisfactory.

Measuring Group a Beta-Hemolytic Streptococcus Bacteria in Saliva Sample:

Results of Overnight Growth in Liquid Media, Assayed by Rapid Strep Test

In some applications of the present invention, group A streptococcus bacteria (GAS) can be detected from saliva swab by Indirect ("Backup") methods. In a clinical experiment performed by the inventors, Backup methods for GAS detection from saliva swab were tested. The experimental data is based on GAS growth simulations and the Clinical Trial data is based on saliva swabs obtained from patients with GAS pharyngitis who were enrolled in phase 2 of a Proof of Concept Clinical Trial (Protocol Number: STRP.P001, SNIH Clinical Trial Number: NCT03231098, Shaare Zedek Medical Center Helsinki IRB Number: SZMC-0181-17).

Materials and Methods

Bacterial Culture: 10 GAS strains were used: 1 standard control strain and 9 wildtype strains. The control GAS strain was American Type Culture Collection ("ATCC") 19615, a strain often used for quality control, and the wildtype GAS strains were isolated during Clinical Trials and labeled WT-1 through WT-9. All GAS bacteria used in experiments were taken from 1-7 days old cultures on blood agar plates stored at 4-8° C.

Growth conditions: The bacteria were routinely grown in a 37° C. incubator, without agitation. Liquid cultures were grown in 4 mL plastic test tubes, with liquid volumes of 0.9-1.1 mL after inoculation. Cultures were incubated for 12-75 hours.

Growth media: Blood plate media: Standard 90 mm plate (Petri dishes) containing TSA+5% sheep blood. Blood plates were purchased from Hylabs (Rehovot, Israel, Cat. No. PD-049).

Liquid media: Todd Hewitt broth ("TH"), which is a media specifically developed to grow Streptococci. TH powder was purchased from Sigma Aldrich (Missouri, USA, Cat. No. T1438-500g). The media was prepared and sterilized by filtration through 0.2 um filtration units. The liquid growth media was prepared with 4.5 times the concentration recommended in the instructions. At this higher concentration, the liquid growth media had the following concentrations: glucose: 9 g/L; nitrogen source: 135 g/L; inorganic molecules: 22.05 g/L; and total solids: 166.5 g/L (as shown in the 4.5 row of Table 11, described hereinbelow.

Swabs: Flocked Swabs: Swabs with a tip of short nylon brush-like fibers designed for efficient absorption and elution, purchased from Puritan Diagnostics (Maine, USA, Cat. No. 25-3306-H). Cotton Swabs: Swabs with a tip comprised of a cotton matrix, purchased from Kodan Medicam (Bet Shemesh, Israel, Cat. No. 1102245).

Polyester Swabs: Swabs with a tip comprised of a polyester matrix, manufactured by Puritan Diagnostics (Guilford, Main, USA), Cat. No. 25-806 1PD SOLID).

Bacterial suspensions: Pure GAS bacterial suspensions were made by transferring GAS colonies from culture into sterile Phosphate Buffer Saline ("PBS").

Gargle spiked with GAS: Throat gargles were obtained by gargling 10-11 mL PBS for approximately 10 seconds and pure GAS suspensions were added to gargle and diluted with gargle as necessary.

Saliva swabs: Saliva swabs were obtained from patients enrolled in the Clinical Trial. Patients were asked to suck on a flocked swab for approximately 10 seconds. Saliva swabs obtained from Clinical Trial subjects were inoculated onto blood plates and beta-hemolytic colonies were counted using a light table. Some saliva swabs were then inoculated into TH culture media and swab was left in culture media during incubation. Both the culture media and the swab were later assayed by Backup methods performed using RST methods.

RST methods: Lateral flow immuno-assay RST kits were purchased from Moore Medical (Connecticut, USA, Cat. No. 82792). Swab sample RST: After incubation, saliva swab was removed from culture media and placed into a tube containing 8 drops of RST solutions, agitated slightly, and removed after 1-3 minutes. RST dipstick was then added to tube and removed after 5 minutes. 0.1 mL sample RST: Similar to swab RST. 0.1 mL of specimen sample was added to tube containing RST solutions instead of a swab. Whole tube RST: In some cases, the 8 drops of RST solutions were added directly into tubes containing GAS in liquid culture media (0.9-1.1 mL) and RST dipstick was added to liquid culture media tube 1-3 minutes after addition of RST solutions. Filter RST: Culture media incubated with saliva swab was filtered, membrane filter was placed into a tube, 8 drops of RST solutions were added, and tube contents were mixed by a blunt tip for 30-45 seconds. The RST dipstick was added to the filter mixture approximately 3 minutes after addition of RST solutions.

Saliva swab simulation 1: Swabs were dipped into tubes containing pure GAS bacteria suspensions and agitated up and down 12-20 times before being removed for testing. Swabs were then inoculated onto blood plates and beta-hemolytic colonies were counted using a light table.

Saliva swab simulation 2: Swabs were dipped 5 times into tubes containing gargle spiked with GAS bacteria and then dipped 5 times into TH culture media to inoculate. Swabs were discarded prior to incubation of the culture media.

Bacterial counts: 0.05 mL or 0.1 mL samples of bacterial suspensions were inoculated onto blood plates using the appropriate limiting dilutions (dilutions of 8,000-fold or 30,000-fold) and beta-hemolytic colonies were counted using a light table.

Summary of Results

GAS was successfully captured from almost all plated saliva swab samples of positive subjects enrolled in phase 2 of the Proof of Concept Clinical Trial, as seen in Table 5 of FIG. 23. The data in Table 5 describe the range of GAS CFU amounts observed on the blood plates inoculated with Clinical Trial phase 2 subject saliva swabs. Most plated saliva swabs from positive subjects successfully captured GAS with a range of 4 CFUs to TNTC, with only one case of false negative (pt. ID #033.VEN), yielding a capture rate of 94.7% (18/19). 84.2% of cases had greater than 20 CFUs, 73.7% of cases had greater than 40 CFUs, and 63.2% of cases had greater than 100 CFUs.

As presented in Table 6 of FIG. 24 (see also the next paragraph), four of the saliva swab samples (Patients 12-15) from the Clinical Trial, after being inoculated onto the blood plates, were also tested using Backup methods performed using RST methods, two of which yielded true positive results. The Filter RST method yielded the strongest RST result (RST 4), and the Whole Tube RST method yielded the weakest RST result (RST 0). The Swab RST method was sensitive enough to yield a positive result even for a patient with a very low amount of GAS in the saliva swab sample (4 CFUs).

After performing the experiment reflected in Table 6, the inventors appreciated that the data presented in Table 6 is invalid due to inaccurate testing. Due to the removal of some of the sample (for inoculating onto blood plates) prior to testing, as described above, the Backup methods using RST methods yielded inaccurate results, because the full sample was not tested. Subsequent clinical trial samples were tested properly utilizing the complete saliva sample (Patients 17-34), as described hereinbelow with reference to Table 8 of FIG. 26.

Saliva swab simulation 1 shows that flocked swabs are the preferred swab for obtaining a salvia swab sample, as can be seen in Table 7 of FIG. 25. The data in Table 7 present an experiment which compared the total absorbance plus elution of GAS onto a plate from three different swab materials: cotton, polyester, and flocked. Swabs were dipped into 0.6 mL of pure GAS liquid suspension and then inoculated onto a blood plate. The flocked swab showed 3 to 5 times more total absorbance plus elution efficiency using three different GAS concentrations.

Saliva swab simulation 2 shows that flocked swabs, when used to inoculate a sample into TH culture broth for a Backup Test performed using RST methods, are as efficient as direct liquid transfer, as can be seen in Table 8 of FIG. 26. The data in Table 8 present an experiment which compared methods for transferring gargle spiked with GAS into culture media ("inoculation methods"). Using a flocked swab for inoculation yielded a positive Backup Test performed using RST methods comparable to using a pipette to transfer 0.2 mL (RST 3).

Almost all saliva swab clinical samples which were inoculated into Todd Hewitt (TH) broth and assayed by Backup methods using RST methods yielded either true positive or true negative results for all subjects enrolled in phase 2 of the Proof of Concept Clinical Trial, seen in Table 9 of FIG. 27. The data presented in Table 9 describe Clinical Trial saliva swabs that were incubated in TH culture broth and were then assayed using Backup Test methods performed using RST methods. The Filter RST method had a sensitivity of 90% and the Swab RST method had a sensitivity of 80%.

Conclusions

These experimental data support the Backup method for GAS detection using a saliva sample via the incubation of a saliva swab in liquid culture media followed by lateral flow RST immunoassay. Plated clinical saliva swab samples displayed a 94.7% successful capture rate of GAS which confirms that saliva samples are a viable alternative to gargling in cases where gargling is not possible. Saliva swab simulations support the concept that Backup Test methods performed using RST methods of saliva swabs incubated in liquid media is an efficient method for GAS detection. Additional saliva swab simulation data shows that flocked swabs increase the uptake and release of specimen samples compared to other swabs.

Clinical data from 18 samples demonstrates that a saliva swab Backup Test performed using RST methods in liquid media has high sensitivity (90%) and specificity (100%). Furthermore, the Filter Backup Test methods performed using RST methods yielded a higher sensitivity (90%) than the Swab Backup method performed using RST methods (80%).

A liquid growth medium and a method of using the liquid growth medium are provided for testing for the presence of group A streptococcus bacteria (GAS) in a sample of oral fluid obtained from a patient, in accordance with respective applications of the present invention. The liquid growth medium and/or the method may be used in combination with any of the techniques described hereinabove in which growth medium is used for testing for the presence of biological particulate, such as strep, e.g., GAS. Although the liquid growth medium and the method are generally described hereinbelow as being appropriate for testing for the presence of GAS, they may also be used to test for other types of streptococcus bacteria, other types of bacteria, a microorganism, a fungus, a spore, a virus, a mite, a biological cell, a biological antigen, a protein, a protein antigen, or a carbohydrate antigen.

The liquid growth medium has a substantially greater total nitrogen source concentration and a substantially greater total solids concentration than conventional liquid growth media used for incubating GAS. The liquid growth medium has a substantially greater osmotic value (indicative of the total concentration of molecules in the media) than conventional liquid growth media. In particular, the liquid growth medium typically has (a) a total nitrogen source concentration between 75 and 300 g/L and (b) a total solids concentration between 92.5 and 370 g/L.

The high-concentration liquid growth medium may be particularly useful for successfully growing low concentrations (typically between 100 and 500 CFU/ml) of GAS present in samples of oral fluid, such as gargled fluid gargled by the patient or saliva not swabbed from a throat of the patient. These samples of oral fluid typically contain many dozens of types (often over 100) of other types of interfering bacteria. As described below, the inventors have found that the use of conventional, lower concentration liquid growth media for testing for the presence of GAS in samples of oral fluid (rather than samples swabbed from the tonsils, as is conventional in strep testing) results in consumption of most of the nutrients in the liquid growth medium by the interfering bacteria, leaving insufficient nutrients to grow the GAS of interest to an extent adequate for accurate testing.

Many bacterial liquid growth media are used commercially to grow Group A streptococcus bacteria.

They all contain at least 2 of the following three types of components:

a. A sugar, usually glucose, as an energy source.

b. Nitrogen sources as building blocks for nitrogen and carbon.

c. Inorganic salts and molecules that serve as nutrients, as buffers to maintain pH during growth and to maintain osmotic balance.

The table below shows the respective concentrations of the abovementioned three components in some of the widely used, commercially available liquid growth media formulations (which can be obtained from many manufactures all over the world). The following are examples of typical formulations.

TABLE 10

| Formulation name | Glucose | Nitrogen Source | Inorganic molecules | Total solids |
| --- | --- | --- | --- | --- |
| Todd Hewitt Broth | 2 g/L | 30 g/L | 4.9 g/L | 37 g/L |
| Brain Heart Infusion | 2 g/L | 27.5 g/L | 7.5 g/L | 37 g/L |
| Tryptic Soy Broth | 2.5 g/L | 20 g/L | 7.5 g/L | 30 g/L |
| Columbia Broth | 2.5 g/L | 23.1 g/L | 9.41 g/L | 35 g/L |
| Nutrient Broth | None | 20 g/L | 5 g/L | 25 g/L |
| Thioglycollate broth | 5.5 g/L | 20.5 g/L | 3 g/L | 29.75 g/L |

Thus, a typical conventional liquid growth media for streptococcal growth will contain=<30 g/L of nitrogen sources, >10 g/L of Inorganic molecules, >40 g/L of total solids. These conventional liquid growth media, having the respective concentrations as shown in Table 10, all enable good growth of GAS in pure form.

Furthermore, the use of a high-concentration liquid growth medium is conventionally believed to depress the growth of GAS. See, for example, Bernheimer, A. W. and Pappenheimer A. M. Jr., "Factors necessary for massive growth of Group A hemolytic Streptococcus". Journal of Bacteriology, Volume 43(4), pages 481-494 (1941).

As described hereinabove, the liquid growth medium of the present application has a substantially greater osmotic value (indicative of the total concentration of molecules in the media) than conventional liquid growth media. For some applications, the total nitrogen source concentration is between 105 and 180 g/L, such as between 120 and 160 g/L, and/or the total solids concentration is between 130 and 222 g/L, such as between 148 and 193 g/L.

Typically, the liquid growth medium has a pH of between 6 and 8.3, such as between 7.0 and 8.0.

For some applications, the liquid growth medium has a total sugar concentration of between 6 and 20, such as between 6 and 12. For some of these applications, the liquid growth medium has a glucose concentration of between 7 and 10, such as between 8 and 9.5.

For some applications, an assembly is provided that includes the liquid growth medium and a sealed sterile container that contains the liquid growth medium.

For some applications, an assembly is provided that includes the liquid growth medium and a container that contains the liquid growth medium and a sample of oral fluid obtained from a patient, such as described above.

For some applications, a kit is provided that includes the liquid growth medium and a lateral flow strep test strip, one or more extraction reagents, and/or a filter.

In an application of the present invention, a method of preparing the liquid growth medium includes adding a quantity of powdered growth medium to a volume of distilled water, and stirring until the powdered growth medium is dissolved in the distilled water to produce the liquid growth medium. The quantity of powdered growth medium and the volume of the distilled water are typically selected such that the liquid growth medium has (a) a total nitrogen source concentration between 75 and 300 g/L and (b) a total solids concentration between 92.5 and 370 g/L. The liquid growth medium may optionally have any of characteristics described above.

In an application of the present invention, a method is provided for testing for the presence of GAS in a sample of oral fluid obtained from a patient, the method including:
  generating a biological product by incubating the sample of oral fluid for between 12 and 50 hours in a container that contains a liquid growth medium, the liquid growth medium having (a) a total nitrogen source concentration between 75 and 300 g/L and (b) a total solids concentration between 92.5 and 370 g/L; and
  thereafter, performing a strep test using a rapid strep test (RST) technique on the biological product.

For some applications, incubating includes incubating for between 16 and 50 hours.

Typically, the container does not contain agar. Alternatively, the container does contain some agar, but it is typically a relatively small amount compared to conventional strep culturing techniques.

For some applications, performing the strep test using the RST technique includes performing a lateral flow test. For some applications, performing the strep test includes applying one or more extraction reagents to the biological product.

Alternatively, for some applications, performing the strep test using the RST technique includes performing an RST technique selected from the group consisting of: an ELISA-based RST, an antibody-coated-beads-based RST, a nucleic-acid-based RST, and a fluorescent immunoassaying (FIA) RST.

Typically, but not necessarily, the sample of oral fluid is selected from the group consisting of: gargled fluid gargled by the patient, and saliva not swabbed from a throat of the patient (e.g., spit by the patient, or sucked onto a swab by the patient).

Alternatively, the sample of oral fluid is saliva swabbed from a tonsil of the patient.

For some applications, generating the biological product further includes filtering the sample of oral fluid and the liquid growth medium after incubating. For some of these applications, performing the strep test using the RST technique includes performing the strep test using the RST technique on the filter. For some of these filtering applications, the sample of oral fluid is saliva swabbed from a tonsil of the patient.

Typically, RST values below 0.25 (average of 5 and 10 minutes readings) are considered to be negative results. An RST value of 0.5 is indicative of a bacteria concentration of at least 10,000 CFU/ml The inventors performed experimentation where the lateral flow values of pure systems grown in TH-1 and TH-10 were compared with the lateral flow values of TH-1 systems with added salt (NaCl) or sugar (Glucose) at increasing concentrations. The Lateral flow value of TH-10 was similar to the values of TH-1+5% NaCl and 30% glucose.

5% Nacl and 30% glucose have similar Osmolarities, and inhibited the Strep to the same extent.

From this a value of about 180 MOsmomolar was calculated, and a demonstration of Osmolarity dependent Strep A growth inhibition was shown, in agreement with scientific literature.

A. The following is an experimental setup as performed by the inventors:
  1. Each system consisted of a 5 ml test tube, containing 1.1 ml growth media.
  2. 0.1 ml bacterial suspensions were added to each system and growth was started by incubation at 35.5° C., in air. Termination was done by withdrawal from the incubator and immediate processing, or by storage at 6-8° C. for up to 2 hours before processing.
  3. The 0.1 ml bacterial suspensions were of 3 types:
    (a) In "pure" systems the bacteria were suspended in sterile Phosphate-Buffered Saline ("PBS").
    (b) In "Gargle" systems the bacteria were suspended in a gargle solution. Gargle was obtained by gargling 10-11 ml of sterile PBS for about 10 seconds and then transferring the gargle to a collection cup.
    (c) In "saliva" systems the bacteria were suspended in saliva. Saliva was obtained by spitting into a collection cup.
  4. Incubation was for a period of at least 4 hours but up to 3 days, depending on the experiment.
  5. Two strains of GAS were used: the well-known "ATCC 19615" strain, which is used as a control strain in many diagnostic applications, and a wild-type strain "WT-9," which was isolated from a patient in a clinical trial performed on behalf of the inventors.
  6. Bacterial stock suspensions were obtained by resuspending in PBS a 1-4-days-old bacterial colony, grown at 35.5° C. on a blood agar plate for 1-2 days and then stored at 6-8° C. till used. The stock was diluted 10-250,000 fold, depending on the experiment, in either PBS, gargle or saliva. Bacterial dilutions of 4,800-20,000 in PBS were plated (50 microliters), grown at least overnight at 35.5° C., and the beta-hemolytic colonies counted.
  7. Processing the samples involved assaying 0.1 ml of sample in an antigen lateral flow, Rapid Strip Test, for Streptococcus Group A. Test strips were obtained from McKesson company, USA, and used in accordance with the manufacture instructions. Estimation of the strength of the positive line was done visually, by experience lab workers.

Example 1

The following Gargle/Saliva growth Media [GSM] were prepared based on the Todd Hewitt formula, with successively increasing concentrations of Glucose, Nitrogen Sources, and Inorganic molecules, as indicated in Table 11 below:

TABLE 11

| Formulation name | Glucose | Nitrogen Source | Inorganic molecules | Total solids |
|---|---|---|---|---|
| Todd Hewitt Broth X 1 (TH-1) | 2 g/L | 30 g/L | 4.9 g/L | 37 g/L |
| Todd Hewitt Broth X 2.5 (GSM -1) | 5 g/L | 75 g/L | 12.25 g/L | 92.5 g/L |
| Todd Hewitt Broth X 4.5 (GSM-2) | 9 g/L | 135 g/L | 22.05 g/L | 166.5 g/L |
| Todd Hewitt Broth X 7 (GSM-3) | 14 g/L | 210 g/L | 34.3 g/L | 259 g/L |
| Todd Hewitt Broth X 10 (GSM-4) | 20 g/L | 300 g/L | 49 g/L | 370 g/L |

1.1 ml of each of the above sterile solutions was placed in a tube.

Bacterial suspensions were prepared by spiking even number of bacteria cells in PBS×1, Gargle fluid and saliva.

0.1 ml of bacterial suspension was added to each of the above growth media shown in Table 11 and incubated at 35.5° C., in air, for 16.5-17.5 hours to obtain cultures.

0.1 ml of each culture was transferred each to a new tube containing Solution A (2M Sodium nitrite) and Solution B (0.2M Acetic acid) followed by a short mix on a Vortex mixer.

McKesson RSTs were dipped into each solution and results were read after 5 and 10 minutes according to arbitrary test line intensity scale. Results are presented as the average between the 2 readings.

Results

Figure 28:
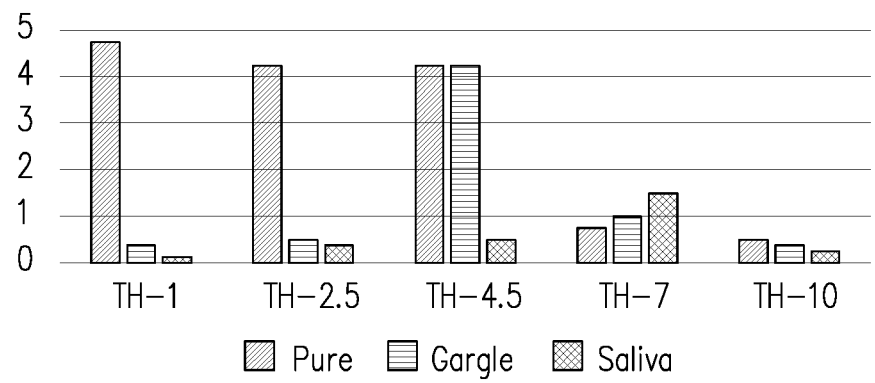
FIGS. 28 and 29 are graphs that present results of experiments conducted in accordance with respective applications of the present invention.

The following Table 12 summarizes test results, which are reflected as well in FIG. 28:

TABLE 12

| Growth Media | Test Line intensity | | |
|---|---|---|---|
| | Pure | Gargle | Saliva |
| TH-1 | 4.8 | 0.4 | 0.1 |
| GSM-1 | 4.3 | 0.5 | 0.4 |
| GSM-2 | 4.3 | 4.3 | 0.5 |
| GSM-3 | 0.75 | 1 | 1.5 |
| GSM-4 | 0.5 | 0.4 | 0.3 |

Conclusions

Both gargle and saliva suspensions grow best in a GSM media having a high concentration of solids.

As per the above results, the highest RST readings for gargle suspension growth resulted when GSM-2 was used.

As per the above results, the highest RST readings for saliva suspension growth resulted when GSM-3 was used.

Thus, the inventors have realized that the optimal range of solids concentrations in liquid growth media for growing gargle and saliva suspensions should be between 4.5-7×TH, i.e., 4.5-7 times the solids concentration in conventional Todd Hewitt liquid growth medium.

In contrast to bacteria sourced from gargle fluid and saliva, the growth of pure GAS culture was inhibited by higher solids concentrations.

Example 2

The following Gargle/Saliva growth Media [SPM] (shown in Table 14 below) were prepared based on a mix of several formulas as indicated in Table 13 below with successively increasing concentrations of Glucose, Nitrogen sources, and Inorganic molecules:

TABLE 13

| Formulation name | Todd Hewitt | Brain Heart Infusion | Tryptic Soy Broth | Beef Extract | Yeast Extract | Glucose |
|---|---|---|---|---|---|---|
| Percentage of total solids for SPMX 1 | 4.44 g/L | 6.66 g/L | 3.9 g/L | 10g /L | 3 g/L | 2 g/L |

TABLE 14

| Formulation name | Glucose | Nitrogen Source | Inorganic molecules | Total solids |
|---|---|---|---|---|
| SPM X 1 (SPM-1) | 2.9 g/L | 24.15 g/L | 2.9 g/L | 30 g/L |
| SPM X 3.5 (SPM-3.5) | 10.15 | 85.525 | 10.15 | 105 g/L |
| SPM X 4.5 (SPM-4.5) | 13.05 | 108.675 | 13.05 | 135 g/L |
| SPM X 6 (SPM-6) | 17.4 | 144.9 | 17.4 | 180 g/L |
| SPM X 7 (SPM-7) | 20.3 | 169.05 | 20.3 | 210 g/L |
| SPM X 8.5 (SPM-8.5) | 24.65 | 205.275 | 24.65 | 255 g/L |
| SPM X 10 (SPM-10) | 29 g/L | 241.5 g/L | 29 g/L | 300 g/L |

1.1 ml of each of the above sterile solutions was placed in a tube.

Bacterial suspensions were prepared by spiking even number of bacteria cells in PBS×1, Gargle fluid and saliva.

0.1 ml of bacterial suspension was added to each of the above growth media shown in Table 14 and incubated at 35.5° C., in air, for 22 hours to obtain cultures.

0.1 ml of each culture was transferred each to a new tube containing Solution A (2M Sodium nitrite) and Solution B (0.2M Acetic acid) followed by a short mix on a Vortex mixer.

McKesson RSTs were dipped into each solution and results were read after 5 and 10 minutes according to arbitrary test line intensity scale. Results are presented as the average between the 2 readings.

Results

Figure 29:
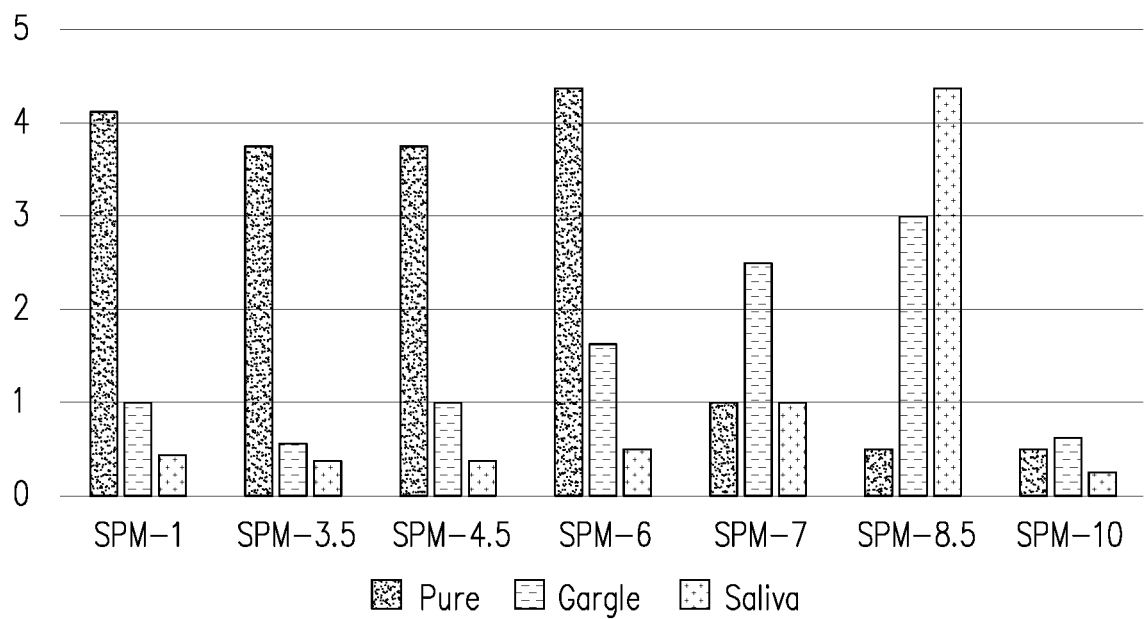

The following Table 15 summarizes test results, which are reflected as well in FIG. 29:

TABLE 15

| Growth Media | Pure | Gargle | Saliva |
|---|---|---|---|
| SPM-1 | 4.1 | 1 | 0.4 |
| SPM-3.5 | 3.8 | 0.6 | 0.4 |
| SPM-4.5 | 3.8 | 1 | 0.4 |
| SPM-6 | 4.4 | 1.6 | 0.5 |
| SPM-7 | 1 | 2.5 | 1 |
| SPM-8.5 | 0.5 | 3 | 4.4 |
| SPM-10 | 0.5 | 0.6 | 0.25 |

Thus, increasing the solids concentration in SPM growth media has a similar effect on GAS growth as shown using the GSM media of Example 1.

Solid concentration of growth media has the same effect in both cases (Example 1 and Example 2) regardless of the media nutrient composition.

Example 3

1.1 ml of the TH-1 and 1.1 ml of GSM-1 growth media were each placed in respective tubes.

Bacterial suspensions were diluted to the final respective cell counts specified in Table 16 below for both growth media formulas.

0.1 ml of each diluted bacterial suspension was added to a tube of TH-1 growth medium and to a tube of GSM-1 growth medium and incubated at 35.5° C., in air, for 23 hours, to obtain cultures.

0.1 ml of each culture was each transferred to a new tube containing Solution A (2M Sodium nitrite) and Solution B (0.2M Acetic acid) followed by a short mix on a Vortex mixer.

McKesson RSTs were dipped in the solution and results were read after 5 and 10 minutes according to arbitrary test line intensity scale. Results are presented as the average between the 2 readings.

Results

Lateral flow values of cultures grown at 35.5° C. for 23h

TABLE 16

| Culture | CFU per tube CFU per ml | Test line intensity TH-1 | Test line intensity TH-4.5 |
|---|---|---|---|
| Pure | 180 | 4.3 | 4 |
|  | 920 | 4 | 3.5 |
|  | 4590 | 4.6 | 4.5 |
|  | 45880 | 4 | 3.6 |
|  | 458800 | 4.2 | 3.9 |
| Gargle | 180 | 0.1 | 4.4 |
|  | 920 | 1 | 4.4 |
|  | 4590 | 2.5 | 4.3 |
|  | 45880 | 4 | 3.4 |
|  | 458800 | 4.6 | 2.8 |

Conclusions

The range of cell numbers per ml in the above experiment represents the variability of cell counts in gargle fluids that were collected during clinical study conducted by Hero Scientific.

GAS cells both from pure culture and gargle fluid grow well in TH×4.5 and can be easily detected by the RST.

TH×1 is inferior to the high-solids concentration broth when gargle fluid is present in the broth at lower cell numbers. At higher cell numbers, even though TH-1 resulted in higher RST readings, TH-4.5 still resulted in sufficiently high readings so as to provide unambiguous results.

In an embodiment, the techniques and apparatus described herein are combined with techniques and apparatus described in one or more of the following patent applications, which are assigned to the assignee of the present application and are incorporated herein by reference:

International Application PCT/IL2018/050225, filed Feb. 28, 2018, which published as WO 2018/158768 to Fruchter et al.;

U.S. Provisional Application 62/727,208, filed Sep. 5, 2018; and/or

International Application PCT/IL2019/050994, filed Sep. 5, 2019, entitled, "Strep testing methods," which published as WO 2020/049566 to Fruchter et al.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising a testing device for testing for the presence of particulate in a liquid, the testing device comprising:

a liquid container for containing the liquid, the liquid container shaped so as to define an upstream opening for receiving the liquid;

a filter;

a waste liquid receptacle;

a liquid-pressure source, which (a) is arranged to apply pressure to drive the liquid contained in the liquid container through the filter and then into the waste liquid receptacle, and (b) comprises a plunger comprising a plunger head that is shaped so as to be insertable into the liquid container via the upstream opening of the liquid container; and a filter-receiving chamber that is (a) disposed downstream of the liquid container when the plunger head is within the liquid container, (b) shaped so as to define an inlet, and (c) in fluid communication with the filter, wherein the filter is removably disposed upstream of the filter-receiving chamber with the filter partially covering the inlet of the filter-receiving chamber, and arranged in the testing device to be movable at least partially into the filter-receiving chamber via the inlet after the liquid has been driven through the filter.

2. The apparatus according to claim 1, wherein the inlet of the filter-receiving chamber has an inlet area that is less than a greatest cross-sectional area of the filter-receiving chamber, the inlet area and the greatest cross-sectional area measured in respective planes parallel to each other.

3. The apparatus according to claim 1, wherein the filter-receiving chamber comprises one or more pressure-activated valves, not disposed at the inlet of the filter-receiving chamber.

4. The apparatus according to claim 1, wherein the apparatus further comprises an elongate member configured to push at least a portion of the filter into the filter-receiving chamber.

5. The apparatus according to claim 1, wherein the plunger head is configured to push at least a portion of the filter into the filter-receiving chamber.

6. The apparatus according to claim 1, wherein the filter-receiving chamber comprises one or more valves, not disposed at the inlet of the filter-receiving chamber.

7. The apparatus according to claim 6, wherein the one or more valves comprise one or more pressure-activated valves.

8. The apparatus according to claim 7, wherein the one or more valves comprise one or more non-pressure-activated valves.

9. The apparatus according to claim 1, wherein the liquid container is shaped so as to define one or more openings through a wall of the liquid container, wherein the one or more openings are downstream of the filter when the filter is removably disposed upstream of the filter-receiving chamber with the filter partially covering the inlet of the filter-receiving chamber, and wherein the filter-receiving chamber is not disposed so as to receive the liquid that is driven through the one or more openings, such that the one or more openings allow the liquid to pass, thereby drawing the liquid through the filter.

10. The apparatus according to claim 1, wherein the apparatus further comprises at least one container comprising an extraction reagent.

11. The apparatus according to claim 10, wherein the apparatus further comprises a test strip.

12. A method comprising:

receiving liquid in a liquid container of a testing device, via an upstream opening of the liquid container;

inserting a plunger head of a plunger into the liquid container via the upstream opening;

applying pressure, by pushing the plunger within the liquid container, to drive the liquid through a filter of the testing device and then into a waste liquid receptacle of the testing device, while (a) the filter is removably disposed upstream of a filter-receiving chamber with the filter partially covering an inlet of the filter-receiving chamber, and (b) the filter-receiving chamber is disposed downstream of the liquid container in fluid communication with the filter;

thereafter, moving at least a portion of the filter into the filter-receiving chamber via the inlet;

thereafter, removing the entire filter from within the filter-receiving chamber and from the testing device; and thereafter, testing the filter, outside the testing device, for the presence of biological particulate trapped by the filter.

13. The method according to claim 12, wherein the liquid includes gargled fluid.

14. The method according to claim 12, wherein the liquid includes saliva not swabbed from a throat of a patient.

15. The method according to claim 12, wherein the liquid includes an incubated culture medium containing a biological sample.

16. The method according to claim 12, wherein the biological particulate is group A streptococcus bacteria.

17. The apparatus according to claim 1, wherein the filter-receiving chamber is nipple-shaped.

18. The apparatus according to claim 1, wherein the waste liquid receptacle is coupled to the liquid container downstream of the filter.

19. The apparatus according to claim 1, wherein the plunger is shaped so as to define the waste liquid receptacle.

20. The apparatus according to claim 19, wherein the plunger is shaped so as to define the filter-receiving chamber, and wherein the filter chamber is laterally surrounded by at least a portion of the waste liquid receptacle.

21. The apparatus according to claim 1, wherein the plunger is shaped so as to define the filter-receiving chamber.

22. The apparatus according to claim 21, wherein the apparatus further comprises an elongate member configured to move at least a portion of the filter into the filter-receiving chamber.

23. The method according to claim 12, wherein the plunger is shaped so as to define the filter-receiving chamber.

24. The method according to claim 12, wherein the waste liquid receptacle is coupled to the liquid container downstream of the filter.

25. The method according to claim 12, wherein the plunger is shaped so as to define the waste liquid receptacle.

26. The method according to claim 25, wherein the plunger is shaped so as to define the filter-receiving chamber, and wherein the filter-receiving chamber is laterally surrounded by at least a portion of the waste liquid receptacle.

27. The method according to claim 12, wherein moving the at least a portion of filter into the filter-receiving chamber comprises moving the at least a portion of filter into the filter-receiving chamber using an elongate member.

28. The method according to claim 12, wherein the liquid includes urine.

29. The method according to claim 12, wherein the liquid is selected from the group consisting of: blood, diluted stool, gastrointestinal (GI) fluid, and bronchoalveolar lavage fluid.

30. The method according to claim 12, wherein the filter-receiving chamber is laterally surrounded by at least a portion of the waste liquid receptacle.

31. The method according to claim 12, wherein the inlet of the filter-receiving chamber has an inlet area that equals no more than 40% of a filter surface area of an upstream side of the filter.

32. The method according to claim 23, wherein moving the at least a portion of filter into the filter-receiving chamber comprises moving the at least a portion of filter into the filter-receiving chamber using an elongate member.

33. The apparatus according to claim 1, wherein the filter-receiving chamber is laterally surrounded by at least a portion of the waste liquid receptacle.

34. The apparatus according to claim 1, wherein the inlet of the filter-receiving chamber has an inlet area that equals no more than 40% of a filter surface area of an upstream side of the filter.

* * * * *